(12) United States Patent
Cihlar et al.

(10) Patent No.: US 11,597,759 B2
(45) Date of Patent: Mar. 7, 2023

(54) MULTISPECIFIC ANTIBODIES THAT TARGET HIV GP120 AND CD3

(71) Applicant: Gilead Sciences, Inc., Foster City, CA (US)

(72) Inventors: Tomas Cihlar, Burlingame, CA (US); Joshua Goldsmith, San Francisco, CA (US); George Kukolj, Mount Royal (CA); Craig S. Pace, Pacifica, CA (US); Doug Rehder, Bonsall, CA (US); Matthew R. Schenauer, Dana Point, CA (US); Derek Dean Sloan, Belmont, CA (US); Heather Theresa Stephenson, San Jose, CA (US); Nathan D. Thomsen, Castro Valley, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 16/867,924

(22) Filed: May 6, 2020

(65) Prior Publication Data

US 2020/0377592 A1 Dec. 3, 2020

Related U.S. Application Data

(63) Continuation of application No. 16/014,153, filed on Jun. 21, 2018, now Pat. No. 10,882,907.

(60) Provisional application No. 62/523,141, filed on Jun. 21, 2017.

(51) Int. Cl.
| | | |
|---|---|---|
| C07K 16/10 | (2006.01) |
| A61K 47/68 | (2017.01) |
| A61K 51/10 | (2006.01) |
| A61P 31/18 | (2006.01) |
| C07K 16/28 | (2006.01) |
| G01N 33/53 | (2006.01) |
| A61K 39/395 | (2006.01) |
| A61K 39/42 | (2006.01) |
| A61K 39/00 | (2006.01) |

(52) U.S. Cl.
CPC ........ *C07K 16/1063* (2013.01); *A61K 39/395* (2013.01); *A61K 39/42* (2013.01); *A61K 47/6841* (2017.08); *A61K 47/6849* (2017.08); *A61K 51/1006* (2013.01); *A61K 51/1042* (2013.01); *A61P 31/18* (2018.01); *C07K 16/283* (2013.01); *C07K 16/2809* (2013.01); *G01N 33/53* (2013.01); *A61K 2039/505* (2013.01); *A61K 2039/572* (2013.01); *C07K 16/2803* (2013.01); *C07K 2317/21* (2013.01); *C07K 2317/31* (2013.01); *C07K 2317/33* (2013.01); *C07K 2317/52* (2013.01); *C07K 2317/524* (2013.01); *C07K 2317/526* (2013.01); *C07K 2317/56* (2013.01); *C07K 2317/565* (2013.01); *C07K 2317/567* (2013.01); *C07K 2317/64* (2013.01); *C07K 2317/71* (2013.01); *C07K 2317/72* (2013.01); *C07K 2317/73* (2013.01); *C07K 2317/732* (2013.01); *C07K 2317/76* (2013.01); *C07K 2317/92* (2013.01); *C07K 2317/94* (2013.01)

(58) Field of Classification Search
CPC ........................ C07K 16/1063; C07K 16/2809
See application file for complete search history.

(56) References Cited

U.S. PATENT DOCUMENTS

| | | | |
|---|---|---|---|
| 6,815,201 B2 | 11/2004 | Pinter |
| 7,041,293 B1 | 5/2006 | Berman et al. |
| 7,317,091 B2 | 1/2008 | Lazar et al. |
| 7,662,925 B2 | 2/2010 | Lazar et al. |
| 8,039,592 B2 | 10/2011 | Lazar et al. |
| 8,088,376 B2 | 1/2012 | Chamberlain et al. |
| 8,093,357 B2 | 1/2012 | Lazar et al. |
| 8,093,359 B2 | 1/2012 | Lazar et al. |
| 8,383,109 B2 | 2/2013 | Lazar et al. |
| 8,388,955 B2 | 3/2013 | Lazar et al. |
| 8,394,925 B2 | 3/2013 | Chamberlain et al. |
| 8,546,543 B2 | 10/2013 | Lazar |
| 8,735,545 B2 | 5/2014 | Lazar et al. |
| 8,840,890 B2 | 9/2014 | Lewis et al. |
| 8,858,937 B2 | 10/2014 | Lazar et al. |
| 8,937,158 B2 | 1/2015 | Lazar et al. |
| 9,040,041 B2 | 5/2015 | Desjarlais et al. |
| 9,051,362 B2 | 6/2015 | Chan-Hui et al. |
| 9,150,663 B2 | 10/2015 | Labrijn et al. |
| 9,353,187 B2 | 5/2016 | Lazar et al. |
| 9,464,131 B2 | 10/2016 | Chan-Hui et al. |
| 9,803,023 B2 | 10/2017 | Chamberlain et al. |
| 10,087,239 B2 | 10/2018 | Chan-Hui et al. |
| 10,184,000 B2 | 1/2019 | Lazar et al. |
| 10,336,818 B2 | 7/2019 | Chamberlain et al. |
| 10,584,176 B2 | 3/2020 | Lazar et al. |

(Continued)

FOREIGN PATENT DOCUMENTS

| | | |
|---|---|---|
| CN | 104271597 A | 1/2015 |
| CO | 11162444 | 11/2011 |

(Continued)

OTHER PUBLICATIONS

Winkler, K., et al., 2000, Changing the antigen-binding specificity by single point mutations of an anti-p24 (HIV-1) antibody, J. Immunol. 165:4505-4514.*

Chen, Z., et al., 2015, Human monoclonal antibodies targeting the haemagglutinin glycoprotein can neutralize H7N9 influenza virus, Nat. Comm. 6:6714, 1-10.*

Sela-Culang, I, et al., Oct. 2013, The structural basis of antibody-antigen recognition, Front. Immunol. 4(Article 302):1-13.*

(Continued)

*Primary Examiner* — Jeffrey S Parkin

(57) ABSTRACT

Multispecific antibodies (e.g., bispecific antibodies) that bind to HIV gp120 and CD3 are disclosed. Also disclosed are methods of using such antibodies to treat or prevent HIV infection.

14 Claims, No Drawings

Specification includes a Sequence Listing.

(56) References Cited

U.S. PATENT DOCUMENTS

| | | |
|---|---|---|
| 2005/0287150 A1 | 12/2005 | Ambrosino et al. |
| 2007/0292390 A1 | 12/2007 | Dimitrov et al. |
| 2008/0279879 A1 | 11/2008 | Zolla-Pazner |
| 2008/0286274 A1 | 11/2008 | Minenkova et al. |
| 2009/0117108 A1 | 5/2009 | Wang et al. |
| 2010/0215691 A1 | 8/2010 | Parks et al. |
| 2011/0044994 A1 | 2/2011 | Chan-Hui et al. |
| 2011/0223615 A1 | 9/2011 | Lewis et al. |
| 2014/0205612 A1 | 7/2014 | Chan-Hui et al. |
| 2015/0152167 A1 | 6/2015 | Ho et al. |
| 2015/0183836 A1 | 7/2015 | Sodroski et al. |
| 2015/0361160 A1 | 12/2015 | Burton et al. |
| 2016/0008374 A1 | 1/2016 | Geleziunas et al. |
| 2017/0190763 A1 | 7/2017 | Balakrishnan et al. |
| 2018/0057570 A1 | 3/2018 | Chan-Hui et al. |
| 2018/0371086 A1 | 12/2018 | Cihlar et al. |
| 2019/0211083 A1 | 7/2019 | Balakrishnan et al. |
| 2020/0024330 A1 | 1/2020 | Chan-Hui et al. |

FOREIGN PATENT DOCUMENTS

| | | |
|---|---|---|
| CO | 13138546 | 6/2013 |
| EP | 2926830 B1 | 8/2017 |
| JP | 2006-315964 A | 11/2006 |
| JP | 2014-240414 A | 12/2014 |
| JP | 2016-512557 A | 4/2016 |
| JP | 2017-505121 A | 2/2017 |
| WO | WO-91/09968 A1 | 7/1991 |
| WO | WO-94/12196 A1 | 6/1994 |
| WO | WO-94/29724 A1 | 12/1994 |
| WO | WO-00/05268 A1 | 2/2000 |
| WO | WO-00/06605 A2 | 2/2000 |
| WO | WO-2004/106381 A1 | 12/2004 |
| WO | WO-2005/077982 A1 | 8/2005 |
| WO | WO-2005/095456 A1 | 10/2005 |
| WO | WO-2006/091693 A2 | 8/2006 |
| WO | WO-2007/042261 A2 | 4/2007 |
| WO | WO-2008/119567 A2 | 10/2008 |
| WO | WO-2010/037835 A2 | 4/2010 |
| WO | WO-2010/037836 A2 | 4/2010 |
| WO | WO-2010/037838 A2 | 4/2010 |
| WO | WO-2010/056898 A2 | 5/2010 |
| WO | WO-2010/107939 A2 | 9/2010 |
| WO | WO-2010/125162 A1 | 11/2010 |
| WO | WO-2012/030904 A2 | 3/2012 |
| WO | WO-2012/068366 A2 | 5/2012 |
| WO | WO-2012/106578 A1 | 8/2012 |
| WO | WO-2013/086533 A1 | 6/2013 |
| WO | WO-2013/163427 A1 | 10/2013 |
| WO | WO-2013/188693 A1 | 12/2013 |
| WO | WO-2014/159940 A1 | 10/2014 |
| WO | WO-2015/001085 A1 | 1/2015 |
| WO | WO-2015/048770 A2 | 4/2015 |
| WO | WO-2015/104346 A1 | 7/2015 |
| WO | WO-2015/143079 A1 | 9/2015 |
| WO | WO-2015/181098 A1 | 12/2015 |
| WO | WO-2015/184203 A1 | 12/2015 |
| WO | WO-2016/116626 A1 | 7/2016 |
| WO | WO-2016/154003 A1 | 9/2016 |
| WO | WO-2016/166629 A1 | 10/2016 |
| WO | WO-2016/168758 A1 | 10/2016 |
| WO | WO-2017/009442 A1 | 1/2017 |
| WO | WO-2017/010874 A1 | 1/2017 |
| WO | WO-2017/074878 A1 | 5/2017 |
| WO | WO-2017/106346 A2 | 6/2017 |
| WO | WO-2017/134197 A1 | 8/2017 |
| WO | WO-2018/146317 A1 | 8/2018 |
| WO | WO-2018/237148 A1 | 12/2018 |

OTHER PUBLICATIONS

Sirin, S., et al., 2016, AB-Bind: Antibody binding mutational database for computational affinity predictions, Prot. Sci. 25:393-409.*

Corrected Notice of Allowability dated Dec. 3, 2020 for U.S. Appl. No. 16/014,153.
Franchini G. and Bosch M. L., (1989) "Genetic relatedness of the human immunodeficiency viruses type 1 and 2 (HIV-1, HIV-2) and the simian immunodeficiency virus (SIV)", Annal. NY Acad. Sci 554(1): 81-87.
He L. et al., (2014), "Toward a more accurate view of human B-cell repertoire by next-generation sequencing, unbiased repertoire capture and single-molecule barcoding", Scientific Reports, vol. 4, No. 1.
Maartens G. et al., (2014), "HIV infection: epidemiology, pathogenesis, treatment, and prevension", The Lancet, 384:258-271.
Notice of Acceptance dated Jun. 16, 2021 for AU Pat. Appl. No. 2018290228.
Notice of Allowance dated Feb. 17, 2021 for Taiwanese Pat. Appl. No. 107121345.
Notice of Allowance dated Sep. 21, 2020 for U.S. Appl. No. 16/014,153.
Office Action dated Dec. 15, 2020 for Korean Pat. Appl. No. 10-2020-7001465.
Office Action dated Feb. 4, 2021 for Canadian Pat. Appl. No. 3065328.
Office Action dated Feb. 16, 2021 for Japanese Pat. Appl. No. 2019-570381.
Office Action dated Jun. 9, 2021 for Korean Pat. Appl. No. 10-2020-7001465.
Office Action dated Aug. 10, 2021 for Japanese Pat. Appl. No. 2019-570381.
Stevenson M., (2003) "HIV-1 pathogenesis", Nat. Med. 9(7):853-860.
Australian Examination Report dated Aug. 9, 2017 for AU2015234345.
Bansal, G. P., 2007, "A summary of the workshop on passive immunization using monoclonal antibodies for HIV/AIDS", held at the National Institute of Allergy and Infectious Diseases, Bethesda, Mar. 10, 2006, Biol. 35:367-371.
Bournazos, S. et al., (2014) "Broadly Neutralizing Anti-HIV-1 Antibodies Require Fc Effector functions for in vivo activity" Cell 158(6):1243-1253.
Brown, M. et al., (1996) "Tolerance of single, but not multiple, amino acid replacements in antibody VH CDR 2: a means of minimizing B cell wastage from somatic hypermutation?" Journal of Immunology 156:3285-3291.
Casadevall, A. et al., (2012) "Immunoglobulin isotype influences affinity and specificity" PNAS 109(31):12272-12273.
Center, R. et al., (2000) "The Human Immunodeficiency Virus Type 1 gp120 V2 Domain Mediates gp41-Independent Intersubunit Contacts" Journal of Virology 74(10):4448-4455.
Chen, C., et al., Sep. 1992, Generation and analysis of random point mutations in an antibody CDR2 sequence: Many mutated antibodies lose their ability to bind antigen, J. Exp. Med. 176:855-866.
Decision/Office Action dated Mar. 31, 2020 for TW Pat. Appl. No. 107121345.
European Examination Report dated Mar. 22, 2018 for EP16206293.9.
European Examination Report dated Dec. 14, 2016 for EP10722810.8.
European Search Report (partial) dated Jun. 22, 2015 for EP140040155.
European Search Report dated Feb. 19, 2018 for EP17194834.2-1116.
European Search Report dated Apr. 21, 2017 for EP16206293.9-1412.
European Search Report dated May 2, 2014 for EP11822530.9-1412/2611465 PCT/US2011/049880.
European Search Report dated Oct. 9, 2015 for EP14004015.5-1412/2926830.
European Search Report dated Oct. 9, 2017 for EP17173548.3-1412.
Fanning, L. et al., (1996) "Development of the Immunoglobulin Repertoire" Journal of Immunology and Immunopathology 79(1):1-14.
Gonzales N R et al. (2005), "Minimizing the immunogenicity of antibodies for clinical application", Tumor Biology, Karger, Basel, CH, vol. 26, No. 1, pp. 31-43.

(56) References Cited

OTHER PUBLICATIONS

Guyader, M. et al., Apr. 1987, "Genome organization and transactivation of the human immunodeficiency virus type 2", Nature 326:662-669.
Igawa T et al. (2011), "Engineering the variable region of therapeutic IgG antibodies", MABS, Landes Bioscience, US, vol. 3, No. 3, pp. 243-252.
Intl. Preliminary Report on Patentability and Written Opinion dated Mar. 5, 2013 for PCT/US2011/049880.
Intl. Preliminary Report on Patentability and Written Opinion dated Sep. 20, 2011 for PCT/US2010/027695.
Intl. Search Report dated Apr. 6, 2011 for PCT/US2010/027695.
Intl. Search Report dated Apr. 6, 2012 for PCT/US2011/049880.
Intl. Search Report dated Aug. 11, 2017 for PCT/US2016/066658.
Intl. Search Report dated Sep. 27, 2018 for PCT/US2018/038760.
Jefferis, R. et al., (2009) "Human Immunoglobulin allotypes" MABS 1(4):332-338.
Julien, J. et al., (2013) "Broadly Neutralizing Antibody PGT121 Allosterically Modulates CD4 Binding via Recognition of the HIV-1 gp120 V3 Base and Multiple Surrounding Glycans" PLoS Pathog 9(5):1-15.
Koefoed, K. et al., (2005) "Molecular characterization of the circulating anti-HIV-1 gp120-specific B cell repertoire using antibody phage display libraries generated from pre-selected HIV-1 gp120 binding PBLs" Journal of Immunological Methods 297:187-201.
Liu, Z., et al., 1999, Fine mapping of the antigen-antibody interaction of scFv215, a recombinant antibody inhibiting RNA polymerase II from Drosophila melanogaster, J. Mol. Recog. 12:103-111.
Lobo E D et al. (2004), "Antibody pharmacokinetics and pharmacodynamics", Warasan Phestchasat Maha Witthayalai Mahidon—Mahidol University Journal of Pharmaceutical Science, Faculty of Pharmacy, Mahidol University, Bangkok, TH, vol. 93, No. 11, pp. 2645-2668.
Lucchese G et al. (2012), "How a single amino acid change may alter the immunological information of a peptide", Frontiers in bioscience: Elite edition, vol. 4, No. 5, pp. 1843-1852.
McConnell A D et al. (2014), "A general approach to antibody thermostabilization", mAbs, vol. 6, No. 5, pp. 1274-1282.
McKeating, J. et al., (1993) "Characterization of Neutralizing Monoclonal Antibodies to Linear and Conformation-Dependent Epitopes within the First and Second Variable Domains of Human Immunodeficiency Virus Type 1 gp120" Journal of Virology 67(8):4932-4944.
Moulard, M. et al., (2002) "'Broadly cross-inactive HIV-1-neutralizing human monoclonal Fab selected for binding to gp120-CD4-CCR5 complexes" PNAS 99(10):6913-6918.
Non-Final Office Action dated Oct. 31, 2019 for U.S. Appl. No. 16/014,153.
Notice of Allowance dated Jan. 8, 2020 for U.S. Appl. No. 16/014,153.
Office Action dated Nov. 27, 2019 for TW Pat. Appl. No. 107121345.
Pantophlet, R. et al., (2006) "GP120: Target for neutralizing HIV-1 antibodies" Annual Review of Immunology 24:739-769.
Pejchal, R. et al., (2010) "Structure and function of broadly reactive antibody PG16 reveal an H3 subdomain that mediates potent neutralization of HIV-1" PNAS 107(25):11483-11488.
Rajpal, A. et al., (2014) "Introduction: Antibody Structure and Function" Therapeutic Fc-Fusion Proteins 1:1-43.
Second Notice of Allowance dated Apr. 2, 2020 for U.S. Appl. No. 16/014,153.
Sela-Culang, I. et al., Oct. 2013, "The structural basis of antibody-antigen recognition", Front. Immunol. 4:Article 202, 1-13.
Sloan, D. et al., (2015) "Targeting HIV Reservoir in Infected CD4 T Cells by Dual-Affinity Re-targeting Molecules (DARTs) that Bind HIV Envelope and Recruit Cytotoxic T Cells" PLoS Pathog 11(11):1-29.

Sok D. et al. (2013), "The Effects of Somatic Hypermutation on Neutralization and Binding in the PGT121 Family of Broadly Neutralizing HIV Antibodies", PLOS Pathogens, vol. 9, No. 11, e1003754.
Stiegler, G. et al., (2001) "A Potent Cross-Clade Neutralizing Human Monoclonal Antibody against a Novel Epitope on gp41 of Human Immunodeficiency Virus Type 1" Aids Research and Human Retroviruses 17(18):1757-1765.
Trkola, A. et al., (1996) "Human Monoclonal Antibody 2G12 Defines a Distinctive Neutralization Epitope on the gp120 Glycoprotein of Human Immunodeficiency Virus Type 1" Journal of Virology 70(2):1100-1108.
Walker, L. et al., (2009) "Broad and Potent Neutralizing Antibodies from an African Donor Reveal a New HIV-1 Vaccine Target" Science 326:285-289.
Walker, L. et al., (2009) Supporting Online Material for "Broad and Potent Neutralizing Antibodies from an African Donor Reveal a New HIV-1 Vaccine Target" Science No. 1178746, 27 pages.
Walker, L. et al., (2011) "Broad neutralization coverage of HIV by multiple highly potent antibodies" Nature 477(7365):466-470.
West, Jr., A. P. et al., Jan. 2012, Single-chain Fv-based anti-HIV proteins: Potential and limitations, J. Virol. 86(1):195-202.
Wiens, G. D., et al., 1997, Somatic mutation in VH complementarity-determining region 2 and framework region 2, J. Immunol. 159:1293-1302.
Winkler, K. et al., (2000) "Changing the Antigen Binding Specificity by Single Point Mutations of an Anti-p24 (HIV-1) Antibody" Journal of Immunology 165:4505-4514.
Written Opinion dated Aug. 11, 2017 for PCT/US2016/066658.
Written Opinion dated Sep. 27, 2018 for PCT/US2018/038760.
Xiang, J. et al., (1991) "Modification in Framework Region I Results in a Decreased Affinity of Chimeric Anti-Tag 72 Antibody" Molecular Immunology 28(1/2):141-148.
Xiang, J. et al., (1995) "Framework Residues 71 and 93 of the Chimeric B72.3 Antibody are Major Determinants of the Conformation of Heavy-chain Hypervariable Loops" J. Mol. Biol. 253:385-390.
Xiang, J. et al., 1999, "Light-chain framework region residue Tyr71 of chimeric B72.3 antibody plays an important role in influencing the TAG72 antigen binding", Prot. Engineer. 12(5):417-421.
Zalevsky, J. et al., (2010) "Enhanced antibody half-life improves in vivo activity" Nature Biotechnology 28(2):157-159.
Zhang, M. et al., (2004) "Identification and Characterization of a New Cross-Reactive Human Immunodeficiency Virus Type 1-Neutralizing Human Monoclonal Antibody" Journal of Virology 78(17):9233-9242.
Zhang, M. et al., (2007) "Novel Approaches for Identification of Broadly Cross-Reactive HIV-1 Neutralizing Human Monoclonal Antibodies and Improvement of Their Potency" Current Pharmaceutical Design 13(2):203-212.
Zhang, M. et al., (2008) "Cross-Reactive Human Immunodeficiency Virus Type 1-Neutralizing Human Monoclonal Antibody That Recognizes a Novel Conformational Epitope on gp41 and Lacks Reactivity against Self-Antigens" Journal of Virology 82(14):6869-6879.
Chinese Office Action and Search Report dated for CN 201880041716.2.
GenBank: JN201894.1, "Homo sapiens isolate PGT121 anti-HIV immunoglobulin heavy chain variable region mRNA, partial cds", Sep. 26, 2011, printed on Apr. 13, 2022.
GenBank: JN201911.1, "Homo sapiens isolate PGT121 anti-HIV immunoglobulin light chain variable region mRNA, partial cds", Sep. 26, 2011, printed on Apr. 13, 2022.
Wang M et al. (1992), "Establishment and preliminary identification of hybridoma cell line with monoclonal antibody against HIV-ENV1 peptide", Monoclonal Antibody Communications, vol. 8, No. 4, pp. 46-50.
First Examination Report dated Jun. 2, 2022 for Indian Pat. Appl. No. 202017000617.
Office Action dated Sep. 26, 2022 for CN 201880041716.2 (10 pages).
Rosa S et al. (2021), "mRNA vaccines manufacturing: Challenges and bottlenecks", Vaccine 39:2190-2200.

(56) References Cited

OTHER PUBLICATIONS

Communication under Rule 164(2)(a) EPC dated Nov. 23, 2022 for EP 18743123.4 (6 pages).
Fischer N et al. (2007), "Bispecific antibodies: Molecules that enable novel therapeutic strategies", Pathobiology, Karger, Basel, CH, vol. 74, No. 1, May 1, 2007 (May 1, 2007), pp. 3-14.
First Examination Report dated Oct. 13, 2020 for AU Pat. Appl. No. 2018290228.
Notice of Allowance dated Jan. 7, 2022 for Japanese Pat. Appl. No. 2019-570381.
Office Action dated Jan. 24, 2022 for Canadian Pat. Appl. No. 3065328.

* cited by examiner

SEQUENCE LISTING

<160> NUMBER OF SEQ ID NOS: 127

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Asp Ser Tyr Trp Ser
1               5

<210> SEQ ID NO 2
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Tyr Val His Lys Ser Gly Asp Thr Asn Tyr Asn Pro Ser Leu Lys Ser
1               5                   10                  15

<210> SEQ ID NO 3
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Thr Leu His Gly Arg Arg Ile Tyr Gly Ile Val Ala Phe Asn Glu Trp
1               5                   10                  15

Phe Thr Tyr Phe Tyr Met Asp Val
            20

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Glu Lys Ser Leu Gly Ser Arg Ala Val Gln
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Asn Asn Gln Asp Arg Pro Ser
1               5

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

His Ile Trp Asp Ser Arg Val Pro Thr Lys Trp Val
1               5                   10

<210> SEQ ID NO 7
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Asn Pro Ser Leu Lys
50                  55                  60

Ser Arg Val His Leu Ser Leu Asp Thr Ser Lys Asn Gln Val Ser Leu
65                  70                  75                  80

Ser Leu Thr Gly Val Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Thr Gly Thr Gln Val
        115                 120                 125

Thr Val Ser Ser
        130

<210> SEQ ID NO 8
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Arg Pro Gly Thr
50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105

<210> SEQ ID NO 9
<211> LENGTH: 462
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Asn Pro Ser Leu Lys
    50                  55                  60

Ser Arg Val His Leu Ser Leu Asp Thr Ser Lys Asn Gln Val Ser Leu
65                  70                  75                  80

Ser Leu Thr Gly Val Thr Ala Ala Asp Ser Gly Lys Tyr Tyr Cys Ala
            85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Thr Gly Thr Gln Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
        180                 185                 190

Gly Leu Tyr Ser Leu Ser Ser Val Val Thr Val Pro Ser Ser Ser Leu
    195                 200                 205

Gly Thr Gln Thr Tyr Ile Cys Asn Val Asn His Lys Pro Ser Asn Thr
210                 215                 220

Lys Val Asp Lys Arg Val Glu Pro Lys Ser Cys Asp Lys Thr His Thr
225                 230                 235                 240

Cys Pro Pro Cys Pro Ala Pro Glu Phe Glu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Ala Val Ser His Glu Asp Pro Glu Val
    275                 280                 285

Lys Phe Asn Trp Tyr Val Asp Gly Val Glu Val His Asn Ala Lys Thr
290                 295                 300

```
Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Gln Gly Asn Val Phe Ser Cys Ser Val Leu His Glu Ala Leu His
        435                 440                 445

Ser His Tyr Thr Gln Lys Ser Leu Ser Leu Ser Pro Gly Lys
    450                 455                 460

<210> SEQ ID NO 10
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Arg Pro Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190
```

```
Gln Val Thr His Glu Gly Ser Thr Val Glu Lys Thr Val Ala Pro Thr
        195                 200                 205

Glu Cys Ser
    210

<210> SEQ ID NO 11
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Thr Tyr Ala Met Asn
1               5

<210> SEQ ID NO 12
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Arg Ile Arg Ser Lys Tyr Asn Asn Tyr Ala Thr Tyr Tyr Ala Asp Ser
1               5                   10                  15

Val Lys Asp

<210> SEQ ID NO 13
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

His Gly Asn Phe Gly Asn Ser Tyr Val Ser Trp Phe Ala Tyr
1               5                   10

<210> SEQ ID NO 14
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Ser Ser Thr Gly Ala Val Thr Thr Ser Asn Tyr Ala Asn
1               5                   10

<210> SEQ ID NO 15
<211> LENGTH: 7
<212> TYPE: PRT
<213> ORGANISM: Homo sapiens

<400> SEQUENCE: 15

Gly Thr Asn Lys Arg Ala Pro
1               5
```

```
<210> SEQ ID NO 16
<211> LENGTH: 9
<212> TYPE: PRT
<213> ORGANISM: Homo sapiens

<400> SEQUENCE: 16

Ala Leu Trp Tyr Ser Asn Leu Trp Val
1               5

<210> SEQ ID NO 17
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 18
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 19
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Ala Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350
```

```
Glu Pro Gln Val Tyr Thr Leu Pro Pro Ser Arg Glu Met Thr Lys
            355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
                420                 425                 430

Cys Ser Val Leu His Glu Ala Leu His Ser His Tyr Thr Gln Lys Ser
            435                 440                 445

Leu Ser Leu Ser Pro Gly Lys
    450                 455

<210> SEQ ID NO 20
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 21
<211> LENGTH: 475
<212> TYPE: PRT
```

<213> ORGANISM: Human immunodeficiency virus 1

<400> SEQUENCE: 21

| | | | | | | | | | | | | | | |
|---|---|---|---|---|---|---|---|---|---|---|---|---|---|---|
| Ala | Glu | Gln | Leu | Trp | Val | Thr | Val | Tyr | Tyr | Gly | Val | Pro | Val | Trp | Arg |
| 1 | | | | 5 | | | | | 10 | | | | | 15 | |
| Glu | Ala | Asn | Thr | Thr | Leu | Phe | Cys | Ala | Ser | Asp | Ala | Lys | Ala | Tyr | Asp |
| | | | 20 | | | | | 25 | | | | | 30 | | |
| Thr | Glu | Val | His | Asn | Val | Trp | Ala | Thr | His | Ala | Cys | Val | Pro | Thr | Asp |
| | | | | 35 | | | | | 40 | | | | | 45 | |
| Pro | Asn | Pro | Gln | Glu | Val | Val | Met | Gly | Asn | Val | Thr | Glu | Asp | Phe | Asn |
| | | 50 | | | | | 55 | | | | | 60 | | | |
| Met | Trp | Lys | Asn | Asn | Met | Val | Glu | Gln | Met | His | Glu | Asp | Ile | Ile | Ser |
| 65 | | | | | 70 | | | | | 75 | | | | | 80 |
| Leu | Trp | Asp | Gln | Ser | Leu | Lys | Pro | Cys | Val | Lys | Leu | Thr | Pro | Leu | Cys |
| | | | | 85 | | | | | 90 | | | | | 95 | |
| Val | Thr | Leu | His | Cys | Thr | Asn | Val | Thr | Ile | Ser | Ser | Thr | Asn | Gly | Ser |
| | | | | 100 | | | | | 105 | | | | | 110 | |
| Thr | Ala | Asn | Val | Thr | Met | Arg | Glu | Glu | Met | Lys | Asn | Cys | Ser | Phe | Asn |
| | | | 115 | | | | | 120 | | | | | 125 | | |
| Thr | Thr | Thr | Val | Ile | Arg | Asp | Lys | Ile | Gln | Lys | Glu | Tyr | Ala | Leu | Phe |
| | | 130 | | | | | 135 | | | | | 140 | | | |
| Tyr | Lys | Leu | Asp | Ile | Val | Pro | Ile | Glu | Gly | Lys | Asn | Thr | Asn | Thr | Ser |
| 145 | | | | | 150 | | | | | 155 | | | | | 160 |
| Tyr | Arg | Leu | Ile | Asn | Cys | Asn | Thr | Ser | Val | Ile | Thr | Gln | Ala | Cys | Pro |
| | | | | 165 | | | | | 170 | | | | | 175 | |
| Lys | Val | Ser | Phe | Glu | Pro | Ile | Pro | Ile | His | Tyr | Cys | Ala | Pro | Ala | Gly |
| | | | 180 | | | | | 185 | | | | | 190 | | |
| Phe | Ala | Ile | Leu | Lys | Cys | Asn | Asn | Lys | Thr | Phe | Asn | Gly | Lys | Gly | Pro |
| | | | | 195 | | | | | 200 | | | | | 205 | |
| Cys | Arg | Asn | Val | Ser | Thr | Val | Gln | Cys | Thr | His | Gly | Ile | Lys | Pro | Val |
| | | 210 | | | | | 215 | | | | | 220 | | | |
| Val | Ser | Thr | Gln | Leu | Leu | Leu | Asn | Gly | Ser | Leu | Ala | Glu | Glu | Asp | Ile |
| 225 | | | | | 230 | | | | | 235 | | | | | 240 |
| Ile | Ile | Arg | Ser | Glu | Asn | Phe | Thr | Asn | Asn | Gly | Lys | Asn | Ile | Ile | Val |
| | | | | 245 | | | | | 250 | | | | | 255 | |
| Gln | Leu | Lys | Glu | Pro | Val | Lys | Ile | Asn | Cys | Thr | Arg | Pro | Gly | Asn | Asn |
| | | | 260 | | | | | 265 | | | | | 270 | | |
| Thr | Arg | Arg | Ser | Ile | Asn | Ile | Gly | Pro | Gly | Arg | Ala | Phe | Tyr | Ala | Thr |
| | | 275 | | | | | 280 | | | | | 285 | | | |
| Gly | Ala | Ile | Ile | Gly | Asp | Ile | Arg | Lys | Ala | His | Cys | Asn | Ile | Ser | Thr |
| | | 290 | | | | | 295 | | | | | 300 | | | |
| Glu | Gln | Trp | Asn | Asn | Thr | Leu | Thr | Gln | Ile | Val | Asp | Lys | Leu | Arg | Glu |
| 305 | | | | | 310 | | | | | 315 | | | | | 320 |
| Gln | Phe | Gly | Asn | Lys | Thr | Ile | Ile | Phe | Asn | Gln | Ser | Ser | Gly | Gly | Asp |
| | | | | 325 | | | | | 330 | | | | | 335 | |
| Pro | Glu | Val | Val | Met | His | Thr | Phe | Asn | Cys | Gly | Gly | Glu | Phe | Phe | Tyr |
| | | | 340 | | | | | 345 | | | | | 350 | | |
| Cys | Asn | Ser | Thr | Gln | Leu | Phe | Asn | Ser | Thr | Trp | Phe | Asn | Asn | Gly | Thr |
| | | | | 355 | | | | | 360 | | | | | 365 | |
| Ser | Thr | Trp | Asn | Ser | Thr | Ala | Asp | Asn | Ile | Thr | Leu | Pro | Cys | Arg | Ile |
| | | 370 | | | | | 375 | | | | | 380 | | | |
| Lys | Gln | Val | Ile | Asn | Met | Trp | Gln | Glu | Val | Gly | Lys | Ala | Met | Tyr | Ala |
| 385 | | | | | 390 | | | | | 395 | | | | | 400 |

```
Pro Pro Ile Arg Gly Gln Ile Asp Cys Ser Ser Asn Ile Thr Gly Leu
                405                 410                 415

Ile Leu Thr Arg Asp Gly Gly Ser Asn Ser Ser Gln Asn Glu Thr Phe
            420                 425                 430

Arg Pro Gly Gly Gly Asn Met Lys Asp Asn Trp Arg Ser Glu Leu Tyr
        435                 440                 445

Lys Tyr Lys Val Val Lys Ile Glu Pro Leu Gly Ile Ala Pro Thr Arg
    450                 455                 460

Ala Lys Arg Arg Val Val Gln Arg Glu Lys Arg
465                 470                 475

<210> SEQ ID NO 22
<211> LENGTH: 35
<212> TYPE: PRT
<213> ORGANISM: Human immunodeficiency virus 1

<400> SEQUENCE: 22

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

<210> SEQ ID NO 23
<211> LENGTH: 462
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190
```

```
Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
        210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 24
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Tyr Val His Lys Ser Gly Asp Thr Asn Tyr Ser Pro Ser Leu Lys Ser
1               5                   10                  15

<210> SEQ ID NO 25
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 25

Gly Ala Ser Ile Ser Asp Ser Tyr
1               5

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Val His Lys Ser Gly Asp Thr
1               5

<210> SEQ ID NO 27
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ala Arg Thr Leu His Gly Arg Arg Ile Tyr Gly Ile Val Ala Phe Asn
1               5                   10                  15

Glu Trp Phe Thr Tyr Phe Tyr Met Asp Val
            20                  25

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Ala Ser Ile Ser Asp Ser
1               5

<210> SEQ ID NO 29
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Leu His Gly Arg Arg Ile Tyr Gly Ile Val Ala Phe Asn Glu Trp Phe
1               5                   10                  15

Thr Tyr Phe Tyr Met Asp
            20

<210> SEQ ID NO 30
<211> LENGTH: 10
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 30

Val Ser Gly Ala Ser Ile Ser Asp Ser Tyr
1               5                   10

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Val His Lys Ser Gly Asp Thr Asn Tyr Ser Pro Ser Leu Lys Ser Arg
1               5                   10                  15

<210> SEQ ID NO 32
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Thr Leu His Gly Arg Arg Ile Tyr Gly Ile Val Ala Phe Asn Glu Trp
1               5                   10                  15

Phe Thr Tyr Phe Tyr Met Asp
            20

<210> SEQ ID NO 33
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Pro Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
            165                 170                 175

Leu Ser Leu Thr Pro Glu Gln Trp Lys Ser His Arg Ser Tyr Ser Cys
        180                 185                 190

Gln Val Thr His Glu Gly Ser Thr Val Glu Lys Thr Val Ala Pro Thr
            195                 200                 205

Glu Cys Ser
        210

<210> SEQ ID NO 34
<211> LENGTH: 6
<212> TYPE: PRT
<213> ORGANISM: Methylobacterium extorquens

<400> SEQUENCE: 34

Ser Leu Gly Ser Arg Ala
1               5

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Trp Asp Ser Arg Val Pro Thr Lys Trp
1               5

<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Glu Lys Ser Leu Gly Ser Arg Ala
1               5

<210> SEQ ID NO 37
<211> LENGTH: 849
<212> TYPE: PRT
<213> ORGANISM: Human immunodeficiency virus 1

<400> SEQUENCE: 37

Met Lys Val Met Gly Thr Lys Lys Asn Tyr Gln His Leu Trp Arg Trp
1               5                   10                  15

Gly Ile Met Leu Leu Gly Met Leu Met Met Ser Ser Ala Ala Glu Gln
            20                  25                  30

Leu Trp Val Thr Val Tyr Tyr Gly Val Pro Val Trp Arg Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

```
Gln Glu Val Val Met Gly Asn Val Thr Glu Asp Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

His Cys Thr Asn Val Thr Ile Ser Ser Thr Asn Gly Ser Thr Ala Asn
130                 135                 140

Val Thr Met Arg Glu Glu Met Lys Asn Cys Ser Phe Asn Thr Thr Thr
145                 150                 155                 160

Val Ile Arg Asp Lys Ile Gln Lys Glu Tyr Ala Leu Phe Tyr Lys Leu
                165                 170                 175

Asp Ile Val Pro Ile Glu Gly Lys Asn Thr Asn Thr Ser Tyr Arg Leu
                180                 185                 190

Ile Asn Cys Asn Thr Ser Val Ile Thr Gln Ala Cys Pro Lys Val Ser
                195                 200                 205

Phe Glu Pro Ile Pro Ile His Tyr Cys Ala Pro Ala Gly Phe Ala Ile
            210                 215                 220

Leu Lys Cys Asn Asn Lys Thr Phe Asn Gly Lys Gly Pro Cys Arg Asn
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Asp Ile Ile Ile Arg
                260                 265                 270

Ser Glu Asn Phe Thr Asn Asn Gly Lys Asn Ile Ile Val Gln Leu Lys
                275                 280                 285

Glu Pro Val Lys Ile Asn Cys Thr Arg Pro Gly Asn Asn Thr Arg Arg
            290                 295                 300

Ser Ile Asn Ile Gly Pro Gly Arg Ala Phe Tyr Ala Thr Gly Ala Ile
305                 310                 315                 320

Ile Gly Asp Ile Arg Lys Ala His Cys Asn Ile Ser Thr Glu Gln Trp
                325                 330                 335

Asn Asn Thr Leu Thr Gln Ile Val Asp Lys Leu Arg Glu Gln Phe Gly
                340                 345                 350

Asn Lys Thr Ile Ile Phe Asn Gln Ser Ser Gly Gly Asp Pro Glu Val
            355                 360                 365

Val Met His Thr Phe Asn Cys Gly Gly Glu Phe Phe Tyr Cys Asn Ser
370                 375                 380

Thr Gln Leu Phe Asn Ser Thr Trp Phe Asn Asn Gly Thr Ser Thr Trp
385                 390                 395                 400

Asn Ser Thr Ala Asp Asn Ile Thr Leu Pro Cys Arg Ile Lys Gln Val
            405                 410                 415

Ile Asn Met Trp Gln Glu Val Gly Lys Ala Met Tyr Ala Pro Pro Ile
                420                 425                 430

Arg Gly Gln Ile Asp Cys Ser Ser Asn Ile Thr Gly Leu Ile Leu Thr
                435                 440                 445

Arg Asp Gly Gly Ser Asn Ser Ser Gln Asn Glu Thr Phe Arg Pro Gly
            450                 455                 460

Gly Gly Asn Met Lys Asp Asn Trp Arg Ser Glu Leu Tyr Lys Tyr Lys
465                 470                 475                 480

Val Val Lys Ile Glu Pro Leu Gly Ile Ala Pro Thr Arg Ala Lys Arg
                485                 490                 495
```

```
Arg Val Val Gln Arg Glu Lys Arg Ala Val Thr Leu Gly Ala Val Phe
                500                 505                 510
Leu Gly Phe Leu Gly Ala Ala Gly Ser Thr Met Gly Ala Ala Ser Leu
            515                 520                 525
Thr Leu Thr Val Gln Ala Arg Leu Leu Leu Ser Gly Ile Val Gln Gln
        530                 535                 540
Gln Ser Asn Leu Leu Arg Ala Ile Glu Ala Gln Gln His Met Leu Gln
545                 550                 555                 560
Leu Thr Val Trp Gly Ile Lys Gln Leu Gln Ala Arg Val Leu Ala Ile
                565                 570                 575
Glu Arg Tyr Leu Lys Asp Gln Gln Leu Leu Gly Ile Trp Gly Cys Ser
            580                 585                 590
Gly Lys Leu Ile Cys Thr Thr Thr Val Pro Trp Asn Thr Ser Trp Ser
        595                 600                 605
Asn Lys Ser Tyr Asp Tyr Ile Trp Asn Asn Met Thr Trp Met Gln Trp
610                 615                 620
Glu Arg Glu Ile Asp Asn Tyr Thr Gly Phe Ile Tyr Thr Leu Ile Glu
625                 630                 635                 640
Glu Ser Gln Asn Gln Gln Glu Lys Asn Glu Leu Glu Leu Leu Glu Leu
            645                 650                 655
Asp Lys Trp Ala Ser Leu Trp Asn Trp Phe Asn Ile Thr Asn Trp Leu
        660                 665                 670
Trp Tyr Ile Lys Leu Phe Ile Met Ile Ile Gly Gly Leu Val Gly Leu
            675                 680                 685
Arg Ile Val Cys Ala Val Leu Ser Ile Val Asn Arg Val Arg Gln Gly
        690                 695                 700
Tyr Ser Pro Leu Ser Phe Gln Thr Arg Leu Pro Asn Pro Arg Gly Pro
705                 710                 715                 720
Asp Arg Pro Glu Glu Thr Glu Gly Glu Gly Gly Glu Arg Asp Arg Asp
                725                 730                 735
Arg Ser Ala Arg Leu Val Asn Gly Phe Leu Ala Ile Ile Trp Asp Asp
            740                 745                 750
Leu Arg Ser Leu Cys Leu Phe Ser Tyr His Arg Leu Arg Asp Leu Leu
        755                 760                 765
Leu Ile Val Ala Arg Val Val Glu Ile Leu Gly Arg Arg Gly Trp Glu
    770                 775                 780
Ile Leu Lys Tyr Trp Trp Asn Leu Leu Lys Tyr Trp Ser Gln Glu Leu
785                 790                 795                 800
Lys Asn Ser Ala Val Ser Leu Leu Asn Val Thr Ala Ile Ala Val Ala
                805                 810                 815
Glu Gly Thr Asp Arg Val Ile Glu Ile Val Gln Arg Ala Val Arg Ala
            820                 825                 830
Ile Leu His Ile Pro Thr Arg Ile Arg Gln Gly Phe Glu Arg Ala Leu
        835                 840                 845
Leu

<210> SEQ ID NO 38
<211> LENGTH: 481
<212> TYPE: PRT
<213> ORGANISM: Human immunodeficiency virus 1

<400> SEQUENCE: 38

Thr Glu Lys Leu Trp Val Thr Val Tyr Tyr Gly Val Pro Val Trp Lys
1               5                   10                  15
```

-continued

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Val Asn Val Thr Glu Asn Phe Asn
    50                  55                  60

Met Trp Lys Asn Asp Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Ser Leu Lys Cys Thr Asp Leu Lys Asn Asp Thr Asn Thr Asn Ser
            100                 105                 110

Ser Ser Gly Arg Met Ile Met Glu Lys Gly Glu Ile Lys Asn Cys Ser
        115                 120                 125

Phe Asn Ile Ser Thr Ser Ile Arg Gly Lys Val Gln Lys Glu Tyr Ala
    130                 135                 140

Phe Phe Tyr Lys Leu Asp Ile Ile Pro Ile Asp Asn Asp Thr Thr Ser
145                 150                 155                 160

Tyr Lys Leu Thr Ser Cys Asn Thr Ser Val Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Asn Asn Lys Thr Phe Asn Gly Thr Gly Pro
        195                 200                 205

Cys Thr Asn Val Ser Thr Val Gln Cys Thr His Gly Ile Arg Pro Val
    210                 215                 220

Val Ser Thr Gln Leu Leu Leu Asn Gly Ser Leu Ala Glu Glu Glu Val
225                 230                 235                 240

Val Ile Arg Ser Val Asn Phe Thr Asp Asn Ala Lys Thr Ile Ile Val
                245                 250                 255

Gln Leu Asn Thr Ser Val Glu Ile Asn Cys Thr Arg Pro Asn Asn Asn
            260                 265                 270

Thr Arg Lys Arg Ile Arg Ile Gln Arg Gly Pro Gly Arg Ala Phe Val
        275                 280                 285

Thr Ile Gly Lys Ile Gly Asn Met Arg Gln Ala His Cys Asn Ile Ser
    290                 295                 300

Arg Ala Lys Trp Asn Asn Thr Leu Lys Gln Ile Ala Ser Lys Leu Arg
305                 310                 315                 320

Glu Gln Phe Gly Asn Asn Lys Thr Ile Ile Phe Lys Gln Ser Ser Gly
                325                 330                 335

Gly Asp Pro Glu Ile Val Thr His Ser Phe Asn Cys Gly Gly Glu Phe
            340                 345                 350

Phe Tyr Cys Asn Ser Thr Gln Leu Phe Asn Ser Thr Trp Phe Asn Ser
        355                 360                 365

Thr Trp Ser Thr Glu Gly Ser Asn Asn Thr Glu Gly Ser Asp Thr Ile
    370                 375                 380

Thr Leu Pro Cys Arg Ile Lys Gln Ile Ile Asn Met Trp Gln Lys Val
385                 390                 395                 400

Gly Lys Ala Met Tyr Ala Pro Pro Ile Ser Gly Gln Ile Arg Cys Ser
                405                 410                 415

Ser Asn Ile Thr Gly Leu Leu Leu Thr Arg Asp Gly Gly Asn Ser Asn
            420                 425                 430

```
Asn Glu Ser Glu Ile Phe Arg Pro Gly Gly Asp Met Arg Asp Asn
        435                 440                 445

Trp Arg Ser Glu Leu Tyr Lys Tyr Lys Val Val Lys Ile Glu Pro Leu
    450                 455                 460

Gly Val Ala Pro Thr Lys Ala Lys Arg Val Val Gln Arg Glu Lys
465                 470                 475                 480

Arg
```

<210> SEQ ID NO 39
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

```
Asn Asn Gln Asp Arg Pro Ser Gly Ile Pro Glu Arg
1               5                   10
```

<210> SEQ ID NO 40
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

```
Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Tyr Arg Pro Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190
```

```
Gln Val Thr His Glu Gly Ser Thr Val Glu Lys Thr Val Ala Pro Thr
        195                 200                 205

Glu Cys Ser
    210

<210> SEQ ID NO 41
<211> LENGTH: 462
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Asn Pro Ser Leu Lys
    50                  55                  60

Ser Arg Val His Leu Ser Leu Asp Thr Ser Lys Asn Gln Val Ser Leu
65                  70                  75                  80

Ser Leu Thr Gly Val Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Thr Gly Thr Gln Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Ala Gly Pro Asp Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320
```

```
Leu Thr Val Leu His Gln Asp Trp Leu Asn Gly Lys Glu Tyr Lys Cys
                325                 330                 335

Lys Val Ser Asn Lys Ala Leu Pro Leu Pro Glu Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Leu His Glu Ala Leu His
        435                 440                 445

Ser His Tyr Thr Gln Lys Ser Leu Ser Leu Ser Pro Gly Lys
    450                 455                 460

<210> SEQ ID NO 42
<211> LENGTH: 171
<212> TYPE: PRT
<213> ORGANISM: Homo sapiens

<400> SEQUENCE: 42

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 43

Gly Phe Thr Phe Asn Thr Tyr Ala
1               5

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ile Arg Ser Lys Tyr Asn Asn Tyr Ala Thr
1               5                   10

<210> SEQ ID NO 45
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Val Arg His Gly Asn Phe Gly Asn Ser Tyr Val Ser Trp Phe Ala Tyr
1               5                   10                  15

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Phe Thr Phe Asn Thr Tyr
1               5

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ser Lys Tyr Asn Asn Tyr
1               5

<210> SEQ ID NO 48
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Asn Phe Gly Asn Ser Tyr Val Ser Trp Phe Ala
1               5                   10

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ala Ser Gly Phe Thr Phe Asn Thr Tyr Ala
1               5                   10

<210> SEQ ID NO 50
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ile Arg Ser Lys Tyr Asn Asn Tyr Ala Thr Tyr Tyr Ala Asp Ser Val
1               5                   10                  15

Lys Asp Arg

<210> SEQ ID NO 51
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

His Gly Asn Phe Gly Asn Ser Tyr Val Ser Trp Phe Ala
1               5                   10

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Thr Gly Ala Val Thr Thr Ser Asn Tyr
1               5

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ser Ser Thr Gly Ala Val Thr Thr Ser Asn Tyr
1               5                   10

<210> SEQ ID NO 54
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Trp Tyr Ser Asn Leu Trp
1               5

<210> SEQ ID NO 55
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Thr Asn Lys Arg Ala Pro Gly Val Pro Ala Arg
1               5                   10

<210> SEQ ID NO 56
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

-continued

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 57
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
            290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
            325                 330

<210> SEQ ID NO 58
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 59
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330

<210> SEQ ID NO 60
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
    115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 61
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
            290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
            325                 330

<210> SEQ ID NO 62
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 63
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Val Leu Asp Ser Asp Gly Ser Phe Leu
            275                 280                 285

Leu Tyr Ser Lys Leu Thr Val Asp Lys Ser Arg Trp Gln Gln Gly Asn
290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330

<210> SEQ ID NO 64
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Glu Pro Lys Ser Cys Asp Lys Thr His Thr Cys Pro Pro Cys Pro Ala
1               5                   10                  15

Pro Glu Phe Glu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Leu Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 65
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 65

```
Glu Pro Lys Ser Cys Asp Lys Thr His Thr Cys Pro Pro Cys Pro Ala
1               5                   10                  15

Pro Glu Phe Glu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Leu Leu Tyr
            180                 185                 190

Ser Lys Leu Thr Val Asp Lys Ser Arg Trp Gln Gln Gly Asn Val Phe
        195                 200                 205

Ser Cys Ser Val Leu His Glu Ala Leu His Ser His Tyr Thr Gln Lys
    210                 215                 220

Ser Leu Ser Leu Ser Pro Gly Lys
225                 230
```

<210> SEQ ID NO 66
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Leu Leu Ala Gly Pro Asp Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 67
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330

<210> SEQ ID NO 68
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 69
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Arg Leu Thr Val Asp Lys Ser Arg Trp Gln Gln Gly Asn
290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
            325                 330

<210> SEQ ID NO 70
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Phe Glu Gly Gly Pro Asp Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 71
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330

<210> SEQ ID NO 72
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Arg Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 73
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Asp Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Arg Leu Thr Val Asp Lys Ser Arg Trp Gln Gln Gly Asn
290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330

<210> SEQ ID NO 74
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Pro Lys Ser Cys Asp Lys Thr His Thr Cys Pro Pro Cys Pro Ala
1               5                   10                  15

Pro Glu Phe Glu Gly Gly Pro Asp Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

-continued

```
<210> SEQ ID NO 75
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Glu Pro Lys Ser Cys Asp Lys Thr His Thr Cys Pro Pro Cys Pro Ala
1               5                   10                  15

Pro Glu Phe Glu Gly Gly Pro Asp Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Gln Gly Asn Val Phe
        195                 200                 205

Ser Cys Ser Val Leu His Glu Ala Leu His Ser His Tyr Thr Gln Lys
    210                 215                 220

Ser Leu Ser Leu Ser Pro Gly Lys
225                 230

<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Gly Gly Gly Ser
1               5

<210> SEQ ID NO 77
<211> LENGTH: 330
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 77

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 78
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

```
Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Phe Arg Pro Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210
```

<210> SEQ ID NO 79
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

```
Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Thr Arg Pro Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu Gly Gln Pro Lys Ala Ala Pro
            100                 105                 110
```

Ser Val Thr Leu Phe Pro Pro Ser Ser Glu Glu Leu Gln Ala Asn Lys
            115                 120                 125

Ala Thr Leu Val Cys Leu Ile Ser Asp Phe Tyr Pro Gly Ala Val Thr
        130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210

<210> SEQ ID NO 80
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Gly Ser Arg Pro Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
            115                 120                 125

Ala Thr Leu Val Cys Leu Ile Ser Asp Phe Tyr Pro Gly Ala Val Thr
        130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210

<210> SEQ ID NO 81
<211> LENGTH: 105

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 81

```
Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Tyr Arg Pro Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105
```

<210> SEQ ID NO 82
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Phe Arg Pro Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105
```

<210> SEQ ID NO 83
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Ser Asp Ile Ser Val Ala Pro Gly Glu Thr Ala Arg Ile Ser Cys Gly
1               5                   10                  15
```

```
Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Thr Arg Pro Gly Thr
 50                  55                  60

Thr Ala Thr Leu Thr Ile Thr Ser Val Glu Ala Gly Asp Glu Ala Asp
 65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105
```

<210> SEQ ID NO 84
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 84

```
Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Gly Ser Arg Pro Gly Thr
 50                  55                  60

Thr Ala Thr Leu Thr Ile Thr Ser Val Glu Ala Gly Asp Glu Ala Asp
 65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105
```

<210> SEQ ID NO 85
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 85

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Val Leu Gln Ser
        35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
65                  70                  75                  80
```

His Lys Leu Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 86
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Leu Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 87
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 88
<211> LENGTH: 106
<212> TYPE: PRT
<213> ORGANISM: Homo sapiens

```
<400> SEQUENCE: 88

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 89
<211> LENGTH: 106
<212> TYPE: PRT
<213> ORGANISM: Homo sapiens

<400> SEQUENCE: 89

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 90
<211> LENGTH: 106
<212> TYPE: PRT
<213> ORGANISM: Homo sapiens

<400> SEQUENCE: 90

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Ala Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95
```

```
Glu Lys Thr Val Ala Pro Thr Glu Cys Ser
            100                 105
```

<210> SEQ ID NO 91
<211> LENGTH: 106
<212> TYPE: PRT
<213> ORGANISM: Homo sapiens

<400> SEQUENCE: 91

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

<210> SEQ ID NO 92
<211> LENGTH: 462
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

```
Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Asn Pro Ser Leu Lys
    50                  55                  60

Ser Arg Val His Leu Ser Leu Asp Thr Ser Lys Asn Gln Val Ser Leu
65                  70                  75                  80

Ser Leu Thr Gly Val Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Thr Gly Thr Gln Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190
```

Gly Leu Tyr Ser Leu Ser Ser Val Thr Val Pro Ser Ser Leu
            195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Phe Glu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Ala Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 93
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Ala Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 94
<211> LENGTH: 462
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 94

```
Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Asn Pro Ser Leu Lys
    50                  55                  60

Ser Arg Val His Leu Ser Leu Asp Thr Ser Lys Asn Gln Val Ser Leu
65                  70                  75                  80

Ser Leu Thr Gly Val Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Thr Gly Thr Gln Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Ala Gly Pro Asp Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Leu Pro Glu Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400
```

Gln Pro Glu Asn Asn Tyr Lys Thr Thr Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Leu His Glu Ala Leu His
        435                 440                 445

Ser His Tyr Thr Gln Lys Ser Leu Ser Leu Ser Pro Gly Lys
    450                 455                 460

<210> SEQ ID NO 95
<211> LENGTH: 287
<212> TYPE: PRT
<213> ORGANISM: Homo sapiens

<400> SEQUENCE: 95

Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Arg Glu Ala Tyr Leu Thr Gln Leu Met Ile Ile Lys
    50                  55                  60

Asn Ser Thr Tyr Arg Glu Ile Gly Arg Arg Leu Lys Phe Trp Asn Glu
65                  70                  75                  80

Thr Asp Pro Glu Phe Val Ile Asp His Met Asp Ala Asn Lys Ala Gly
                85                  90                  95

Arg Tyr Gln Cys Gln Tyr Arg Ile Gly His Tyr Arg Phe Arg Tyr Ser
            100                 105                 110

Asp Thr Leu Glu Leu Val Val Thr Gly Leu Tyr Gly Lys Pro Phe Leu
        115                 120                 125

Ser Ala Asp Arg Gly Leu Val Leu Met Pro Gly Glu Asn Ile Ser Leu
    130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile His Gln Asp Tyr Thr
    210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285

<210> SEQ ID NO 96
<211> LENGTH: 119
<212> TYPE: PRT

<213> ORGANISM: Homo sapiens

<400> SEQUENCE: 96

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Val Leu His Trp Val Arg Gln Ala Pro Gly Lys Gly Leu Asp Trp Val
        35                  40                  45

Ala Val Ile Ser Asp Asp Gly Arg Asn Lys Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Gly Tyr Ser Gly Ser Trp Phe Asp Tyr Trp Gly Gln Gly
            100                 105                 110

Thr Leu Val Thr Val Ser Ser
            115

<210> SEQ ID NO 97
<211> LENGTH: 449
<212> TYPE: PRT
<213> ORGANISM: Homo sapiens

<400> SEQUENCE: 97

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Val Leu His Trp Val Arg Gln Ala Pro Gly Lys Gly Leu Asp Trp Val
        35                  40                  45

Ala Val Ile Ser Asp Asp Gly Arg Asn Lys Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Glu Gly Tyr Ser Gly Ser Trp Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

```
Thr His Thr Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Ala Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Leu Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ser His Tyr Thr Gln Lys Ser Leu Ser Leu Ser Pro Gly
        435                 440                 445

Lys

<210> SEQ ID NO 98
<211> LENGTH: 5
<212> TYPE: PRT
<213> ORGANISM: Homo sapiens

<400> SEQUENCE: 98

Ser Tyr Val Leu His
1               5

<210> SEQ ID NO 99
<211> LENGTH: 17
<212> TYPE: PRT
<213> ORGANISM: Homo sapiens

<400> SEQUENCE: 99

Val Ile Ser Asp Asp Gly Arg Asn Lys Tyr Phe Ala Asp Ser Val Lys
1               5                   10                  15

Gly

<210> SEQ ID NO 100
<211> LENGTH: 10
<212> TYPE: PRT
<213> ORGANISM: Homo sapiens

<400> SEQUENCE: 100

Glu Gly Tyr Ser Gly Ser Trp Phe Asp Tyr
1               5                   10
```

<210> SEQ ID NO 101
<211> LENGTH: 107
<212> TYPE: PRT
<213> ORGANISM: Homo sapiens

<400> SEQUENCE: 101

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Gly Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105
```

<210> SEQ ID NO 102
<211> LENGTH: 214
<212> TYPE: PRT
<213> ORGANISM: Homo sapiens

<400> SEQUENCE: 102

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Gly Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 103
<211> LENGTH: 11
<212> TYPE: PRT
<213> ORGANISM: Homo sapiens

<400> SEQUENCE: 103

Arg Ala Ser Gln Gly Ile Ser Ser Ala Leu Ala
1               5                   10

<210> SEQ ID NO 104
<211> LENGTH: 7
<212> TYPE: PRT
<213> ORGANISM: Homo sapiens

<400> SEQUENCE: 104

Gly Ala Ser Ser Leu Glu Gly
1               5

<210> SEQ ID NO 105
<211> LENGTH: 9
<212> TYPE: PRT
<213> ORGANISM: Homo sapiens

<400> SEQUENCE: 105

Gln Gln Phe Asn Ser Tyr Pro Phe Thr
1               5

<210> SEQ ID NO 106
<211> LENGTH: 8
<212> TYPE: PRT
<213> ORGANISM: Homo sapiens

<400> SEQUENCE: 106

Gly Phe Thr Phe Ser Ser Tyr Val
1               5

<210> SEQ ID NO 107
<211> LENGTH: 8
<212> TYPE: PRT
<213> ORGANISM: Homo sapiens

<400> SEQUENCE: 107

Ile Ser Asp Asp Gly Arg Asn Lys
1               5

<210> SEQ ID NO 108
<211> LENGTH: 12
<212> TYPE: PRT
<213> ORGANISM: Homo sapiens

<400> SEQUENCE: 108

Val Arg Glu Gly Tyr Ser Gly Ser Trp Phe Asp Tyr
1               5                   10

<210> SEQ ID NO 109
<211> LENGTH: 7
<212> TYPE: PRT
<213> ORGANISM: Homo sapiens

<400> SEQUENCE: 109

Gly Phe Thr Phe Ser Ser Tyr
1               5
```

```
<210> SEQ ID NO 110
<211> LENGTH: 4
<212> TYPE: PRT
<213> ORGANISM: Homo sapiens

<400> SEQUENCE: 110

Asp Asp Gly Arg
1

<210> SEQ ID NO 111
<211> LENGTH: 8
<212> TYPE: PRT
<213> ORGANISM: Homo sapiens

<400> SEQUENCE: 111

Gly Tyr Ser Gly Ser Trp Phe Asp
1               5

<210> SEQ ID NO 112
<211> LENGTH: 10
<212> TYPE: PRT
<213> ORGANISM: Homo sapiens

<400> SEQUENCE: 112

Ala Ser Gly Phe Thr Phe Ser Ser Tyr Val
1               5                   10

<210> SEQ ID NO 113
<211> LENGTH: 17
<212> TYPE: PRT
<213> ORGANISM: Homo sapiens

<400> SEQUENCE: 113

Ile Ser Asp Asp Gly Arg Asn Lys Tyr Phe Ala Asp Ser Val Lys Gly
1               5                   10                  15

Arg

<210> SEQ ID NO 114
<211> LENGTH: 9
<212> TYPE: PRT
<213> ORGANISM: Homo sapiens

<400> SEQUENCE: 114

Glu Gly Tyr Ser Gly Ser Trp Phe Asp
1               5

<210> SEQ ID NO 115
<211> LENGTH: 6
<212> TYPE: PRT
<213> ORGANISM: Homo sapiens

<400> SEQUENCE: 115

Gln Gly Ile Ser Ser Ala
1               5

<210> SEQ ID NO 116
<211> LENGTH: 3
<212> TYPE: PRT
<213> ORGANISM: Homo sapiens

<400> SEQUENCE: 116

Gly Ala Ser
1
```

```
<210> SEQ ID NO 117
<211> LENGTH: 9
<212> TYPE: PRT
<213> ORGANISM: Homo sapiens

<400> SEQUENCE: 117

Gln Gln Phe Asn Ser Tyr Pro Phe Thr
1               5

<210> SEQ ID NO 118
<211> LENGTH: 7
<212> TYPE: PRT
<213> ORGANISM: Homo sapiens

<400> SEQUENCE: 118

Ser Gln Gly Ile Ser Ser Ala
1               5

<210> SEQ ID NO 119
<211> LENGTH: 3
<212> TYPE: PRT
<213> ORGANISM: Homo sapiens

<400> SEQUENCE: 119

Gly Ala Ser
1

<210> SEQ ID NO 120
<211> LENGTH: 6
<212> TYPE: PRT
<213> ORGANISM: Homo sapiens

<400> SEQUENCE: 120

Phe Asn Ser Tyr Pro Phe
1               5

<210> SEQ ID NO 121
<211> LENGTH: 8
<212> TYPE: PRT
<213> ORGANISM: Homo sapiens

<400> SEQUENCE: 121

Ala Ser Gln Gly Ile Ser Ser Ala
1               5

<210> SEQ ID NO 122
<211> LENGTH: 12
<212> TYPE: PRT
<213> ORGANISM: Homo sapiens

<400> SEQUENCE: 122

Gly Ala Ser Ser Leu Glu Gly Gly Val Pro Ser Arg
1               5                   10

<210> SEQ ID NO 123
<211> LENGTH: 6
<212> TYPE: PRT
<213> ORGANISM: Homo sapiens

<400> SEQUENCE: 123

Phe Asn Ser Tyr Pro Phe
1               5

<210> SEQ ID NO 124
<211> LENGTH: 16
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Val His Lys Ser Gly Asp Thr Asn Tyr Asn Pro Ser Leu Lys Ser Arg
1               5                   10                  15

<210> SEQ ID NO 125
<211> LENGTH: 207
<212> TYPE: PRT
<213> ORGANISM: Homo sapiens

<400> SEQUENCE: 125

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 126
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45
```

```
Gly Tyr Val His Lys Ser Gly Asp Thr Asn Tyr Ser Pro Ser Leu Lys
        50                  55                  60

Ser Arg Val Asn Leu Ser Leu Asp Thr Ser Lys Asn Gln Val Ser Leu
65                      70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
            115                 120                 125

Thr Val Ser Ser
        130

<210> SEQ ID NO 127
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
                20                  25                  30

Gly Gln Ala Pro Ser Leu Ile Ile Tyr Asn Asn Gln Asp Arg Pro Ser
            35                  40                  45

Gly Ile Pro Glu Arg Phe Ser Gly Ser Pro Asp Ser Pro Phe Gly Thr
        50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu Gly
            100                 105
```

US 11,597,759 B2

MULTISPECIFIC ANTIBODIES THAT TARGET HIV GP120 AND CD3

CROSS-REFERENCE TO RELATED APPLICATIONS

This application is a continuation application of U.S. application Ser. No. 16/014,153, filed on Jun. 21, 2018, which claims priority to U.S. Provisional Patent Application Ser. No. 62/523,141, filed on Jun. 21, 2017, which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jun. 20, 2018, is named 35648-0054WO1_SL.txt and is 164,114 bytes in size.

FIELD

This disclosure relates to antibodies for the treatment and prevention of human immunodeficiency virus (HIV) infection. In particular, provided herein are multispecific antibodies comprising broadly neutralizing anti-HIV antibodies, and methods for using these antibodies to reduce HIV replication and in the treatment and prevention of HIV infection.

BACKGROUND

Human immunodeficiency virus (HIV) infection and related diseases are a major public health problem worldwide. Most currently approved therapies for HIV infection target the viral reverse transcriptase, protease enzymes, and integrase, but resistance of HIV to these existing drugs, long term toxicity, and lack of patient adherence to daily dosing regimens have proven to be problems associated with these therapies. Therefore, it is important to discover and develop new HIV drugs.

WO2012/030904 describes human anti-HIV antibodies derived from memory B cells of HIV-infected donors, which are capable of inhibiting infection by HIV-1 species from a plurality of clades. However, the therapeutic use of these antibodies is limited due to issues with immunogenicity, pharmacokinetics, antigen specificity, effector function, and manufacturing. Accordingly, there is a need in the art for novel anti-HIV antibodies with advantageous properties for therapeutic uses.

SUMMARY

The present disclosure provides, inter alia, compositions and methods for treating or preventing HIV. More specifically, provided herein are multispecific antibodies that target human immunodeficiency virus (HIV) envelope (Env) glycoprotein GP120 (gp120), and a second antigen (e.g., Cluster of Differentiation 3 (CD3); anti-IgA receptor (CD89)), and uses thereof.

In one aspect, this disclosure provides a multispecific antibody that binds to human immunodeficiency virus-1 (HIV-1) Envelope (Env) glycoprotein gp 120 (gp120) and human CD3 (e.g., human CD3ε). The antibody comprises a first antigen-binding domain that comprises a first heavy chain variable domain (VH) and a first light chain variable domain (VL). The first antigen-binding domain binds to gp120 and comprises a first VH-complementarity determining region (CDR) 1 comprising the amino acid sequence of SEQ ID NO:1; a first VH-CDR2 comprising the amino acid sequence of SEQ ID NO:2; a first VH-CDR3 comprising the amino acid sequence of SEQ ID NO:3; a first VL-CDR1 comprising the amino acid sequence of SEQ ID NO:4; a first VL-CDR2 comprising the amino acid sequence of SEQ ID NO:5; and a first VL-CDR3 comprising the amino acid sequence of SEQ ID NO:6. This antibody also comprises a second antigen-binding domain that binds to human CD3 (e.g., human CDR). In certain embodiments, the anti-gp120 antibody binds a protein comprising or consisting the amino acid sequence set forth in SEQ ID NO: 21. In some instances, the anti-gp120 antibody binds a protein comprising or consisting the amino acid sequence set forth in SEQ ID NO: 38. In some instances, the anti-gp120 antibody binds free HIV-1 virus. In some instances, the anti-gp120 antibody binds an HIV-1 infected cell. In some instances, the anti-gp120 antibody binds both free HIV-1 virus and an HIV-1 infected cell. In certain cases, the anti-gp120 antibody binds at least two different strains of HIV-1 (e.g., Group M, Group N, Group O, or Group P). In one embodiment, the anti-gp120 antibody binds pWITO.c/2474 (Accession number JN944948 and NIH AIDS Reagent Program catalogue number 11739). In another embodiment, the anti-gp120 antibody binds pCH058.c/2960 (Accession number JN944940 and NIH AIDS Reagent Program catalogue number 700010058).

In another aspect, this disclosure provides a multispecific antibody that binds to human immunodeficiency virus-1 (HIV-1) Envelope (Env) glycoprotein gp 120 (gp120) and the IgA receptor, CD89. The antibody comprises a first antigen-binding domain that comprises a first heavy chain variable domain (VH) and a first light chain variable domain (VL). The first antigen-binding domain binds to gp120 and comprises a first VH-complementarity determining region (CDR) 1 comprising the amino acid sequence of SEQ ID NO:1; a first VH-CDR2 comprising the amino acid sequence of SEQ ID NO:2; a first VH-CDR3 comprising the amino acid sequence of SEQ ID NO:3; a first VL-CDR1 comprising the amino acid sequence of SEQ ID NO:4; a first VL-CDR2 comprising the amino acid sequence of SEQ ID NO:5; and a first VL-CDR3 comprising the amino acid sequence of SEQ ID NO:6. This antibody also comprises a second antigen-binding domain that binds to CD89 (e.g., human CD89/FCAR; UniProtKB-P24071). In certain embodiments, the anti-gp120 antibody binds a protein comprising or consisting the amino acid sequence set forth in SEQ ID NO: 21. In some instances, the anti-gp120 antibody binds a protein comprising or consisting the amino acid sequence set forth in SEQ ID NO: 38. In some instances, the anti-gp120 antibody binds free HIV-1 virus. In some instances, the anti-gp120 antibody binds an HIV-1 infected cell. In some instances, the anti-gp120 antibody binds both free HIV-1 virus and an HIV-1 infected cell. In certain cases, the anti-gp120 antibody binds at least two different strains of HIV-1 (e.g., Group M, Group N, Group O, or Group P). In one embodiment, the anti-gp120 antibody binds pWITO.c/2474 (Accession number JN944948 and NIH AIDS Reagent Program catalogue number 11739). In another embodiment, the anti-gp120 antibody binds pCH058.c/2960 (Accession number JN944940 and NIH AIDS Reagent Program catalogue number 700010058).

In some embodiments of the above two aspects, the first VH comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:7. In some embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:8. In certain instances of these embodiments, the amino acids at one or more of positions 66, 67, 67A, and 67C (Kabat numbering) of SEQ ID NO:8 are unaltered. In certain embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:81. In certain embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:82. In certain embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:83. In certain embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:84. In certain instances, the VH's described above are linked directly, or via an intervening amino acid(s) (e.g., a G-S linker sequence) to one of the amino acid sequences set forth in SEQ ID NOs.: 56-65. In other instances, the VH's described above are linked directly, or via an intervening amino acid(s) (e.g., a G-S linker sequence) to one of the amino acid sequences set forth in SEQ ID NOs.: 66-75. In some instances, the VH's described above, are linked directly, or via an intervening amino acid(s) (e.g., a G-S linker sequence) to an amino acid sequence with 0-10 amino acid substitutions (e.g., substitutions that increase half-life and/or decrease effector function) within SEQ ID NO:77. In certain embodiments, the VH's described above are linked directly, or via an intervening amino acid(s) (e.g., a G-S linker sequence) to an amino acid sequence comprising a CH1 domain, CH2 domain, and a CH3 domain from IgG1 (e.g., human IgG1, e.g., IgG1m3 allotype) and an IgG3 hinge region (e.g., an "open" IgG3 hinge variant "IgG3 C-" described in WO2017/096221).

In some embodiments of the above two aspects, the first antigen-binding domain comprises a heavy chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:9. In some embodiments, the first antigen-binding domain comprises a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:10. In some embodiments, the first antigen-binding domain comprises a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:40. In some embodiments, the first antigen-binding domain comprises a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:78. In some embodiments, the first antigen-binding domain comprises a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:79. In some embodiments, the first antigen-binding domain comprises a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:80.

In certain embodiments of the above two aspects, the first VH comprises the amino acid sequence of SEQ ID NO:7 and the first VL comprises the amino acid sequence of SEQ ID NO:8. In other embodiments, the first VH comprises the amino acid sequence of SEQ ID NO:7 and the first VL comprises the amino acid sequence of SEQ ID NO:81. In other embodiments, the first VH comprises the amino acid sequence of SEQ ID NO:7 and the first VL comprises the amino acid sequence of SEQ ID NO:82. In other embodiments, the first VH comprises the amino acid sequence of SEQ ID NO:7 and the first VL comprises the amino acid sequence of SEQ ID NO:83. In other embodiments, the first VH comprises the amino acid sequence of SEQ ID NO:7 and the first VL comprises the amino acid sequence of SEQ ID NO:84. In certain instances, the VH's described above are linked directly, or via an intervening amino acid(s) (e.g., a G-S linker sequence) to one of the amino acid sequences set forth in SEQ ID NOs.:56-65. In other instances, the VH's described above are linked directly, or via an intervening amino acid(s) (e.g., a G-S linker sequence) to one of the amino acid sequences set forth in SEQ ID NOs.:66-75. In some instances, the VH's described above, are linked directly, or via an intervening amino acid(s) (e.g., a G-S linker sequence) to an amino acid sequence with 0-10 amino acid substitutions (e.g., substitutions that increase half-life and/or decrease effector function) within SEQ ID NO:77. In certain cases, the VH's described above are linked directly, or via an intervening amino acid(s) (e.g., a G-S linker sequence) to an amino acid sequence comprising a CH1 domain, CH2 domain, and a CH3 domain from IgG1 (e.g., human IgG1, e.g., IgG1m3 allotype) and an IgG3 hinge region (e.g., an "open" IgG3 hinge variant "IgG3 C-" described in WO2017/096221).

In some embodiments of the above two aspects, the first antigen-binding domain comprises a heavy chain having an amino acid sequence that has the amino acid sequence set forth in SEQ ID NO:9 and comprises a light chain having an amino acid sequence set forth in SEQ ID NO:10. In some embodiments, the first antigen-binding domain comprises a heavy chain having an amino acid sequence that has the amino acid sequence set forth in SEQ ID NO:9 and comprises a light chain having an amino acid sequence set forth in SEQ ID NO:40, In some embodiments, the first antigen-binding domain comprises a heavy chain having an amino acid sequence that has the amino acid sequence set forth in SEQ ID NO:9 and comprises a light chain having an amino acid sequence set forth in SEQ ID NO:78. In some embodiments, the first antigen-binding domain comprises a heavy chain having an amino acid sequence that has the amino acid sequence set forth in SEQ ID NO:9 and comprises a light chain having an amino acid sequence set forth in SEQ ID NO:79. In some embodiments, the first antigen-binding domain comprises a heavy chain having an amino acid sequence that has the amino acid sequence set forth in SEQ ID NO:9 and comprises a light chain having an amino acid sequence set forth in SEQ ID NO:80.

In certain embodiments, the multispecific antibody is a bispecific antibody.

In certain embodiments, the second antigen-binding domain binds human CD3 and comprises a second VH and a second VL. The second VH comprises a second VH-CDR1 comprising the amino acid sequence of SEQ ID NO:11; a second VH-CDR2 comprising the amino acid sequence of SEQ ID NO:12; and a second VH-CDR3 comprising the amino acid sequence of SEQ ID NO:13. In some embodiments, the second VL comprises a second VL-CDR1 comprising the amino acid sequence of SEQ ID NO:14; a second VL-CDR2 comprising the amino acid sequence of SEQ ID NO:15; and a second VL-CDR3 comprising the amino acid sequence of SEQ ID NO:16.

In certain embodiments, the second antigen-binding domain binds human CD3 and comprises a second VH and a second VL, wherein the second VH comprises a second VH-CDR1 comprising the amino acid sequence of SEQ ID NO:11; a second VH-CDR2 comprising the amino acid sequence of SEQ ID NO:12; and a second VH-CDR3 comprising the amino acid sequence of SEQ ID NO:13; and wherein the second VL comprises a second VL-CDR1 comprising the amino acid sequence of SEQ ID NO:14; a second VL-CDR2 comprising the amino acid sequence of SEQ ID NO:15; and a second VL-CDR3 comprising the amino acid sequence of SEQ ID NO:16.

In certain embodiments, the second antigen-binding domain binds human CD89 and comprises a second VH and a second VL. The second VH comprises a second VH-CDR1 comprising the amino acid sequence of SEQ ID NO:98; a second VH-CDR2 comprising the amino acid sequence of SEQ ID NO:99; and a second VH-CDR3 comprising the amino acid sequence of SEQ ID NO:100. In some embodiments, the second VL comprises a second VL-CDR1 comprising the amino acid sequence of SEQ ID NO:103; a second VL-CDR2 comprising the amino acid sequence of SEQ ID NO:104; and a second VL-CDR3 comprising the amino acid sequence of SEQ ID NO:105.

In certain embodiments, the second antigen-binding domain binds human CD89 and comprises a second VH and a second VL, wherein the second VH comprises a second VH-CDR1 comprising the amino acid sequence of SEQ ID NO:98; a second VH-CDR2 comprising the amino acid sequence of SEQ ID NO:99; and a second VH-CDR3 comprising the amino acid sequence of SEQ ID NO:100; and wherein the second VL comprises a second VL-CDR1 comprising the amino acid sequence of SEQ ID NO:103; a second VL-CDR2 comprising the amino acid sequence of SEQ ID NO:104; and a second VL-CDR3 comprising the amino acid sequence of SEQ ID NO:105.

In some embodiments, the second VH comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:17. In some embodiments, the second VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:18.

In one embodiment, the second VH comprises an amino acid sequence set forth in SEQ ID NO:17 and the second VL comprises an amino acid sequence set forth in SEQ ID NO:18.

In some embodiments, the second VH comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:96. In some embodiments, the second VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:101.

In one embodiment, the second VH comprises an amino acid sequence set forth in SEQ ID NO:96 and the second VL comprises an amino acid sequence set forth in SEQ ID NO:101.

In certain embodiments, the second antigen-binding domain comprises a heavy chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:19. In some embodiments, the second antigen-binding domain comprises a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:20.

In certain embodiments, the second antigen-binding domain comprises a heavy chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:97. In some embodiments, the second antigen-binding domain comprises a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:102.

In some embodiments, the antibody is a kappa-lambda body, a dual-affinity re-targeting molecule (DART), a knob-in-hole, a strand-exchange engineered domain body (SEED-body), a Bispecific T cell engager (BiTe), a CrossMab, an Fcab, a Diabody, a Tandem diabody (TandAb), or a Duo-Body®.

In certain embodiments, the first antigen-binding domain is fused directly, or via an intervening amino acid sequence, to a first heavy chain constant region selected from the group consisting of human IgG1, human IgG2, human IgG3, human IgG4, human IgA1, and human IgA2. In some instances, the first antigen-binding domain is fused directly, or via an intervening amino acid sequence, to a first heavy chain constant region, wherein the constant region is from human IgG1 (e.g., IgG1m3 allotype) with the exception that the IgG1 hinge region is replaced with an IgG3 hinge region (e.g., an "open" IgG3 hinge variant "IgG3 C-" described in WO2017/096221). In some embodiments, the second antigen-binding domain is fused directly, or via an intervening amino acid sequence, to a second heavy chain constant region selected from the group consisting of human IgG1, human IgG2, human IgG3, human IgG4, human IgA1, and human IgA2. In some instances, the second antigen-binding domain is fused directly, or via an intervening amino acid sequence, to a second heavy chain constant region, wherein the constant region is from human IgG1 (e.g., IgG1m3 allotype) with the exception that the IgG1 hinge region is replaced with an IgG3 hinge region (e.g., an "open" IgG3 hinge variant "IgG3 C-" described in WO2017/096221).

In a specific embodiment, the first heavy chain constant region is a human IgG1, and the second heavy chain constant region is a human IgG1.

In some embodiments, the first antigen-binding domain is fused directly, or via an intervening amino acid sequence, to a first light chain constant region that is a human lambda constant region. In other embodiments, the second antigen-binding domain is fused directly, or via an intervening amino acid sequence, to a second light chain constant region that is a human lambda constant region.

In one embodiment, the first heavy chain constant region comprises one of the following: F405L, F405A, F405D, F405E, F405H, F405I, F405K, F405M, F405N, F405Q, F405S, F405T, F405V, F405W, or F405Y amino acid mutations and the second heavy chain constant region comprises a K409R amino acid mutation. In one instance, the first heavy chain constant region comprises a F405L amino acid mutation and the second heavy chain constant region comprises a K409R amino acid mutation. In another instance, the first heavy chain constant region comprises a F405A amino acid mutation and the second heavy chain constant region comprises a K409R amino acid mutation. In another instance, the first heavy chain constant region comprises a F405D amino acid mutation and the second heavy chain constant region comprises a K409R amino acid mutation. In another instance, the first heavy chain constant region comprises a F405E amino acid mutation and the second heavy chain constant region comprises a K409R amino acid mutation. In another instance, the first heavy chain constant region comprises a F405H amino acid mutation and the second heavy chain constant region comprises a K409R amino acid mutation. In another instance, the first heavy chain constant region comprises a F405I amino acid mutation and the second heavy chain constant region comprises a K409R amino acid mutation. In another instance, the first heavy chain constant region comprises a F405K amino acid mutation and the second heavy chain constant region comprises a K409R amino acid mutation. In another instance, the first heavy chain constant region comprises a F405M amino acid mutation and the second heavy chain constant region comprises a K409R amino acid mutation. In another instance, the first heavy chain constant region comprises a F405N amino acid mutation and the second heavy chain constant region comprises a K409R amino acid mutation. In another instance, the first heavy chain constant region comprises a F405Q amino acid mutation and the second heavy chain constant region comprises a K409R amino acid mutation. In another instance, the first heavy chain constant region comprises a F405S amino acid mutation and the second heavy chain constant region comprises a K409R amino acid mutation. In another instance, the first heavy chain constant region comprises a F405T amino acid mutation and the second heavy chain constant region comprises a K409R amino acid mutation. In another instance, the first heavy chain constant region comprises a F405V amino acid mutation and the second heavy chain constant region comprises a K409R amino acid mutation. In another instance, the first heavy chain constant region comprises a F405W amino acid mutation and the second heavy chain constant region comprises a K409R amino acid mutation. In another instance, the first heavy chain constant region comprises a F405Y amino acid mutation and the second heavy chain constant region comprises a K409R amino acid mutation.

In another embodiment, the first heavy chain constant region comprises a K409R amino acid mutation and the second heavy chain constant region comprises one of the following: F405L, F405A, F405D, F405E, F405H, F405I, F405K, F405M, F405N, F405Q, F405S, F405T, F405V, F405W, or F405Y amino acid mutations. In one instance, the first heavy chain constant region comprises a K409R amino acid mutation and the second heavy chain constant region comprises an F405L amino acid mutation. In another instance, the first heavy chain constant region comprises a K409R amino acid mutation and the second heavy chain constant region comprises an F405A amino acid mutation. In one instance, the first heavy chain constant region comprises a K409R amino acid mutation and the second heavy chain constant region comprises an F405D amino acid mutation. In one instance, the first heavy chain constant region comprises a K409R amino acid mutation and the second heavy chain constant region comprises an F405E amino acid mutation. In one instance, the first heavy chain constant region comprises a K409R amino acid mutation and the second heavy chain constant region comprises an F405H amino acid mutation. In one instance, the first heavy chain constant region comprises a K409R amino acid mutation and the second heavy chain constant region comprises an F405I amino acid mutation. In one instance, the first heavy chain constant region comprises a K409R amino acid mutation and the second heavy chain constant region comprises an F405K amino acid mutation. In one instance, the first heavy chain constant region comprises a K409R amino acid mutation and the second heavy chain constant region comprises an F405M amino acid mutation. In one instance, the first heavy chain constant region comprises a K409R amino acid mutation and the second heavy chain constant region comprises an F405N amino acid mutation. In one instance, the first heavy chain constant region comprises a K409R amino acid mutation and the second heavy chain constant region comprises an F405Q amino acid mutation. In one instance, the first heavy chain constant region comprises a K409R amino acid mutation and the second heavy chain constant region comprises an F405S amino acid mutation. In one instance, the first heavy chain constant region comprises a K409R amino acid mutation and the second heavy chain constant region comprises an F405T amino acid mutation. In one instance, the first heavy chain constant region comprises a K409R amino acid mutation and the second heavy chain constant region comprises an F405V amino acid mutation. In one instance, the first heavy chain constant region comprises a K409R amino acid mutation and the second heavy chain constant region comprises an F405W amino acid mutation. In one instance, the first heavy chain constant region comprises a K409R amino acid mutation and the second heavy chain constant region comprises an F405Y amino acid mutation.

In certain embodiments, the effector function of the first heavy chain constant region and the second heavy chain constant region are reduced or abrogated (e.g., relative to the effector function of the antibody with a wild type IgG1 Fc).

In some embodiments, the first heavy chain constant region comprises a human IgG1 heavy chain constant region that comprises a N297A mutation or a N297Q mutation and/or the second heavy chain constant region comprises a human IgG1 heavy chain constant region that comprises a N297A mutation or a N297Q mutation.

In another aspect, this disclosure provides a bispecific antibody that binds to gp120 and human CD3. The bispecific antibody comprises a first arm that binds to gp120. The first arm comprises a first heavy chain comprising a first heavy chain constant region comprising a first mutation that is either one of F405L, F405A, F405D, F405E, F405H, F405I, F405K, F405M, F405N, F405Q, F405S, F405T, F405V, F405W, or an F405Y amino acid mutation, or a K409R mutation; and a first VH comprising a VH-CDR1 comprising the amino acid sequence of SEQ ID NO:1; a VH-CDR2 comprising the amino acid sequence of SEQ ID NO:2; and a VH-CDR3 comprising the amino acid sequence of SEQ ID NO:3. In one instance, the first arm comprises a first heavy chain comprising a first heavy chain constant region comprising a first mutation that is either one of F405L or K409R mutation. The first arm also comprises a first light chain comprising a first light chain constant region; and a first VL comprising a VL-CDR1 comprising the amino acid sequence of SEQ ID NO:4; a VL-CDR2 comprising the amino acid sequence of SEQ ID NO:5; and a VL-CDR3 comprising the amino acid sequence of SEQ ID NO:6. The bispecific antibody comprises a second arm that binds to CD3 (e.g., human CD3 (e.g., human CDR). The second arm comprises a second heavy chain comprising a second heavy chain constant region comprising a second mutation that is either one of F405L, F405A, F405D, F405E, F405H, F405I, F405K, F405M, F405N, F405Q, F405S, F405T, F405V, F405W, or an F405Y amino acid mutation, or a K409R mutation; and a second VH comprising a VH-CDR1 comprising the amino acid sequence of SEQ ID NO:11; a VH-CDR2 comprising the amino acid sequence of SEQ ID NO:12; and a VH-CDR3 comprising the amino acid sequence of SEQ ID NO:13. In one instance, the second arm comprises a second heavy chain comprising a second heavy chain constant region comprising a second mutation that is either one of F405L or K409R mutation. The second arm comprises a second light chain comprising a second light chain constant region; and a second VL comprising a VL-CDR1 comprising the amino acid sequence of SEQ ID NO:14; a VL-CDR2 comprising the amino acid sequence of SEQ ID NO:15; and a VL-CDR3 comprising the amino acid sequence of SEQ ID NO:16. The first mutation and the second mutation are different mutations.

In another aspect, this disclosure provides a bispecific antibody that binds to gp120 and human CD89. The bispecific antibody comprises a first arm that binds to gp120. The first arm comprises a first heavy chain comprising a first heavy chain constant region comprising a first mutation that is either one of F405L, F405A, F405D, F405E, F405H, F405I, F405K, F405M, F405N, F405Q, F405S, F405T, F405V, F405W, or an F405Y amino acid mutation, or a K409R mutation; and a first VH comprising a VH-CDR1 comprising the amino acid sequence of SEQ ID NO:1; a VH-CDR2 comprising the amino acid sequence of SEQ ID NO:2; and a VH-CDR3 comprising the amino acid sequence of SEQ ID NO:3. In one instance, the first arm comprises a first heavy chain comprising a first heavy chain constant region comprising a first mutation that is either one of F405L or K409R mutation. The first arm also comprises a first light chain comprising a first light chain constant region; and a first VL comprising a VL-CDR1 comprising the amino acid sequence of SEQ ID NO:4; a VL-CDR2 comprising the amino acid sequence of SEQ ID NO:5; and a VL-CDR3 comprising the amino acid sequence of SEQ ID NO:6. The bispecific antibody comprises a second arm that binds to CD89 (e.g., human CD89). The second arm comprises a second heavy chain comprising a second heavy chain constant region comprising a second mutation that is either one of F405L, F405A, F405D, F405E, F405H, F405I, F405K, F405M, F405N, F405Q, F405S, F405T, F405V, F405W, or an F405Y amino acid mutation, or a K409R mutation; and a second VH comprising a VH-CDR1 comprising the amino acid sequence of SEQ ID NO:98; a VH-CDR2 comprising the amino acid sequence of SEQ ID NO:99; and a VH-CDR3 comprising the amino acid sequence of SEQ ID NO:100. In one instance, the second arm comprises a second heavy chain comprising a second heavy chain constant region comprising a second mutation that is either one of F405L or K409R mutation. The second arm comprises a second light chain comprising a second light chain constant region; and a second VL comprising a VL-CDR1 comprising the amino acid sequence of SEQ ID NO:103 a VL-CDR2 comprising the amino acid sequence of SEQ ID NO:104; and a VL-CDR3 comprising the amino acid sequence of SEQ ID NO:105. The first mutation and the second mutation are different mutations.

In certain embodiments of the above two aspects, the anti-gp120 antibody arm binds a protein comprising or consisting the amino acid sequence set forth in SEQ ID NO: 21. In some instances, the anti-gp120 antibody arm binds a protein comprising or consisting the amino acid sequence set forth in SEQ ID NO: 38. In some instances, the anti-gp120 antibody arm binds free HIV-1 virus. In some instances, the anti-gp120 antibody binds an HIV-1 infected cell. In some instances, the anti-gp120 antibody arm binds both free HIV-1 virus and an HIV-1 infected cell. In certain cases, the anti-gp120 antibody binds at least two different strains of HIV-1 (e.g., Group M, Group N, Group O, or Group P). In one embodiment, the anti-gp120 antibody arm binds pWI-TO.c/2474 (Accession number JN944948 and NIH AIDS Reagent Program catalogue number 11739). In another embodiment, the anti-gp120 antibody arm binds pCH058.c/2960 (Accession number JN944940 and NIH AIDS Reagent Program catalogue number 700010058).

In some embodiments, the first VH comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:7. In some embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:8. In certain instances of these embodiments, the amino acids at one or more of positions 66, 67, 67A, and 67C (Kabat numbering) of SEQ ID NO:8 are unaltered. In certain embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:81. In certain embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:82. In certain embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 9'7%, at least 98%, at least 99%, or 100% identical to SEQ ID NO:83. In certain embodiments, the first VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:84. In some instances, the VH's described above, are linked directly, or via an intervening amino acid(s) (e.g., a G-S linker sequence) to an amino acid sequence with 1-10 amino acid substitutions (e.g., substitutions that increase half-life and/or decrease effector function) within SEQ ID NO:77.

In some embodiments, the first heavy chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:9. In some embodiments, the first light chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:10. In some embodiments, the first light chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:40. In some embodiments, the first light chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:78. In some embodiments, the first light chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:79. In some embodiments, the first light chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:80.

In certain embodiments, the second VH comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:17. In some embodiments, the second VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:18.

In certain embodiments, the second VH comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:96. In some embodiments, the second VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:101.

In some embodiments, the second heavy chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:19. In certain embodiments, the second light chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:20.

In some embodiments, the second heavy chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:97. In certain embodiments, the second light chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:102.

In one embodiment, the first VH comprises the amino acid sequence of SEQ ID NO:7 and the first VL comprises the amino acid sequence of SEQ ID NO:8 and/or the second VH comprises the amino acid sequence of SEQ ID NO:17 and the second VL comprises the amino acid sequence of SEQ ID NO:18.

In one embodiment, the first VH comprises the amino acid sequence of SEQ ID NO:7 and the first VL comprises the amino acid sequence of SEQ ID NO:8 and/or the second VH comprises the amino acid sequence of SEQ ID NO:96 and the second VL comprises the amino acid sequence of SEQ ID NO:101.

In another embodiment, the first VH comprises the amino acid sequence of SEQ ID NO:7 and the first VL comprises the amino acid sequence of SEQ ID NO:81 and/or the second VH comprises the amino acid sequence of SEQ ID NO:17 and the second VL comprises the amino acid sequence of SEQ ID NO:18.

In another embodiment, the first VH comprises the amino acid sequence of SEQ ID NO:7 and the first VL comprises the amino acid sequence of SEQ ID NO:81 and/or the second VH comprises the amino acid sequence of SEQ ID NO:96 and the second VL comprises the amino acid sequence of SEQ ID NO:101.

In a further embodiment, the first VH comprises the amino acid sequence of SEQ ID NO:7 and the first VL comprises the amino acid sequence of SEQ ID NO:82 and/or the second VH comprises the amino acid sequence of SEQ ID NO:17 and the second VL comprises the amino acid sequence of SEQ ID NO:18.

In a further embodiment, the first VH comprises the amino acid sequence of SEQ ID NO:7 and the first VL comprises the amino acid sequence of SEQ ID NO:82 and/or the second VH comprises the amino acid sequence of SEQ ID NO:96 and the second VL comprises the amino acid sequence of SEQ ID NO:101.

In another embodiment, the first VH comprises the amino acid sequence of SEQ ID NO:7 and the first VL comprises the amino acid sequence of SEQ ID NO:83 and/or the second VH comprises the amino acid sequence of SEQ ID NO:17 and the second VL comprises the amino acid sequence of SEQ ID NO:18.

In another embodiment, the first VH comprises the amino acid sequence of SEQ ID NO:7 and the first VL comprises the amino acid sequence of SEQ ID NO:83 and/or the second VH comprises the amino acid sequence of SEQ ID NO:96 and the second VL comprises the amino acid sequence of SEQ ID NO:101.

In yet another embodiment, the first VH comprises the amino acid sequence of SEQ ID NO:7 and the first VL comprises the amino acid sequence of SEQ ID NO:84 and/or the second VH comprises the amino acid sequence of SEQ ID NO:17 and the second VL comprises the amino acid sequence of SEQ ID NO:18.

In yet another embodiment, the first VH comprises the amino acid sequence of SEQ ID NO:7 and the first VL comprises the amino acid sequence of SEQ ID NO:84 and/or the second VH comprises the amino acid sequence of SEQ ID NO:96 and the second VL comprises the amino acid sequence of SEQ ID NO:101.

In another embodiment, the first heavy chain comprises the amino acid sequence of SEQ ID NO:9 and the first light chain comprises the amino acid sequence of SEQ ID NO:10 and/or the second heavy chain comprises the amino acid sequence of SEQ ID NO:19 and the second light chain comprises the amino acid sequence of SEQ ID NO:20.

In yet another embodiment, the first VH comprises the amino acid sequence of SEQ ID NO:7 and the first VL comprises the amino acid sequence of SEQ ID NO:84 and/or the second VH comprises the amino acid sequence of SEQ ID NO:96 and the second VL comprises the amino acid sequence of SEQ ID NO:101.

In another embodiment, the first heavy chain comprises the amino acid sequence of SEQ ID NO:9 and the first light chain comprises the amino acid sequence of SEQ ID NO:40 and/or the second heavy chain comprises the amino acid sequence of SEQ ID NO:19 and the second light chain comprises the amino acid sequence of SEQ ID NO:20.

In another embodiment, the first heavy chain comprises the amino acid sequence of SEQ ID NO:9 and the first light chain comprises the amino acid sequence of SEQ ID NO:40 and/or the second heavy chain comprises the amino acid sequence of SEQ ID NO:97 and the second light chain comprises the amino acid sequence of SEQ ID NO:102.

In another embodiment, the first heavy chain comprises the amino acid sequence of SEQ ID NO:9 and the first light chain comprises the amino acid sequence of SEQ ID NO:78 and/or the second heavy chain comprises the amino acid sequence of SEQ ID NO:19 and the second light chain comprises the amino acid sequence of SEQ ID NO:20.

In another embodiment, the first heavy chain comprises the amino acid sequence of SEQ ID NO:9 and the first light chain comprises the amino acid sequence of SEQ ID NO:78 and/or the second heavy chain comprises the amino acid sequence of SEQ ID NO:97 and the second light chain comprises the amino acid sequence of SEQ ID NO:102.

In yet another embodiment, the first heavy chain comprises the amino acid sequence of SEQ ID NO:9 and the first light chain comprises the amino acid sequence of SEQ ID NO:79 and/or the second heavy chain comprises the amino acid sequence of SEQ ID NO:19 and the second light chain comprises the amino acid sequence of SEQ ID NO:20.

In yet another embodiment, the first heavy chain comprises the amino acid sequence of SEQ ID NO:9 and the first light chain comprises the amino acid sequence of SEQ ID NO:79 and/or the second heavy chain comprises the amino acid sequence of SEQ ID NO:97 and the second light chain comprises the amino acid sequence of SEQ ID NO:102.

In a further embodiment, the first heavy chain comprises the amino acid sequence of SEQ ID NO:9 and the first light chain comprises the amino acid sequence of SEQ ID NO:80 and/or the second heavy chain comprises the amino acid sequence of SEQ ID NO:19 and the second light chain comprises the amino acid sequence of SEQ ID NO:20.

In a further embodiment, the first heavy chain comprises the amino acid sequence of SEQ ID NO:9 and the first light chain comprises the amino acid sequence of SEQ ID NO:80 and/or the second heavy chain comprises the amino acid sequence of SEQ ID NO:97 and the second light chain comprises the amino acid sequence of SEQ ID NO:102.

In certain embodiments of all of the above aspects and embodiments, the antibody further comprises a cytotoxic agent, a radioisotope, a therapeutic agent, an anti-viral agent, or a detectable label.

In a further aspect, this disclosure provides a composition comprising a nucleic acid molecule encoding the first light chain variable region or first light chain of the first antigen-binding domain of an antibody disclosed above. In another aspect, this disclosure provides a composition comprising a nucleic acid molecule encoding the first heavy chain variable region or first heavy chain of the first antigen-binding domain of an antibody disclosed above. In yet another aspect, this disclosure provides a composition comprising a nucleic acid molecule encoding the first light chain variable region or first light chain of the second antigen-binding domain of an antibody disclosed above. In yet another aspect, this disclosure provides a composition comprising a nucleic acid molecule encoding the second heavy chain variable region or second heavy chain of the second antigen-binding domain of an antibody disclosed above.

In another aspect, the disclosure features host cells comprising one or more of the nucleic acids described above. In certain instances, the host cell comprises all four chains of the bispecific antibody. In other instances, the host cell comprises the nucleic acids encoding the gp120-binding arm of the bispecific antibody. In other instances, the host cell comprises the nucleic acids encoding the CD3-binding arm of the bispecific antibody. In yet other instances, the host cell comprises the nucleic acids encoding the CD89-binding arm of the bispecific antibody. In some embodiments, the host cell is selected from the group consisting of *E. coli, Pseudomonas, Bacillus, Streptomyces*, yeast (e.g., *Pichia, Saccharomyces*), CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, a plant cell, an insect cell, and a human cell in tissue culture.

In yet another aspect, featured are methods of producing an antibody that binds to gp120 and human CD3 (or an antibody that binds to gp120 and human CD89). The method comprising culturing the host cell described above under conditions such that the nucleic acid molecules are expressed and the antibody is produced.

In another aspect, disclosed are methods for detecting cells expressing gp120 and CD3 (or CD89) in a sample. The method involves contacting the sample with an antibody described herein.

In yet another aspect, this disclosure provides a pharmaceutical composition comprising an antibody described herein and a pharmaceutically acceptable excipient.

In a further embodiment, this disclosure features a kit comprising an antibody described herein and a) a detection reagent, b) a gp120 and/or CD3 and/or CD89 antigen, c) a notice that reflects approval for use or sale for human administration, or d) a combination thereof.

Also provided are methods of treating or preventing human immunodeficiency virus infection in a human subject in need thereof. The method involves administering to the human subject a therapeutically effective amount of an antibody or pharmaceutical composition disclosed herein. In some embodiments, the human immunodeficiency virus infection is an HIV-1 infection. In some embodiments, the virus in the patient has an Env that is N332 PNG positive. In certain embodiments, the HIV is of clade B, G, A, AC, or AE.

In another aspect, the disclosure features an antibody that binds to gp120. This antibody comprises a VH and a VL. The VH comprises a VH-CDR1 comprising the amino acid sequence of SEQ ID NO:1, a VH-CDR2 comprising the amino acid sequence of SEQ ID NO:2, a VH-CDR3 comprising the amino acid sequence of SEQ ID NO:3. The VL comprises a VL-CDR1 comprising the amino acid sequence of SEQ ID NO:4, a VL-CDR2 comprising the amino acid sequence of SEQ ID NO:5, and a VL-CDR3 comprising the amino acid sequence of SEQ ID NO:6. In addition, the VL comprises a tyrosine, phenylalanine, or threonine at position 67A (Kabat numbering), or a glycine at position 67 (Kabat numbering).

In certain embodiments, the anti-gp120 antibody binds a protein comprising or consisting the amino acid sequence set forth in SEQ ID NO: 21. In some instances, the anti-gp120 antibody binds a protein comprising or consisting the amino acid sequence set forth in SEQ ID NO: 38. In some instances, the anti-gp120 antibody binds free HIV-1 virus. In some instances, the anti-gp120 antibody binds an HIV-1 infected cell. In some instances, the anti-gp120 antibody binds both free HIV-1 virus and an HIV-1 infected cell. In certain cases, the anti-gp120 antibody binds at least two different strains of HIV-1 (e.g., Group M, Group N, Group O, or Group P). In one embodiment, the anti-gp120 antibody binds pWITO.c/2474 (Accession number JN944948 and NIH AIDS Reagent Program catalogue number 11739). In another embodiment, the anti-gp120 antibody binds pCH058.c/2960 (Accession number JN944940 and NIH AIDS Reagent Program catalogue number 700010058).

In some embodiments, the VH comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:7. In some embodiments, the VH is linked directly or via an intervening amino acid sequence (e.g., a G-S linker) to a human IgG1 constant region (e.g., IgG1m3 allotype) that contains 0-10 (e.g., 1, 2, 3, 4, 5, 6, 7, 8, 9, or 10) amino acid substitutions that reduce effector function and/or increase pharmacokinetic half-life of the antibody. In some instances, the antibody has a hinge region from an IgG3 antibody (e.g., an "open" IgG3C-hinge variant disclosed in WO 2017/096221) and a CH1, CH2, and CH3 region from a human IgG1 antibody (e.g., IgG1m3 allotype).

In certain embodiments, the VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:81, 82, 83, or 84.

In some embodiments, the heavy chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:9.

In certain embodiments, the light chain comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 40, 78, 79, or 80.

In one embodiment, the antibody comprises a heavy chain comprising the amino acid sequence set forth in SEQ ID NO:9, and a light chain comprising the amino acid sequence set forth in any one of SEQ ID NO:40.

In another embodiment, the antibody comprises a heavy chain comprising the amino acid sequence set forth in SEQ ID NO:9, and a light chain comprising the amino acid sequence set forth in any one of SEQ ID NO:78.

In yet another embodiment, the antibody comprises a heavy chain comprising the amino acid sequence set forth in SEQ ID NO:9, and a light chain comprising the amino acid sequence set forth in any one of SEQ ID NO:79.

In another embodiment, the antibody comprises a heavy chain comprising the amino acid sequence set forth in SEQ ID NO:9, and a light chain comprising the amino acid sequence set forth in any one of SEQ ID NO:80.

In some embodiments, the antibodies described above further comprise a cytotoxic agent, a radioisotope, a therapeutic agent, an anti-viral agent, or a detectable label.

In another aspect, the disclosure features a pharmaceutical composition comprising an antibody of this aspect and pharmaceutically acceptable carrier.

In another aspect, the disclosure relates to a nucleic acid or nucleic acids encoding an antibody of this aspect.

In another aspect, this disclosure provides a vector or vectors comprising the nucleic acid or nucleic acids described above.

In yet another aspect, the disclosure features a host cell comprising the vector or vectors described above.

In a further aspect, the disclosure provides a method for producing an anti-gp120 antibody. The method involves culturing the host cell described above under conditions such that the nucleic acid or nucleic acids are expressed and the antibody is produced.

Also featured is a method of treating or preventing human immunodeficiency virus infection in a human subject in need thereof. The method comprises administering to the human subject a therapeutically effective amount of the antibody or the pharmaceutical composition of this aspect. In some embodiments, the human immunodeficiency virus infection is an HIV-1 infection. In some embodiments, the HIV in the patient has an Env that is N332 PNG positive. In certain embodiments, the HIV is of clade B, G, A, AC, or AE.

In another aspect, the disclosure features an antibody fragment that binds to gp120. This antibody fragment comprises a VH and a VL. The VH comprises a VH-CDR1 comprising the amino acid sequence of SEQ ID NO:1, a VH-CDR2 comprising the amino acid sequence of SEQ ID NO:2, a VH-CDR3 comprising the amino acid sequence of SEQ ID NO:3. The VL comprises a VL-CDR1 comprising the amino acid sequence of SEQ ID NO:4, a VL-CDR2 comprising the amino acid sequence of SEQ ID NO:5, and a VL-CDR3 comprising the amino acid sequence of SEQ ID NO:6. In addition, the VL comprises a tyrosine, phenylalanine, or threonine at position 67A (Kabat numbering), or a glycine at position 67 (Kabat numbering).

In certain embodiments, the anti-gp120 antibody fragment binds a protein comprising or consisting the amino acid sequence set forth in SEQ ID NO: 21. In some instances, the anti-gp120 antibody fragment binds a protein comprising or consisting the amino acid sequence set forth in SEQ ID NO: 38. In some instances, the anti-gp120 antibody fragment binds free HIV-1 virus. In some instances, the anti-gp120 antibody binds an HIV-1 infected cell. In some instances, the anti-gp120 antibody fragment binds both free HIV-1 virus and an HIV-1 infected cell. In certain cases, the anti-gp120 antibody binds at least two different strains of HIV-1 (e.g., Group M, Group N, Group O, or Group P). In one embodiment, the anti-gp120 antibody fragment binds pWITO.c/2474 (Accession number JN944948 and NIH AIDS Reagent Program catalogue number 11739). In another embodiment, the anti-gp120 antibody fragment binds pCH058.c/2960 (Accession number JN944940 and NIH AIDS Reagent Program catalogue number 700010058).

In some embodiments, the VH comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:7.

In certain embodiments, the VL comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:81, 82, 83, or 84.

In some embodiments, the antibody fragment is a Fab, an F(ab)2, Fv, a scFv, a sc(Fv)2, or a diabody.

In some embodiments, the antibody fragments described above further comprise a cytotoxic agent, a radioisotope, a therapeutic agent, an anti-viral agent, or a detectable label.

In another aspect, the disclosure features a pharmaceutical composition comprising an antibody fragment of this aspect and pharmaceutically acceptable carrier.

In another aspect, the disclosure relates to a nucleic acid or nucleic acids encoding an antibody fragment of this aspect.

In another aspect, this disclosure provides a vector or vectors comprising the nucleic acid or nucleic acids described above.

In yet another aspect, the disclosure features a host cell comprising the vector or vectors described above.

In a further aspect, the disclosure provides a method for producing an anti-gp120 antibody fragment. The method involves culturing the host cell described above under conditions such that the nucleic acid or nucleic acids are expressed and the antibody fragment is produced.

In another aspect, the disclosure features a method for treating or preventing HIV in a human subject in need thereof. The method comprises administering to the human subject a therapeutically effective amount of the antibody fragment or the pharmaceutical composition of this aspect. In some embodiments, the human immunodeficiency virus infection is an HIV-1 infection. In some embodiments, the HIV in the patient has an Env that is N332 PNG positive. In certain embodiments, the HIV is of clade B, G, A, AC, or AE.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

DETAILED DESCRIPTION

The multispecific antibodies described herein bind to human immunodeficiency virus (HIV) envelope (Env) protein gp120 (gp120) and the Cluster of Differentiation 3 (CD3) (e.g., CD3ε) and are effective in killing HIV-infected cells. For example, the multispecific antibody is a bispecific antibody that has two antigen-binding arms, wherein the bispecific antibody binds with one arm an antigen on an HIV-infected cell (e.g., gp120) and with the other arm an antigen on T cells (e.g., CD3) can target T cells (e.g., CD4$^+$ T cells and/or CD8$^+$ T cells) to the HIV-infected cell, resulting in the killing of the HIV-infected cell. A bispecific antibody binding CD3 and gp120 can redirect CD8$^+$ and CD4$^+$ T cells to kill gp120-expressing cells (e.g., HIV-infected cells). The T cells kill HIV-infected cells independent of their T cell receptor specificity. In one embodiment, the bispecific antibody is an anti-gp120 X anti-CD3 Duobody®. The Duobodies of the present disclosure have significant advantages over other bispecific platforms known in the art. A major advantage of the Duobody® platform over, e.g., the DART platform is that the Duobodies disclosed herein can recruit CD4$^+$ T cells to kill target cells (e.g., HIV-infected cells). CD4$^+$ T cell-mediated killing is not observed with DARTs (see, Sloan et al., *PLOS Pathogens*, 11(11):e1005233. doi:10.1371/journal.ppat.1005233 (2015)). This is a significant advantage since the targets in HIV treatments are also CD4$^+$ T cells. One concern with using antibodies that require innate effector cells for activity for HIV treatment is that the effector cells may not be present in the tissue where the latently infected CD4$^+$ T cells reside, which is less of an issue if CD4$^+$ T cells themselves can be effector cells.

HIV-1 is the main family of HIV and accounts for 95% of all infections worldwide. HIV-2 is mainly seen in a few West African countries.

HIV viruses are divided into specific groups, M, N, O and P, of which M is the "major" group and responsible for majority of HIV/AIDS globally. Based on their genetic sequence, Group M is further subdivided into subtypes (also called clades) with prevalence in distinct geographical locations.

A Group M "subtype" or "clade" is a subtype of HIV-1 group M defined by genetic sequence data. Examples of Group M subtypes include Subtypes A-K. Some of the subtypes are known to be more virulent or are resistant to different medications. There are also "circulating recombinant forms" or CRFs derived from recombination between viruses of different subtypes, which are each given a number. CRF12_BF, for example, is a recombination between subtypes B and F. Subtype A is common in West Africa. Subtype B is the dominant form in Europe, the Americas, Japan, Thailand, and Australia. Subtype C is the dominant form in Southern Africa, Eastern Africa, India, Nepal, and parts of China. Subtype D is generally only seen in Eastern and central Africa. Subtype E has never been identified as a nonrecombinant, only recombined with subtype A as CRF01_AE. Subtype F has been found in central Africa, South America and Eastern Europe. Subtype G (and the CRF02_AG) have been found in Africa and central Europe. Subtype H is limited to central Africa. Subtype I was originally used to describe a strain that is now accounted for as CRF04_cpx, with the cpx for a "complex" recombination of several subtypes. Subtype J is primarily found in North, Central and West Africa, and the Caribbean Subtype K is limited to the Democratic Republic of Congo and Cameroon. These subtypes are sometimes further split into sub-subtypes such as A1 and A2 or F1 and F2. In 2015, the strain CRF19, a recombinant of subtype A, subtype D, and subtype G, with a subtype D protease was found to be strongly associated with rapid progression to AIDS in Cuba.

This disclosure provides, inter alia, neutralizing antibodies (e.g., broadly neutralizing Abs) that target the gp120 polypeptide on the surface of HIV-infected cells. Neutralizing antibodies against viral envelope proteins provide adaptive immune defense against HIV-1 exposure by blocking the infection of susceptible cells. Broad neutralization indicates that the antibodies can neutralize HIV-1 isolates from different clades. Thus, the antibodies encompassed by this disclosure have cross-clade binding activity.

gp120

Envelope glycoprotein gp120 (or gp120) is a 120 kDa glycoprotein that is part of the outer layer of HIV. It presents itself as viral membrane spikes consisting of three molecules of gp120 linked together and anchored to the membrane by gp41 protein. Gp120 is essential for viral infection as it facilitates HIV entry into the host cell through its interaction with cell surface receptors. These receptors include DC-SIGN, Heparan Sulfate Proteoglycan, and the CD4 receptor. Binding to CD4 on helper T-cells induces the start of a cascade of conformational changes in gp120 and gp41 that lead to the fusion of the virus with the host cell membrane.

Gp120 is encoded by the HIV env gene. The env gene encodes a gene product of around 850 amino acids. The primary env product is the protein gp160, which gets cleaved to gp120 (about 480 amino acids) and gp41 (about 345 amino acids) in the endoplasmic reticulum by the cellular protease furin.

The amino acid sequence of an exemplary gp160 polypeptide of HIV clone WITO is provided below (the V3 hypervariable loop is boldened and the N332 potential N-linked glycosylation site is boldened and underlined):

```
                                                 (SEQ ID NO: 37)
MKVMGTKKNYQHLWRWGIMLLGMLMMSSAAEQLWVTVYYGVPVWREANTT

LFCASDAKAYDTEVHNVWATHACVPTDPNPQEVVMGNVTEDFNMWKNNMV

EQMHEDIISLWDQSLKPCVKLTPLCVTLHCTNVTISSTNGSTANVTMREE

MKNCSFNTTTVIRDKIQKEYALFYKLDIVPIEGKNTNTSYRLINCNTSVI

TQACPKVSFEPIPIHYCAPAGFAILKCNNKTFNGKGPCRNVSTVQCTHGI

KPVVSTQLLLNGSLAEEDIIIRSENFTNNGKNIIVQLKEPVKINCTRPGN

NTRRSINIGPGRAFYATGAIIGDIRKAHCNISTEQWNNTLTQIVDKLREQ

FGNKTIIFNQSSGGDPEVVMHTFNCGGEFFYCNSTQLFNSTWFNNGTSTW

NSTADNITLPCRIKQVINMWQEVGKAMYAPPIRGQIDCSSNITGLILTRD

GGSNSSQNETFRPGGGNMKDNWRSELYKYKVVKIEPLGIAPTRAKRRVVQ

REKRAVTLGAVFLGFLGAAGSTMGAASLTLTVQARLLLSGIVQQQSNLLR

AIEAQQHMLQLTVWGIKQLQARVLAIERYLKDQQLLGIWGCSGKLICTTT

VPWNTSWSNKSYDYIWNNMTWMQWEREIDNYTGFIYTLIEESQNQQEKNE

LELLELDKWASLWNWFNITNWLWYIKLFIMIIGGLVGLRIVCAVLSIVNR

VRQGYSPLSFQTRLPNPRGPDRPEETEGEGGERDRDRSARLVNGFLAIIW

DDLRSLCLFSYHRLRDLLLIVARVVEILGRRGWEILKYWWNLLKYWSQEL

KNSAVSLLNVTAIAVAEGTDRVIEIVQRAVRAILHIPTRIRQGFERALL
```

The amino acid sequence of an exemplary gp120 polypeptide is provided below:

```
                                                 (SEQ ID NO: 21)
AEQLWVIVYYGVPVWREANTTLFCASDAKAYDTEVHNVWATHACVPTDPN

PQEVVMGNVTEDFNMWKNNMVEQMHEDIISLWDQSLKPCVKLTPLCVTLH

CTNVTISSTNGSTANVTMREEMKNCSFNTTTVIRDKIQKEYALFYKLDIV

PIEGKNTNTSYRLINCNTSVITQACPKVSFEPIPIHYCAPAGFAILKCNN

KTFNGKGPCRNVSTVQCTHGIKPVVSTQLLLNGSLAEEDIIIRSENFTNN

GKNIIVQLKEPVKINCTRPGNNTRRSINIGPGRAFYATGAIIGDIRKAHC

NISTEQWNNTLTQIVDKLREQFGNKTIIFNQSSGGDPEVVMHTFNCGGEF

FYCNSTQLFNSTWFNNGTSTWNSTADNITLPCRIKQVINMWQEVGKAMYA

PPIRGQIDCSSNITGLILTRDGGSNSSQNETFRPGGGNMKDNWRSELYKY

KVVKIEPLGIAPTRAKRRVVQREKR.
```

The amino acid sequence of another exemplary gp120 polypeptide (see, www.bioafrica.net/proteomics/ENV-GP120prot.html) is provided below:

```
                                            (SEQ ID NO: 38)
TEKLWVTVYY  GVPVWKEATT  TLFCASDAKA  YDTEVHNVWA

THACVPTDPN  PQEVVLVNVT  ENFNMWKNDM  VEQMHEDIIS

LWDQSLKPCV  KLTPLCVSLK  CTDLKNDTNT  NSSSGRMIME

KGEIKNCSFN  ISTSIRGKVQ  KEYAFFYKLD  IIPIDNDTTS

YKLTSCNTSV  ITQACPKVSF  EPIPIHYCAP  AGFAILKCNN

KTFNGTGPCT  NVSTVQCTHG  IRPVVSTQLL  LNGSLAEEEV

VIRSVNFTDN  AKTIIVQLNT  SVEINCTRPN  NNTRKRIRIQ

RGPGRAFVTI  GKIGNMRQAH  CNISRAKWNN  TLKQIASKLR

EQFGNNKTII  FKQSSGGDPE  IVTHSFNCGG  EFFYCNSTQL

FNSTWFNSTW  STEGSNNTEG  SDTITLPCRI  KQIINMWQKV

GKAMYAPPIS  GQIRCSSNIT  GLLLTRDGGN  SNNESEIFRP

GGGDMRDNWR  SELYKYKVVK  IEPLGVAPTK  AKRRVVQREK R
```

Genomic diversity among independent human immunodeficiency virus type 1 (HIV-1) isolates, to a lesser degree among sequential isolates from the same patients, and even within a single patient isolate is a well-known feature of HIV-1. Although this sequence heterogeneity is distributed throughout the genome, most of the heterogeneity is located in the env gene. Comparison of predicted amino acid sequences from several different isolates has shown that sequence heterogeneity is clustered in five variable regions (designated V1 through V5) of the surface glycoprotein, gp120. The V3 region, although only 35 amino acids long, exhibits considerable sequence variability. Interestingly, in spite of this variability, the V3 region includes determinants that mediate interactions with $CD4^+$ cells. The increase in gp120 variability results in higher levels of viral replication, suggesting an increase in viral fitness in individuals infected by diverse HIV-1 variants. Variability in potential N-linked glycosylation sites (PNGSs) also result in increased viral fitness. PNGSs allow for the binding of long-chain carbohydrates to the high variable regions of gp120. Thus, the number of PNGSs in env might affect the fitness of the virus by providing more or less sensitivity to neutralizing antibodies.

A consensus sequence of the V3 region of gp120 (Milich et al., *J Virol.,* 67(9):5623-5634 (1993) is provided below:

(SEQ ID NO: 22)
CTRPNNNTRKSIHIGPGRAFYTTGEIIGDIRQAHC.

Anti-gp120 Antibodies

This disclosure features anti-gp120 antibodies. In certain embodiments, these antibodies bind to HIV-1 antigens expressed on a cell surface and eliminate or kill the infected cell.

In certain embodiments, these antibodies are neutralizing antibodies (e.g., monoclonal) that target HIV-1. A "neutralizing antibody" is one that can neutralize the ability of HIV to initiate and/or perpetuate an infection in a host and/or in target cells in vitro. The disclosure provides neutralizing monoclonal human antibodies, wherein the antibody recognizes an antigen from HIV, e.g., a gp120 polypeptide. In certain embodiments, a "neutralizing antibody" may inhibit the entry of HIV-1 virus, e.g., SF162 and/or JR-CSF, with a neutralization index >1.5 or >2.0 (Kostrikis L G et al., *J. Virol.,* 70(1): 445-458 (1996)).

In some embodiments, these antibodies are broadly neutralizing antibodies (e.g., monoclonal) that target HIV-1. By "broadly neutralizing antibodies" are meant antibodies that neutralize more than one HIV-1 virus species (from diverse clades and different strains within a clade) in a neutralization assay. A broad neutralizing antibody may neutralize at least 2, 3, 4, 5, 6, 7, 8, 9 or more different strains of HIV-1, the strains belonging to the same or different clades. In particular embodiments, a broad neutralizing antibody may neutralize multiple HIV-1 species belonging to at least 2, 3, 4, 5, or 6 different clades. In certain embodiments, the inhibitory concentration of the antibody may be less than about 0.0001 μg/ml, less than about 0.001 μg/ml, less than about 0.01 μg/ml, less than about 0.1 μg/ml, less than about 0.5 μg/ml, less than about 1.0 μg/ml, less than about 5 μg/ml, less than about 10 μg/ml, less than about 25 μg/ml, less than about 50 μg/ml, or less than about 100 μg/ml to neutralize about 50% of the input virus in the neutralization assay.

In one embodiment, the anti-gp120 antibodies of this disclosure are related to the antibody described as PGT-121 LO6 in PCT Application Publication No. WO 2012/030904. Table 1 below provides the relevant sequence information for the PGT-121 LO6 antibody.

TABLE 1

| | |
|---|---|
| Clone Designation | PGT121 LO6 |
| Heavy Chain | QMQLQESGPGLVKPSETLSLTCSVSGASISDSYWSWIRRSPGKGLEW IGYVHKSGDTNYSPSLKSRVNLSLDTSKNQVSLSLVAATAADSGKYY CARTLHGRRIYGIVAFNEWFTYFYMDVWGNGTQVTVSSASTKGPSVF PLAPSSKSISGGTAALGCLVKDYFPEPVTVSWNSGALTSGVHTFPAV LQSSGLYSLSSVVTVPSSSLGTQTYICNVNHKPSNTKVDKKVEPKSC DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVMHEALHNHYTQKSLSLSPGK (SEQ ID NO: 23) |
| Heavy CDR1 Kabat | DSYWS (SEQ ID NO: 1) |
| Heavy CDR2 Kabat | YVHKSGDTNYSPSLKS (SEQ ID NO : 24) |
| Heavy CDR3 Kabat | TLHGRRIYGIVAFNEWFTYFYMDV (SEQ ID NO: 3) |
| Heavy CDR1 IMGT | GASISDSY (SEQ ID NO: 25) |
| Heavy CDR2 IMGT | VHKSGDT (SEQ ID NO: 26) |
| Heavy CDR3 IMGT | ARTLHGRRIYGIVAFNEWFTYFYMDV (SEQ ID NO : 27) |
| Heavy CDR1 Chothia | GASISDS (SEQ ID NO: 28) |
| Heavy CDR2 Chothia | KSG |
| Heavy CDR3 Chothia | LHGRRIYGIVAFNEWFTYFYMD (SEQ ID NO: 29) |
| Heavy CDR1 Honegger | VSGASISDSY (SEQ ID NO: 30) |
| Heavy CDR2 Honegger | VHKSGDTNYSPSLKSR (SEQ ID NO: 31) |
| Heavy CDR3 Honegger | TLHGRRIYGIVAFNEWFTYFYMD (SEQ ID NO: 32) |
| Light Chain | SDISVAPGETARISCGEKSLGSRAVQWYQHRAGQAPSLIIYNNQDRP SGIPERFSGSPDSPFGTTATLTITSVEAGDEADYYCHIWDSRVPTKW VFGGGTTLTVLGQPKAAPSVTLFPPSSEELQANKATLVCLISDFYPG AVTVAWKADSSPVKAGVETTTPSKQSNNKYAASSYLSLTPEQWKSHR SYSCQVTHEGSTVEKTVAPTECS (SEQ ID NO: 33) |
| Light CDR1 Kabat | GEKSLGSRAVQ (SEQ ID NO: 4) |
| Light CDR2 Kabat | NNQDRPS (SEQ ID NO: 5) |

TABLE 1-continued

```
Light CDR3 Kabat      HIWDSRVPTKWV (SEQ ID NO: 6)

Light CDR1 IMGT       SLGSRA (SEQ ID NO: 34)

Light CDR2 IMGT       NNQ

Light CDR3 IMGT       HIWDSRVPTKWV (SEQ ID NO: 6)

Light CDR1 Chothia    EKSLGSRA (SEQ ID NO: 36)

Light CDR2 Chothia    NNQ

Light CDR3 Chothia    WDSRVPTKW (SEQ ID NO: 35)

Light CDR1 Honegger   EKSLGSRA (SEQ ID NO: 36)

Light CDR2 Honegger   NNQDRPSGIPER (SEQ ID NO: 39)

Light CDR3 Honegger   WDSRVPTKW (SEQ ID NO: 35)
```

Crystal structure and experimental analysis of an antibody highly related to the PGT-121 LO6 antibody—i.e., PGT-122—revealed that PGT122 also utilizes amino acid residues outside of the CDRs to bind antigen (together with the CDRs). For example, this antibody appears to have additional regions in the framework region that contact antigens (see, e.g., Experimental Validation for PGT121 and related antibodies: Sok et al., *PLOS Pathogens*, 9, e1003754 (2013)). High resolution structures of PGT122 bound to the Env viral antigen have been determined (see, e.g., Julien J. P. et al., *Science*, 342, 14777-14783 (2013), and Pancera, M. et al., *Nature*, 514, 455-461 (2014)). The structure of PGT121 is described in Julien J P et al., *PLOS Pathogens* 9, e1003342 (2013), and Mouquet H et al., *PNAS*, 109, E3268-E3277 (2012). The structure of PGT122 is described in Julien J P et al., *PLOS Pathogens* 9, e1003342 (2013), PDB ID 4JY5; and the structure of PGT123 is described in Julien J P et al., *PLOS Pathogens* 9, e1003342 (2013). The PGT122 and PGT123 antibodies are closely related to the PGT121 antibody, so the PGT122/Env structure, together with knowledge of the PGT121, PGT122, and PGT123 structures, can be used to model the structure of PGT121 bound to Env very accurately and predict with high confidence the residues of PGT121 involved in binding to Env. The predicted residues of the PGT121 LO6 antibody that contact the gp120 antigen based on similarity to PGT122 and the PGT122/Env structure are provided below with framework residues shown in bold (Kabat numbering):

VH (Kabat numbering):
33, 56, 58, 99, 100, 100A, 100B, 100C, 100D, 100E, 100G, 100I, 100J, 100K, 100L; and VL (Kabat numbering):
28, 29, 30, 50, 51, 52, 66, 67, 67A, 67C, 91, 92, 93, 94, 95, 95A, 95B.

The PGT-121 LO6 antibody has been shown to bind to many different variants of antigen, e.g., different viral strains, which may contact the antibody at unknown amino acid positions in addition to those listed above. Different viral strains have different Env (i.e., antigen) sequences and different glycosylation patterns, and even a single Env sequence can have heterogeneous glycosylation patterns, requiring a broadly binding or neutralizing antibody to recognize Env proteins of different HIV-1 variants or even different glycosylation patterns on the same Env protein. For example, the epitope of PGT121 is comprised of the Env V3 loop, in particular an N-linked glycan at position N332. The V3 loop is the major determinant of cellular tropism and viral clade. Among 117 CCR5-tropic viruses of multiple clades, the presence of a potential N-linked glycosylation (PNG) motif in the viral DNA sequence encoding for the N332 glycan was statistically significantly associated with susceptibility to neutralization by PGT121 amongst viruses of clades B, G, A, AC and AE. Among 50 clade B Env sequences isolated from patients participating in Gilead-sponsored clinical trials, 94% of CCR5-tropic Envs harboring the N332 PNG motif were susceptible to neutralization by PGT121 compared to only 26% of viruses that were not CCR5-tropic, N332 PNG positive ($P<0.0001$). Thus, genetic determination of Env clade, tropism and presence of the N332 PNG motif is highly predictive of neutralization susceptibility by PGT121 and may be useful as a marker to predict viral susceptibility to neutralization by PGT121 and its derivatives.

The present disclosure provides variants of the PGT-121 LO6 antibody. In certain embodiments, these variants have substantially the same or increased binding affinity for gp120 compared to the PGT-121 LO6 antibody. Binding affinity may be determined using any assay known in the art including ELISA, SPR, BLI, or flow cytometry. In certain embodiments, these variants have increased binding affinity to FcRn at pH 6.0 compared to the PGT-121 LO6 antibody. In some embodiments, these variants have increased neutralization of HIV-1 relative to the PGT-121 LO6 antibody. In certain embodiments, the variants have reduced immunogenicity as compared to the PGT-121 LO6 antibody. In certain embodiments, binding of the variants of this disclosure to the Env protein is predicted to involve regions of Env in or around the following residues (HIV Env HXB2 numbering): V3 loop (324-328, 330) and associated N332 glycan and a portion of the V1-loop (135-137) and associated N137 glycan, residues 415-417. The antibody paratope for Env binding is predicted to involve residues in the following regions that make direct contact with the antigen (Kabat numbering): CDRH1 (33), CDRH2 (50, 56, 58), CDRH3 (99, 100, 100A, 100B, 100C, 100D, 100E, 100G, 100I, 100L), CDRL1 (28, 29, 30), CDRL2 (50, 51, 52), LFR3 (66, 67 67A, 67B, and 67C) and CDRL3 (93, 94, 95A, 95B).

PGT-121 LO6 heavy chain variable domain sequence (with Kabat numbering) (SEQ ID NO: 126)

| Q | M | Q | L | Q | E | S | G | P | G | L | V | K | P | S | E | T | L | S |
|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 |
| L | T | C | S | V | S | G | A | S | I | S | D | S | Y | W | S | W | I | R |
| 20 | 21 | 22 | 23 | 24 | 25 | 26 | 27 | 28 | 29 | 30 | 31 | 32 | 33 | 34 | 35 | 36 | 37 | 38 |
| R | S | P | G | K | G | L | E | W | I | G | Y | V | H | K | S | G | D | T |
| 39 | 40 | 41 | 42 | 43 | 44 | 45 | 46 | 47 | 48 | 49 | 50 | 51 | 52 | 53 | 54 | 55 | 56 | 57 |
| N | Y | S | P | S | L | K | S | R | V | N | L | S | L | D | T | S | K | N |
| 58 | 59 | 60 | 61 | 62 | 63 | 64 | 65 | 66 | 67 | 68 | 65 | 75 | 71 | 72 | 73 | 74 | 75 | 76 |
| Q | V | S | L | S | L | V | A | A | T | A | A | D | S | G | K | Y | Y | C |
| 77 | 78 | 79 | 80 | 81 | 82 | 82A | 82B | 82C | 83 | 84 | 85 | 86 | 87 | 88 | 89 | 90 | 91 | 92 |
| A | R | T | L | H | G | R | R | I | Y | G | I | V | A | F | N | E | W | F |
| 93 | 94 | 95 | 96 | 97 | 98 | 99 | 100 | 100A | 100B | 100C | 100D | 100E | 100F | 100G | 100H | 100I | 100J | 100K |
| T | Y | F | Y | M | D | V | W | G | N | G | T | Q | V | T | V | S | S | |
| 100L | 100M | 100N | 100O | 100P | 101 | 102 | 103 | 104 | 105 | 106 | 107 | 108 | 109 | 110 | 111 | 112 | 113 | |

PGT-121 LO6 light chain variable domain sequence (with Kabat numbering; Note that the VL ends at position 107 (V); i.e., G108 is not part of the VL) (SEQ ID NO: 127)

| — | — | — | — | — | — | — | S | D | I | S | V | A | P | G | E | T | A | R | I | S | C | G | E | K | S | L | G | S | R |
|---|---|---|---|---|---|---|---|---|---|---|---|---|---|---|---|---|---|---|---|---|---|---|---|---|---|---|---|---|---|
| 1 | 2 | 3 | 4 | 5 | 6 | 7 | 8 | 9 | 11 | 12 | 13 | 14 | 15 | 16 | 17 | 18 | 19 | 20 | 21 | 22 | 23 | 24 | 25 | 26 | 27 | 28 | 29 | 30 | 31 |
| A | V | Q | W | Y | Q | H | R | A | G | Q | A | P | S | L | I | I | Y | N | N | Q | D | R | P | S | G | I | P | E | R |
| 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 |
| F | S | G | S | P | D | S | P | F | G | T | T | A | T | L | T | I | T | S | V | E | A | G | D | E | A | D | Y | Y | C |
| 62 | 63 | 64 | 65 | 66 | 67 | 67a | 67b | 67c | 68 | 69 | 70 | 71 | 72 | 73 | 74 | 75 | 76 | 77 | 78 | 79 | 80 | 81 | 82 | 83 | 84 | 85 | 86 | 87 | 88 |
| H | I | W | D | S | R | V | P | T | K | W | V | F | G | G | G | T | T | L | T | V | L | G | | | | | | | |
| 89 | 90 | 91 | 92 | 93 | 94 | 95 | 95a | 95b | 95c | 96 | 97 | 98 | 99 | 100 | 101 | 102 | 103 | 104 | 105 | 106 | 107 | 108 | | | | | | | |

One exemplary variant of the PGT-121 LO6 antibody is the PGT-121.60 antibody, the relevant sequence information of which is provided in Table 2 below.

TABLE 2

| Clone Designation | PGT121.60 hIgG1/hLambda |
|---|---|
| Heavy Chain | QMQLQESGPGLVKPSETLSLTCSVSGASISDSYWSWIRRSPGKGLEW IGYVHKSGDTNYNPSLKSRVHLSLDTSKNQVSLSLTGVTAADSGKYY CARTLHGRRIYGIVAFNEWFTYFYMDVWGTGTQVTVSSASTKGPSVF PLAPSSKSTSGGTAALGCLVKDYFPEPVTVSWNSGALTSGVHTFPAV LQSSGLYSLSSVVTVPSSSLGTQTYICNVNHKPSNTKVDKKVEPKSC DKTHTCPPCPAPELLAGPDVFLFPPKPKDTLMISRTPEVTCVVVDVS HEDPEVKFNWYVDGVEVHNAKTKPREEQYNSTYRVVSVLTVLHQDWL NGKEYKCKVSNKALPLPEEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVLHEALHSHYTQKSLSLSPGK (SEQ ID NO: 41) |
| Heavy CDR1 Kabat | DSYWS (SEQ ID NO: 1) |
| Heavy CDR2 Kabat | YVHKSGDTNYNPSLKS (SEQ ID NO: 2) |
| Heavy CDR3 Kabat | TLHGRRIYGIVAFNEWFTYFYMDV (SEQ ID NO: 3) |
| Heavy CDR1 IMGT | GASISDSY (SEQ ID NO: 25) |
| Heavy CDR2 IMGT | VHKSGDT (SEQ ID NO: 26) |
| Heavy CDR3 IMGT | ARTLHGRRIYGIVAFNEWFTYFYMDV (SEQ ID NO: 27) |
| Heavy CDR1 Chothia | GASISDS (SEQ ID NO: 28) |
| Heavy CDR2 Chothia | KSG |
| Heavy CDR3 Chothia | LHGRRIYGIVAFNEWFTYFYMD (SEQ ID NO: 29) |
| Heavy CDR1 Honegger | VSGASISDSY (SEQ ID NO: 30) |
| Heavy CDR2 Honegger | VHKSGDTNYNPSLKSR (SEQ ID NO: 124) |
| Heavy CDR3 Honegger | TLHGRRIYGIVAFNEWFTYFYMD (SEQ ID NO: 32) |

TABLE 2-continued

| | |
|---|---|
| Light Chain | SDISVAPGETARISCGEKSLGSRAVQWYQHRAGQAPSLIIYNNQDRP SGIPERFSGSPDSRPGTTATLTITSVEAGDEADYYCHIWDSRVPTKW VFGGGTTLTVLGQPKAAPSVTLFPPSSEELQANKATLVCLISDFYPG AVTVAWKADSSPVKAGVETTTPSKQSNNKYAASSYLSLTPEQWKSHR SYSCQVTHEGSTVEKTVAPTECS (SEQ ID NO: 10) |
| Light CDR1 Kabat | GEKSLGSRAVQ (SEQ ID NO: 4) |
| Light CDR2 Kabat | NNQDRPS (SEQ ID NO: 5) |
| Light CDR3 Kabat | HIWDSRVPTKWV (SEQ ID NO: 6) |
| Light CDR1 IMGT | SLGSRA (SEQ ID NO: 34) |
| Light CDR2 IMGT | NNQ |
| Light CDR3 IMGT | HIWDSRVPTKWV (SEQ ID NO: 6) |
| Light CDR1 Chothia | EKSLGSRA (SEQ ID NO: 3 6) |
| Light CDR2 Chothia | NNQ |
| Light CDR3 Chothia | WDSRVPTKW (SEQ ID NO: 35) |
| Light CDR1 Honegger | EKSLGSRA (SEQ ID NO: 36) |
| Light CDR2 Honegger | NNQDRPSGIPER (SEQ ID NO: 39) |
| Light CDR3 Honegger | WDSRVPTKW (SEQ ID NO: 35) |

Exemplary Anti-120 Antibody 1

Exemplary anti-gp120 Antibody 1 is related to the PGT-121.60 antibody. The relevant amino acid sequences of an Exemplary anti-gp120 Antibody 1 (PGT121.60 human IgG1 FEARLS/human Lambda) are provided in Table 3.

TABLE 3

| | |
|---|---|
| Clone Designation | PGT121.60 hIgG1 FEARLS/hLambda |
| VH | QMQLQESGPGLVKPSETLSLTCSVSGASISDSYWSWIRRSPGKGLEW IGYVHKSGDTNYNPSLKSRVHLSLDTSKNQVSLSLTGVTAADSGKYY CARTLHGRRIYGIVAFNEWFTYFYMDVWGTGTQVTVSS (SEQ ID NO: 7) |
| Heavy Chain | QMQLQESGPGLVKPSETLSLTCSVSGASISDSYWSWIRRSPGKGLEW IGYVHKSGDTNYNPSLKSRVHLSLDTSKNQVSLSLTGVTAADSGKYY CARTLHGRRIYGIVAFNEWFTYFYMDVWGTGTQVTVSSASTKGPSVF PLAPSSKSTSGGTAALGCLVKDYFPEPVTVSWNSGALTSGVHTFPAV LQSSGLYSLSSVVTVPSSSLGTQTYICNVNHKPSNTKVDKRVEPKSC DKTHTCPPCPAPEFEGGPSVFLFPPKPKDTLMISRTPEVTCVVVAVS HEDPEVKFNWYVDGVEVHNAKTKPREEQYNSTYRVVSVLTVLHQDWL NGKEYKCKVSNKALPAPIEKTISKAKGQPREPQVYTLPPSREEMTKN QVSLTCLVKGFYPSDIAVEWESNGQPENNYKTTPPVLDSDGSFFLYS RLTVDKSRWQQGNVFSCSVLHEALHSHYTQKSLSLSPGK (SEQ ID NO: 9) |
| Heavy CDR1 Kabat | DSYWS (SEQ ID NO: 1) |
| Heavy CDR2 Kabat | YVHKSGDTNYNPSLKS (SEQ ID NO: 2) |
| Heavy CDR3 Kabat | TLHGRRIYGIVAFNEWFTYFYMDV (SEQ ID NO: 3) |
| Heavy CDR1 IMGT | GASISDSY (SEQ ID NO: 25) |
| Heavy CDR2 IMGT | VHKSGDT (SEQ ID NO: 26) |
| Heavy CDR3 IMGT | ARTLHGRRIYGIVAFNEWFTYFYMDV (SEQ ID NO: 27) |
| Heavy CDR1 Chothia | GASISDS (SEQ ID NO: 28) |
| Heavy CDR2 Chothia | KSG |
| Heavy CDR3 Chothia | LHGRRIYGIVAFNEWFTYFYMD (SEQ ID NO: 29) |
| Heavy CDR1 Honegger | VSGASISDSY (SEQ ID NO: 30) |
| Heavy CDR2 Honegger | VHKSGDTNYNPSLKSR (SEQ ID NO: 124) |

TABLE 3-continued

```
Heavy CDR3 Honegger  TLHGRRIYGIVAFNEWFTYFYMD (SEQ ID NO: 32)

VL                   SDISVAPGETARISCGEKSLGSRAVQWYQHRAGQAPSLIIYNNQDRP
                     SGIPERFSGSPDSRPGTTATLTITSVEAGDEADYYCHIWDSRVPTKW
                     VFGGGTTLTVL (SEQ ID NO: 8)

Light Chain          SDISVAPGETARISCGEKSLGSRAVQWYQHRAGQAPSLIIYNNQDRP
                     SGIPERFSGSPDSRPGTTATLTITSVEAGDEADYYCHIWDSRVPTKW
                     VFGGGTTLTVLGQPKAAPSVTLFPPSSEELQANKATLVCLISDFYPG
                     AVTVAWKADSSPVKAGVEITTPSKQSNNKYAASSYLSLIPEQWKSHR
                     SYSCQVTHEGSTVEKTVAPTECS (SEQ ID NO: 10)

Light CDR1 Kabat     GEKSLGSRAVQ (SEQ ID NO: 4)

Light CDR2 Kabat     NNQDRPS (SEQ ID NO: 5)

Light CDR3 Kabat     HIWDSRVPTKWV (SEQ ID NO: 6)

Light CDR1 IMGT      SLGSRA (SEQ ID NO: 34)

Light CDR2 IMGT      NNQ

Light CDR3 IMGT      HIWDSRVPTKWV (SEQ ID NO: 6)

Light CDR1 Chothia   EKSLGSRA (SEQ ID NO: 36)

Light CDR2 Chothia   NNQ

Light CDR3 Chothia   WDSRVPTKW (SEQ ID NO : 35)

Light CDR1 Honegger  EKSLGSRA (SEQ ID NO: 36)

Light CDR2 Honegger  NNQDRPSGIPER (SEQ ID NO: 39)

Light CDR3 Honegger  WDSRVPTKW (SEQ ID NO: 35)
```

The anti-gp120 antibodies can encompass the heavy chain CDR 1, CDR2, and CDR3 and the light chain CDR 1, CDR2, and CDR3 of Exemplary anti-gp120 Antibody 1. In one embodiment, the CDRs are defined based on the Kabat definition. In another embodiment, the CDRs are defined based on the Chothia definition. In a specific embodiment, the Chothia definition is from Discovery Studio which uses the definitions from Chothia and Lesk, *J Mol Biol.* 196(4): 901-17 (1987) and Morea et al., Methods, 20:267-279 (2000). In another specific embodiment, the Chothia definition is based on the Chothia from Abysis definition. In another embodiment, the CDRs are defined based on the IMGT definition. In another embodiment, the CDRs are defined based on the Honegger definition. In another embodiment, the CDRs are defined based on the contact definition. In some instances, the anti-gp120 antibodies of this disclosure bind a protein comprising or consisting the amino acid sequence set forth in SEQ ID NO: 21. In some instances, the anti-gp120 antibodies of this disclosure bind a protein comprising or consisting the amino acid sequence set forth in SEQ ID NO: 38. In some instances, the anti-gp120 antibodies of this disclosure bind free HIV-1 virus. In some instances, the anti-gp120 antibodies of this disclosure bind an HIV-1 infected cell. In some instances, the anti-gp120 antibodies of this disclosure bind both free HIV-1 virus and an HIV-1 infected cell. In certain cases, the anti-gp120 antibodies of this disclosure bind at least two different strains of HIV-1 (e.g., Group M, Group N, Group O, or Group P). In one embodiment, the anti-gp120 antibodies of this disclosure, bind pWITO.c/2474 (Accession number JN944948 and NIH AIDS Reagent Program catalogue number 11739). In another embodiment, the anti-gp120 antibodies of this disclosure, bind pCH058.c/2960 (Accession number JN944940 and NIH AIDS Reagent Program catalogue number 700010058).

In certain instances, the anti-gp120 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable heavy chain of Exemplary anti-gp120 Antibody 1. In some embodiments, the anti-gp120 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the heavy chain of Exemplary anti-gp120 Antibody 1. In certain instances, the anti-gp120 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable light chain of Exemplary anti-gp120 Antibody 1. In certain instances, the anti-gp120 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the light chain of Exemplary anti-gp120 Antibody 1. In certain embodiments, the anti-gp120 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable heavy chain and the variable light chain of Exemplary anti-gp120 Antibody 1. In some embodiments, the anti-gp120 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the heavy chain and comprise an amino acid sequence having at least 80%, 85%, 86%, 87%, 88%, 89%, 90%, 91%, 92%, 93%, 94%, 95%, 96%, 97%, 98%, 99%, or 100% identity to the light chain of Exemplary anti-gp120 Antibody 1. In some instances, the anti-gp120 antibodies of this disclosure bind a protein comprising or consisting the amino acid sequence set forth in SEQ ID NO: 21. In some instances, the anti-gp120 antibodies of this disclosure bind a protein comprising or consisting the amino acid sequence set forth in SEQ ID NO: 38. In some instances, the anti-gp120 antibodies of this disclosure bind free HIV-1 virus. In some instances, the anti-gp120 antibodies of this disclosure bind an HIV-1 infected cell. In some instances, the anti-gp120 antibodies of this disclosure bind both free HIV-1 virus and an HIV-1 infected cell. In certain cases, the anti-gp120 antibodies of this disclosure bind at least two different strains of HIV-1 (e.g., Group M, Group N, Group O, or Group P). In one embodiment, the anti-gp120 antibodies of this disclosure, bind pWITO.c/2474 (Accession number JN944948 and NIH AIDS Reagent Program catalogue number 11739). In another embodiment, the anti-gp120 antibodies of this disclosure, bind pCH058.c/2960 (Accession number JN944940 and NIH AIDS Reagent Program catalogue number 700010058).

In some embodiments, the variable heavy chain of Exemplary Anti-gp120 Antibody 1 is linked to a heavy chain constant region comprising a CH1 domain and a hinge region. In some embodiments, the variable heavy chain of Exemplary Anti-gp120 Antibody 1 is linked to a heavy chain constant region comprising a CH3 domain. In certain embodiments, the variable heavy chain of Exemplary Anti-gp120 Antibody 1 is linked to a heavy chain constant region comprising a CH1 domain, hinge region, and CH2 domain from IgG4 and a CH3 domain (e.g., from IgG1). In certain embodiments, the variable heavy chain of Exemplary Anti-gp120 Antibody 1 is linked to a heavy chain constant region comprising a CH1 domain, CH2 domain, and a CH3 domain from IgG1 (e.g., human IgG1, e.g., IgG1m3 allotype) and an IgG3 hinge region (e.g., an "open" IgG3 hinge variant designated "IgG3 C-" in WO 2017/096221 (see, e.g., FIG. 2A of this PCT publication)). This IgG3 hinge variant is expected to exhibit improved Fab arm flexibility and the ability to span over a 200A° distance that is sufficient for intra-trimeric interactions. In certain embodiments, such a chimeric antibody contains one or more additional mutations in the heavy chain constant region that increase the stability of the chimeric antibody. In certain embodiments, the heavy chain constant region includes substitutions that modify the properties of the antibody (e.g., decrease Fc receptor binding, increase or decrease antibody glycosylation, decrease binding to C1q, increase half-life, decrease effector function).

In certain embodiments, the anti-gp120 antibody is an IgG antibody. In one embodiment, the antibody is IgG1. In another embodiment, the antibody is IgG2. In some embodiments, the antibody has a chimeric heavy chain constant region (e.g., having the CH1, hinge, and CH2 regions of IgG4 and CH3 region of IgG1).

IgG antibodies exist in various allotypes and isoallotypes. In particular embodiments, antibodies of the present disclosure include an IgG1 heavy chain having an allotype of G1m1; nG1m2; G1m3; G1m17,1; G1m17,1,2; G1m3,1; or G1m17. Each of these allotypes or isoallotypes is characterized by the following amino acid residues at the indicated positions within the IgG1 heavy chain constant region (Fc) (EU numbering):

G1m1: D356, L358;
nG1m1: E356, M358;
G1m3: R214, E356, M358, A431;
G1m17,1: K214, D356, L358, A431;
G1m17,1,2: K214, D356, L358, G431;
G1m3,1: R214, D356, L358, A431; and
G1m17: K214, E356, M358, A431.

In a specific embodiment, the VH of Exemplary Anti-gp120 Antibody 1 is directly linked to, or linked via an intervening amino acid sequence (e.g., a G-S linker), to a wild type IgG1m3 sequence provided below (representative allotype-determining residues are indicated in bold).

```
                                            (SEQ ID NO: 77)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In certain embodiments, a VH of Exemplary Anti-gp120 Antibody 1 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a mutant IgG1m3 sequence with 1 to 10 (e.g., 1, 2, 3, 4, 5, 6, 7, 8, 9, 10) amino acid substitutions in SEQ ID NO:77 (e.g., substitutions made to reduce effector function and/or to increase half-life). Exemplary amino acid substitutions are described later in this disclosure.

In certain embodiments, the anti-gp120 antibody is a human IgG1/human kappa antibody. In some embodiments, antibodies of this disclosure comprise a kappa light chain having an allotype selected from Km1; Km1,2; or Km3. Each of these allotypes is characterized by the following amino acid residues at the indicated positions within the IgG1 light chain (EU numbering):

Km1: V153, L191;
Km1,2: A153, L191; and
Km3: A153, V191.

In certain embodiments, an antibody of this disclosure comprises an IgG1 kappa light chain comprising one of the following amino acid sequences, in which representative allotype-determining residues are indicated in bold:

```
Km1:
                                            (SEQ ID NO: 85)
TVAAPSVFIFPPSDEQLKSGTASVVCLLNNFYPREAKVQWKVDNVLQSGN

SQESVTEQDSKDSTYSLSSTLTLSKADYEKHKLYACEVTHQGLSSPVTKS

FNRGEC;

Km1, 2:
                                            (SEQ ID NO: 86)
TVAAPSVFIFPPSDEQLKSGTASVVCLLNNFYPREAKVQWKVDNALQSGN

SQESVTEQDSKDSTYSLSSTLTLSKADYEKHKLYACEVTHQGLSSPVTKS

FNRGEC;
or

Km3:
                                            (SEQ ID NO: 87)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.
```

In certain embodiments, the anti-gp120 antibody is a human IgG1/human lambda antibody. Each individual human includes between seven and eleven different lambda light chain genes, which encode light chains selected from Lambda1, Lambda2, Lambda3, Lambda4, Lambda5, Lambda6, and Lambda7. In particular embodiments, antibodies of the present disclosure comprise a lambda light chain selected from Lambda1, Lambda2, Lambda3, Lambda4, Lambda5, Lambda6, and Lambda7. In particular embodiments, an antibody described herein comprises a lambda light chain comprising one of the following amino acid sequences, in which representative lambda-determining residues are indicated in bold:

Lambda1:
(SEQ ID NO: 88)
GQPKANPTVTLFPPSSEELQANKATLVCLISDFYPGAVTVAWKADGSPVK

AGVETTKPSKQSNNKYAASSYLSLTPEQWKSHRSYSCQVTHEGSTVEKTV

APTECS;

Lambda2:
(SEQ ID NO: 89)
GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTV

APTECS;

Lambda3:
(SEQ ID NO: 90)
GQPKAAPSVTLFPPSSEELQANKATLVCLISDFYPGAVTVAWKADSSPAK

AGVETTTPSKQSNNKYAASSYLSLTPEQWKSHKSYSCQVTHEGSTVEKTV

APTECS;
or

Lambda7:
(SEQ ID NO: 91)
GQPKAAPSVTLFPPSSEELQANKATLVCLVSDFYPGAVTVAWKADGSPVK

VGVETTKPSKQSNNKYAASSYLSLTPEQWKSHRSYSCRVTHEGSTVEKTV

APAECS.

In a specific embodiment, a VL of Exemplary Anti-gp120 Antibody 1 (e.g., an amino acid sequence that has at least 80%, 85%, 90%, 95%, 96%, 97%, 98%, 99%, or 100% identity to SEQ ID NO: 8, or that has 0 to 5 (i.e., 1, 2, 3, 4, or 5) amino acid substitutions (e.g., conservative substitutions within SEQ ID NO: 8) is directly linked to, or linked via an intervening amino acid sequence (e.g., a G-S linker), to a wild type human lambda 2 sequence (SEQ ID NO:89). In certain embodiments, the VL of Exemplary Anti-gp120 Antibody 1 is directly linked to, or linked via an intervening amino acid sequence (e.g., a G-S linker), to a mutant human lambda 2 sequence having 1 to 5 (i.e., 1, 2, 3, 4, 5) substitutions within SEQ ID NO:89.

In a particular embodiment, the anti-gp120 antibody is a human IgG1m3/human lambda2 antibody.

Antibodies, such as Exemplary anti-gp120 Antibody 1 can be made, for example, by preparing and expressing nucleic acids that encode the amino acid sequences of the antibody.

Exemplary Anti-120 Antibody 2

Another exemplary anti-gp120 antibody, Exemplary Anti-gp120 Antibody 2, has the same six CDRs as Exemplary Anti-gp120 Antibody 1. This antibody comprises a VH sequence comprising or consisting of the amino acid sequence set forth in SEQ ID NO:7 and a VL sequence comprising or consisting of the amino acid sequence set forth below:

(SEQ ID NO: 81)
SDISVAPGETARISCGEKSLGSRAVQWYQHRAGQAPSLITYNNQDRPSGI

PERFSGSPDYRPGTTATLTITSVEAGDEADYYCHIWDSRVPTKWVFGGGT

TLTVL.

In certain instances, the VL is directly linked to, or linked via an intervening amino acid sequence (e.g., a G-S linker) to a human lambda constant region.

Exemplary Anti-gp120 Antibody 2 comprises a heavy chain comprising or consisting of the amino acid sequence set forth in SEQ ID NO:9, and a light chain comprising or consisting of the amino acid sequence set forth below:

(SEQ ID NO: 40)
SDISVAPGETARISCGEKSLGSRAVQWYQHRAGQAPSLIIYNNQDRPSGI

PERFSGSPDYRPGTTATLTITSVEAGDEADYYCHIWDSRVPTKWVFGGGT

TLTVLGQPKAAPSVTLFPPSSEELQANKATLVCLISDFYPGAVTVAWKAD

SSPVKAGVETTTPSKQSNNKYAASSYLSLTPEQWKSHRSYSCQVTHEGST

VEKTVAPTECS

In some instances, the anti-gp120 antibodies of this disclosure bind a protein comprising or consisting the amino acid sequence set forth in SEQ ID NO: 21. In some instances, the anti-gp120 antibodies of this disclosure bind a protein comprising or consisting the amino acid sequence set forth in SEQ ID NO: 38. In some instances, the anti-gp120 antibodies of this disclosure bind free HIV-1 virus. In some instances, the anti-gp120 antibodies of this disclosure bind an HIV-1 infected cell. In some instances, the anti-gp120 antibodies of this disclosure bind both free HIV-1 virus and an HIV-1 infected cell. In certain cases, the anti-gp120 antibodies of this disclosure bind at least two different strains of HIV-1 (e.g., Group M, Group N, Group O, or Group P). In one embodiment, the anti-gp120 antibodies of this disclosure, bind pWITO.c/2474 (Accession number JN944948 and NIH AIDS Reagent Program catalogue number 11739). In another embodiment, the anti-gp120 antibodies of this disclosure, bind pCH058.c/2960 (Accession number JN944940 and NIH AIDS Reagent Program catalogue number 700010058).

In some embodiments, a variable heavy chain of Exemplary Anti-gp120 Antibody 2 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is linked to a heavy chain constant region comprising a CH1 domain and a hinge region. In some embodiments, a variable heavy chain of Exemplary Anti-gp120 Antibody 2 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is linked to a heavy chain constant region comprising a CH3 domain. In certain embodiments, a variable heavy chain of Exemplary Anti-gp120 Antibody 2 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is linked to a heavy chain constant region comprising a CH1 domain, hinge region, and CH2 domain from IgG4 and a CH3 domain (e.g., from IgG1). In certain embodiments, the variable heavy chain of Exemplary Anti-gp120 Antibody 1 is linked to a heavy chain constant region comprising a CH1 domain, CH2 domain, and a CH3 domain from IgG1 (e.g., human IgG1, e.g., IgG1m3 allotype) and an IgG3 hinge region (e.g., an "open" IgG3 hinge variant "IgG3 C-" described in WO2017/096221). In certain embodiments such a chimeric antibody contains one or more additional mutations in the heavy chain constant region that increase the stability of the chimeric antibody. In certain embodiments, the heavy chain constant region includes substitutions that modify the properties of the antibody (e.g., decrease Fc receptor binding, increase or decrease antibody glycosylation, decrease binding to C1q, increase half-life, decrease effector function).

In certain embodiments, the anti-gp120 antibody is an IgG antibody. In one embodiment, the antibody is IgG1. In another embodiment, the antibody is IgG2. In some embodiments, the antibody has a chimeric heavy chain constant region (e.g., having the CH1, hinge, and CH2 regions of IgG4 and CH3 region of IgG1).

In particular embodiments, antibodies of the present disclosure include an IgG1 heavy chain having an allotype of G1m1; nG1m2; G1m3; G1m17,1; G1m17,1,2; G1m3,1; or G1m17.

In certain embodiments, the anti-gp120 antibody is a human IgG1/human kappa antibody. In some embodiments, antibodies of this disclosure comprise a kappa light chain having an allotype selected from Km1; Km1,2; or Km3. In certain embodiments, the anti-gp120 antibody is a human IgG1/human lambda antibody. In some embodiments, antibodies of this disclosure comprise a lambda light chain selected from Lambda1, Lambda2, Lambda3, Lambda4, Lambda5, Lambda6, and Lambda1.

In a particular embodiment, the anti-gp120 antibody is a human IgG1m3/human lambda2 antibody.

In some embodiments, a VH of Exemplary Anti-gp120 Antibody 2 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a wild type IgG1m3 sequence (SEQ ID NO:77). In certain embodiments, the VH of Exemplary Anti-gp120 Antibody 2 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a mutant IgG1m3 sequence with 1 to 10 (e.g., 1, 2, 3, 4, 5, 6, 7, 8, 9, 10) amino acid substitutions in SEQ ID NO:77 (e.g., substitutions to reduce effector function and/or to increase half-life). Exemplary amino acid substitutions are described later in this disclosure.

In some embodiments, a VL of Exemplary Anti-gp120 Antibody 2 (e.g., an amino acid sequence that has at least 80%, 85%, 90%, 95%, 96%, 97%, 98%, 99%, or 100% identity to SEQ ID NO: 81, or that has 0 to 5 (i.e., 1, 2, 3, 4, or 5) amino acid substitutions (e.g., conservative substitutions within SEQ ID NO: 81) is directly linked to, or linked via an intervening amino acid sequence (e.g., a G-S linker), to a wild type human lambda 2 sequence (SEQ ID NO:89). In certain embodiments, a VL of Exemplary Anti-gp120 Antibody 2 (e.g., an amino acid sequence that has at least 80%, 85%, 90%, 95%, 96%, 97%, 98%, 99%, or 100% identity to SEQ ID NO: 81, or that has 0 to 5 (i.e., 1, 2, 3, 4, or 5) amino acid substitutions (e.g., conservative substitutions within SEQ ID NO: 81) is directly linked to, or linked via an intervening amino acid sequence (e.g., a G-S linker), to a mutant human lambda 2 sequence having 1 to 5 (i.e., 1, 2, 3, 4, 5) substitutions within SEQ ID NO:89.

Exemplary Anti-gp120 Antibody 2 can be used either as a monospecific or a multispecific antibody (e.g., a bispecific antibody). The whole antibody or an antigen-binding fragment (e.g., Fab, F(ab)2, Fv, scFv, sc(Fv)2, diabody) are encompassed by this disclosure.

Antibodies, such as Exemplary anti-gp120 Antibody 2 can be made, for example, by preparing and expressing nucleic acids that encode the amino acid sequences of the antibody.

Exemplary Anti-120 Antibody 3

Another exemplary anti-gp120 antibody, Exemplary Anti-gp120 Antibody 3, has the same six CDRs as Exemplary Anti-gp120 Antibody 1. This antibody comprises a VH sequence comprising or consisting of the amino acid sequence set forth in SEQ ID NO:7 and a VL sequence comprising or consisting of the amino acid sequence provided below:

```
                                          (SEQ ID NO: 82)
SDISVAPGETARISCGEKSLGSRAVQWYQHRAGQAPSLIIYNNQDRPSGI

PERFSGSPDFRPGTTATLTITSVEAGDEADYYCHIWDSRVPTKWVFGGGT

TLTVL
```

In certain instances, the VL is directly linked to, or linked via an intervening amino acid sequence (e.g., a G-S linker) to a human lambda constant region.

Exemplary Anti-gp120 Antibody 3 comprises a heavy chain comprising or consisting of the amino acid sequence set forth in SEQ ID NO:9, and a light chain comprising or consisting of the amino acid sequence set forth below:

```
                                          (SEQ ID NO: 78)
    SDISVAPGETARISCGEKSLGSRAVQWYQHRAGQAPSLIIYNNQDR

PSGIPERFSGSPDFRPGTTATLTITSVEAGDEADYYCHIWDSRVPT

KWVFGGGTTLTVLGQPKAAPSVTLFPPSSEELQANKATLVCLISDF

YPGAVTVAWKADSSPVKAGVETTTPSKQSNNKYAASSYLSLTPEQW

KSHRSYSCQVTHEGSTVEKTVAPTECS
```

In some instances, the anti-gp120 antibodies of this disclosure bind a protein comprising or consisting the amino acid sequence set forth in SEQ ID NO: 21. In some instances, the anti-gp120 antibodies of this disclosure bind a protein comprising or consisting the amino acid sequence set forth in SEQ ID NO: 38. In some instances, the anti-gp120 antibodies of this disclosure bind free HIV-1 virus. In some instances, the anti-gp120 antibodies of this disclosure bind an HIV-1 infected cell. In some instances, the anti-gp120 antibodies of this disclosure bind both free HIV-1 virus and an HIV-1 infected cell. In certain cases, the anti-gp120 antibodies of this disclosure bind at least two different strains of HIV-1 (e.g., Group M, Group N, Group O, or Group P). In one embodiment, the anti-gp120 antibodies of this disclosure, bind pWITO.c/2474 (Accession number JN944948 and NIH AIDS Reagent Program catalogue number 11739). In another embodiment, the anti-gp120 antibodies of this disclosure, bind pCH058.c/2960 (Accession number JN944940 and NIH AIDS Reagent Program catalogue number 700010058).

In some embodiments, the variable heavy chain of Exemplary Anti-gp120 Antibody 3 is linked to a heavy chain constant region comprising a CH1 domain and a hinge region. In some embodiments, the variable heavy chain of Exemplary Anti-gp120 Antibody 3 is linked to a heavy chain constant region comprising a CH3 domain. In certain embodiments, the variable heavy chain of Exemplary Anti-gp120 Antibody 3 is linked to a heavy chain constant region comprising a CH1 domain, hinge region, and CH2 domain from IgG4 and a CH3 domain (e.g., from IgG1). In certain embodiments, the variable heavy chain of Exemplary Anti-gp120 Antibody 1 is linked to a heavy chain constant region comprising a CH1 domain, CH2 domain, and a CH3 domain from IgG1 (e.g., human IgG1, e.g., IgG1m3 allotype) and an IgG3 hinge region (e.g., an "open" IgG3 hinge variant "IgG3 C-" described in WO2017/096221). In certain embodiments such a chimeric antibody contains one or more additional mutations in the heavy chain constant region that increase the stability of the chimeric antibody. In certain embodiments, the heavy chain constant region includes substitutions that modify the properties of the antibody (e.g., decrease Fc receptor binding, increase or decrease antibody glycosylation, decrease binding to C1q, increase half-life, decrease effector function).

In certain embodiments, the anti-gp120 antibody is an IgG antibody. In one embodiment, the antibody is IgG1. In another embodiment, the antibody is IgG2. In some embodiments, the antibody has a chimeric heavy chain constant region (e.g., having the CH1, hinge, and CH2 regions of IgG4 and CH3 region of IgG1).

In particular embodiments, antibodies of the present disclosure include an IgG1 heavy chain having an allotype of G1m1; nG1m2; G1m3; G1m17,1; G1m17,1,2; G1m3,1; or G1m17. In certain embodiments, the anti-gp120 antibody is a human IgG1/human kappa antibody. In some embodiments, antibodies of this disclosure comprise a kappa light chain having an allotype selected from Km1; Km1,2; or Km3. In certain embodiments, the anti-gp120 antibody is a human IgG1/human lambda antibody. In some embodiments, antibodies of this disclosure comprise a lambda light chain selected from Lambda1, Lambda2, Lambda3, Lambda4, Lambda5, Lambda6, and Lambda1.

In a particular embodiment, the anti-gp120 antibody is a human IgG1m3/human lambda2 antibody.

In some embodiments, a VH of Exemplary Anti-gp120 Antibody 3 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a wild type IgG1m3 sequence (SEQ ID NO:77). In certain embodiments, a VH of Exemplary Anti-gp120 Antibody 3 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a mutant IgG1m3 sequence with 1 to 10 (e.g., 1, 2, 3, 4, 5, 6, 7, 8, 9, 10) amino acid substitutions in SEQ ID NO:77 (e.g., to reduce effector function and/or to increase half-life). Exemplary amino acid substitutions are described later in this disclosure.

In some embodiments, the VL of Exemplary Anti-gp120 Antibody 3 (e.g., an amino acid sequence that has at least 80%, 85%, 90%, 95%, 96%, 97%, 98%, 99%, or 100% identity to SEQ ID NO: 82, or that has 0 to 5 (i.e., 1, 2, 3, 4, or 5) amino acid substitutions (e.g., conservative substitutions within SEQ ID NO: 82) is directly linked to, or linked via an intervening amino acid sequence (e.g., a G-S linker), to a wild type human lambda 2 sequence (SEQ ID NO:89). In certain embodiments, a VL of Exemplary Anti-gp120 Antibody 3 (e.g., an amino acid sequence that has at least 80%, 85%, 90%, 95%, 96%, 97%, 98%, 99%, or 100% identity to SEQ ID NO: 82, or that has 0 to 5 (i.e., 1, 2, 3, 4, or 5) amino acid substitutions (e.g., conservative substitutions within SEQ ID NO: 82) is directly linked to, or linked via an intervening amino acid sequence (e.g., a G-S linker), to a mutant human lambda 2 sequence having 1 to 5 (i.e., 1, 2, 3, 4, 5) substitutions within SEQ ID NO:89.

Exemplary Anti-gp120 Antibody 3 can be used either as a monospecific or a multispecific antibody (e.g., a bispecific antibody). The whole antibody or an antigen-binding fragment (e.g., Fab, F(ab)2, Fv, scFv, sc(Fv)2, diabody) are encompassed by this disclosure.

Antibodies, such as Exemplary anti-gp120 Antibody 3 can be made, for example, by preparing and expressing nucleic acids that encode the amino acid sequences of the antibody.

Exemplary Anti-120 Antibody 4

Another exemplary anti-gp120 antibody, Exemplary Anti-gp120 Antibody 4, has the same six CDRs as Exemplary Anti-gp120 Antibody 1. This antibody comprises a VH sequence comprising or consisting of the amino acid sequence set forth in SEQ ID NO:7 and a VL sequence comprising or consisting of the amino acid sequence shown below:

```
                                       (SEQ ID NO: 83)
SDISVAPGETARISCGEKSLGSRAVQWYQHRAGQAPSLIIYNNQDR

PSGIPERFSGSPDTRPGTTATLTITSVEAGDEADYYCHIWDSRVPT

KWVFGGGTTLTVL
```

In certain instances, the VL is directly linked to, or linked via an intervening amino acid sequence (e.g., a G-S linker) to a human lambda constant region.

Exemplary Anti-gp120 Antibody 4 comprises a heavy chain comprising or consisting of the amino acid sequence set forth in SEQ ID NO:9, and a light chain comprising or consisting of the amino acid sequence set forth below:

```
                                       (SEQ ID NO: 79)
SDISVAPGETARISCGEKSLGSRAVQWYQHRAGQAPSLIIYNNQDR

PSGIPERFSGSPDTRPGTTATLTITSVEAGDEADYYCHIWDSRVPT

KWVFGGGTTLTVLGQPKAAPSVTLFPPSSEELQANKATLVCLISDF

YPGAVTVAWKADSSPVKAGVETTTPSKQSNNKYAASSYLSLTPEQW

KSHRSYSCQVTHEGSTVEKTVAPTECS
```

In some instances, the anti-gp120 antibodies of this disclosure bind a protein comprising or consisting the amino acid sequence set forth in SEQ ID NO: 21. In some instances, the anti-gp120 antibodies of this disclosure bind a protein comprising or consisting the amino acid sequence set forth in SEQ ID NO: 38. In some instances, the anti-gp120 antibodies of this disclosure bind free HIV-1 virus. In some instances, the anti-gp120 antibodies of this disclosure bind an HIV-1 infected cell. In some instances, the anti-gp120 antibodies of this disclosure bind both free HIV-1 virus and an HIV-1 infected cell. In certain cases, the anti-gp120 antibodies of this disclosure bind at least two different strains of HIV-1 (e.g., Group M, Group N, Group O, or Group P). In one embodiment, the anti-gp120 antibodies of this disclosure, bind pWITO.c/2474 (Accession number JN944948 and NIH AIDS Reagent Program catalogue number 11739). In another embodiment, the anti-gp120 antibodies of this disclosure, bind pCH058.c/2960 (Accession number JN944940 and NIH AIDS Reagent Program catalogue number 700010058).

In some embodiments, the variable heavy chain of Exemplary Anti-gp120 Antibody 4 is linked to a heavy chain constant region comprising a CH1 domain and a hinge region. In some embodiments, the variable heavy chain of Exemplary Anti-gp120 Antibody 4 is linked to a heavy chain constant region comprising a CH3 domain. In certain embodiments, the variable heavy chain of Exemplary Anti-gp120 Antibody 4 is linked to a heavy chain constant region comprising a CH1 domain, hinge region, and CH2 domain from IgG4 and a CH3 domain (e.g., from IgG1). In certain embodiments, the variable heavy chain of Exemplary Anti-gp120 Antibody 1 is linked to a heavy chain constant region comprising a CH1 domain, CH2 domain, and a CH3 domain from IgG1 (e.g., human IgG1, e.g., IgG1m3 allotype) and an IgG3 hinge region (e.g., an "open" IgG3 hinge variant "IgG3 C-" described in WO2017/096221). In certain embodiments such a chimeric antibody contains one or more additional mutations in the heavy chain constant region that increase the stability of the chimeric antibody. In certain embodiments, the heavy chain constant region includes substitutions that modify the properties of the antibody (e.g., decrease Fc receptor binding, increase or decrease antibody glycosylation, decrease binding to C1q, increase half-life, decrease effector function).

In certain embodiments, the anti-gp120 antibody is an IgG antibody. In one embodiment, the antibody is IgG1. In another embodiment, the antibody is IgG2. In some embodiments, the antibody has a chimeric heavy chain constant region (e.g., having the CH1, hinge, and CH2 regions of IgG4 and CH3 region of IgG1).

In particular embodiments, antibodies of the present disclosure include an IgG1 heavy chain having an allotype of G1m1; nG1m2; G1m3; G1m17,1; G1m17,1,2; G1m3,1; or G1m17. In certain embodiments, the anti-gp120 antibody is a human IgG1/human kappa antibody. In some embodiments, antibodies of this disclosure comprise a kappa light chain having an allotype selected from Km1; Km1,2; or Km3. In certain embodiments, the anti-gp120 antibody is a human IgG1/human lambda antibody. In some embodiments, antibodies of this disclosure comprise a lambda light chain selected from Lambda1, Lambda2, Lambda3, Lambda4, Lambda5, Lambda6, and Lambda1.

In some embodiments, a VH of Exemplary Anti-gp120 Antibody 4 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a wild type IgG1m3 sequence (SEQ ID NO:77). In certain embodiments, a VH of Exemplary Anti-gp120 Antibody 4 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a mutant IgG1m3 sequence with 1 to 10 (e.g., 1, 2, 3, 4, 5, 6, 7, 8, 9, 10) amino acid substitutions in SEQ ID NO:77 (e.g., to reduce effector function and/or to increase half-life). Exemplary amino acid substitutions are described later in this disclosure.

In some embodiments, a VL of Exemplary Anti-gp120 Antibody 4 (e.g., an amino acid sequence that has at least 80%, 85%, 90%, 95%, 96%, 97%, 98%, 99%, or 100% identity to SEQ ID NO: 83, or that has 0 to 5 (i.e., 1, 2, 3, 4, or 5) amino acid substitutions (e.g., conservative substitutions within SEQ ID NO: 83) is directly linked to, or linked via an intervening amino acid sequence (e.g., a G-S linker), to a wild type human lambda 2 sequence (SEQ ID NO:89). In certain embodiments, a VL of Exemplary Anti-gp120 Antibody 4 (e.g., an amino acid sequence that has at least 80%, 85%, 90%, 95%, 96%, 97%, 98%, 99%, or 100% identity to SEQ ID NO: 83, or that has 0 to 5 (i.e., 1, 2, 3, 4, or 5) amino acid substitutions (e.g., conservative substitutions within SEQ ID NO: 83) is directly linked to, or linked via an intervening amino acid sequence (e.g., a G-S linker), to a mutant human lambda 2 sequence having 1 to 5 (i.e., 1, 2, 3, 4, 5) substitutions within SEQ ID NO:89.

In a particular embodiment, the anti-gp120 antibody is a human IgG1m3/human lambda2 antibody.

Exemplary Anti-gp120 Antibody 4 can be used either as a monospecific or a multispecific antibody (e.g., a bispecific antibody). The whole antibody or an antigen-binding fragment (e.g., Fab, F(ab)2, Fv, scFv, sc(Fv)2, diabody) may be employed.

Antibodies, such as Exemplary anti-gp120 Antibody 4 can be made, for example, by preparing and expressing nucleic acids that encode the amino acid sequences of the antibody.

Exemplary Anti-120 Antibody 5

Another exemplary anti-gp120 antibody, Exemplary Anti-gp120 Antibody 5, has the same six CDRs as Exemplary Anti-gp120 Antibody 1. This antibody comprises a VH sequence comprising or consisting of the amino acid sequence set forth in SEQ ID NO:7 and a VL sequence comprising or consisting of the amino acid sequence provided below:

```
                                         (SEQ ID NO: 84)
SDISVAPGETARISCGEKSLGSRAVQWYQHRAGQAPSLIIYNNQDR

PSGIPERFSGSPGSRPGTTATLTITSVEAGDEADYYCHIWDSRVPT

KWVFGGGTTLTVL
```

In certain instances, the VL is directly linked to, or linked via an intervening amino acid sequence (e.g., a G-S linker) to a human lambda constant region.

Exemplary Anti-gp120 Antibody 5 comprises a heavy chain comprising or consisting of the amino acid sequence set forth in SEQ ID NO:9, and a light chain comprising or consisting of the amino acid sequence set forth below:

```
                                         (SEQ ID NO: 80)
SDISVAPGETARISCGEKSLGSRAVQWYQHRAGQAPSLIIYNNQDR

PSGIPERFSGSPGSRPGTTATLTITSVEAGDEADYYCHIWDSRVPT

KWVFGGGTTLTVLGQPKAAPSVTLFPPSSEELQANKATLVCLISDF
```

-continued

YPGAVTVAWKADSSPVKAGVETTTPSKQSNNKYAASSYLSLTPEQW

KSHRSYSCQVTHEGSTVEKTVAPTECS

In some instances, the anti-gp120 antibodies of this disclosure bind a protein comprising or consisting the amino acid sequence set forth in SEQ ID NO: 21. In some instances, the anti-gp120 antibodies of this disclosure bind a protein comprising or consisting the amino acid sequence set forth in SEQ ID NO: 38. In some instances, the anti-gp120 antibodies of this disclosure bind free HIV-1 virus. In some instances, the anti-gp120 antibodies of this disclosure bind an HIV-1 infected cell. In some instances, the anti-gp120 antibodies of this disclosure bind both free HIV-1 virus and an HIV-1 infected cell. In certain cases, the anti-gp120 antibodies of this disclosure bind at least two different strains of HIV-1 (e.g., Group M, Group N, Group O, or Group P). In one embodiment, the anti-gp120 antibodies of this disclosure, bind pWITO.c/2474 (Accession number JN944948 and NIH AIDS Reagent Program catalogue number 11739). In another embodiment, the anti-gp120 antibodies of this disclosure, bind pCH058.c/2960 (Accession number JN944940 and NIH AIDS Reagent Program catalogue number 700010058).

In some embodiments, the variable heavy chain of Exemplary Anti-gp120 Antibody 5 is linked to a heavy chain constant region comprising a CH1 domain and a hinge region. In some embodiments, the variable heavy chain of Exemplary Anti-gp120 Antibody 5 is linked to a heavy chain constant region comprising a CH3 domain. In certain embodiments, the variable heavy chain of Exemplary Anti-gp120 Antibody 5 is linked to a heavy chain constant region comprising a CH1 domain, hinge region, and CH2 domain from IgG4 and a CH3 domain (e.g., from IgG1). In certain embodiments, the variable heavy chain of Exemplary Anti-gp120 Antibody 1 is linked to a heavy chain constant region comprising a CH1 domain, CH2 domain, and a CH3 domain from IgG1 (e.g., human IgG1, e.g., IgG1m3 allotype) and an IgG3 hinge region (e.g., an "open" IgG3 hinge variant "IgG3 C-" described in WO2017/096221). In certain embodiments such a chimeric antibody contains one or more additional mutations in the heavy chain constant region that increase the stability of the chimeric antibody. In certain embodiments, the heavy chain constant region includes substitutions that modify the properties of the antibody (e.g., decrease Fc receptor binding, increase or decrease antibody glycosylation, decrease binding to C1q, increase half-life, decrease effector function).

In certain embodiments, the anti-gp120 antibody is an IgG antibody. In one embodiment, the antibody is IgG1. In another embodiment, the antibody is IgG2. In some embodiments, the antibody has a chimeric heavy chain constant region (e.g., having the CH1, hinge, and CH2 regions of IgG4 and CH3 region of IgG1).

In particular embodiments, antibodies of the present disclosure include an IgG1 heavy chain having an allotype of G1m1; nG1m2; G1m3; G1m17,1; G1m17,1,2; G1m3,1; or G1m17.

In certain embodiments, the anti-gp120 antibody is a human IgG1/human kappa antibody. In some embodiments, antibodies of this disclosure comprise a kappa light chain having an allotype selected from Km1; Km1,2; or Km3. In certain embodiments, the anti-gp120 antibody is a human IgG1/human lambda antibody. In some embodiments, antibodies of this disclosure comprise a lambda light chain selected from Lambda1, Lambda2, Lambda3, Lambda4, Lambda5, Lambda6, and Lambda1.

In some embodiments, a VH of Exemplary Anti-gp120 Antibody 5 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a wild type IgG1m3 sequence (SEQ ID NO:77). In certain embodiments, a VH of Exemplary Anti-gp120 Antibody 5 (e.g., an amino acid sequence that has at least 80%, 85%, 90%, 95%, 96%, 97%, 98%, 99%, or 100% identity to SEQ ID NO: 7, or that has 0 to 5 (i.e., 1, 2, 3, 4, or 5) amino acid substitutions (e.g., conservative substitutions within SEQ ID NO: 7) is directly linked to, or linked via an intervening amino acid sequence (e.g., a G-S linker), to a mutant IgG1m3 sequence with 1 to 10 (e.g., 1, 2, 3, 4, 5, 6, 7, 8, 9, 10) amino acid substitutions in SEQ ID NO:77 (e.g., to reduce effector function and/or to increase half-life). Exemplary amino acid substitutions are described later in this disclosure.

In some embodiments, a VL of Exemplary Anti-gp120 Antibody 5 (e.g., an amino acid sequence that has at least 80%, 85%, 90%, 95%, 96%, 97%, 98%, 99%, or 100% identity to SEQ ID NO: 84, or that has 0 to 5 (i.e., 1, 2, 3, 4, or 5) amino acid substitutions (e.g., conservative substitutions within SEQ ID NO: 84) is directly linked to, or linked via an intervening amino acid sequence (e.g., a G-S linker), to a wild type human lambda 2 sequence (SEQ ID NO:89). In certain embodiments, a VL of Exemplary Anti-gp120 Antibody 5 (e.g., an amino acid sequence that has at least 80%, 85%, 90%, 95%, 96%, 97%, 98%, 99%, or 100% identity to SEQ ID NO: 84, or that has 0 to 5 (i.e., 1, 2, 3, 4, or 5) amino acid substitutions (e.g., conservative substitutions within SEQ ID NO: 84) is directly linked to, or linked via an intervening amino acid sequence (e.g., a G-S linker), to a mutant human lambda 2 sequence having 1 to 5 (i.e., 1, 2, 3, 4, 5) substitutions within SEQ ID NO:89.

In a particular embodiment, the anti-gp120 antibody is a human IgG1m3/human lambda2 antibody.

Exemplary Anti-gp120 Antibody 5 can be used either as a monospecific or a multispecific antibody (e.g., a bispecific antibody). The whole antibody or an antigen-binding fragment (e.g., Fab, F(ab)2, Fv, scFv, sc(Fv)2, diabody) are encompassed by this disclosure.

Antibodies, such as Exemplary anti-gp120 Antibody 5 can be made, for example, by preparing and expressing nucleic acids that encode the amino acid sequences of the antibody.

CD3

Cluster of Differentiation (CD3) is a multimeric protein complex that is composed of four distinct polypeptide chains: epsilon (ε), gamma (γ), delta (δ) and zeta (ζ), that assemble and function as three pairs of dimers (εγ, εδ, ζζ). CD3 proteins have an N-terminal extracellular region, a transmembrane domain, and a cytoplasmic tail where the immunoreceptor tyrosine activation motifs (ITAMs) are located. The extracellular domains of CD3 ε, γ and δ contain an immunoglobulin-like domain and thus are considered part of the immunoglobulin superfamily. The CD3/T-cell co-receptor helps to activate both CD8$^+$ T cells and also CD4$^+$ T cells.

The amino acid sequence of human CD3ε can be found at UniProtKB-P07766 and is provided below (the signal sequence is underlined):

```
                                            (SEQ ID NO: 125)
MQSGTHWRVL GLCLLSVGVW GQDGNEEMGG ITQTPYKVSI

SGTTVILTCP QYPGSEILWQ HNDKNIGGDE DDKNIGSDED

HLSLKEFSEL EQSGYYVCYP RGSKPEDANF YLYLRARVCE

NCMEMDVMSV ATIVIVDICI TGGLLLLVYY WSKNRKAKAK

PVTRGAGAGG RQRGQNKERP PPVPNPDYEP IRKGQRDLYS

GLNQRRI
```

The amino acid sequence of human CD3δ can be found at UNiProtKB-P04234 and is provided below (the signal sequence is underlined):

```
                                            (SEQ ID NO: 42)
MEHSTFLSGL VLATLLSQVS PFKIPIEELE DRVFVNCNTS

ITWVEGTVGT LLSDITRLDL GKRILDPRGI YRCNGTDIYK

DKESTVQVHY RMCQSCVELD PATVAGIIVT DVIATLLLAL

GVFCFAGHET GRLSGAADTQ ALLRNDQVY QPLRDRDDAQY

SHLGGNWARN K
```

Antibodies that bind human CD3 are well-known in the art (see, e.g., Kuhn & Weiner, Immunotherapy, 8(8):889-906 (2016); WO 2015/104346)). OKT3 (Muromab), an anti-CD3 antibody directed against CD3ε, has been clinically approved for use in humans for the induction of immunosuppression in solid organ transplantation for the prevention and treatment of rejection (Norman, *Therapeutic Drug Monitoring*, 17, 615-620 (1995)). Teplizumab, also known under the names hOKT3γ1 (Ala-Ala) and MGA031, is a humanized IgG1 antibody that was developed by grafting the complementarity determining region of OKT3 into a human IgG1 backbone. Introduction of two point mutations in its Fc portion decreases binding to FcR. Otelixizumab (ChAglyCD3, TRX4, GSK2136525) was derived from the rat antibody YTH12.5. This humanized IgG1 bears a single mutation in the γ1 Fc portion to avoid glycosylation and thus inhibit FcR binding. Visilizumab (Nuvion, HuM291) is a humanized IgG2 antibody that is rendered non-mitogenic by two point mutations in its Fc region. Foralumab (28F11-AE; NI-0401) is an entirely human anti-CD3 mAb; the Fc portion of this human IgG1 was mutated such that the mAb is non FcR binding in vitro and exhibits only minor cytokine release in vivo while maintaining modulation of the CD3/TCR and T-cell depletion.

Non-limiting examples of anti-CD3 antibodies are also disclosed in US 2016/0333095A1.

In certain embodiments, the anti-CD3 antibodies of this disclosure bind human CD3. In some instances, the anti-CD3 antibodies of this disclosure bind human CD3ε. In other embodiments, the anti-CD3 antibodies of this disclosure bind human CD3δ.

Exemplary Anti-CD3 Antibody 1

The relevant sequence information of an Exemplary anti-CD3 Antibody 1 is provided in Table 4.

TABLE 4

| Clone Designation | Anti-CD3 human IgG1 FEALLS/human lambda |
|---|---|
| VH | EVKLVESGGGLVQPGGSLRLSCAA SGFTFNTYAMNWVRQAPGKGLEWV ARIRSKYNNYATYYADSVKDRFTI SRDDSKSSLYLQMNNLKTEDTAMY YCVRHGNFGNSYVSWFAYWGQGTL VTVSS (SEQ ID NO: 17) |
| Heavy Chain | EVKLVESGGGLVQPGGSLRLSCAA SGFTFNTYAMNWVRQAPGKGLEWV ARIRSKYNNYATYYADSVKDRFTI SRDDSKSSLYLQMNNLKTEDTAMY YCVRHGNFGNSYVSWFAYWGQGTL VTVSSASTKGPSVFPLAPSSKSTS GGTAALGCLVKDYFPEPVTVSWNS SGALTSGVHTFPAVLQSSGLYLSS VVTVPSSSLGTQTYICNVNHKPSN TKVDKRVEPKSCDKTHTCPPCPAP EFEGGPSVFLFPPKPKDTLMISRT PEVTCVVVAVSHEDPEVKFNWYVD GVEVHNAKTKPREEQYNSTYRVVS VLTVLHQDWLNGKEYKCKVSNKAL PAPIEKTISKAKGQPREPQVYTLP PSREEMTKNQVSLTCLVKGFYPSD IAVEWESNGQPENNYKTTPPVLDS DGSFLLYSKLTVDKSRWQQGNVFS CSVLHEALHSHYTQKSLSLSPGK (SEQ ID NO: 19) |
| Heavy CDR1 Kabat | TYAMN (SEQ ID NO: 11) |
| Heavy CDR2 Kabat | RIRSKYNNYATYYADSVKD (SEQ ID NO: 12) |
| Heavy CDR3 Kabat | HGNFGNSYVSWFAY (SEQ ID NO: 13) |
| Heavy CDR1 IMGT | GFTFNTYA (SEQ ID NO: 43) |
| Heavy CDR2 IMGT | IRSKYNNYAT (SEQ ID NO: 44) |
| Heavy CDR3 IMGT | VRHGNFGNSYVSWFAY (SEQ ID NO: 45) |
| Heavy CDR1 Chothia | GFTFNTY (SEQ ID NO: 46) |
| Heavy CDR2 Chothia | SKYNNY (SEQ ID NO: 47) |
| Heavy CDR3 Chothia | GNFGNSYVSWFA (SEQ ID NO: 48) |
| Heavy CDR1 Honegger | ASGFTFNTYA (SEQ ID NO: 49) |
| Heavy CDR2 Honegger | IRSKYNNYATYYADSVKDR (SEQ ID NO: 50) |
| Heavy CDR3 Honegger | HGNFGNSYVSWFA (SEQ ID NO: 51) |
| VL | QAVVTQEPSFSVSPGGTVTLTCRS STGAVTTSNYANWVQQTPGQAFRG LIGGTNKRAPGVPARFSGSLIGDK AALTITGAQADDESIYFCALWYSN LWVFGGGTKLTVL (SEQ ID NO: 18) |
| Light Chain | QAVVTQEPSFSVSPGGTVTLTCRS STGAVTTSNYANWVQQTPGQAFRG LIGGTNKRAPGVPARFSGSLIGDK AALTITGAQADDESIYFCALWYSN LWVFGGGTKLTVLGQPKAAPSVTL FPPSSEELQANKATLVCLISDFYP GAVTVAWKADSSPVKAGVETTTPS KQSNNKYAASSYLSLTPEQWKSHR SYSCQVTHEGSTVEKTVAPTECS (SEQ ID NO: 20) |
| Light CDR1 Kabat | RSSTGAVTTSNYAN (SEQ ID NO: 14) |

TABLE 4-continued

| Clone Designation | Anti-CD3 human IgG1 FEALLS/human lambda |
|---|---|
| Light CDR2 Kabat | GTNKRAP (SEQ ID NO: 15) |
| Light CDR3 Kabat | ALWYSNLWV (SEQ ID NO: 16) |
| Light CDR1 IMGT | TGAVTTSNY (SEQ ID NO: 52) |
| Light CDR2 IMGT | GTN |
| Light CDR3 IMGT | ALWYSNLWV (SEQ ID NO: 16) |
| Light CDR1 Chothia | SSTGAVTTSNY (SEQ ID NO: 53) |
| Light CDR2 Chothia | GTN |
| Light CDR3 Chothia | WYSNLW (SEQ ID NO: 54) |
| Light CDR1 Honegger | SSTGAVTTSNY (SEQ ID NO: 53) |
| Light CDR2 Honegger | GTNKRAPGVPAR (SEQ ID NO: 55) |
| Light CDR3 Honegger | WYSNLW (SEQ ID NO: 54) |

The anti-CD3 antibodies can encompass the heavy chain CDR 1, CDR2, and CDR3 and the light chain CDR 1, CDR2, and CDR3 of Exemplary anti-CD3 Antibody 1. In one embodiment, the CDRs are defined based on the Kabat definition. In another embodiment, the CDRs are defined based on the Chothia definition. In another embodiment, the CDRs are defined based on the IMGT definition. In another embodiment, the CDRs are defined based on the Honegger definition. In another embodiment, the CDRs are defined based on the Chothia from Abysis definition. In another embodiment, the CDRs are defined based on the Chothia/AbM CDR. In another embodiment, the CDRs are defined based on the contact definition. These CDRs can be determined, e.g., by using the AbYsis database (www.bioinforg.uk/abysis/sequence_input/key_annotation/key_annotation.cgi).

In certain instances, the anti-CD3 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable heavy chain of Exemplary anti-CD3 Antibody 1. In some embodiments, the anti-CD3 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the heavy chain of Exemplary anti-CD3 Antibody 1. In certain instances, the anti-CD3 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable light chain of Exemplary anti-CD3 Antibody 1. In certain instances, the anti-CD3 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the light chain of Exemplary anti-CD3 Antibody 1. In certain embodiments, the anti-CD3 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable heavy chain and the variable light chain of Exemplary anti-CD3 Antibody 1. In some embodiments, the anti-CD3 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the heavy chain and comprise an amino acid sequence having at least 80%, 85%, 86%, 87%, 88%, 89%, 90%, 91%, 92%, 93%, 94%, 95%, 96%, 97%, 98%, 99%, or 100% identity to the light chain of Exemplary anti-CD3 Antibody 1.

In some embodiments, the variable heavy chain of Exemplary Anti-CD3 Antibody 1 is linked to a heavy chain constant region comprising a CH1 domain and a hinge region. In some embodiments, the variable heavy chain of Exemplary Anti-CD3 Antibody 1 is linked to a heavy chain constant region comprising a CH3 domain. In certain embodiments, the variable heavy chain of Exemplary Anti-CD3 Antibody 1 is linked to a heavy chain constant region comprising a CH1 domain, hinge region, and CH2 domain from IgG4 and a CH3 domain (e.g., from IgG1). In certain embodiments, the variable heavy chain of Exemplary Anti-gp120 Antibody 1 is linked to a heavy chain constant region comprising a CH1 domain, CH2 domain, and a CH3 domain from IgG1 (e.g., human IgG1, e.g., IgG1m3 allotype) and an IgG3 hinge region (e.g., an "open" IgG3 hinge variant "IgG3 C-" described in WO2017/096221). In certain embodiments such a chimeric antibody contains one or more additional mutations in the heavy chain constant region that increase the stability of the chimeric antibody. In certain embodiments, the heavy chain constant region includes substitutions that modify the properties of the antibody (e.g., decrease Fc receptor binding, increase or decrease antibody glycosylation, decrease binding to C1q, increase half-life, decrease effector function).

In certain embodiments, the anti-CD3 antibody is an IgG antibody. In one embodiment, the antibody is IgG1. In another embodiment, the antibody is IgG2. In some embodiments, the antibody has a chimeric heavy chain constant region (e.g., having the CH1, hinge, and CH2 regions of IgG4 and CH3 region of IgG1).

In particular embodiments, antibodies of this disclosure include an IgG1 heavy chain having an allotype of G1m1; nG1m2; G1m3; G1m17,1; G1m17,1,2; G1m3,1; or G1m17.

In a specific embodiment, the VH of Exemplary Anti-CD3 Antibody 1 is linked to a wild type IgG1m3 Fc (SEQ ID NO:77). In certain instances, the VH of Exemplary Anti-CD3 Antibody 1 is linked to a mutated IgG1m3 sequence with 1 to 10 (e.g., 1, 2, 3, 4, 5, 6, 7, 8, 9, 10) amino acid substitutions made in SEQ ID NO:77 (e.g., to reduce effector function and/or to increase half-life). Exemplary amino acid substitutions are described below.

In a specific embodiment, the VL of Exemplary Anti-CD3 Antibody 1 is linked to a human lambda 2 sequence (SEQ ID NO:89). In certain instances, the VL of Exemplary Anti-CD3 Antibody 1 is linked to a mutated human lambda 2 sequence with 1 to 10 (e.g., 1, 2, 3, 4, 5, 6, 7, 8, 9, 10) amino acid substitutions are made in SEQ ID NO:89. Such amino acid substitutions are described below.

In certain embodiments, the anti-CD3 antibody is a human IgG1/human lambda antibody.

Antibodies, such as Exemplary anti-CD3 Antibody 1 can be made, for example, by preparing and expressing nucleic acids that encode the amino acid sequences of the antibody.

CD89

CD89 (Cluster of Differentiation 89) also known as Fc fragment of IgA receptor (FCAR) is the transmembrane receptor FcαRI. FcαRI binds the heavy-chain constant region of Immunoglubulin A (IgA) antibodies. FcαRI is expressed on the cell surface of myeloid lineage cells, including neutrophils, monocytes, macrophages, and eosinophils.

The amino acid sequence of human CD89 from UniProtKB-P24071 is provided below:

```
                                            (SEQ ID NO: 95)
MDPKQTTLLC LVLCLGQRIQ AQEGDFPMPF ISAKSSPVIP
LDGSVKIQCQ AIREAYLTQL MIIKNSTYRE IGRRLKFWNE
TDPEFVIDHM DANKAGRYQC QYRIGHYRFR YSDTLELVVT
GLYGKPFLSA DRGLVLMPGE NISLTCSSAH IPFDRFSLAK
EGELSLPQHQ SGEHPANFSL GPVDLNVSGI YRCYGWYNRS
PYLWSFPSNA LELVVTDSIH QDYTTQNLIR MAVAGLVLVA
LLAILVENWH SHTALNKEAS ADVAEPSWSQ QMCQPGLTFA
RTPSVCK
```

Antibodies that bind human CD89 are well-known in the art (see, e.g., Fishwild et al., Nature Biotechnol., 14(7):845-851 (1996); Duval et al., J. Virol., 82(9): 4671-4674 (2008); US 2003/0082643). In some embodiments, the anti-CD89 antibody is one of 14.1, 7.4, or 8.2 (also referred to as 14A8, 7F12, and 8D2, respectively). Any of these antibodies or variants thereof may be employed in the multispecific antibodies disclosed herein.

In certain embodiments, the anti-CD89 antibodies of this disclosure or the multispecific antibodies disclosed herein bind to a polypeptide comprising or consisting of the amino acid sequence set forth in SEQ ID NO:95.

Exemplary Anti-CD89 Antibody 1

The relevant sequence information of an Exemplary anti-CD89 Antibody 1 is provided in the Table below.

| Designation | Anti-CD89 Antibody human IgG1 FEALLS/human lambda |
|---|---|
| VH | QVQLVESGGGVVQPGRSLRLSCAASGFTFSSYVLHWVRQAPGKGLDWVAVISDDGRNKYFADSVKGRFTISRDNSKNTLYLQMNSLRAEDTAVYYCVREGYSGSWFDYWGQGTLVTVSS (SEQ ID NO:96) |
| Heavy Chain | QVQLVESGGGVVQPGRSLRLSCAASGFTFSSYVLHWVRQAPGKGLDWVAVISDDGRNKYFADSVKGRFTISRDNSKNTLYLQMNSLRAEDTAVYYCVREGYSGSWFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEFEGGPSVFLFPPKPKDTLMISRTPEVTCVVVAVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFLLYSKLTVDKSRWQQGNVFSCSVLHEALHSHYTQKSLSLSPGK (SEQ ID NO: 97) |
| Heavy CDR1 Kabat | SYVLH (SEQ ID NO: 98) |
| Heavy CDR2 Kabat | VISDDGRNKYFADSVKG (SEQ ID NO: 99) |
| Heavy CDR3 Kabat | EGYSGSWFDY (SEQ ID NO: 100) |
| Heavy CDR1 IMGT | GFTFSSYV (SEQ ID NO: 106) |
| Heavy CDR2 IMGT | ISDDGRNK (SEQ ID NO: 107) |
| Heavy CDR3 IMGT | VREGYSGSWFDY (SEQ ID NO: 108) |
| Heavy CDR1 Chothia | GFTFSSY (SEQ ID NO: 109) |
| Heavy CDR2 Chothia | DDGR (SEQ ID NO: 110) |
| Heavy CDR3 Chothia | GYSGSWFD (SEQ ID NO: 111) |
| Heavy CDR1 Honegger | ASGFTFSSYV (SEQ ID NO: 112) |
| Heavy CDR2 Honegger | ISDDGRNKYFADSVKGR (SEQ ID NO: 113) |
| Heavy CDR3 Honegger | EGYSGSWFD (SEQ ID NO: 114) |
| VL | AIQLTQSPSSLSASVGDRVTITCRASQGISSALAWYQQKPGKAPKLLIYGASSLEGGVPSRFSGSGSGTDFTLTISSLQPEDFATYYCQQFNSYPFTFGPGTKVDIK (SEQ ID NO: 101) |
| Light Chain | AIQLTQSPSSLSASVGDRVTITCRASQGISSALAWYQQKPGKAPKLLIYGASSLEGGVPSRFSGSGSGTDFTLTISSLQPEDFATYYCQQFNSYPFTFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 102) |
| Light CDR1 Kabat | RASQGISSALA (SEQ ID NO: 103) |
| Light CDR2 Kabat | GASSLEG (SEQ ID NO: 104) |
| Light CDR3 Kabat | QQFNSYPFT (SEQ ID NO: 105) |
| Light CDR1 IMGT | QGISSA (SEQ ID NO: 115) |
| Light CDR2 IMGT | GAS (SEQ ID NO: 116) |
| Light CDR3 IMGT | QQFNSYPFT (SEQ ID NO: 117) |
| Light CDR1 Chothia | SQGISSA (SEQ ID NO: 118) |
| Light CDR2 Chothia | GAS (SEQ ID NO: 119) |
| Light CDR3 Chothia | FNSYPF (SEQ ID NO: 120) |
| Light CDR1 Honegger | ASQGISSA (SEQ ID NO: 121) |
| Light CDR2 Honegger | GASSLEGGVPSR (SEQ ID NO: 122) |
| Light CDR3 Honegger | FNSYPF (SEQ ID NO: 123) |

The anti-CD89 antibodies can encompass the heavy chain CDR 1, CDR2, and CDR3 and the light chain CDR 1, CDR2, and CDR3 of Exemplary anti-CD89 Antibody 1. In one embodiment, the CDRs are defined based on the Kabat definition. In another embodiment, the CDRs are defined based on the Chothia definition. In another embodiment, the CDRs are defined based on the IMGT definition. In another embodiment, the CDRs are defined based on the Honegger definition. In another embodiment, the CDRs are defined based on the Chothia from Abysis definition. In another embodiment, the CDRs are defined based on the Chothia/AbM CDR. In another embodiment, the CDRs are defined based on the contact definition. These CDRs can be determined, e.g., by using the AbYsis database (www.bioinforg.uk/abysis/sequence_input/key_annotation/key_annotation.cgi).

In certain instances, the anti-CD89 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable heavy chain of Exemplary anti-CD89 Antibody 1. In some embodiments, the anti-CD89 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the heavy chain of Exemplary anti-CD89 Antibody 1. In certain instances, the anti-CD89 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable light chain of Exemplary anti-CD89 Antibody 1. In certain instances, the anti-CD89 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the light chain of Exemplary anti-CD89 Antibody 1. In certain embodiments, the anti-CD89 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the variable heavy chain and the variable light chain of Exemplary anti-CD89 Antibody 1. In some embodiments, the anti-CD89 antibodies comprise an amino acid sequence having at least 80%, 85%, 86%, 87%, 88%, 89%, 90%, 91%, 92%, 93%, 94%, 95%, 96%, 97%, 98%, 99%, or 100% identity to the heavy chain and comprise an amino acid sequence having at least 80%, 85%, 86%, 87%, 88%, 89%, 90%, 91%, 92%, 93%, 94%, 95%, 96%, 97%, 98%, 99%, or 100% identity to the light chain of Exemplary anti-CD89 Antibody 1.

In some embodiments, the variable heavy chain of Exemplary Anti-CD89 Antibody 1 is linked to a heavy chain constant region comprising a CH1 domain and a hinge region. In some embodiments, the variable heavy chain of Exemplary Anti-CD89 Antibody 1 is linked to a heavy chain constant region comprising a CH3 domain. In certain embodiments, the variable heavy chain of Exemplary Anti-CD89 Antibody 1 is linked to a heavy chain constant region comprising a CH1 domain, hinge region, and CH2 domain from IgG4 and a CH3 domain (e.g., from IgG1). In certain embodiments, the variable heavy chain of Exemplary Anti-CD89 Antibody 1 is linked to a heavy chain constant region comprising a CH1 domain, CH2 domain, and a CH3 domain from IgG1 (e.g., human IgG1, e.g., IgG1m3 allotype) and an IgG3 hinge region (e.g., an "open" IgG3 hinge variant "IgG3 C-" described in WO2017/096221). In certain embodiments, such a chimeric antibody contains one or more additional mutations in the heavy chain constant region that increase the stability of the chimeric antibody. In certain embodiments, the heavy chain constant region includes substitutions that modify the properties of the antibody (e.g., decrease Fc receptor binding, increase or decrease antibody glycosylation, decrease binding to C1q, increase half-life, decrease effector function).

In certain embodiments, the anti-CD89 antibody is an IgG antibody. In one embodiment, the antibody is IgG1. In another embodiment, the antibody is IgG2. In some embodiments, the antibody has a chimeric heavy chain constant region (e.g., having the CH1, hinge, and CH2 regions of IgG4 and CH3 region of IgG1).

In particular embodiments, antibodies of this disclosure include an IgG1 heavy chain having an allotype of G1m1; nG1m2; G1m3; G1m17,1; G1m17,1,2; G1m3,1; or G1m17.

In a specific embodiment, the VH of Exemplary Anti-CD89 Antibody 1 is linked to a wild type IgG1m3 Fc (SEQ ID NO:77). In certain instances, the VH of Exemplary Anti-CD89 Antibody 1 is linked to a mutated IgG1m3 sequence with 1 to 10 (e.g., 1, 2, 3, 4, 5, 6, 7, 8, 9, 10) amino acid substitutions made in SEQ ID NO:77 (e.g., to reduce effector function and/or to increase half-life). Exemplary amino acid substitutions are described below.

In a specific embodiment, the VL of Exemplary Anti-CD89 Antibody 1 is linked to a human lambda 2 sequence (SEQ ID NO:89). In certain instances, the VL of Exemplary Anti-CD89 Antibody 1 is linked to a mutated human lambda 2 sequence with 1 to 10 (e.g., 1, 2, 3, 4, 5, 6, 7, 8, 9, 10) amino acid substitutions are made in SEQ ID NO:89. Such amino acid substitutions are described below.

In certain embodiments, the anti-CD89 antibody is a human IgG1/human lambda antibody.

Antibodies, such as Exemplary anti-CD89 Antibody 1 can be made, for example, by preparing and expressing nucleic acids that encode the amino acid sequences of the antibody.

Multispecific Antibodies

In another aspect, this disclosure features multispecific antibodies. Multispecific antibodies are antibodies which binds two or more different epitopes (e.g., bispecific antibodies, trivalent antibodies, tetravalent antibodies). The anti-gp120 and anti-CD3 antibodies or the anti-gp120 and anti-CD89 described above can be comprised as part of multispecific antibodies. The multispecific antibodies may have binding sites to at least one other antigen or one other epitope that is not bound by the anti-gp120 or anti-CD3 (or anti-CD89) antibody binding sites of the multispecific antibody. The anti-gp120/anti-CD3 multispecific antibody or the anti-gp120/anti-CD89 multispecific antibody can comprise a dimerization domain and three or more (e.g., three, four, five, six) antigen binding sites. An exemplary dimerization domain comprises (or consists of) an Fc region. An anti-gp120/anti-CD3 multispecific antibody or anti-gp120/anti-CD89 multispecific antibody can comprise (or consist of) three to about eight (i.e., three, four, five, six, seven, eight) antigen binding sites. The multispecific antibody optionally comprises at least one polypeptide chain (e.g., two polypeptide chains, three polypeptide chains), wherein the polypeptide chain(s) comprise three or more variable domains. For instance, the polypeptide chain(s) may comprise, e.g., VD1-(X1)$_n$-VD2-(X2)$_n$-Fc, or VD1-(X1)$_n$-VD2-(X2)$_n$-VD3-(X3)$_n$-Fc, wherein VD1 is a first variable domain, VD2 is a second variable domain, VD3 is a third variable domain Fc is a polypeptide chain of an Fc region, X1, X2, and X3 represent an amino acid or peptide spacer, and n is 0 or 1. In certain instances, the variable domains may each be an scFv. Multispecific antibodies can be readily produced by recombinant expression of nucleic acid encoding the polypeptide chains of the antibody.

Bispecific Antibodies

In one aspect, the multispecific antibody is a bispecific antibody. Bispecific antibodies are antibodies that have binding specificities for two different epitopes. A bispecific antibody has two "arms." One arm of the bispecific antibody binds one epitope and the other arm another epitope. In one embodiment, one arm of the bispecific antibody binds a first antigen and the other arm of the bispecific antibody binds a second antigen. In another embodiment, the two arms of the bispecific antibody bind to two different epitopes of the same antigen.

In one aspect, this disclosure features a bispecific antibody that specifically binds to gp120 and specifically binds to a second antigen (e.g., a triggering molecule on a leukocyte, such as a T-cell receptor molecule (e.g., CD3), or Fc receptors for IgG (FcγR), such as FcγRI (CD64), FcγRII (CD32), FcγRIII (CD16), or CD89) so as to focus and localize cellular defense mechanisms to the infected cell)).

In a particular embodiment, one arm of the bispecific antibody specifically binds to gp120 and the other arm specifically binds to CD3 (e.g., a human CD3 (e.g., human CD3ε, human CD3δ)). In another particular embodiment, one arm of the bispecific antibody specifically binds to gp120 and the other arm specifically binds to CD89 (e.g., a human CD89). In certain embodiments, the arm of the bispecific antibody that binds to gp120 comprises the six CDRs of Exemplary anti-gp120 Antibody 1. In some cases, the CDRs are defined according to Kabat. In other embodiments, the CDRs are defined according to Chothia. In yet other embodiments, the CDRs are defined according to the IMGT definition. In yet other embodiments, the CDRs are defined according to the Honegger definition. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:7) of Exemplary anti-gp120 Antibody 1. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VL (SEQ ID NO:8) of Exemplary anti-gp120 Antibody 1. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:7) and the VL (SEQ ID NO:8), respectively, of Exemplary anti-gp120 Antibody 1. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:7) and the VL (SEQ ID NO:81), respectively, of Exemplary anti-gp120 Antibody 2. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:7) and the VL (SEQ ID NO:82), respectively, of Exemplary anti-gp120 Antibody 3. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:7) and the VL (SEQ ID NO:83), respectively, of Exemplary anti-gp120 Antibody 4. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:7) and the VL (SEQ ID NO:84), respectively, of Exemplary anti-gp120 Antibody 5. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:9) of Exemplary anti-gp120 Antibody 1. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the light chain (SEQ ID NO:10) of Exemplary anti-gp120 Antibody 1. In certain embodiments, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:9) and the light chain (SEQ ID NO:10), respectively, of Exemplary anti-gp120 Antibody 1. In certain instances, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:9) and the light chain (SEQ ID NO:40), respectively, of Exemplary anti-gp120 Antibody 2. In certain instances, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:9) and the light chain (SEQ ID NO:78), respectively, of Exemplary anti-gp120 Antibody 3. In certain instances, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:9) and the light chain (SEQ ID NO:79), respectively, of Exemplary anti-gp120 Antibody 4. In certain instances, the arm of the bispecific antibody that binds to gp120 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:9) and the light chain (SEQ ID NO:80), respectively, of Exemplary anti-gp120 Antibody 5. In one embodiment, the arm of the bispecific antibody that binds to gp120 comprises an amino acid sequence of SEQ ID NO:7 and SEQ ID NO:8. In another embodiment, the arm of the bispecific antibody that binds to gp120 comprises an amino acid sequence of SEQ ID NO:7 and SEQ ID NO:81. In another embodiment, the arm of the bispecific antibody that binds to gp120 comprises an amino acid sequence of SEQ ID NO:7 and SEQ ID NO:82. In yet another embodiment, the arm of the bispecific antibody that binds to gp120 comprises an amino acid sequence of SEQ ID NO:7 and SEQ ID NO:83. In a further embodiment, the arm of the bispecific antibody that binds to gp120 comprises an amino acid sequence of SEQ ID NO:7 and SEQ ID NO:84. In one particular embodiment, the arm of the bispecific antibody that binds to gp120 comprises an amino acid sequence of SEQ ID NO:9 and SEQ ID NO:10. In another particular embodiment, the arm of the bispecific antibody that binds to gp120 comprises an amino acid sequence of SEQ ID NO:9 and SEQ ID NO:40. In yet another particular embodiment, the arm of the bispecific antibody that binds to gp120 comprises an amino acid sequence of SEQ ID NO:9 and SEQ ID NO:78. In a further embodiment, the arm of the bispecific antibody that binds to gp120 comprises an amino acid sequence of SEQ ID NO:9 and SEQ ID NO:79. In another embodiment, the arm of the bispecific antibody that binds to gp120 comprises an amino acid sequence of SEQ ID NO:9 and SEQ ID NO:80. In some instances, the arm of the bispecific antibody that binds to gp120 binds a protein comprising or consisting the amino acid sequence set forth in SEQ ID NO: 21. In some instances, the arm of the bispecific antibody that binds to gp120 binds a protein comprising or consisting the amino acid sequence set forth in SEQ ID NO: 38. In some instances, the arm of the bispecific antibody that binds to gp120 binds free HIV-1 virus. In some instances, the arm of the bispecific antibody that binds to gp120 binds an HIV-1 infected cell. In some instances, the arm of the bispecific antibody that binds to gp120 binds both free HIV-1 virus and an HIV-1 infected cell. In certain cases, the arm of the bispecific antibody that binds to gp120 binds at least two different strains of HIV-1 (e.g., Group M, Group N, Group O, or Group P). In one embodiment, the arm of the bispecific antibody that binds to gp120 binds pWITO.c/2474 (Accession number JN944948 and NIH AIDS Reagent Program catalogue number 11739). In another embodiment, the arm of the bispecific antibody that binds to gp120 binds pCH058.c/2960 (Accession number JN944940 and NIH AIDS Reagent Program catalogue number 700010058).

In certain embodiments, the arm of the bispecific antibody that binds to human CD3 comprises the six CDRs of Exemplary anti-human CD3 Antibody 1. In some cases, the CDRs are defined according to Kabat. In other embodiments, the CDRs are defined according to Chothia. In yet other embodiments, the CDRs are defined according to the IMGT definition. In yet other embodiments, the CDRs are defined according to the Honegger definition. In certain embodiments, the arm of the bispecific antibody that binds to human CD3 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:17) of Exemplary anti-CD3 Antibody 1. In certain embodiments, the arm of the bispecific antibody that binds to human CD3 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VL (SEQ ID NO:18) of Exemplary anti-CD3 Antibody 1. In certain embodiments, the arm of the bispecific antibody that binds to human CD3 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:17) and the VL (SEQ ID NO:18), respectively, of Exemplary anti-human CD3 Antibody 1. In certain embodiments, the arm of the bispecific antibody that binds to human CD3 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:19) of Exemplary anti-human CD3 Antibody 1. In certain embodiments, the arm of the bispecific antibody that binds to CD3 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the light chain (SEQ ID NO:20) of Exemplary anti-human CD3 Antibody 1. In certain embodiments, the arm of the bispecific antibody that binds to human CD3 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:19) and the light chain (SEQ ID NO:20), respectively, of Exemplary anti-human CD3 Antibody 1. In a particular embodiment, the arm of the bispecific antibody that binds to human CD3 comprises an amino acid sequence of SEQ ID NO:17 and SEQ ID NO:18. In another particular embodiment, the arm of the bispecific antibody that binds to human CD3 comprises an amino acid sequence of SEQ ID NO:19 and SEQ ID NO:20. In certain embodiments, the arm of the bispecific antibody that binds to human CD3 binds to human CD3ε.

In certain embodiments, the arm of the bispecific antibody that binds to human CD89 comprises the six CDRs of Exemplary anti-human CD89 Antibody 1. In some cases, the CDRs are defined according to Kabat. In other embodiments, the CDRs are defined according to Chothia. In yet other embodiments, the CDRs are defined according to the IMGT definition. In yet other embodiments, the CDRs are defined according to the Honegger definition. In certain embodiments, the arm of the bispecific antibody that binds to human CD89 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:96) of Exemplary anti-CD89 Antibody 1. In certain embodiments, the arm of the bispecific antibody that binds to human CD89 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VL (SEQ ID NO:101) of Exemplary anti-CD89 Antibody 1. In certain embodiments, the arm of the bispecific antibody that binds to human CD89 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the VH (SEQ ID NO:96) and the VL (SEQ ID NO:101), respectively, of Exemplary anti-human CD89 Antibody 1. In certain embodiments, the arm of the bispecific antibody that binds to human CD89 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:97) of Exemplary anti-human CD89 Antibody 1. In certain embodiments, the arm of the bispecific antibody that binds to CD89 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the light chain (SEQ ID NO:102) of Exemplary anti-human CD89 Antibody 1. In certain embodiments, the arm of the bispecific antibody that binds to human CD89 comprises an amino acid sequence that is at least 75%, 80%, 85%, 86%, 87%, 88%, 89%, 90%, 91%, 92%, 93%, 94%, 95%, 96%, 97%, 98%, 99%, or 100% identical to the heavy chain (SEQ ID NO:97) and the light chain (SEQ ID NO:102), respectively, of Exemplary anti-human CD89 Antibody 1. In a particular embodiment, the arm of the bispecific antibody that binds to human CD89 comprises an amino acid sequence of SEQ ID NO:96 and SEQ ID NO:101. In another particular embodiment, the arm of the bispecific antibody that binds to human CD89 comprises an amino acid sequence of SEQ ID NO:97 and SEQ ID NO:102. In certain embodiments, the arm of the bispecific antibody that binds to human CD89 binds to human CD89.

In certain embodiments, one arm of the bispecific antibody comprises an scFv that binds gp120. In certain embodiments, one arm of the bispecific antibody comprises an scFv that binds human CD3. In certain embodiments, one arm of the bispecific antibody comprises an scFv that binds human CD89. In certain embodiments, a bispecific antibody can include a chimeric antibody or a humanized antibody. In certain embodiments, a bispecific antibody can comprise a F(ab')2 fragment.

In one aspect, a bispecific antibody of this disclosure binds to gp120 and human CD3 (e.g., CD3ε, CD3δ) and can effectuate the killing of HIV-1 infected cells. In one instance, such a bispecific antibody that binds to gp120 contains VH-CDR1 of SEQ ID NO:1, VH-CDR2 of SEQ ID NO:2, VH-CDR3 of SEQ ID NO:3, VL-CDR1 of SEQ ID NO:4, VL-CDR2 of SEQ ID NO:5, and VL-CDR3 of SEQ ID NO:6. In one instance, such a bispecific antibody that binds to human CD3 contains VH-CDR1 of SEQ ID NO:11, VH-CDR2 of SEQ ID NO:12, VH-CDR3 of SEQ ID NO:13, VL-CDR1 of SEQ ID NO:14, VL-CDR2 of SEQ ID NO:15, and VL-CDR3 of SEQ ID NO:16. In another instance, a bispecific antibody that binds to gp120 and human CD3 contains on its gp120-binding arm: VH-CDR1 of SEQ ID NO:1, VH-CDR2 of SEQ ID NO:2, VH-CDR3 of SEQ ID NO:3, VL-CDR1 of SEQ ID NO:4, VL-CDR2 of SEQ ID NO:5, and VL-CDR3 of SEQ ID NO:6; and contains on its human CD3-binding arm: VH-CDR1 of SEQ ID NO:11, VH-CDR2 of SEQ ID NO:12, VH-CDR3 of SEQ ID NO:13, VL-CDR1 of SEQ ID NO:14, VL-CDR2 of SEQ ID NO:15, and VL-CDR3 of SEQ ID NO:16.

In another instance, such a bispecific antibody contains, on its gp120-binding arm, a VH that has an amino acid sequence that is at least 90%, 91%, 92%, 93%, 94%, 95%, 96%, 97% or at least 98% identical to SEQ ID NO:7. In another instance, such a bispecific antibody contains, on its gp120-binding arm, a VH that has an amino acid sequence that is identical to SEQ ID NO:7 except for 1 to 10 (i.e., 1, 2, 3, 4, 5, 6, 7, 8, 9, 10) substitutions, insertions and/or deletions. In another instance, such a bispecific antibody contains, on its gp120-binding arm, a VH that has an amino acid sequence that is identical to SEQ ID NO:7 except for 1 to 10 (i.e., 1, 2, 3, 4, 5, 6, 7, 8, 9, 10) substitutions. In another instance, such a bispecific antibody contains, on its gp120-binding arm, a VL that has an amino acid sequence that is at least 90%, 91%, 92%, 93%, 94%, 95%, 96%, 97% or at least 98% identical to SEQ ID NO:8, 81, 82, 83, or 84. In another instance, such a bispecific antibody contains, on its gp120-binding arm, a VL that has an amino acid sequence that is identical to SEQ ID NO:8, 81, 82, 83, or 84 except for 1 to 10 (i.e., 1, 2, 3, 4, 5, 6, 7, 8, 9, 10) substitutions, insertions and/or deletions. In another instance, such a bispecific antibody contains, on its gp120-binding arm, a VL that has an amino acid sequence that is identical to SEQ ID NO:8, 81, 82, 83, or 84 except for 1 to 10 (i.e., 1, 2, 3, 4, 5, 6, 7, 8, 9, 10) substitutions. In another instance, such a bispecific antibody contains, on its gp120-binding arm, a heavy chain that has an amino acid sequence that is at least 90%, 91%, 92%, 93%, 94%, 95%, 96%, 97% or at least 98% identical to SEQ ID NO:9. In another instance, such a bispecific antibody contains, on its gp120-binding arm, a heavy chain that has an amino acid sequence that is identical to SEQ ID NO:9 except for 1 to 10 (i.e., 1, 2, 3, 4, 5, 6, 7, 8, 9, 10) substitutions, insertions and/or deletions. In another instance, such a bispecific antibody contains, on its gp120-binding arm, a heavy chain that has an amino acid sequence that is identical to SEQ ID NO:9 except for 1 to 10 (i.e., 1, 2, 3, 4, 5, 6, 7, 8, 9, 10) substitutions. In another instance, such a bispecific antibody contains, on its gp120-binding arm, a light chain that has an amino acid sequence that is at least 90%, 91%, 92%, 93%, 94%, 95%, 96%, 97% or at least 98% identical to SEQ ID NO:10, 40, 78, 79, or 80. In another instance, such a bispecific antibody contains, on its gp120-binding arm, a light chain that has an amino acid sequence that is identical to SEQ ID NO:10, 40, 78, 79, or 80 except for 1 to 10 (i.e., 1, 2, 3, 4, 5, 6, 7, 8, 9, 10) substitutions, insertions and/or deletions. In another instance, such a bispecific antibody contains, on its gp120-binding arm, a light chain that has an amino acid sequence that is identical to SEQ ID NO:10, 40, 78, 79, or 80 except for 1 to 10 (i.e., 1, 2, 3, 4, 5, 6, 7, 8, 9, 10) substitutions.

In another instance, such a bispecific antibody contains, on its human CD3-binding arm, a VH that has an amino acid sequence that is at least 90%, 91%, 92%, 93%, 94%, 95%, 96%, 97% or at least 98% identical to SEQ ID NO:17. In another instance, such a bispecific antibody contains, on its human CD3-binding arm, a VH that has an amino acid sequence that is identical to SEQ ID NO:17 except for 1 to 10 (i.e., 1, 2, 3, 4, 5, 6, 7, 8, 9, 10) substitutions, insertions and/or deletions. In another instance, such a bispecific antibody contains, on its human CD3-binding arm, a VH that has an amino acid sequence that is identical to SEQ ID NO:17 except for 1 to 10 (i.e., 1, 2, 3, 4, 5, 6, 7, 8, 9, 10) substitutions. In another instance, such a bispecific antibody contains, on its human CD3-binding arm, a VL that has an amino acid sequence that is at least 90%, 91%, 92%, 93%, 94%, 95%, 96%, 97% or at least 98% identical to SEQ ID NO:18. In another instance, such a bispecific antibody contains, on its human CD3-binding arm, a VL that has an amino acid sequence that is identical to SEQ ID NO:18 except for 1 to 10 (i.e., 1, 2, 3, 4, 5, 6, 7, 8, 9, 10) substitutions, insertions and/or deletions. In another instance, such a bispecific antibody contains, on its human CD3-binding arm, a VL that has an amino acid sequence that is identical to SEQ ID NO:18 except for 1 to 10 (i.e., 1, 2, 3, 4, 5, 6, 7, 8, 9, 10) substitutions. In another instance, such a bispecific antibody contains, on its human CD3-binding arm, a heavy chain that has an amino acid sequence that is at least 90%, 91%, 92%, 93%, 94%, 95%, 96%, 97% or at least 98% identical to SEQ ID NO:19. In another instance, such a bispecific antibody contains, on its human CD3-binding arm, a heavy chain that has an amino acid sequence that is identical to SEQ ID NO:19 except for 1 to 10 (i.e., 1, 2, 3, 4, 5, 6, 7, 8, 9, 10) substitutions, insertions and/or deletions. In another instance, such a bispecific antibody contains, on its human CD3-binding arm, a heavy chain that has an amino acid sequence that is identical to SEQ ID NO:19 except for 1 to 10 (i.e., 1, 2, 3, 4, 5, 6, 7, 8, 9, 10) substitutions. In another instance, such a bispecific antibody contains, on its human CD3-binding arm, a light chain that has an amino acid sequence that is at least 90%, 91%, 92%, 93%, 94%, 95%, 96%, 97% or at least 98% identical to SEQ ID NO:20. In another instance, such a bispecific antibody contains, on its human CD3-binding arm, a light chain that has an amino acid sequence that is identical to SEQ ID NO:20 except for 1 to 10 (i.e., 1, 2, 3, 4, 5, 6, 7, 8, 9, 10) substitutions, insertions and/or deletions. In another instance, such a bispecific antibody contains, on its human CD3-binding arm, a light chain that has an amino acid sequence that is identical to SEQ ID NO:20 except for 1 to 10 (i.e., 1, 2, 3, 4, 5, 6, 7, 8, 9, 10) substitutions.

In one aspect, a bispecific antibody of this disclosure binds to gp120 and human CD89 and can effectuate the killing of HIV-1 infected cells. CD89 is the IgA receptor predominantly expressed on neutrophils and thus this bispecific antibody would enhance recruitment of neutrophils to kill HIV-infected cells. In one instance, such a bispecific antibody that binds to gp120 contains VH-CDR1 of SEQ ID NO:1, VH-CDR2 of SEQ ID NO:2, VH-CDR3 of SEQ ID NO:3, VL-CDR1 of SEQ ID NO:4, VL-CDR2 of SEQ ID NO:5, and VL-CDR3 of SEQ ID NO:6. In one instance, such a bispecific antibody that binds to human CD89 contains VH-CDR1 of SEQ ID NO:98, VH-CDR2 of SEQ ID NO:99, VH-CDR3 of SEQ ID NO:100, VL-CDR1 of SEQ ID NO:103, VL-CDR2 of SEQ ID NO:104, and VL-CDR3 of SEQ ID NO:105. In another instance, a bispecific antibody that binds to gp120 and human CD89 contains on its gp120-binding arm: VH-CDR1 of SEQ ID NO:1, VH-CDR2 of SEQ ID NO:2, VH-CDR3 of SEQ ID NO:3, VL-CDR1 of SEQ ID NO:4, VL-CDR2 of SEQ ID NO:5, and VL-CDR3 of SEQ ID NO:6; and contains on its human CD89-binding arm: VH-CDR1 of SEQ ID NO:98, VH-CDR2 of SEQ ID NO:99, VH-CDR3 of SEQ ID NO:100, VL-CDR1 of SEQ ID NO:103, VL-CDR2 of SEQ ID NO:104, and VL-CDR3 of SEQ ID NO:105.

In another instance, such a bispecific antibody contains, on its gp120-binding arm, a VH that has an amino acid sequence that is at least 90%, 91%, 92%, 93%, 94%, 95%, 96%, 97% or at least 98% identical to SEQ ID NO:7. In another instance, such a bispecific antibody contains, on its gp120-binding arm, a VH that has an amino acid sequence that is identical to SEQ ID NO:7 except for 1 to 10 (i.e., 1, 2, 3, 4, 5, 6, 7, 8, 9, 10) substitutions, insertions and/or deletions. In another instance, such a bispecific antibody contains, on its gp120-binding arm, a VH that has an amino acid sequence that is identical to SEQ ID NO:7 except for 1 to 10 (i.e., 1, 2, 3, 4, 5, 6, 7, 8, 9, 10) substitutions. In another instance, such a bispecific antibody contains, on its gp120-binding arm, a VL that has an amino acid sequence that is at least 90%, 91%, 92%, 93%, 94%, 95%, 96%, 97% or at least 98% identical to SEQ ID NO:8, 81, 82, 83, or 84. In another instance, such a bispecific antibody contains, on its gp120-binding arm, a VL that has an amino acid sequence that is identical to SEQ ID NO:8, 81, 82, 83, or 84 except for 1 to 10 (i.e., 1, 2, 3, 4, 5, 6, 7, 8, 9, 10) substitutions, insertions and/or deletions. In another instance, such a bispecific antibody contains, on its gp120-binding arm, a VL that has an amino acid sequence that is identical to SEQ ID NO:8, 81, 82, 83, or 84 except for 1 to 10 (i.e., 1, 2, 3, 4, 5, 6, 7, 8, 9, 10) substitutions. In another instance, such a bispecific antibody contains, on its gp120-binding arm, a heavy chain that has an amino acid sequence that is at least 90%, 91%, 92%, 93%, 94%, 95%, 96%, 97% or at least 98% identical to SEQ ID NO:9. In another instance, such a bispecific antibody contains, on its gp120-binding arm, a heavy chain that has an amino acid sequence that is identical to SEQ ID NO:9 except for 1 to 10 (i.e., 1, 2, 3, 4, 5, 6, 7, 8, 9, 10) substitutions, insertions and/or deletions. In another instance, such a bispecific antibody contains, on its gp120-binding arm, a heavy chain that has an amino acid sequence that is identical to SEQ ID NO:9 except for 1 to 10 (i.e., 1, 2, 3, 4, 5, 6, 7, 8, 9, 10) substitutions. In another instance, such a bispecific antibody contains, on its gp120-binding arm, a light chain that has an amino acid sequence that is at least 90%, 91%, 92%, 93%, 94%, 95%, 96%, 97% or at least 98% identical to SEQ ID NO:10, 40, 78, 79, or 80. In another instance, such a bispecific antibody contains, on its gp120-binding arm, a light chain that has an amino acid sequence that is identical to SEQ ID NO:10, 40, 78, 79, or 80 except for 1 to 10 (i.e., 1, 2, 3, 4, 5, 6, 7, 8, 9, 10) substitutions, insertions and/or deletions. In another instance, such a bispecific antibody contains, on its gp120-binding arm, a light chain that has an amino acid sequence that is identical to SEQ ID NO:10, 40, 78, 79, or 80 except for 1 to 10 (i.e., 1, 2, 3, 4, 5, 6, 7, 8, 9, 10) substitutions.

In another instance, such a bispecific antibody contains, on its human CD89-binding arm, a VH that has an amino acid sequence that is at least 90%, 91%, 92%, 93%, 94%, 95%, 96%, 97% or at least 98% identical to SEQ ID NO:96. In another instance, such a bispecific antibody contains, on its human CD89-binding arm, a VH that has an amino acid sequence that is identical to SEQ ID NO:96 except for 1 to 10 (i.e., 1, 2, 3, 4, 5, 6, 7, 8, 9, 10) substitutions, insertions and/or deletions. In another instance, such a bispecific antibody contains, on its human CD89-binding arm, a VH that has an amino acid sequence that is identical to SEQ ID NO:96 except for 1 to 10 (i.e., 1, 2, 3, 4, 5, 6, 7, 8, 9, 10) substitutions. In another instance, such a bispecific antibody contains, on its human CD89-binding arm, a VL that has an amino acid sequence that is at least 90%, 91%, 92%, 93%, 94%, 95%, 96%, 97% or at least 98% identical to SEQ ID NO:101. In another instance, such a bispecific antibody contains, on its human CD89-binding arm, a VL that has an amino acid sequence that is identical to SEQ ID NO:101 except for 1 to 10 (i.e., 1, 2, 3, 4, 5, 6, 7, 8, 9, 10) substitutions, insertions and/or deletions. In another instance, such a bispecific antibody contains, on its human CD89-binding arm, a VL that has an amino acid sequence that is identical to SEQ ID NO:101 except for 1 to 10 (i.e., 1, 2, 3, 4, 5, 6, 7, 8, 9, 10) substitutions. In another instance, such a bispecific antibody contains, on its human CD89-binding arm, a heavy chain that has an amino acid sequence that is at least 90%, 91%, 92%, 93%, 94%, 95%, 96%, 97% or at least 98% identical to SEQ ID NO:97. In another instance, such a bispecific antibody contains, on its human CD89-binding arm, a heavy chain that has an amino acid sequence that is identical to SEQ ID NO:97 except for 1 to 10 (i.e., 1, 2, 3, 4, 5, 6, 7, 8, 9, 10) substitutions, insertions and/or deletions. In another instance, such a bispecific antibody contains, on its human CD89-binding arm, a heavy chain that has an amino acid sequence that is identical to SEQ ID NO:97 except for 1 to 10 (i.e., 1, 2, 3, 4, 5, 6, 7, 8, 9, 10) substitutions. In another instance, such a bispecific antibody contains, on its human CD89-binding arm, a light chain that has an amino acid sequence that is at least 90%, 91%, 92%, 93%, 94%, 95%, 96%, 97% or at least 98% identical to SEQ ID NO:102. In another instance, such a bispecific antibody contains, on its human CD89-binding arm, a light chain that has an amino acid sequence that is identical to SEQ ID NO:102 except for 1 to 10 (i.e., 1, 2, 3, 4, 5, 6, 7, 8, 9, 10) substitutions, insertions and/or deletions. In another instance, such a bispecific antibody contains, on its human CD89-binding arm, a light chain that has an amino acid sequence that is identical to SEQ ID NO:102 except for 1 to 10 (i.e., 1, 2, 3, 4, 5, 6, 7, 8, 9, 10) substitutions.

In certain embodiments, the bispecific antibody has an Fc domain from a human IgG1 antibody with 0-10 amino acid substitutions therein. The Fc domain contains one "leg" (hinge-CH2-CH3) from one component (e.g., gp120 binding portion) of the bispecific antibody and another "leg" (hinge-CH2-CH3) from the second component (e.g., CD3- or CD89-binding portion) of the bispecific antibody. The substitutions may be in one or both "legs." In certain embodiments, the Fc domain has one or more (1, 2, 3, 4, or 5) of the following mutations (EU numbering) in one or both "legs": N297A or N297Q, L234F, L235E, D265A, or P331S.

A bispecific antibody that binds to gp120 and CD3, or to gp120 and CD89, as disclosed herein can be prepared by chemically linking two different monoclonal antibodies or by fusing two hybridoma cell lines to produce a hybrid-hybridoma. Other bispecific antibodies technology platforms that can be employed include, for example, Kλ-bodies, SMIPs, DNLs, Covx-bodies, peptibodies, strand-exchange engineered domain bodies (SEEDbodies), dAbs, diabodies, Affibodies, Fynomers, Kunitz Domains, Tand-Abs, nanobodies, Albu-dabs, DARTs, DVD-IG, scFv-Igs, SVD-Igs, dAb-Igs, Knobs-in-Holes, BiTe platform, CrossMab® platform, DuoBodies® and TriomAbs®. Non-limiting examples of bispecific formats that can be employed in making the bispecific antibodies disclosed herein are provided in Del Bano et al., *Antibodies,* 5:1 (2016); Garber et al., *Nature Reviews Drug Discovery,* 13:799-801 (2014).

In one embodiment, a bispecific antibody molecule of this disclosure comprises a single antibody that has two arms comprising different antigen-binding regions, one arm with a specificity to a first antigen such as gp120 and the second arm with a specificity to a second antigen such as human CD3 or human CD89. In another embodiment, a bispecific antibody molecule of this disclosure comprises a single antibody that has one antigen-binding region or arm specific to a first antigen such as gp120 and a second antigen-binding region or arm specific to a second antigen such as human CD3 or human CD89. In yet another embodiment, a bispecific antibody molecule of this disclosure comprises a single chain antibody that has a first specificity to a first antigen such as gp120 and a second specificity to a second antigen such as human CD3 or human CD89, e.g., via two scFvs linked in tandem by an extra peptide linker. In a further embodiment, a bispecific antibody molecule of this disclosure includes a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)). In some embodiments, the bispecific antibody is a chemically-linked bispecific (Fab')2 fragment. In other embodiments, the bispecific antibody comprises a Tandab (i.e., a fusion of two single chain diabodies resulting in a tetravalent bispecific antibody that has two binding sites for each of the target antigens). In certain embodiments, the bispecific antibody is a flexibody, which is a combination of scFvs with a diabody resulting in a multivalent molecule. In yet another embodiment, the bispecific antibody comprises a "dock and lock" molecule, based on the "dimerization and docking domain" in Protein Kinase A, which, when applied to Fabs, can yield a trivalent bispecific binding protein consisting of two identical Fab fragments linked to a different Fab fragment. In another instance, the bispecific antibodies of this disclosure comprise a "Scorpion molecule," comprising, e.g., two scFvs fused to both termini of a human Fab-arm. In yet another embodiment, the bispecific antibody of this disclosure comprises a diabody.

Exemplary classes of bispecific antibodies include but are not limited to IgG-like molecules with complementary CH3 domains to force heterodimerization; IgG fusion molecules, wherein full length IgG antibodies are fused to extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; recombinant IgG-like dual targeting molecules, wherein the two sides of the molecule each contain the Fab fragment or part of the Fab fragment of at least two different antibodies; scFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

Examples of Fab fusion bispecific antibodies include but are not limited to F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech).

Examples of scFv-, diabody-based and domain antibodies include but are not limited to Bispecific T Cell Engager (BITE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), and dual targeting heavy chain only domain antibodies.

Duobodies

The bispecific antibody of this disclosure can be a Duobody® that binds to gp120 and a second antigen (e.g., human CD3 such as human CD3ε or human CD3δ; human CD89). A Duobody® is a bispecific IgG1 antibody that comprises a K409R mutation in the CH3 region of the constant region of one heavy chain of the bispecific antibody and a mutation selected from the group consisting of F405L, F405A, F405D, F405E, F405H, F405I, F405K, F405M, F405N, F405Q, F405S, F405T, F405V, F405W, and F405Y, in the CH3 region of the constant region of the other heavy chain. In a specific embodiment, a Duobody® is a bispecific IgG1 antibody that comprises a K409R mutation in the CH3 region of the constant region of one heavy chain of the bispecific antibody and a F405L mutation in the CH3 region of the constant region of the other heavy chain.

In certain embodiments, a first antigen binding domain that binds to gp120 as described above comprises a human IgG1 heavy chain constant region comprising a mutation selected from the group consisting of F405L, F405A, F405D, F405E, F405H, F405I, F405K, F405M, F405N, F405Q, F405S, F405T, F405V, F405W, and F405Y, and a second antigen binding domain that binds to human CD3 (or human CD89) as described above comprises a human IgG1 heavy chain constant region comprising a K409R mutation.

In one embodiment, a first antigen binding domain that binds to gp120 as described above comprises a human IgG1 heavy chain constant region comprising a F405L mutation, and a second antigen binding domain that binds to human CD3 as described above comprises a human IgG1 heavy chain constant region comprising a K409R mutation.

In other embodiments, a first antigen binding domain that binds to gp120 as described above comprises a human IgG1 heavy chain constant region comprising a K409R mutation, and a second antigen binding domain that binds to human CD3 (or human CD89) as described above comprises a human IgG1 heavy chain constant region comprising a mutation selected from the group consisting of F405L, F405A, F405D, F405E, F405H, F405I, F405K, F405M, F405N, F405Q, F405S, F405T, F405V, F405W, and F405Y.

In one embodiment, a first antigen binding domain that binds to gp120 as described above comprises a human IgG1 heavy chain constant region comprising a K409R mutation, and a second antigen binding domain that binds to human CD3 (or human CD89) as described above comprises a human IgG1 heavy chain constant region comprising a F405L mutation.

The CDRs and the VH and VL of the Duobody® can be any of the anti-gp120, anti-CD3, or anti-CD89 amino acid sequences described in detail above.

In one embodiment, the gp120-binding arm of the Duobody® comprises a VH-CDR1 of SEQ ID NO:1, a VH-CDR2 of SEQ ID NO:2, a VH-CDR3 of SEQ ID NO:3, a VL-CDR1 of SEQ ID NO:4, a VL-CDR2 of SEQ ID NO:5, and a VL-CDR3 of SEQ ID NO:6. In one embodiment, the CD3-binding arm of the Duobody® comprises a VH-CDR1 of SEQ ID NO:11, a VH-CDR2 of SEQ ID NO:12, a VH-CDR3 of SEQ ID NO:13, a VL-CDR1 of SEQ ID NO:14, a VL-CDR2 of SEQ ID NO:15, and a VL-CDR3 of SEQ ID NO:16. In another instance, a Duobody® that binds to gp120 and human CD3 contains on its gp120-binding arm: a VH-CDR1 of SEQ ID NO:1, a VH-CDR2 of SEQ ID NO:2, a VH-CDR3 of SEQ ID NO:3, a VL-CDR1 of SEQ ID NO:4, a VL-CDR2 of SEQ ID NO:5, and a VL-CDR3 of SEQ ID NO:6; and contains on its human CD3-binding arm: a VH-CDR1 of SEQ ID NO:11, a VH-CDR2 of SEQ ID NO:12, a VH-CDR3 of SEQ ID NO:13, a VL-CDR1 of SEQ ID NO:14, a VL-CDR2 of SEQ ID NO:15, and a VL-CDR3 of SEQ ID NO:16.

In one embodiment, the gp120-binding arm of the Duobody® comprises a VH of SEQ ID NO:7 and a VL of SEQ ID NO:8. In one embodiment, the gp120-binding arm of the Duobody® comprises a VH of SEQ ID NO:7 and a VL of SEQ ID NO:81. In one embodiment, the gp120-binding arm of the Duobody® comprises a VH of SEQ ID NO:7 and a VL of SEQ ID NO:82. In one embodiment, the gp120-binding arm of the Duobody® comprises a VH of SEQ ID NO:7 and a VL of SEQ ID NO:83. In one embodiment, the gp120-binding arm of the Duobody® comprises a VH of SEQ ID NO:7 and a VL of SEQ ID NO:84. In one embodiment, the CD3-binding arm of the Duobody® comprises a VH of SEQ ID NO:17 and a VL of SEQ ID NO:18. In one embodiment, the CD89-binding arm of the Duobody® comprises a VH of SEQ ID NO:96 and a VL of SEQ ID NO:101. In another instance, a Duobody® that binds to gp120 and human CD3 contains on its gp120-binding arm: a VH of SEQ ID NO:7 and a VL of SEQ ID NO:8, and contains on its human CD3-binding arm: a VH of SEQ ID NO:17 and a VL of SEQ ID NO:18. In another instance, a Duobody® that binds to gp120 and human CD89 contains on its gp120-binding arm: a VH of SEQ ID NO:7 and a VL of SEQ ID NO:8, and contains on its human CD89-binding arm: a VH of SEQ ID NO:96 and a VL of SEQ ID NO:101. In one instance, a Duobody® that binds to gp120 and human CD3 contains on its gp120-binding arm: a VH of SEQ ID NO:7 and a VL of SEQ ID NO:81, and contains on its human CD3-binding arm: a VH of SEQ ID NO:17 and a VL of SEQ ID NO:18. In one instance, a Duobody® that binds to gp120 and human CD89 contains on its gp120-binding arm: a VH of SEQ ID NO:7 and a VL of SEQ ID NO:81, and contains on its human CD3-binding arm: a VH of SEQ ID NO:96 and a VL of SEQ ID NO:101. In one instance, a Duobody® that binds to gp120 and human CD3 contains on its gp120-binding arm: a VH of SEQ ID NO:7 and a VL of SEQ ID NO:82, and contains on its human CD3-binding arm: a VH of SEQ ID NO:17 and a VL of SEQ ID NO:18. In one instance, a Duobody® that binds to gp120 and human CD89 contains on its gp120-binding arm: a VH of SEQ ID NO:7 and a VL of SEQ ID NO:82, and contains on its human CD3-binding arm: a VH of SEQ ID NO:96 and a VL of SEQ ID NO:101. In one instance, a Duobody® that binds to gp120 and human CD3 contains on its gp120-binding arm: a VH of SEQ ID NO:7 and a VL of SEQ ID NO:83, and contains on its human CD3-binding arm: a VH of SEQ ID NO:17 and a VL of SEQ ID NO:18. In one instance, a Duobody® that binds to gp120 and human CD89 contains on its gp120-binding arm: a VH of SEQ ID NO:7 and a VL of SEQ ID NO:83, and contains on its human CD89-binding arm: a VH of SEQ ID NO:96 and a VL of SEQ ID NO:101. In one instance, a Duobody® that binds to gp120 and human CD3 contains on its gp120-binding arm: a VH of SEQ ID NO:7 and a VL of SEQ ID NO:84, and contains on its human CD3-binding arm: a VH of SEQ ID NO:17 and a VL of SEQ ID NO:18. In one instance, a Duobody® that binds to gp120 and human CD89 contains on its gp120-binding arm: a VH of SEQ ID NO:7 and a VL of SEQ ID NO:84, and contains on its human CD89-binding arm: a VH of SEQ ID NO:96 and a VL of SEQ ID NO:101. In another embodiment, a Duobody® that binds to gp120 and human CD3 comprises a first heavy chain of SEQ ID NO:9 and a first light chain of SEQ ID NO:10; and a second heavy chain of SEQ ID NO:19 and a second light chain of SEQ ID NO:20. In another embodiment, a Duobody® that binds to gp120 and human CD89 comprises a first heavy chain of SEQ ID NO:9 and a first light chain of SEQ ID NO:10; and a second heavy chain of SEQ ID NO:97 and a second light chain of SEQ ID NO:102. In another embodiment, a Duobody® that binds to gp120 and human CD3 comprises a first heavy chain of SEQ ID NO:9 and a first light chain of SEQ ID NO:40; and a second heavy chain of SEQ ID NO:19 and a second light chain of SEQ ID NO:20. In another embodiment, a Duobody® that binds to gp120 and human CD89 comprises a first heavy chain of SEQ ID NO:9 and a first light chain of SEQ ID NO:40; and a second heavy chain of SEQ ID NO:97 and a second light chain of SEQ ID NO:102. In another embodiment, a Duobody® that binds to gp120 and human CD3 comprises a first heavy chain of SEQ ID NO:9 and a first light chain of SEQ ID NO:78; and a second heavy chain of SEQ ID NO:19 and a second light chain of SEQ ID NO:20. In another embodiment, a Duobody® that binds to gp120 and human CD89 comprises a first heavy chain of SEQ ID NO:9 and a first light chain of SEQ ID NO:78; and a second heavy chain of SEQ ID NO:97 and a second light chain of SEQ ID NO:102. In another embodiment, a Duobody® that binds to gp120 and human CD3 comprises a first heavy chain of SEQ ID NO:9 and a first light chain of SEQ ID NO:79; and a second heavy chain of SEQ ID NO:19 and a second light chain of SEQ ID NO:20. In another embodiment, a Duobody® that binds to gp120 and human CD89 comprises a first heavy chain of SEQ ID NO:9 and a first light chain of SEQ ID NO:79; and a second heavy chain of SEQ ID NO:97 and a second light chain of SEQ ID NO:102. In another embodiment, a Duobody® that binds to gp120 and human CD3 comprises a first heavy chain of SEQ ID NO:9 and a first light chain of SEQ ID NO:80; and a second heavy chain of SEQ ID NO:19 and a second light chain of SEQ ID NO:20. In another embodiment, a Duobody® that binds to gp120 and human CD89 comprises a first heavy chain of SEQ ID NO:9 and a first light chain of SEQ ID NO:80; and a second heavy chain of SEQ ID NO:97 and a second light chain of SEQ ID NO:102. In one embodiment, one of the heavy chains of the anti-gp120 x CD3 Duobody® or of the anti-gp120 x CD89 Duobody® comprises an amino acid sequence that is at least 80%, 85%, 90%, 91%, 92%, 93%, 94%, or 95%, 96%, 97%, 98%, 99%, or 100% identical to one amino acid sequence set out below, or is identical to one of the amino acid sequences provided below except for 1 to 10 (i.e., 1, 2, 3, 4, 5, 6, 7, 8, 9, or 10) amino acid substitutions:

(SEQ ID NO: 56)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

ELLAGPDVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVMHEALHNHYTQKSLSLSPGK

```
                                                (SEQ ID NO: 57)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

ELLAGPDVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVLHEALHSHYTQKSLSLSPGK (SEQ ID NO: 58)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

ELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVMHEALHNHYTQKSLSLSPGK (SEQ ID NO: 59)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

ELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVLHEALHSHYTQKSLSLSPGK (SEQ ID NO: 60)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

EFEGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVMHEALHNHYTQKSLSLSPGK (SEQ ID NO: 61)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

EFEGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVLHEALHSHYTQKSLSLSPGK (SEQ ID NO: 62)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

EFEGGPSVFLFPPKPKDTLMISRTPEVTCVVVAVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVMHEALHNHYTQKSLSLSPGK
```

(SEQ ID NO: 63)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

EFEGGPSVFLFPPKPKDTLMISRTPEVTCVVVAVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVLHEALHSHYTQKSLSLSPGK (SEQ ID NO: 64)
EPKSCDKTHTCPPCPAP

EFEGGPSVFLFPPKPKDTLMISRTPEVTCVVVAVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVMHEALHNHYTQKSLSLSPGK (SEQ ID NO: 65)
EPKSCDKTHTCPPCPAP

EFEGGPSVFLFPPKPKDTLMISRTPEVTCVVVAVSHEDPEVKFNWYVDGVEVHNAKTKPR

EEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFLLYSKLTV

DKSRWQQGNVFSCSVLHEALHSHYTQKSLSLSPGK

In one embodiment, one of the heavy chains of the anti-gp120 x CD3 Duobody® or the anti-gp120 x CD89 Duobody® comprises an amino acid sequence that is at least 80%, 85%, 90%, 91%, 92%, 93%, 94%, or 95%, 96%, 97%, 98%, 99%, or 100% identical to one amino acid sequence set out below, or is identical to one amino acid sequence provided below except for 1 to 10 (i.e., 1, 2, 3, 4, 5, 6, 7, 8, 9, or 10) amino acid substitutions:

(SEQ ID NO: 66)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHT

CPPCPAPELLAGPDVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVMHEALHNHYTQKSLSLSPGK (SEQ ID NO: 67)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHT

CPPCPAPELLAGPDVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVLHEALHSHYTQKSLSLSPGK (SEQ ID NO: 68)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHT

CPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPRE

-continued

PQVYTLPPSREEMTKNQVSLTCLVKGFYPSDIAVEWESNGQPENNYKTTPPVLDSDGSFF

LYSRLTVDKSRWQQGNVFSCSVMHEALHNHYTQKSLSLSPGK (SEQ ID NO: 69)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHT

CPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVLHEALHSHYTQKSLSLSPGK (SEQ ID NO: 70)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHT

CPPCPAPEFEGGPDVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVMHEALHNHYTQKSLSLSPGK (SEQ ID NO: 71)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHT

CPPCPAPEFEGGPDVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVLHEALHSHYTQKSLSLSPGK (SEQ ID NO: 72)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHT

CPPCPAPEFEGGPDVFLFPPKPKDTLMISRTPEVTCVVVAVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVMHEALHNHYTQKSLSLSPGK (SEQ ID NO: 73)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHT

CPPCPAPEFEGGPDVFLFPPKPKDTLMISRTPEVTCVVVAVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVLHEALHSHYTQKSLSLSPGK (SEQ ID NO: 74)
EPKSCDKTHT

CPPCPAPEFEGGPDVFLFPPKPKDTLMISRTPEVTCVVVAVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVMHEALHNHYTQKSLSLSPGK (SEQ ID NO: 75)
EPKSCDKTHT

CPPCPAPEFEGGPDVFLFPPKPKDTLMISRTPEVTCVVVAVSHEDPEVKFNWYVDGVEVH

NAKTKPREEQYNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTPPVLDSDGSFF

LYSRLTVDKSRWQQGNVFSCSVLHEALHSHYTQKSLSLSPGK

In one embodiment, one heavy chain constant region of the Duobody® comprises the amino acid sequence set forth in SEQ ID NO:64 and the other heavy chain constant region of the Duobody® comprises the amino acid sequence set forth in SEQ ID NO:74. In another embodiment, one heavy chain constant region of the Duobody® comprises the amino acid sequence set forth in SEQ ID NO:65 and the other heavy chain constant region of the Duobody® comprises the amino acid sequence set forth in SEQ ID NO:75. In another embodiment, one heavy chain constant region of the Duobody® comprises the amino acid sequence set forth in SEQ ID NO:62 and the other heavy chain constant region of the Duobody® comprises the amino acid sequence set forth in SEQ ID NO:72. In yet another embodiment, one heavy chain constant region of the Duobody® comprises the amino acid sequence set forth in SEQ ID NO:63 and the other heavy chain constant region of the Duobody® comprises the amino acid sequence set forth in SEQ ID NO:73.

In one embodiment, the heavy chain of the gp120-binding arm of the Duobody® has the amino acid sequence set forth in SEQ ID NO:9 and the light chain of the gp120-binding arm of the Duobody® has the amino acid sequence set forth in SEQ ID NO:10. In another embodiment, the heavy chain of the gp120-binding arm of the Duobody® has the amino acid sequence set forth in SEQ ID NO: 9 and the light chain of the gp120-binding arm of the Duobody® has the amino acid sequence set forth in SEQ ID NO: 40. In another embodiment, the heavy chain of the gp120-binding arm of the Duobody® has the amino acid sequence set forth in SEQ ID NO: 9 and the light chain of the gp120-binding arm of the Duobody® has the amino acid sequence set forth in SEQ ID NO: 78. In another embodiment, the heavy chain of the gp120-binding arm of the Duobody® has the amino acid sequence set forth in SEQ ID NO: 9 and the light chain of the gp120-binding arm of the Duobody® has the amino acid sequence set forth in SEQ ID NO: 79. In yet another embodiment, the heavy chain of the gp120-binding arm of the Duobody® has the amino acid sequence set forth in SEQ ID NO: 9 and the light chain of the gp120-binding arm of the Duobody® has the amino acid sequence set forth in SEQ ID NO: 80.

In one embodiment, the heavy chain of the CD3-binding arm of the gp120 X CD3 Duobody® comprises or consists of the amino acid sequence set forth in SEQ ID NO:19 and the light chain of the CD3-binding arm of the Duobody® comprises or consists of the amino acid sequence set forth in SEQ ID NO:20.

In one embodiment, the heavy chain of the CD89-binding arm of the gp120 X CD89 Duobody® comprises or consists of the amino acid sequence set forth in SEQ ID NO:97 and the light chain of the CD3-binding arm of the Duobody® comprises or consists of the amino acid sequence set forth in SEQ ID NO:102.

In one embodiment, the gp120 X CD3 Duobody® comprises two arms, the first arm comprising a heavy and light chain that bind gp120, wherein the heavy chain of the gp120-binding arm of the Duobody® comprises an amino acid sequence that is at least 80%, 81%, 82%, 83%, 84%, 85%, 86%, 87%, 88%, 89%, 90%, 91%, 92%, 93%, 94%, 95%, 96%, 97%, or 98% identical to the amino acid sequence set forth in SEQ ID NO:9 and the light chain of the gp120-binding arm comprises an amino acid sequence that is at least 80%, 81%, 82%, 83%, 84%, 85%, 86%, 87%, 88%, 89%, 90%, 91%, 92%, 93%, 94%, 95%, 96%, 97%, or 98% identical to the amino acid sequence set forth in SEQ ID NO:10, 40, 78, 79, or 80, and the second arm comprising a heavy and light chain that bind CD3, wherein the heavy chain of the CD3-binding arm of the Duobody® comprises an amino acid sequence that is at least 80%, 81%, 82%, 83%, 84%, 85%, 86%, 87%, 88%, 89%, 90%, 91%, 92%, 93%, 94%, 95%, 96%, 97%, or 98% identical to the amino acid sequence set forth in SEQ ID NO:19 and the light chain of the CD3-binding arm comprises an amino acid sequence that is at least 80%, 81%, 82%, 83%, 84%, 85%, 86%, 87%, 88%, 89%, 90%, 91%, 92%, 93%, 94%, 95%, 96%, 97%, or 98% identical to the amino acid sequence set forth in SEQ ID NO:20.

In one embodiment, the gp120 X CD89 Duobody® comprises two arms, the first arm comprising a heavy and light chain that bind gp120, wherein the heavy chain of the gp120-binding arm of the Duobody® comprises an amino acid sequence that is at least 80%, 81%, 82%, 83%, 84%, 85%, 86%, 87%, 88%, 89%, 90%, 91%, 92%, 93%, 94%, 95%, 96%, 97%, or 98% identical to the amino acid sequence set forth in SEQ ID NO:9 and the light chain of the gp120-binding arm comprises an amino acid sequence that is at least 80%, 81%, 82%, 83%, 84%, 85%, 86%, 87%, 88%, 89%, 90%, 91%, 92%, 93%, 94%, 95%, 96%, 97%, or 98% identical to the amino acid sequence set forth in SEQ ID NO:10, 40, 78, 79, or 80, and the second arm comprising a heavy and light chain that bind CD89, wherein the heavy chain of the CD89-binding arm of the Duobody® comprises an amino acid sequence that is at least 80%, 81%, 82%, 83%, 84%, 85%, 86%, 87%, 88%, 89%, 90%, 91%, 92%, 93%, 94%, 95%, 96%, 97%, or 98% identical to the amino acid sequence set forth in SEQ ID NO:97 and the light chain of the CD89-binding arm comprises an amino acid sequence that is at least 80%, 81%, 82%, 83%, 84%, 85%, 86%, 87%, 88%, 89%, 90%, 91%, 92%, 93%, 94%, 95%, 96%, 97%, or 98% identical to the amino acid sequence set forth in SEQ ID NO:102.

In one specific embodiment, the gp120 X CD3 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:10, and the second arm comprising a heavy and light chain that bind CD3, wherein the heavy chain of the CD3-binding arm of the Duobody® comprises the amino acid sequence set forth in SEQ ID NO:19 and the light chain of the CD3-binding arm comprises the amino acid sequence set forth in SEQ ID NO:20. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In one specific embodiment, the gp120 X CD89 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:10, and the second arm comprising a heavy and light chain that bind CD89, wherein the heavy chain of the CD89-binding arm of the Duobody® comprises the amino acid sequence set forth in SEQ ID NO:97 and the light chain of the CD89-binding arm comprises the amino acid sequence set forth in SEQ ID NO:102. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In another specific embodiment, the gp120 X CD3 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:40, and the second arm comprising a heavy and light chain that bind CD3, wherein the heavy chain of the CD3-binding arm of the Duobody® comprises the amino acid sequence set forth in SEQ ID NO:19 and the light chain of the CD3-binding arm comprises the amino acid sequence set forth in SEQ ID NO:20. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In another specific embodiment, the gp120 X CD89 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:40, and the second arm comprising a heavy and light chain that bind CD89, wherein the heavy chain of the CD89-binding arm of the Duobody® comprises the amino acid sequence set forth in SEQ ID NO:97 and the light chain of the CD89-binding arm comprises the amino acid sequence set forth in SEQ ID NO:102. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In another specific embodiment, the gp120 X CD3 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:78, and the second arm comprising a heavy and light chain that bind CD3, wherein the heavy chain of the CD3-binding arm of the Duobody® comprises the amino acid sequence set forth in SEQ ID NO:19 and the light chain of the CD3-binding arm comprises the amino acid sequence set forth in SEQ ID NO:20. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In another specific embodiment, the gp120 X CD89 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:78, and the second arm comprising a heavy and light chain that bind CD89, wherein the heavy chain of the CD89-binding arm of the Duobody® comprises the amino acid sequence set forth in SEQ ID NO:97 and the light chain of the CD89-binding arm comprises the amino acid sequence set forth in SEQ ID NO:102. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In another specific embodiment, the gp120 X CD3 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:79, and the second arm comprising a heavy and light chain that bind CD3, wherein the heavy chain of the CD3-binding arm of the Duobody® comprises the amino acid sequence set forth in SEQ ID NO:19 and the light chain of the CD3-binding arm comprises the amino acid sequence set forth in SEQ ID NO:20. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In another specific embodiment, the gp120 X CD89 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:79, and the second arm comprising a heavy and light chain that bind CD89, wherein the heavy chain of the CD89-binding arm of the Duobody® comprises the amino acid sequence set forth in SEQ ID NO:97 and the light chain of the CD89-binding arm comprises the amino acid sequence set forth in SEQ ID NO:102. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In another specific embodiment, the gp120 X CD3 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:80, and the second arm comprising a heavy and light chain that bind CD3, wherein the heavy chain of the CD3-binding arm of the Duobody® comprises the amino acid sequence set forth in SEQ ID NO:19 and the light chain of the CD3-binding arm comprises the amino acid sequence set forth in SEQ ID NO:20. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In another specific embodiment, the gp120 X CD89 Duobody® comprises two arms, the first arm comprising a heavy and light chain that bind gp120, wherein the heavy chain of the gp120-binding arm of the Duobody® comprises an the amino acid sequence set forth in SEQ ID NO:9 and the light chain of the gp120-binding arm comprises the amino acid sequence set forth in SEQ ID NO:80, and the second arm comprising a heavy and light chain that bind CD89, wherein the heavy chain of the CD89-binding arm of the Duobody® comprises the amino acid sequence set forth in SEQ ID NO:97 and the light chain of the CD89-binding arm comprises the amino acid sequence set forth in SEQ ID NO:102. In certain embodiments 1-10 (i.e., 1, 2, 3, 4, 5, 6, 7, 8, 9, or 10) amino acids substitutions may be made within any component (e.g., CH1, hinge, CH2, CH3) of one or both of the heavy chain constant regions of the Duobody®. In certain instances, the amino acid substitutions alter (e.g., reduce) the effector function and/or increase the half-life relative to the unaltered polypeptide. In certain embodiments, these substitutions may be conservative amino acid substitutions.

In particular embodiments, the antibodies are afucosylated. In some embodiments, the antibodies comprise one or more tags. In certain embodiments, the one or more tags comprise an avidin tag.

Fc Modifications

In certain embodiments, the antibodies (e.g., Duobodies®) of this disclosure include one or more amino acid sequence modifications in the heavy chain constant region (Fc) as compared to the IgG1m3 amino acid sequence (i.e., SEQ ID NO:77). In certain embodiments, the antibodies (e.g., Duobodies®) of this disclosure include one or more amino acid sequence modifications in the heavy chain constant region (Fc) as compared to the PGT-121.60 antibody. In particular embodiments, these modifications increase stability or increase binding affinity of the modified antibody as compared to the PGT-121 LO6 antibody. In particular embodiments, these modifications increase stability or increase binding affinity of the modified antibody as compared to the PGT-121.60 antibody. In particular embodiments, certain of these modifications, increase half-life of the antibody. In certain embodiments, certain of these modifications, decrease antibody effector function. In other embodiments, certain of these modifications, decrease antibody effector function and increase half-life of the antibody.

In certain embodiments, the one or more modifications are selected from the following Fc amino acid substitutions (EU numbering) or combinations thereof: L234F; L235E; G236A; S239D; F243L; D265E; D265A; S267E; H268F; R292P; N297Q; N297A; S298A; S324T; I332E; S239D; A330L; L234F; L235E; P331S; F243L; Y300L; V305I; P396L; S298A; E333A; K334A; E345R; L235V; F243L; R292P; Y300L; P396L; M428L; E430G; N434S; G236A, S267E, H268F, S324T, and I332E; G236A, S239D, and I332E; S239D, A330L, I332E; L234F, L235E, and P331S; F243L, R292P, Y300L, V305I, and P396L; G236A, H268F, S324T, and I332E; S239D, H268F, S324T, and I332E; S298A, E333A, and K334A; L235V, F243L, R292P, Y300L, and P396L; S239D, I332E; S239D, S298A, and I332E; G236A, S239D, I332E, M428L, and N434S; G236A, S239D, A330L, I332E, M428L, and N434S; S239D, I332E, G236A and A330L; M428L and N4343S; M428L, N434S; G236A, S239D, A330L, and I332E; and G236A and I332E. In certain embodiments, the one or more modifications is selected from the group consisting of: N297A, D265A, L234F, L235E, N297Q, and P331S. In certain embodiments, the one or more modifications is N297A or D265A. In certain embodiments the one or more modifications are L234F and L235E. In certain embodiments, the one or more modifications are L234F, L234E, and D265A. In certain embodiments, the one or more modifications are L234F, L234E, and N297Q. In certain embodiments, the one or more modifications are L234F, L235E, and P331S. In certain embodiments, the one or more modifications are D265A and N297Q. In certain embodiments, the one or more modifications are L234F, L235E, D265A, N297Q, and P331S.

Mutations that reduce Fc-receptor binding include, for example, N297A; N297Q; D265A; L234F/L235E; L234F/L235E/N297Q; L234F/L235E/P331S; D265A/N297Q; and L234F/L235E/D265A/N297Q/P331S (all EU numbering). In certain embodiments the antibodies disclosed herein (e.g., Duobodies) comprise L234F and L235E mutations. In certain embodiments the antibodies disclosed herein (e.g., Duobodies) comprise L234F, L235E, and D265A mutations. In certain embodiments the antibodies disclosed herein (e.g., Duobodies) comprise L234F, L235E, and D265A mutations. In certain embodiments the antibodies disclosed herein (e.g., Duobodies) comprise an N297A or N297Q mutation. In certain embodiments the antibodies disclosed herein (e.g., Duobodies) comprise an N297A or N297Q mutation as well as L234F, L235E, and D265A mutations. In certain embodiments, one, two, three, four, or more amino acid substitutions are introduced into a Fc region to alter the effector function of the antibody. For example, these substitutions are located at positions selected from the group consisting of amino acid residues 234, 235, 236, 237, 265, 297, 318, 320, and 322, (according to EU numbering). These positions can be replaced with a different amino acid residue such that the antibody has an altered (e.g., reduced) affinity for an effector ligand (e.g., an Fc receptor or the C1 component of complement), but retains the antigen-binding ability of the parent antibody. In certain embodiments, the antibodies disclosed herein (e.g., Duobodies) comprise E233P, L234V, L235A, and G236A mutations (EU numbering). In some embodiments, the antibodies comprise A327G, A330S, and P331S mutations (EU numbering). In some embodiments, the antibodies comprise K322A mutations (EU numbering). In some embodiments, the antibodies comprise E318A, K320A, and K322A (EU numbering) mutations. In certain embodiments, the antibodies comprise a L235E (EU numbering) mutation.

Mutations that increase the half-life of an antibody are known in the art. In one embodiment, the constant region of an antibody described herein (e.g., Duobodies®) comprises a methionine to tyrosine substitution at position 252 (EU numbering), a serine to threonine substitution at position 254 (EU numbering), and a threonine to glutamic acid substitution at position 256 9EU numbering). See, e.g., U.S. Pat. No. 7,658,921. This type of mutant, designated as a "YTE mutant" exhibits a four-fold increased half-life relative to wild-type versions of the same antibody (Dall'Acqua t al., *J Biol Chem*, 281: 23514-24 (2006); Robbie et al., *Antimicrob Agents Chemotherap.*, 57(12):6147-6153 (2013)). In certain embodiments, an antibody comprises an IgG constant domain comprising one, two, three or more amino acid substitutions of amino acid residues at positions 251-257, 285-290, 308-314, 385-389, and 428-436 (EU numbering). In other embodiments, an antibody described herein (e.g., Duobodies®) comprises a M428L and N4343 S substitution (EU numbering). In other embodiments, an antibody described herein (e.g., Duobodies®) comprises T250Q and M428L (EU numbering) mutations. In other embodiments, an antibody described herein (e.g., Duobodies®) comprises H433K and N434F (EU numbering) mutations.

In particular embodiments, the antibodies (e.g., Duobodies®) comprise two or more, three or more, four or more, five or more, six or more, six or fewer, five or fewer, four or fewer, three or fewer, two or fewer, or one modified Fc amino acid residue(s). In certain embodiments, the antibodies comprise the L234F, L235E, D264A mutations, which are collectively referred to as "FEA." In certain embodiments, the antibodies comprise the L234F, L235E, D264A, and F405L mutations, which are collectively referred to as "FEAL." In certain embodiments, the antibodies comprise the L234F, L235E, D264A, and a mutation selected from the group consisting of F405L, F405A, F405D, F405E, F405H, F405I, F405K, F405M, F405N, F405Q, F405S, F405T, F405V, F405W, and F405Y. In certain embodiments, the antibodies comprise the L234F, L235E, D264A, and K409R mutations, which are collectively referred to as "FEAR." In certain embodiments, FEAL and FEAR are comprised in a bispecific antibody (e.g., Duobodies®) described herein. In certain embodiments, the antibodies comprise the M428L and N434S mutations, which are collectively referred to as "LS. In certain embodiments, the antibodies comprise the L234F, L235E, D264A, F405L, M428L, and N434S mutations, which are collectively referred to as "FEALLS." In certain embodiments, the antibodies comprise the L234F, L235E, D264A, M428L, and N434S mutations along with one further mutation selected from the group consisting of F405L, F405A, F405D, F405E, F405H, F405I, F405K, F405M, F405N, F405Q, F405S, F405T, F405V, F405W, and F405Y. In certain embodiments, the antibodies comprise the L234F, L235E, D264A, K409R, M428L, and N434S mutations which are collectively referred to as "FEARLS." In certain embodiments, FEALLS and FEARLS are comprised in a bispecific antibody (e.g., Duobodies®) described herein. In certain embodiments, the antibodies comprise the S239D, I332E, G236A, A330L ("DEAL"). In certain embodiments, the antibodies comprise the S239D, I332E, G236A, A330L, M428L and N434S mutations ("DEALLS"). The FEA mutations decrease or abrogate effector function while the DEAL mutations increase or enhance effector function by enhancing the binding of the Fc to activating FcγRs. The LS mutations increase the pharmacokinetic half-life of the antibody.

By reducing or abrogating effector function, the CD3 X gp120 multispecific/bispecific antibody (i) it ensures that the T cells bound by the bispecific molecule, which will include those not infected with HIV, are not killed by innate effector cells e.g., NK cells, macrophages; and (ii) by not binding or having reduced binding to FcγRs on innate effector cells, it also ensures the T cells are not activated in the absence of target cells. Activation of T cells in the absence of target cells would lead to a cytokine response and would not be tolerable. Binding of the bispecific molecule to FcγRs on innate effector cells would lead to clustering of the CD3 molecules on the T cells, resulting in antigen-independent T cell activation.

Conjugated Antibodies

Any of the antibodies disclosed herein may be conjugated antibodies which are bound to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g. $^{90}Y$, $^{131}I$, $^{125}I$, $^{35}S$, $^{3}H$, $^{121}In$, $^{99}Tc$), fluorescent substances (e.g., fluorescein and rhodamine), luminescent substances (e.g., luminol), haptens, enzymes (e.g., glucose oxidase), metal chelates, biotin, avidin, and drugs.

The above-described conjugated antibodies can be prepared by performing chemical modifications on the antibodies or the lower molecular weight forms thereof described herein. Methods for modifying antibodies are well known in the art (e.g., U.S. Pat. Nos. 5,057,313 and 5,156,840).

Nucleic Acids

This disclosure also features polynucleotides comprising a nucleotide sequence encoding a multispecific antibody described herein that binds to gp120 and human CD3 antigen, or that binds to gp120 and human CD89 antigen, vectors comprising such polynucleotides, and host cells (e.g., mammalian cells, yeast, *E. coli*) comprising such polynucleotides or expression vectors. Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

In one aspect, this disclosure provides polynucleotides comprising nucleotide sequences encoding the VH, VL or VH and VL of the antibodies which bind to gp120 (e.g., Exemplary anti-gp120 Antibody 2; Exemplary anti-gp120 Antibody 3; Exemplary anti-gp120 Antibody 4; Exemplary anti-gp120 Antibody 5).

In another aspect, this disclosure provides polynucleotides comprising nucleotide sequences encoding antibodies, which bind to gp120 and human CD3 polypeptides and comprises an amino acid sequence as described herein.

In another aspect, this disclosure provides polynucleotides comprising nucleotide sequences encoding antibodies, which bind to gp120 and human CD89 polypeptides and comprises an amino acid sequence as described herein.

In another aspect, this disclosure provides polynucleotides or nucleic acid molecules encoding an antibody or antigen-binding fragment thereof according to the present invention. In some embodiments, the nucleic acid molecules encode an antibody light chain (or a fragment thereof) or an antibody light chain (or a fragment thereof), or both of the present application. In other embodiments, the nucleic acid is a DNA, a cDNA, or an mRNA. In some other embodiments, the nucleic acid molecule is codon-optimized to enhance expression in a host cell.

In another aspect, provided herein are polynucleotides comprising a nucleotide sequence encoding the CDRs, light chain, or heavy chain of an antibody described herein. The polynucleotides can comprise nucleotide sequences encoding a light chain or light chain variable domain comprising the VL CDRs of antibodies described herein (see, e.g., Tables above). The polynucleotides can comprise nucleotide sequences encoding a heavy chain or heavy chain variable domain comprising the VH CDRs of antibodies described herein (see, e.g., Tables above). In one embodiment, a polynucleotide described herein encodes a variable light chain or light chain with the VL-CDRs comprising the amino acid sequence set forth in SEQ ID NOs: 4, 5, and 6, respectively; or 14, 15, and 16, respectively. In another embodiment, a polynucleotide described herein encodes a variable heavy chain or heavy chain with VH-CDRs comprising the amino acid sequence set forth in SEQ ID NOs: 1, 2, and 3, respectively; or 11, 12, and 13, respectively. In one embodiment, a polynucleotide described herein encodes a VL domain comprising the amino acid sequence set forth in SEQ ID NO:8, 18, or 101. In another embodiment, a polynucleotide described herein encodes a VH domain comprising the amino acid sequence set forth in SEQ ID NO:7, 17, or 96. In yet another embodiment, a polynucleotide described herein encodes a light chain comprising the amino acid sequence set forth in SEQ ID NO:10, 20, or 102. In another embodiment, a polynucleotide described herein encodes a heavy chain comprising the amino acid sequence set forth in SEQ ID NO:9, 19, or 97.

Also encompassed by this disclosure are polynucleotides encoding an anti-gp120 and an anti-CD3 (or an anti-CD89) antibody that are optimized, e.g., by codon optimization, replacement with heterologous signal sequences, and elimination of mRNA instability elements. Methods to generate optimized nucleic acids can be carried out by adapting the methods described in, e.g., U.S. Pat. Nos. 5,965,726; 6,174,666; 6,291,664; 6,414,132; and 6,794,498.

Vectors and Host Cells

This disclosure also encompasses vectors comprising a nucleic acid(s) disclosed herein. A vector can be of any type, for example, a recombinant vector such as an expression vector. Vectors include, but are not limited to, plasmids, cosmids, bacterial artificial chromosomes (BAC) and yeast artificial chromosomes (YAC) and vectors derived from bacteriophages or plant or animal (including human) viruses. Vectors can comprise an origin of replication recognized by the proposed host cell and in the case of expression vectors, promoter and other regulatory regions recognized by the host cell. In particular embodiments, a vector comprises a polynucleotide encoding an antibody of the disclosure operably linked to a promoter and optionally additional regulatory elements. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. Vectors include, but are not limited to, those suitable for recombinant production of the antibodies disclosed herein.

The choice of the vector is dependent on the recombinant procedures followed and the host used. Introduction of vectors into host cells can be effected by inter alia calcium phosphate transfection, virus infection, DEAE-dextran-mediated transfection, lipofectamine transfection or electroporation. Vectors may be autonomously replicating or may replicate together with the chromosome into which they have been integrated. In certain embodiments, the vectors contain one or more selection markers. The choice of the markers may depend on the host cells of choice. These include, but are not limited to, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the antibodies described herein, operably linked to one or more nucleic acid molecules encoding proteins or peptides that can be used to isolate the antibodies, are also covered by the disclosure. These proteins or peptides include, but are not limited to, glutathione-S-transferase, maltose binding protein, metal-binding polyhistidine, green fluorescent protein, luciferase and beta-galactosidase.

In particular embodiments, the vector that is used is pcDNA™3.1+(ThermoFisher, MA).

The disclosure also provides host cells comprising a nucleic acid or a vector described herein. Any of a variety of host cells can be used. In one embodiment, a host cell is a prokaryotic cell, for example, E. coli. In another embodiment, a host cell is a eukaryotic cell, for example, a mammalian cell, such as a Chinese Hamster Ovary (CHO) cell, COS cells, BHK cells, NSO cells or Bowes melanoma cells. Examples of human host cells are, inter alia, HeLa, 911, AT1080, A549, 293 and HEK293T cells.

The term "nucleic acid molecule" refers to a polymeric form of nucleotides and includes both sense and anti-sense strands of RNA, cDNA, genomic DNA, and synthetic forms and mixed polymers of the above. As used herein, the term nucleic acid molecule may be interchangeable with the term polynucleotide. In some embodiments, a nucleotide refers to a ribonucleotide, deoxynucleotide or a modified form of either type of nucleotide, and combinations thereof. The terms also include, but are not limited to, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-optimized nucleic acids.

The term "operably linked" refers to two or more nucleic acid sequence elements that are usually physically linked and are in a functional relationship with each other. For instance, a promoter is operably linked to a coding sequence if the promoter is able to initiate or regulate the transcription or expression of a coding sequence, in which case, the coding sequence should be understood as being "under the control of" the promoter.

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. "Isolated nucleic acid encoding an antibody or fragment thereof" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Some vectors are suitable for delivering the nucleic acid molecule or polynucleotide of the present application. Certain vectors are capable of directing the expression of nucleic acids to which they are operatively linked. Such vectors are referred to herein as expression vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art. In one embodiment, the antibody or the antigen binding fragment thereof includes Variant 1, Variant 2, Variant 3, and/or Variant 4. In some embodiments, the antibody or antigen binding fragment thereof includes Variant 1. In some embodiments, the antibody or antigen binding fragment thereof includes Variant 2. In some embodiments, the antibody or antigen binding fragment thereof includes Variant 3. In some embodiments, the antibody or antigen binding fragment thereof includes Variant 4.

The term "variant" may also refer to any naturally occurring or engineered molecule comprising one or more nucleotide or amino acid mutations. In one embodiment, the molecule is an antibody. For example, somatic variants may encompass all related naturally occurring antibodies that are part of or derived from the same B-cell lineage. Engineered variants may encompass all single mutations or combinatorial mutations made to an antibody.

Methods of Producing Antibodies

Monospecific antibodies that bind to gp120 and bispecific antibodies that bind to gp120 and human CD3 (e.g., human CD3ε or human CD3δ) can be produced by any method known in the art for the synthesis of antibodies, for example, by chemical synthesis or by recombinant expression techniques.

Methods of making monospecific antibodies are very well known in the art. Methods of making bispecific antibodies are described, for example, in U.S. Pat. Nos. 5,731,168; 5,807,706; 5,821,333; and U.S. Appl. Publ. Nos. 2003/020734 and 2002/0155537. Bispecific tetravalent antibodies, and methods of making them are described, e.g., in WO 02/096948 and WO 00/44788, the disclosures of both of which are herein incorporated by reference in its entirety. In addition, other publications relating to making bispecific antibodies include WO 91/00360, WO 92/08802, WO92/05793, and WO 93/17715; Tutt et al., *J. Immunol.* 147:60-69 (1991); U.S. Pat. Nos. 4,474,893; 4,714,681; 4,925,648; 5,573,920; 5,601,819 and 9,212,230; and Kostelny et al., *J. Immunol.* 148:1547-1553 (1992).

In one embodiment, a bispecific antibody of this disclosure is a Duobody®. Duobodies can be made by the DuoBody® technology platform (Genmab A/S) as described, e.g., in International Publication Nos. WO 2008/119353, WO 2011/131746, WO 2011/147986, and WO 2013/060867, Labrijn A F et al., *PNAS,* 110(13): 5145-5150 (2013), Gramer et al., mAbs, 5(6): 962-973 (2013), and Labrijn et al., *Nature Protocols,* 9(10): 2450-2463 (2014). This technology can be used to combine one half of a first monospecific antibody containing two heavy and two light chains with one half of a second monospecific antibody containing two heavy and two light chains. The resultant heterodimer contains one heavy chain and one light chain from the first antibody paired with one heavy chain and one light chain from the second antibody. When both of the monospecific antibodies recognize different epitopes on different antigens, the resultant heterodimer is a bispecific antibody.

For the DuoBody® platform, each of the monospecific antibodies includes a heavy chain constant region with a single point mutation in the CH3 domain. These point mutations permit a stronger interaction between the CH3 domains in the resulting bispecific antibody than between the CH3 domains in either of the monospecific antibodies without the mutations. The single point mutation in each monospecific antibody can be at residue 366, 368, 370, 399, 405, 407, or 409 (EU numbering) in the CH3 domain of the heavy chain constant region (see, WO 2011/131746). Furthermore, the single point mutation is located at a different residue in one monospecific antibody relative to the other monospecific antibody. For example, one monospecific antibody can comprise the mutation F405L (EU numbering; phenylalanine to leucine mutation at residue 405), or one of F405A, F405D, F405E, F405H, F405I, F405K, F405M, F405N, F405Q, F405S, F405T, F405V, F405W, and F405Y mutations, while the other monospecific antibody can comprise the mutation K409R (EU numbering; lysine to arginine mutation at residue 409). The heavy chain constant regions of the monospecific antibodies can be an IgG1, IgG2, IgG3, or IgG4 isotype (e.g., a human IgG1 isotype), and a bispecific antibody produced by the DuoBody® technology can be modified to alter (e.g., reduce) Fc-mediated effector functions and/or improve half-life. One method of making a Duobody® involves the following: (i) separate expression of two parental IgG1s containing single matching point mutations (i.e., K409R and F405L (or one of F405A, F405D, F405E, F405H, F405I, F405K, F405M, F405N, F405Q, F405S, F405T, F405V, F405W, and F405Y mutations) (EU numbering)) in the CH3 domain; (ii) mixing of parental IgG1s under permissive redox conditions in vitro to enable recombination of half-molecules; (iii) removal of the reductant to allow reoxidation of interchain disulfide bonds; and (iv) analysis of exchange efficiency and final product using chromatography-based or mass spectrometry (MS)-based methods (see, Labrijn et al., *Nature Protocols*, 9(10): 2450-2463 (2014)).

Another exemplary method of making bispecific antibodies is by the knobs-into-holes technology (Ridgway et al., *Protein Eng.*, 9:617-621 (1996); WO 2006/028936). The mispairing problem of Ig heavy chains that is a chief drawback for making bispecific antibodies is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some instances, antibodies of the disclosure have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass or different subclasses. In one instance, a bispecific antibody that binds to gp120 and CD3 comprises a T366W (EU numbering) mutation in the "knobs chain" and T366S, L368A, Y407V 9EU numbering) mutations in the "hole chain." In certain embodiments, an additional interchain disulfide bridge is introduced between the CH3 domains by, e.g., introducing a Y349C mutation into the "knobs chain" and a E356C mutation or a S354C mutation into the "hole chain." In certain embodiments, R409D, K370E mutations are introduced in the "knobs chain" and D399K, E357K mutations in the "hole chain." In other embodiments, Y349C, T366W mutations are introduced in one of the chains and E356C, T366S, L368A, Y407V mutations in the counterpart chain. In some embodiments. Y349C, T366W mutations are introduced in one chain and S354C, T366S, L368A, Y407V mutations in the counterpart chain. In some embodiments, Y349C, T366W mutations are introduced in one chain and S354C, T366S, L368A, Y407V mutations in the counterpart chain. In yet other embodiments, Y349C, T366W mutations are introduced in one chain and S354C, T366S, L368A, Y407V mutations in the counterpart chain (all EU numbering).

Another exemplary method of making bispecific antibodies is by using the Bispecific T-cell Engagers (BiTEs®) platform. BiTEs are made by genetically fusing a first scFv (e.g., an scFv that binds gp120) to a second scFv (e.g., an scFv that binds human CD3) via flexible peptide linker (e.g., GGGGS (SEQ ID NO:76)). See, e.g., Staerz et al., *Nature*, 314:628-631 (1985); Mack et al., PNAS, 92:7021-7025 (1995); Huehls et al., *Immunol. Cell Biol.*, 93:290-296 (2015).

Another exemplary method of making bispecific antibodies is by using the Dual-Affinity Re-targeting (DART) platform. This technology is based on the diabody format of Holliger et al. (*PNAS*, 90:6444-6448 (1993)) and further improved for stability and optimal pairing of the VH and VL chains (Johnson et al., *J Mol. Biol.*, 399:436-449 (2010); Sung et al., *J Clin Invest.*, 125(11): 4077-4090 (2015)).

Yet another exemplary method of making bispecific antibodies is by using the Trifunctional Hybrid Antibodies platform—Triomab®. This platform employs a chimeric construction made up of half of two full-length antibodies of different isotypes, mouse IgG2a and rat IgG2b. This technology relies on species-preferential heavy/light chain pairing associations. See, Lindhofer et al., *J Immunol.*, 155:219-225 (1995).

A further exemplary method of making bispecific antibodies is by using the TandAb® platform. This technology is based on the diabody concept but are designed as a single polypeptide chain VH1-VL2-VH2-VL1 comprising short linkers to prevent intra-chain pairing. Head-to-tail dimerization of this single chain results in the formation of a tetravalent homodimer (Kipriyanov et al., *J Mol. Biol.*, 293:41-56 (1999)).

Yet another method for making bispecific antibodies is the CrossMab technology. CrossMab are chimeric antibodies constituted by the halves of two full-length antibodies. For correct chain pairing, it combines two technologies: (i) the knob-into-hole which favors a correct pairing between the two heavy chains; and (ii) an exchange between the heavy and light chains of one of the two Fabs to introduce an asymmetry which avoids light-chain mispairing. See, Ridgway et al., *Protein Eng.*, 9:617-621 (1996); Schaefer et al., *PNAS*, 108:11187-11192 (2011). CrossMabs can combine two or more antigen-binding domains for targeting two or more targets or for introducing bivalency towards one target such as the 2:1 format.

The multispecific antibodies of this disclosure may be produced in bacterial or eukaryotic cells. Antibodies can also be produced in eukaryotic cells such as transformed cell lines (e.g., CHO, 293E, 293T, COS, NIH3T3). In addition, antibodies (e.g., scFv's) can be expressed in a yeast cell such as *Pichia* (see, e.g., Powers et al., *J Immunol Methods.* 251:123-35 (2001)), *Hanseula*, or *Saccharomyces*. In one embodiment, the bispecific antibodies described herein are produced in a CHO cell line. To produce the antibody of interest, a polynucleotide encoding the antibody is constructed, introduced into an expression vector, and then expressed in suitable host cells. Standard molecular biology techniques are used to prepare the recombinant expression vector, transfect the host cells, select for transformants, culture the host cells, and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341: 544-546 (1989), araB promoter (Better et al., *Science*, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., *J. Bacteriol.*, 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, and NIH3T3 cells, the expression vector includes a promoter necessary for expression in these cells, for example, an SV40 promoter (Mulligan et al., *Nature*, 277:108 (1979)), MMLV-LTR promoter, EF1α promoter (Mizushima et al., *Nucleic Acids Res.*, 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including dhfr$^-$ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

In an exemplary system for antibody expression, recombinant expression vectors encoding the antibody heavy chain and the antibody light chain of a bispecific antibody of this disclosure are introduced into dhfr$^-$ CHO cells by calcium phosphate-mediated transfection. In a specific embodiment, the dhfr– CHO cells are cells of the DG44 cell line, such as DG44i (see, e.g., Derouaz et al., *Biochem Biophys Res Commun.*, 340(4):1069-77 (2006)). Within the recombinant expression vectors, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vectors also carry a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

The multispecific antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly. Animals are also provided comprising one or more of the nucleic acids described herein.

The multispecific antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Pharmaceutical Compositions

This disclosure also includes pharmaceutical compositions comprising an antibody described herein, or a polynucleotide encoding an antibody described herein, and a pharmaceutically acceptable diluent, carrier or excipient. In certain embodiments, the pharmaceutical composition comprises a therapeutically effective amount of the antibody or polynucleotide.

Various pharmaceutically acceptable diluents, carriers, and excipients, and techniques for the preparation and use of pharmaceutical compositions will be known to those of skill in the art in light of the present disclosure. Illustrative pharmaceutical compositions and pharmaceutically acceptable diluents, carriers, and excipients are also described in Remington: The Science and Practice of Pharmacy 20th Ed.

(Lippincott, Williams & Wilkins 2003). In particular embodiments, each carrier, diluent or excipient is "acceptable" in the sense of being compatible with the other ingredients of the pharmaceutical composition and not injurious to the subject. Often, the pharmaceutically acceptable carrier is an aqueous pH-buffered solution. Some examples of materials which can serve as pharmaceutically-acceptable carriers, diluents or excipients include: sterile water; buffers, e.g., phosphate-buffered saline; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The formulation of and delivery methods of pharmaceutical compositions will generally be adapted according to the site and the disease to be treated. Exemplary formulations include, but are not limited to, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays.

Methods of Use

This disclosure provides methods for treating or preventing an HIV infection or a related disease or disorder in a subject in need thereof (e.g., a human subject), comprising providing to a subject in need thereof an effective amount of an antibody described herein, or a polynucleotide encoding the antibody. As used herein, the term "effective amount" in the context of the administration of a therapy to a subject refers to the amount of a therapy that achieves a desired prophylactic or therapeutic effect. The polynucleotide may be present in a vector, e.g., a viral vector. In particular embodiments, the related disease or disorder is caused by infection with HIV. In particular embodiments, it is acquired immune deficiency syndrome (AIDS). In particular embodiments, the subject is a virologically suppressed HIV-infected mammal, while is other embodiments, the subject is a treatment-naïve HIV-infected mammal. In certain embodiments, a treatment-naïve subject has a viral load between $10^3$ and $10^5$ copies/ml, and in certain embodiments, a virologically suppressed subject has a viral load <50 copies/ml. In particular embodiments, the subject is a mammal, e.g., a human. In certain embodiments, the subject has been diagnosed with an HIV, e.g., HIV-1 or HIV-2, infection or a related disease or disorder, e.g., AIDS, or is considered at risk for developing an HIV, e.g., HIV-1 or HIV-2, infection or a related disease or disorder, e.g., AIDS. Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

Also provided are methods for preventing or inhibiting an increase in HIV virus titer, virus replication, virus proliferation or an amount of an HIV viral DNA, HIV proviral DNA, or HIV viral protein in a subject (e.g., a human subject). In one embodiment, the method comprises providing to the subject in need thereof an amount of an antibody described herein, or a polynucleotide encoding the antibody, effective to prevent an increase in HIV titer, virus replication or an amount of an HIV protein of one or more HIV strains or isolates in the subject. In certain embodiments, the method further comprises measuring an amount of HIV viral or proviral DNA or protein at one or more time points, e.g., before and after the subject in provided with an antibody of the present disclosure. Methods and biomarkers for determining an amount of HIV viral or proviral DNA or protein in a subject are known and available in the art, and described for example, in Siliciano, J. D. et al., *Curr Opin. HIV AIDS*, 5(6):491-7 (2010), and Rouzioux, C. et al., *Curr Opin HIV AIDS*, 8(3):170-5 (2013).

The Duobody® described herein can reactivate latent HIV ex vivo in CD4$^+$ T cells isolated from combination antiretroviral therapy (cART)-suppressed patients and thus may actually increase HIV virus titer. This is a benefit of the Duobody® since it would activate latently-infected cells to express gp120 and would then potentially be targeted for elimination. Binding to CD3 can induce a partial T cell activation phenotype and activation of a latently-infected CD4$^+$ T cell leads to virus expression. Thus, also featured are methods of reversing latency of HIV in a subject in need thereof. The method involves administering to a human subject in need thereof a gp120 X CD3 Duobody® described herein. In certain embodiments, the method further comprises measuring an amount of HIV RNA, viral or proviral DNA or protein at one or more time points, e.g., before and after the subject is provided with a Duobody® of the present disclosure.

In certain aspect, the antibodies of the present disclosure may be used in, for example, methods of inhibiting certain viruses such as HIV isolates described herein, prophylactic inhibiting or preventing infections of certain viruses such as HIV isolates described herein, detection of certain viruses such as HIV isolates described herein in a sample, inhibiting certain viruses such as HIV isolates described herein, diagnosis of certain viruses such as HIV isolates described herein.

For in vivo treatment of mammalian subject, e.g., humans, the subject may be administered or provided a pharmaceutical composition comprising a multispecific antibody described herein. When used for in vivo therapy, the antibodies described herein are typically administered or provided to the patient in therapeutically effective amounts (i.e., amounts that eliminate or reduce the patient's viral burden and/or viral reservoir). The antibodies are administered or provided to a mammalian subject, e.g., a human, in accord with known methods, such as, but not limited to, intravenous administration, e.g., as a bolus or by continuous infusion over a period of time, by intramuscular, intraperitoneal, intracerebrospinal, subcutaneous, intraarticular, intrasynovial, intrathecal, oral, topical, or inhalation routes. The antibodies may be administered parenterally, when possible, at the target cell site, or intravenously. In one embodiment, administration of the antibody to the subject is via an intravenous route. In another embodiment, administration of the antibody to the subject is via a subcutaneous route. In particular embodiments, pharmaceutical compositions of the disclosure are administered to a subject systemically, parenterally, or locally.

In certain embodiments, the present disclosure provides a method for treating an HIV infection, comprising administering to a patient in need thereof a therapeutically effective amount of an antibody disclosed herein.

Combination Therapy

In certain embodiments, a method for treating or preventing an HIV infection in a human having or at risk of having the infection is provided, comprising administering to the human a therapeutically effective amount of an antibody disclosed herein, or a pharmaceutical composition thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of an antibody disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising an antibody disclosed herein, or a pharmaceutical composition thereof, in combination with one or more (e.g., one, two, three, one or two, or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of an antibody disclosed herein, or a pharmaceutical composition thereof, in combination with a therapeutically effective amount of one or more additional therapeutic agents which are suitable for treating an HIV infection.

In certain embodiments, an antibody disclosed herein, or a pharmaceutical composition thereof, is combined with one, two, three, four, or more additional therapeutic agents. In certain embodiments, an antibody disclosed herein, or a pharmaceutical composition thereof, is combined with two additional therapeutic agents. In other embodiments, an antibody disclosed herein, or a pharmaceutical composition thereof, is combined with three additional therapeutic agents. In further embodiments, an antibody disclosed herein, or a pharmaceutical composition thereof, is combined with four additional therapeutic agents. The one, two, three, four, or more additional therapeutic agents can be different therapeutic agents selected from the same class of therapeutic agents, and/or they can be selected from different classes of therapeutic agents.

In certain embodiments, an antibody disclosed herein is administered with one or more additional therapeutic agents. Co-administration of an antibody disclosed herein with one or more additional therapeutic agents generally refers to simultaneous or sequential administration of a compound disclosed herein and one or more additional therapeutic agents, such that therapeutically effective amounts of the antibody disclosed herein and the one or more additional therapeutic agents are both present in the body of the patient. When administered sequentially, the combination may be administered in two or more administrations.

Co-administration includes administration of unit dosages of the antibodies disclosed herein before or after administration of unit dosages of one or more additional therapeutic agents. For example, the antibody disclosed herein may be administered within seconds, minutes, or hours of the administration of the one or more additional therapeutic agents. In some embodiments, a unit dose of an antibody disclosed herein is administered first, followed within seconds or minutes by administration of a unit dose of one or more additional therapeutic agents. Alternatively, a unit dose of one or more additional therapeutic agents is administered first, followed by administration of a unit dose of an antibody disclosed herein within seconds or minutes. In other embodiments, a unit dose of an antibody disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of an antibody disclosed herein.

In certain embodiments, an antibody disclosed herein is combined with one or more additional therapeutic agents in a unitary dosage form for simultaneous administration to a patient, for example as a solid dosage form for oral administration.

In certain embodiments, an antibody of this disclosure is formulated as a liquid, which may optionally contain an additional therapeutic agent(s) useful for treating HIV. In certain embodiments, the liquid can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such formulations are suitable for once daily dosing. In the above embodiments, the additional therapeutic agent may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cistrans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

Examples of combination drugs that can be employed with an antibody of this disclosure include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812.

Examples of other drugs for treating HIV that can be combined with an antibody of this disclosure include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

Examples of HIV protease inhibitors that can be combined with an antibody of this disclosure include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

Examples of HIV nucleoside or non-nucleotide inhibitors of reverse transcriptase that can be combined with an antibody of this disclosure include dapivirine, delavirdine, delavirdine mesylate, doravirine, efavirenz, etravirine, lentinan, nevirapine, rilpivirine, ACC-007, AIC-292, KM-023, and VM-1500.

Examples of HIV nucleoside or nucleotide inhibitors of reverse transcriptase that can be combined with an antibody of this disclosure include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

Examples of HIV integrase inhibitors that can be combined with an antibody of this disclosure include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) that can be combined with an antibody of this disclosure include CX-05045, CX-05168, and CX-14442.

Examples of HIV entry (fusion) inhibitors that can be combined with an antibody of this disclosure include cenicriviroc, CCR5 inhibitors, gp41 inhibitors, CD4 attachment inhibitors, gp120 inhibitors, and CXCR4 inhibitors.

Examples of CCR5 inhibitors that can be combined with an antibody of this disclosure include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors that can be combined with an antibody of this disclosure include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors that can be combined with an antibody of this disclosure include ibalizumab and CADA analogs.

Examples of gp120 inhibitors that can be combined with an antibody of this disclosure include Radha-108 (receptol) 3B3-PE38, BanLec, bentonite-based nanomedicine, fostemsavir tromethamine, IQP-0831, and BMS-663068

Examples of CXCR4 inhibitors that can be combined with an antibody of this disclosure include plerixafor, ALT-1188, N15 peptide, and vMIP (Haimipu).

Examples of HIV maturation inhibitors that can be combined with an antibody of this disclosure include BMS-955176 and GSK-2838232.

Examples of latency reversing agents that can be combined with an antibody of this disclosure include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), NIZ-985, IL-15, JQ1, disulfiram, amphotericin B, and ubiquitin inhibitors such as largazole analogs, and GSK-343. Examples of HDAC inhibitors include romidepsin, vorinostat, and panobinostat. Examples of PKC activators include indolactam, prostratin, ingenol B, and DAG-lactones.

Examples of capsid inhibitors that can be combined with an antibody of this disclosure include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

Examples of immune-based therapies that can be combined with an antibody of this disclosure include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (PD-1) modulators; programmed death-ligand 1 (PD-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103.

Examples of PI3K inhibitors that can be combined with an antibody of this disclosure include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Examples of Integrin alpha-4/beta-7 antagonists that can be combined with an antibody of this disclosure include PTG-100, TRK-170, abrilumab, etrolizumab, carotegrast methyl, and vedolizumab.

Examples of HIV antibodies, bispecific antibodies, and "antibody-like" therapeutic proteins that can be combined with an antibody of this disclosure include DARTs®, DUOBODIES®, BITES®, XmAbs®, TandAbs®, Fab derivatives, bNAbs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66. Examples of those targeting HIV in such a manner include bavituximab, UB-421, C2F5, C2G12, C4E10, C2F5+C2G12+C4E10, 3BNC-117, PGT145, PGT121, PGDM1400, MDX010 (ipilimumab), VRC01, A32, 7B2, 10E8, VRC-07-523, VRC-HIVMAB080-00-AB, MGD-014 and VRC07. Additional examples of antibodies targeting HIV include PGT122, PGT123, PGT124, 10-1074, PGT133, PGT134, PG16, PG9, PGT151, or the like.

Examples of pharmacokinetic enhancers that can be combined with an antibody of this disclosure include cobicistat and ritonavir.

Examples of additional therapeutic agents that can be combined with an antibody of this disclosure include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006592 (Pharma Resources), US 20140221356 (Gilead Sciences), US 20100143301 (Gilead Sciences) and WO 2013/091096 (Boehringer Ingelheim).

Examples of HIV vaccines that can be combined with an antibody of this disclosure include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3 S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HW-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVax-Tat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVlCH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine.

Therapeutic agents used for birth control (contraceptive) that can be combined with an antibody of this disclosure include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In a particular embodiment, an antibody disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a specific embodiment, an antibody disclosed herein, or a pharmaceutical composition thereof, is combined with an HIV nucleoside or nucleotide inhibitor of reverse transcriptase and an HIV non-nucleoside inhibitor of reverse transcriptase. In another specific embodiment, an antibody disclosed herein, or a pharmaceutical composition thereof, is combined with an HIV nucleoside or nucleotide inhibitor of reverse transcriptase, and an HIV protease inhibiting compound. In an additional embodiment, an antibody disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an antibody disclosed herein, or a pharmaceutical composition thereof, is combined with at least one HIV nucleoside inhibitor of reverse transcriptase, an integrase inhibitor, and a pharmacokinetic enhancer. In another embodiment, an antibody disclosed herein, or a pharmaceutical composition thereof, is combined with two HIV nucleoside or nucleotide inhibitors of reverse transcriptase.

In a particular embodiment, an antibody disclosed herein, or a pharmaceutical composition thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, an antibody disclosed herein, or a pharmaceutical composition thereof, is combined with tenofovir, tenofovir disoproxil, tenofovir disoproxil fumarate, tenofovir alafenamide, or tenofovir alafenamide hemifumarate.

In a particular embodiment, an antibody disclosed herein, or a pharmaceutical composition thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, an antibody disclosed herein, or a pharmaceutical composition thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In another particular embodiment, an antibody disclosed herein, or a pharmaceutical composition thereof, is combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Kits

This disclosure also encompasses kits comprising one or more antibodies described herein or conjugates thereof. In one instance, provided herein is a pharmaceutical pack or kit comprising one or more containers filled with one or more of the ingredients of the pharmaceutical compositions described herein, such as one or more antibodies provided herein. In some instances, the kits contain a pharmaceutical composition described herein. In one embodiment, kits comprising an antibody disclosed herein, or a pharmaceutical composition thereof, in combination with one or more (e.g., one, two, three, one or two, or one to three) additional therapeutic agents (such as those disclosed above) are provided. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Virus Neutralization Activity

PGT121 is a highly potent neutralizing antibody with broad coverage of HIV subtype B isolates (IC50 0.03 μg/ml, 80% breadth). The potency (measured as IC50 or IC95) and breadth (% of isolates neutralized from the panel tested) of neutralization of PGT121 and variants thereof were examined using two different published assay formats:

i) the CEM-NKr-CCR5-LucR reporter cell-line based assay (Li et al. 2005. J Vir 79(16): 10108-10125), which is compatible for screening antibodies against pseudotyped as well as replication competent HIV isolates; and ii) the Monogram HIV PhenoSense Neutralization Assay (Monogram Biosciences) which uses a luciferase reporter virus pseudotyped with HIV Env variants of interest (Richman et al. 2003. *PNAS* 100(7): 4144-4149).

In the reporter cell-line-based CEM-NKr-CCR5-LucR neutralization assay, a multicycle viral replication assay (Spenlehauer et al. 2001. Virology, doi:10.1006/viro.2000.0780), antibodies were screened against a panel of five replication competent clinical isolates including the lab adapted HIV-1 BaL strain and subtype B isolates 93HT593, 92US657, 92US712 and 92US727 amplified from patient plasma samples (NIH AIDS Reagent Program).

Neutralization potencies of several variant PGT-121 antibodies were observed to be comparable to that of PGT-121 (also referred to as PGT-121 LO6 herein) for the five viruses tested, suggesting that the modifications present in these antibodies as compared to PGT-121 had minimal impact on the determinants of antigen recognition and binding (Table 5 below with the CEM-NKr-CCR5-Luc cells). Other variants (e.g. PGT121.60 and PGT121.61) exhibited a 2-3-fold increase in neutralization potency against this limited virus panel, as compared to PGT121.

subtype B viruses isolated from pre-ART baseline plasma samples from ART naïve HIV patients enrolled in clinical trials and included 113 CCR5-tropic (R5) viruses, 28 viruses of dual or mixed-tropism (DM) and one CXCR4 tropic (X4) virus. Given that HIV-1 Env exhibits significant diversity among patient isolates, between clades, as well as within a clade, neutralization activity of PGT121 and variants was also profiled against viruses representing non-B clades using a panel of viruses from Monogram's library collection. The Monogram HIV PhenoSense Neutralization Assay was utilized to profile large collections of patient isolates, thereby enabling a more rigorous profiling of both breadth and potency of PGT121 and the variants generated. The results are shown in Tables 6-9. Results showed that variants of PGT121 such as PGT121.60 showed enhanced neutralization activity against select viruses.

TABLE 6

Neutralization activity ($IC_{50}$) of PGT121 and PGT121.60 against subtype B viruses

| Isolate | Tropism | PGT121 IC50 (μg/mL) | PGT121.60 IC50 (μg/mL) | PGT121 IC50/ PGT121.60 IC50 |
|---|---|---|---|---|
| MGRM-B-106 | DM | 0.0041 | 0.0010 | 4.1 |
| MGRM-B-112 | DM | 0.0145 | 0.0058 | 2.5 |
| MGRM-B-136 | X4 | 0.0087 | 0.0071 | 1.2 |
| MGRM-B-105 | DM | 0.0219 | 0.0076 | 2.9 |
| MGRM-B-132 | X4 | 0.0092 | 0.0077 | 1.2 |
| MGRM-B-110 | DM | 0.0373 | 0.0113 | 3.3 |
| MGRM-B-115 | DM | 0.2362 | 0.1412 | 1.7 |
| MGRM-B-111 | DM | 2.1336 | 0.9549 | 2.2 |
| MGRM-B-118 | DM | 2.4658 | 3.3142 | 0.7 |

TABLE 5

Neutralization activity of PGT121, and select variants against HIV-1 strains BaL, HT593, US657, US712 and US727, as observed using the CEM.NKr.CCR5.LucR based assay. Data represents mean of 2 to 3 repeats

| mAb | Neutralization Potency, $IC_{50}$ (μg/mL) | | | | | PGT121 $IC_{50}$/Variant $IC_{50}$ | | | | |
|---|---|---|---|---|---|---|---|---|---|---|
| | BaL | HT593 | US657 | US712 | US727 | BaL | HT593 | US657 | US712 | US727 |
| PGT121 | 0.020 | 0.216 | 0.111 | 0.017 | 0.013 | 1 | 1 | 1 | 1 | 1 |
| PGT121.42 | 0.015 | 0.155 | 0.096 | 0.020 | 0.015 | 1.3 | 1.4 | 1.2 | 0.9 | 0.9 |
| PGT121.43 | 0.013 | 0.127 | 0.092 | 0.016 | 0.012 | 1.5 | 1.7 | 1.2 | 1.1 | 1.1 |
| PGT121.56 | 0.02 | 0.164 | 0.142 | 0.019 | 0.011 | 1.0 | 1.3 | 0.8 | 0.9 | 1.2 |
| PGT121.60 | 0.007 | 0.141 | 0.062 | 0.008 | 0.007 | 2.9 | 1.5 | 1.8 | 2.1 | 1.9 |
| PGT121.61 | 0.008 | 0.343 | 0.072 | 0.008 | 0.005 | 2.5 | 0.6 | 1.5 | 2.1 | 2.6 |

In the Monogram neutralization assay, the Env (gp160) coding region was amplified from plasma viral RNA isolated from HIV+ART naïve viremic patients and cloned into an expression vector, such that the virus quasispecies distribution present in the patient plasma samples is maintained. The expression vectors were then used to generate HIV-1 pseudovirus swarms expressing the patient-derived Env proteins. Two panels of clade B clinical isolates were generated for the Monogram neutralization assay: Panel 1 (Monogram Clinical Isolates panel) comprised 63 isolates from the Monogram library collection, and included 33 or more CCR5-tropic viruses, 15 or more CXCR4-tropic (X4) and 15 or more viruses of dual-mixed (DM) tropism; and Panel 2 (Gilead clinical isolates panel) comprised 142

TABLE 7

Neutralization potency of PGT121 and PGT121.60 against subtype B viruses

| Virus ID | PGT121 IC50 (μg/mL) | PGT121.60 IC50 (μg/mL) | PGT121 IC50/PGT121.60 IC50 |
|---|---|---|---|
| 15-124986 | 0.0048 | 0.0015 | 3.2 |
| 15-124918 | 0.0054 | 0.0018 | 3.0 |
| 15-124914 | 0.0059 | 0.0020 | 3.0 |
| 15-124964 | 0.0092 | 0.0026 | 3.5 |
| 15-124906 | 0.0550 | 0.0103 | 5.3 |
| 15-124904 | 0.0375 | 0.0121 | 3.1 |
| 15-102514 | 0.0450 | 0.0128 | 3.5 |

TABLE 7-continued

Neutralization potency of PGT121 and PGT121.60 against subtype B viruses

| Virus ID | PGT121 IC50 (μg/mL) | PGT121.60 IC50 (μg/mL) | PGT121 IC50/PGT121.60 IC50 |
|---|---|---|---|
| 15-101757 | 0.0621 | 0.0132 | 4.7 |
| 15-124987 | 0.0510 | 0.0163 | 3.1 |
| 15-124962 | 0.0955 | 0.0277 | 3.4 |
| 15-124970 | 0.1101 | 0.0285 | 3.9 |
| 15-124950 | 0.2996 | 0.0995 | 3.0 |
| 15-124975 | 0.5775 | 0.1052 | 5.5 |
| 15-124934 | 9.6415 | 0.7973 | 12.1 |
| 15-101608 | 6.7016 | 1.8392 | 3.6 |
| 15-124963 | 16.8855 | 2.0546 | 8.2 |

TABLE 8

Neutralization potency and coverage of PGT121 and select variants against 92 subtype B viruses

| mAb | Median IC95 (μg/mL) | PGT121 IC50/Variant IC50 | Coverage (%) |
|---|---|---|---|
| PGT121 | 0.329 | 1.0 | 57.6 |
| PGT121.13 | 0.629 | 0.5 | 51.1 |
| PGT121.42 | 0.277 | 1.2 | 63.0 |
| PGT121.43 | 0.266 | 1.2 | 62.0 |
| PGT121.54 | 0.283 | 1.2 | 63.0 |
| PGT121.55 | 0.275 | 1.2 | 63.0 |
| PGT121.56 | 0.265 | 1.2 | 62.0 |
| PGT121.58 | 0.244 | 1.3 | 58.7 |
| PGT121.59 | 0.253 | 1.3 | 60.9 |
| PGT121.60 | 0.177 | 1.9 | 59.8 |
| PGT121.61 | 0.327 | 1.0 | 58.7 |
| PGT121.62 | 0.254 | 1.3 | 63.0 |
| PGT121.63 | 0.379 | 0.9 | 60.9 |
| PGT121.64 | 0.129 | 2.6 | 59.8 |
| PGT121.65 | 0.165 | 2.0 | 59.8 |

TABLE 9

Neutralization activity of PGT121 and PGT121.60 against multiclade viruses

| Virus ID | PGT121 IC50 (μg/mL) | PGT121.60 IC50 (μg/mL) | PGT121 IC50/PGT121.60 IC50 |
|---|---|---|---|
| MGRM-Chronic-B-004 | 0.0078 | 0.0013 | 6.0 |
| MGRM-Acute-B-005 | 0.0043 | 0.0014 | 3.1 |
| MGRM-Acute-B-009 | 0.0037 | 0.0016 | 2.3 |
| MGRM-Chronic-B-020 | 0.0038 | 0.0018 | 2.1 |
| MGRM-Chronic-B-006 | 0.0056 | 0.0020 | 2.8 |
| MGRM-Chronic-B-023 | 0.0043 | 0.0034 | 1.3 |
| MGRM-Chronic-B-008 | 0.0111 | 0.0056 | 2.0 |
| MGRM-Chronic-B-010 | 0.0154 | 0.0074 | 2.1 |
| MGRM-Chronic-B-003 | 0.0080 | 0.0079 | 1.0 |
| MGRM-Chronic-B-009 | 0.0224 | 0.0112 | 2.0 |
| MGRM-Acute-B-003 | 0.0361 | 0.0179 | 2.0 |
| MGRM-Acute-B-007 | 0.0466 | 0.0255 | 1.8 |
| MGRM-Chronic-B-016 | 0.0583 | 0.0283 | 2.1 |
| MGRM-Acute-B-001 | 0.0739 | 0.0313 | 2.4 |
| MGRM-Acute-B-010 | 0.0466 | 0.0328 | 1.4 |
| MGRM-Chronic-B-012 | 0.0914 | 0.0409 | 2.2 |
| MGRM-Acute-B-004 | 0.0933 | 0.0497 | 1.9 |
| MGRM-Chronic-B-002 | 0.1010 | 0.0649 | 1.6 |
| MGRM-Chronic-B-005 | 0.0866 | 0.0720 | 1.2 |
| MGRM-Acute-B-006 | 0.1307 | 0.0966 | 1.4 |
| MGRM-Chronic-B-001 | 0.1257 | 0.0985 | 1.3 |
| MGRM-Chronic-B-014 | 0.2879 | 0.1334 | 2.2 |
| MGRM-Chronic-B-015 | 0.2736 | 0.1855 | 1.5 |
| MGRM-Chronic-B-019 | 0.3462 | 0.1993 | 1.7 |
| MGRM-Chronic-B-007 | 2.1241 | 2.5544 | 0.8 |
| MGRM-Chronic-B-022 | >50 | 11.4677 | |
| MGRM-C-026 | 0.0016 | 0.0004 | 4.0 |
| MGRM-C-011 | 0.0028 | 0.0012 | 2.3 |
| MGRM-C-006 | 0.0091 | 0.0030 | 3.0 |
| MGRM-C-027 | 0.0054 | 0.0038 | 1.4 |
| MGRM-C-022 | 0.0101 | 0.0038 | 2.7 |
| MGRM-C-023 | 0.0179 | 0.0044 | 4.1 |
| MGRM-C-008 | 0.0075 | 0.0044 | 1.7 |
| MGRM-C-017 | 0.0087 | 0.0058 | 1.5 |
| MGRM-C-004 | 0.0118 | 0.0064 | 1.8 |
| MGRM-C-005 | 0.0145 | 0.0078 | 1.9 |
| MGRM-C-002 | 0.0219 | 0.0095 | 2.3 |
| MGRM-C-016 | 0.0083 | 0.0137 | 0.6 |
| MGRM-C-012 | 0.1060 | 0.0338 | 3.1 |
| MGRM-C-024 | 0.1703 | 0.0826 | 2.1 |
| MGRM-C-007 | 0.2868 | 0.1993 | 1.4 |
| MGRM-C-028 | 1.3581 | 0.7440 | 1.8 |
| MGRM-C-018 | 28.1619 | 10.3254 | 2.7 |
| MGRM-C-013 | 36.4162 | 12.2616 | 3.0 |
| MGRM-C-020 | >50 | 14.8835 | |
| MGRM-A-014 | 0.0032 | 0.0010 | 3.2 |
| MGRM-A-002 | 0.0199 | 0.0047 | 4.2 |
| MGRM-A-009 | 0.0072 | 0.0074 | 1.0 |
| MGRM-A-012 | 0.1364 | 0.0397 | 3.4 |
| MGRM-A-013 | 0.6126 | 0.0561 | 10.9 |
| MGRM-A-003 | 0.2001 | 0.0865 | 2.3 |
| MGRM-A-010 | 1.1108 | 0.7452 | 1.5 |
| MGRM-A-006 | 1.0250 | 4.0544 | 0.3 |
| MGRM-AG-006 | 0.0242 | 0.0106 | 2.3 |
| MGRM-AG-009 | 0.1000 | 0.0868 | 1.2 |
| MGRM-AG-007 | 0.1649 | 0.1082 | 1.5 |
| MGRM-AG-005 | 1.5876 | 0.2029 | 7.8 |
| MGRM-AG-001 | 4.6658 | 1.4409 | 3.2 |
| MGRM-AG-008 | 1.7322 | 1.7064 | 1.0 |
| MGRM-D-002 | 0.0049 | 0.0015 | 3.3 |
| MGRM-D-014 | 0.0068 | 0.0019 | 3.6 |
| MGRM-D-011 | 0.0122 | 0.0043 | 2.8 |
| MGRM-D-001 | 0.7988 | 0.4310 | 1.9 |
| MGRM-F1-010 | 0.0092 | 0.0125 | 0.7 |
| MGRM-F1-018 | 0.0244 | 0.0201 | 1.2 |
| MGRM-F1-020 | 0.0603 | 0.0410 | 1.5 |
| MGRM-F1-014 | 0.0551 | 0.0509 | 1.1 |
| MGRM-F1-013 | 0.0547 | 0.0871 | 0.6 |
| MGRM-F1-016 | 0.9707 | 0.5219 | 1.9 |
| MGRM-F1-004 | 4.7363 | 0.5474 | 8.7 |
| MGRM-F1-012 | 2.3340 | 1.1877 | 2.0 |
| MGRM-F1-006 | 8.8384 | 2.3278 | 3.8 |
| MGRM-F1-015 | 32.6175 | 11.5867 | 2.8 |
| MGRM-G-014 | 0.0035 | 0.0034 | 1.0 |
| MGRM-G-001 | 0.0022 | 0.0050 | 0.4 |
| MGRM-G-019 | 0.0079 | 0.0091 | 0.9 |
| MGRM-G-024 | 0.0240 | 0.0119 | 2.0 |
| MGRM-G-017 | 0.0258 | 0.0255 | 1.0 |
| MGRM-G-004 | 0.3741 | 0.0460 | 8.1 |
| MGRM-G-013 | 1.8198 | 1.4978 | 1.2 |
| MGRM-G-011 | 2.1778 | 1.9067 | 1.1 |

These experiments demonstrated an unexpected improvement in X4-tropic HIV neutralization by Fc enhanced PGT121. HIV can utilize two co-receptors in addition to CD4 for entry into T cells—either CXCR4 or CCR5. The co-receptor binding is mediated by Env, the target of the broadly neutralizing antibodies described herein. Different strains of HIV with different sequences thus preferentially use CXCR4 (known as X4-tropic), CCR5 (known as R5-tropic) or both (known as X4/R5 or dual-tropic). Virus pools showing both R5 and X4 tropism (referred to as Dual-Mixed or DM) may contain mixtures of R5, X4 and or dual tropic strains. PGT121 generally shows poor sensitivity (low potency and breadth) against X4 isolates, preferentially neutralizing R5 tropic viruses. Addition of the Fc mutations DEAL+LS into PGT121 (PGT121.56) specifically enhanced its neutralization activity against DM and X4 tropic viruses (median IC50 enhancement of 2-fold and up to about 20-fold enhancement for at least one isolate. While some PGT121 Fab variants (e.g. PGT121.13 and PGT121.22) exhibited reduced neutralization potency against R5 DM and X4 viruses, several of the engineered PGT121 Fab variants carrying the DEAL+LS Fc mutations, including PGT121.56 with the WT Fab were more potent at neutralizing DM and X4 viruses compared to R5 viruses (P<0.0001) (data not shown). This is highly unexpected as HIV neutralization is thought to be mediated exclusively by the Fab domain rather than the Fc domain. Among R5 isolates, a 2- to 3-fold enhancement in neutralization was observed in about 46% of isolates tested. The DEAL+LS mutation is present in certain antibodies and fragments thereof of the present disclosure. Additional modifications introduced to PGT121.56 further improved neutralization activity of select variants (e.g., PGT121.60).

Breadth of coverage was calculated as the percentage of viruses neutralized at an IC95 <15 µg/ml. Potency was determined by calculating median IC95 values across viruses with IC95 <15 µg/ml. When tested against both panels of HIV-1 isolates, comprising 89 clade B isolates in total, antibodies of the present disclosure exhibited no loss in neutralization activity compared to PGT121 (data not shown). Potency of certain antibodies was near identical to PGT121, with a slightly improved neutralization breadth. The neutralization profiling also served as a surrogate assessment of the ability of the antibodies relative to PGT-121 to recognize and bind diverse Env antigens from a wide range of HIV-1 clinical isolates. Data from profiling of various antibodies showed that antibodies with reduced neutralization potency also exhibited reduced ADCC activity (data not shown), suggesting a positive correlation between the neutralization activity and ADCC activity of the antibodies, and supporting the use of neutralization breadth as a surrogate for the assessment of ADCC breadth.

Example 2: Immunogenicity Studies

Three methods were used to assess immunogenicity and guide engineering to remove immunogenic motifs in PGT121. In silico prediction tools were used to identify sites of potential risk of immunogenicity in the PGT121 antibody, and also to guide engineering efforts to improve manufacturability (e.g. removal of glycosylation sites, improvement of low pH hold stability) while preventing introduction of novel T cell epitopes. Based on this analysis, modifications of the framework regions were made in antibodies of the present disclosure to reduce immunogenicity which had a low risk of impacting functional activity. In addition, to further identify potentially immunogenic motifs within the variable domain of one antibody of the present disclosure, an ex vivo human T cell activation assay, the EpiScreen™ (Antitope, Ltd., Cambridge, UK) was employed. CD4+ T cells responses induced in 50 healthy donors, representing a variety of HLA haplotypes, in response to overlapping 15 amino acid peptides derived from the antibody, and KLH (keyhole limpet hemocyanin, positive control) were assessed using H-thymidine incorporation assay to measure T-cell proliferation. The assay enabled the localization of specific T cell epitopes in the primary antibody sequence to guide antibody engineering. It also provided a ranking of the relative immunogenicity of T cell epitopes with tested antibodies (data not shown).

To assess clinical immunogenicity risk of selected antibody variants, the EpiScreen™ time course T-cell assay (Antitope, Ltd., Cambridge, UK) was used to measure T-cell activation induced by intact antibodies. The whole molecule assay was conducted as described (Baker and Jones 2007. Curr. Opin. Drug Discov. Devel. 10: 219-227). Thus, this assay takes into account not just T-cell epitope content, but also the processing of the native IgG. Unlike the in silico and peptide scanning assays, the whole molecule ex vivo T-cell activation assay can provide an assessment of the relative clinical risk of a given antibody, and in certain cases may be used to predict clinical immunogenicity rates as described (Baker and Jones 2007 Curr. Opin. Drug Discov. Devel. 10:219-227).

Many clinical stage antibodies have been run in this assay, and antibodies showing little to no clinical immunogenicity have scores near or below 10% in this assay while antibodies showing high clinical immunogenicity such as Alemtuzumab and Infliximab show scores in the 25-40% range (Baker and Jones 2007. Curr. Opin. Drug Discov. Devel. 10:219-227). PGT121.42, PGT121.60, PGT121.61 and PGT121.65 showed reduced donor response rates when compared to PGT121 WT (i.e., PGT-121 L06), supporting a reduced risk of clinical immunogenicity for these variants (data not shown).

Example 3: FcRn Binding

The neonatal Fc receptor (FcRn) is an Fc receptor that has been shown to play a major role in regulating the pharmacokinetic s of IgG molecules in human and preclinical species. Following endocytosis, at acidic pH (<6.5), FcRn binds to the Fc portion of IgG with high affinity. FcRn bound IgG is recycled back to the extracellular space, where at physiological pH IgG binding affinity is reduced and IgG is released back into the circulation. Free IgG that is not salvaged by the FcRn pathway is degraded in the lysosome to endogenous amino acids. The relative binding affinity characteristics of IgG to FcRn at pH 6.0/7.0 has become a well-established correlate for ranking the half-life of IgGs in vivo and a design feature for pharmacokinetic optimization.

The binding of antibodies to FcRn of various antibody variants at different pHs was determined. A 96-well Maxisorp plate was coated with 100 ul of 5 µg/ml FcRn. The plate was incubated overnight at 4° C., and then blocked with 4% skim milk for 2 hr at room temperature after washing 3 times with 0.05% Tween 20 washing buffer. The plate was incubated with 3-fold serial dilution of primary antibody for 1 hr at room temperature. The plate was then washed 3 times and 100 µL of Fab-anti-human Fab-HRP or Goat anti-human IgG-HRP secondary antibody diluted in 4% skimmed milk was added. Plates were then incubated 50 min at room temperature, washed three times, and 100 µL fresh TMB substrate was added. Plates were developed for 3 minutes on bench with gentle shaking. Plate was quenched with 100 µL 1M HCl, shaken briefly, read at A450 on a spectramax m5 plate reader.

Relative to PGT-121, antibodies of the present disclosure comprising LS mutations in the Fc portion of IgG that interacts with FcRn showed a significant improvement in FcRn binding at pH 6.0 with lesser impact on binding at neutral pH of 7.0, as represented by the ratio of pH 7.0/6.0 for Human FcRn. The improved binding was attributed to the presence of the LS mutations and is predicted to provide for a prolonged half-life in humans relative to PGT-121. Data is shown in Table 10.

TABLE 10

Human FcRn binding data for PGT121 and variants

| PGT121 Variants | pH 6.0 $EC_{50}$ (nM) | pH 7.0 $EC_{50}$ (nM) | Ratio pH 7.0/6.0 | Fold vs PGT121 |
|---|---|---|---|---|
| PGT121 | 10.9 | 358 | 33 | 1 |
| 121.42 | 0.41 | 69.8 | 170 | 5 |
| 121.56 | 0.47 | 102.2 | 217 | 7 |
| 121.60 | 0.22 | 78 | 355 | 11 |
| 121.61 | 0.13 | 139.5 | 1073 | 33 |
| 121.64 | 1.59 | 125.1 | 79 | 2 |
| 121.65 | 0.57 | 103.6 | 182 | 6 |

This data shows significant improvement of PGT121.60 and 61 over PGT121.56 or PGT121.42. PGT121.56 is the WT Fab with DEAL+LS Fc. This suggests that the Fab mutations in PGT121.60 and 61 improve FcRn binding. PGT121.64 and PGT121.65 do not show this improvement, suggesting that the Fab modifications in these two variants may actually reduce FcRn binding.

Example 4: In Vivo Profiling

PGT121 and several antibodies from the present application were assayed to characterize their basic pharmacokinetic profiles to ensure that the Fab/Fc modifications present in the antibodies of the present disclosure enhanced, and did not significantly perturb, the PGT121 intrinsic pharmacokinetic behavior. The in vivo disposition of PGT121 and several other antibodies of disclosure were characterized after a single intravenous (IV) 1.0 mg/kg dose in two male naïve cynomolgus monkeys (n=2). Serum samples were collected from monkeys and analyzed using a bioanalytical method (described herein) to determine serum concentration-time profiles and mean serum pharmacokinetic parameters by non-compartmental pharmacokinetic analysis (NCA).

In a separate study, the intrinsic pharmacokinetic behavior of PGT121, PGT121 LS, and new lots of PGT121.42 and PGT121.60 were characterized after a single IV 10.0 mg/kg dose in three male naïve cynomolgus monkeys (n=3). Serum samples were collected and analyzed using a bioanalytical method (described herein) to determine serum concentration-time profiles and mean serum pharmacokinetic parameters by non-compartmental pharmacokinetic analysis (NCA). The mean serum pharmacokinetic parameters of PGT121, PGT121.42, PGT121.43, PGT121.60, and PGT121.61 were determined from the non-compartmental pharmacokinetic analysis of the concentration-time profiles and are depicted in Table 11. All antibodies of the disclosure that were tested in vivo had comparable or improved pharmacokinetics (as defined herein) relative to PGT121.

TABLE 11

Pharmacokinetic parameters of PGT121 and variants after IV administration (1 mg/kg) in naïve cynomolgus monkeys (n = 2)

| mAb Variant | $AUC_{0-\infty}$ (day*ug/mL) | Cl (mL/day/kg) | $V_d$ (mL/kg) | $t_{1/2}$ (day) |
|---|---|---|---|---|
| PGT121 | 120 | 8.38 | 89.9 | 7.5 |
| PGT121.42 | 217 | 4.63 | 77.9 | 11.8 |
| PGT121.43 | 191 | 5.25 | 70.0 | 9.1 |
| PGT121.60 | 127 | 7.95 | 113 | 9.9 |
| PGT121.61 | 117 | 8.76 | 127 | 10.5 |

The mean serum pharmacokinetic parameters of PGT121, PGT121 LS, PGT121.42, and PGT121.60 were determined from the non-compartmental pharmacokinetic analysis of the concentration-time profiles and are depicted in Table 12.

TABLE 12

Pharmacokinetic parameters of PGT121, PGT121 LS, PGT121.42, and PGT121.60 after IV administration (10 mg/kg) in naïve cynomolgus monkeys (n = 3)

| Test Article | $AUC_{0-\infty}$ (day*µg/mL) | Cl (mL/day/kg) | $V_d$ (mL/kg) | $t_{1/2}$ (day) |
|---|---|---|---|---|
| PGT121 | 1510 | 7.0 | 111 | 11.4 |
| PGT121 LS | 3670 | 2.8 | 95.1 | 24.3 |
| PGT121.42 | 1240 | 8.2 | 97.9 | 8.2 |
| PGT121.60 | 1490 | 7.0 | 96.4 | 9.7 |

All antibodies of the disclosure that were tested in vivo had comparable or improved pharmacokinetics (as defined herein) relative to PGT121. PGT121.60 showed increased potency against the tested viruses, compared to PGT121 (data not shown). PGT121 variants such as PGT121.60, PGT121.64 and PGT121.65 exhibited improved potency across all viral isolates tested (data not shown). This suggests that the modifications made (likely the modifications made to the antigen contact residues outside the CDRs) improved neutralization potency. PGT121.60 showed increased neutralizing activities against the viruses representing B and non-B subtypes, compared to PGT121 (data not shown).

Example 5: Assessing the Ability of a Gp120 X CD3 Duobody to Kill HIV-Infected Cells The killing activity of an Exemplary gp120 X CD3 Duobody® (the heavy chain sequence of the gp120 portion of the Duobody® is provided below, the light chain of the gp120 portion of the Duobody® had the sequence set forth in SEQ ID NO: 10; the heavy chain sequence of the CD3 portion of the Duobody® is provided below, the light chain of the CD3 portion of the Duobody® had the sequence set forth in SEQ ID NO.: 20) and the monospecific PGT121.60 (SEQ ID NOs.: 41 and 10) was assessed against 22 primary HIV-1 isolates or clones. Each virus was assessed with an average of 4 healthy PBMC donors (see, Table 13). The proportion of infected cells killed (Emax) was significantly higher with the Exemplary gp120 X CD3 Duobody® (mean±SD; 70%±11%) than with PGT121.60 (mean±SD; 56%±16%; paired T-test, P=0.001). The Exemplary gp120 X CD3 Duobody® was also significantly more potent than PGT121.60, achieving $EC_{50}$ values of 0.129 µg/mL±0.074 µg/mL compared to 1.034 µg/mL 1.408 µg/mL for PGT121.60 (paired T-test, P=0.007). The mean fold change in $EC_{50}$ of the Exemplary gp120 X CD3 Duobody® compared to PGT121.60 was 21-fold.

TABLE 13

Summary table of killing activity of Exemplary gp120 X CD3 Duobody® and PGT-121.60

| | | Emax | | | | EC50 (µg/mL) | | | | |
|---|---|---|---|---|---|---|---|---|---|---|
| | # of donors | Exemplary gp120 X CD3 Duobody® | | PGT-121.60 | | Exemplary gp120 X CD3 Duobody® | | PGT-121.60 | | Fold change in |
| Virus ID | in tested | Mean | SD | Mean | SD | Mean | SD | Mean | SD | EC$_{50}$ |
| 593 | 2 | 42 | 12 | 56 | 20 | 0.015 | 0.0003 | 0.912 | 0.547 | 61 |
| 7051 | 3 | 50 | 16 | 49 | 20 | 0.018 | 0.022 | 0.394 | 0.487 | 22 |
| 7015 | 3 | 53 | 17 | 55 | 25 | 0.191 | 0.105 | 0.516 | 0.428 | 3 |
| 8339 | 5 | 56 | 17 | 13 | 17 | 0.670 | 0.246 | 3.814 | 3.809 | 6 |
| REJO | 5 | 56 | 26 | 0 | 10 | 0.435 | 0.264 | 2.595 | 4.490 | 6 |
| 8176 | 2 | 60 | 15 | 56 | 16 | 0.029 | 0.037 | 1.007 | 1.280 | 35 |
| 7467 | 5 | 62 | 20 | 54 | 24 | 0.039 | 0.055 | 0.139 | 0.143 | 4 |
| 8320 | 2 | 64 | 4 | 0 | 18 | 0.906 | 0.389 | 2.122 | 2.932 | 2 |
| CH106 | 5 | 64 | 14 | 46 | 43 | 0.392 | 0.375 | 6.167 | 12.462 | 16 |
| 7406 | 3 | 66 | 5 | 63 | 11 | 0.009 | 0.006 | 0.090 | 0.109 | 10 |
| 8089 | 5 | 72 | 17 | 64 | 16 | 0.024 | 0.037 | 0.226 | 0.374 | 9 |
| 727 | 5 | 74 | 7 | 66 | 12 | 0.003 | 0.003 | 0.034 | 0.028 | 13 |
| 657 | 5 | 75 | 17 | 62 | 17 | 0.029 | 0.023 | 1.442 | 1.470 | 50 |
| 7552 | 8 | 77 | 13 | 66 | 13 | 0.008 | 0.005 | 0.011 | 0.005 | 1 |
| 7576 | 4 | 79 | 5 | 71 | 6 | 0.005 | 0.001 | 0.016 | 0.003 | 3 |
| CH058 | 2 | 79 | 5 | 71 | 8 | 0.004 | 0.001 | 0.160 | 0.000 | 45 |
| WITO | 2 | 82 | 5 | 71 | 23 | 0.046 | 0.049 | 2.517 | 1.858 | 55 |
| 712 | 2 | 84 | 0 | 71 | 9 | 0.003 | 0.0001 | 0.084 | 0.044 | 26 |
| 1489 | 4 | 85 | 11 | 70 | 8 | 0.007 | 0.001 | 0.276 | 0.339 | 40 |
| 8106 | 3 | 85 | 6 | 75 | 8 | 0.005 | 0.003 | 0.110 | 0.141 | 24 |
| 8398 | 5 | 87 | 5 | 76 | 11 | 0.010 | 0.004 | 0.067 | 0.021 | 7 |
| BaL | 2 | 89 | 4 | 73 | 12 | 0.002 | 0.001 | 0.048 | 0.010 | 20 |
| mean | 4 | 70 | 11 | 56 | 16 | 0.129 | 0.074 | 1.034 | 1.408 | 21 |

In sum, the Exemplary gp120 X CD3 Duobody® kills a significantly greater proportion of HIV-infected cells at significantly lower concentrations than PGT121.60.

Heavy Chain Sequence of gp120 portion of Duobody®:

(SEQ ID NO: 92)
QMQLQESGPGLVKPSETLSLTCSVSGASISDSYWSWIRRSP

GKGLEWIGYVHKSGDTNYNPSLKSRVHLSLDTSKNQVSLSL

TGVTAADSGKYYCARTLHGRRIYGIVAFNEWFTYFYMDVWG

TGTQVTVSSASTKGPSVFPLAPSSKSTSGGTAALGCLVKDY

FPEPVTVSWNSGALTSGVHTFPAVLQSSGLYSLSSVVTVPS

SSLGTQTYICNVNHKPSNTKVDKRVEPKSCDKTHTCPPCPA

PEFEGGPSVFLFPPKPKDTLMISRTPEVTCVVVAVSHEDPE

VKFNWYVDGVEVHNAKTKPREEQYNSTYRVVSVLTVLHQDW

LNGKEYKCKVSNKALPAPIEKTISKAKGQPREPQVYTLPPS

REEMTKNQVSLTCLVKGFYPSDIAVEWESNGQPENNYKTTP

PVLDSDGSFFLYSRLTVDKSRWQQGNVFSCSVMHEALHNHY

TQKSLSLSPGK

Heavy Chain Sequence of CD3 portion of Duobody®:

(SEQ ID NO: 93)
EVKLVESGGGLVQPGGSLRLSCAASGFTFNTYAMNWVRQAP

GKGLEWVARIRSKYNNYATYYADSVKDRFTISRDDSKSSLY

LQMNNLKTEDTAMYYCVRHGNFGNSYVSWFAYWGQGTLVTV

SSASTKGPSVFPLAPSSKSTSGGTAALGCLVKDYFPEPVTV

SWNSGALTSGVHTFPAVLQSSGLYSLSSVVTVPSSSLGTQT

YICNVNHKPSNTKVDKRVEPKSCDKTHTCPPCPAPEFEGGP

SVFLFPPKPKDTLMISRTPEVTCVVVAVSHEDPEVKFNWYV

DGVEVHNAKTKPREEQYNSTYRVVSVLTVLHQDWLNGKEYK

CKVSNKALPAPIEKTISKAKGQPREPQVYTLPPSREEMTKN

QVSLTCLVKGFYPSDIAVEWESNGQPENNYKTTPPVLDSDG

SFLLYSKLTVDKSRWQQGNVFSCSVMHEALHNHYTQKSLSL

SPGK

Methods

Infected-Cell Killing by PBMC Effector Cells

Exemplary gp120 X CD3 Duobody®- and PGT-121.60-dependent killing of HIV-infected CD4 T-cells was investigated in vitro using primary quiescent HIV-infected CD4$^+$ T-cells as target cells and autologous PBMCs as effector cells. Primary CD4$^+$ T cells were infected by spinfection with 50-100 rig p24/million cells at 1200×g for 2 hours and cultured for 5 days at 37° C. in RPM media (supplemented with 10% FBS and 1% Penicillin/Streptomycin) with 30 U/mL IL-2 (Roche Cat #11011456001). Following a 5 day rest to allow de novo antigen expression, the spinfected CD4$^+$ T-cell culture was washed 3 times to remove free virus, plated in 96-well plates at 2×10$^5$ cells/well and incubated with 10-fold serial dilutions of 7 concentrations of the Exemplary gp120 X CD3 Duobody® or PGT-121.60 in the presence of human serum IgG (5 mg/mL final concentration) for 1 hour. While the CD4$^+$ T-cell targets were opsonizing, the effector cells were prepared. Cryopreserved autologous PBMCs were thawed and membrane-stained using PKH67 according to the manufacturer's instructions and added to the opsonizing target cells at 4×10$^5$ cells/well to yield an E:T ratio of 2:1. Effector cells were co-cultured with the opsonized target cells in a final volume of 200 μL per well for 24-48 hours.

Killing of HIV-infected target cells were determined by flow cytometry. At the end of the co-culture period, cells were washed 2× with PBS, stained with 100 μL Live/Dead Aqua (1/1000 diluted in PBS) for 10 minutes until stain was inactivated with addition of 100 μL FACS buffer (PBS+2% FBS). Cells were then washed with FACS Buffer and incubated with anti-CD4-PE/Cy7 mAb (1/50 dilution in FACS buffer) for 20 mins, then washed 3X with FACS Buffer and fixed and permeabilized with 100 μL of Cytofix/Cytoperm for 10 mins. Cells were then washed once with PermWash and incubated with anti-p24-PE mAb in FACS buffer+10% PermWash for 25 mins. Finally, cells were washed 3X with FACS buffer, resuspended in 120 of FACS buffer and flow cytometry data acquired on a LSR Fortessa or X20 FACS (BD Biosciences, San Jose, Calif.) and analyzed using FlowJo software (TreeStar).

Data Analysis

In the killing of infected primary $CD4^+$ T-cells by PBMCs, the enumeration of HIV-infected target cells by flow cytometry used the following gating strategy: lymphocytes were selected based on forward and side scatter and live lymphocytes by negative staining for Live/Dead Aqua. The PKH67-negative live lymphocytes, representing the inoculated $CD4^+$ T-cells, were then selected and HIV-infected cells were identified as p24 Gag+, $CD4^{low}$ (due to HIV-mediated CD4 down-modulation) cells. The percent HIV-infection was represented by the percent of the inoculated (PKH67-negative) $CD4^+$ T cells that were HIV-infected (p24 $Gag^+$, $CD4^{low}$ positive).

The percent of HIV-infected target cells in Exemplary gp120 X CD3 Duobody®- or PGT-121.60-treated wells was compared to the mean percent of HIV-infected target cells in the untreated wells (treated with human serum IgG only, n=2-10 per 96-well plate). The percent killing of HIV-infected target-cells was calculated using the following equation:

100−((% HIV-infected target cells in treated wells/% HIV-infected target cells in untreated wells) *100).

The maximal fraction of infected cells killed by Exemplary gp120 X CD3 Duobody®- or PGT-121.60 (Emax) and the concentration that gave half maximal killing ($EC_{50}$) were obtained from dose-response curves fitted by three parameter nonlinear regression (equation 1), using GraphPad Prism (La Jolla, Calif.) software.

$$Y = Bottom + \frac{Top - Bottom}{1 + 10^{(LogEC50-X)}} \quad \text{Equation 1}$$

where Y=% killing, X=antibody concentration, Bottom=response in absence of antibody, and Top=maximal response.

The dose-response curves that had apparent Emax<40%, the $EC_{50}$ values were reported as >100m/mL and the Emax with absolute value of ≤0% were assigned 0%.

Example 6: Assessing Anti-gp120 Antibody Variants

Under accelerated stress conditions (25° C., 40° C.), the aspartate at position 59 of the light chain variable domain of PGT-121.60 undergoes isomerization to IsoAsp. Asp59 forms part of the HIV Env N332 binding motif and is critical to gp120 binding by PGT-121.60 leading to a loss of Antibody Dependent Cell-mediated Cytotoxicity (ADCC). This chemical liability was mitigated by lyophilization of the drug product.

PGT-121.60 was selected as one of the arms of a Duobody® molecule. Although lyophilization is a successful commercial strategy, removing the isomerization liability from PGT-121.60 was desired in order to streamline development and manufacturing, improve lot-to-lot consistency, and enable a liquid formulation for the Duobody® format. The engineering goals were to remove the aspartate isomerization site while maintaining bioactivity and without re-introducing a T cell epitope. Four of the top variants from engineering (Variant 1, Variant 2, Variant 3, and Variant 4) were moved forward for characterization including binding and potency testing using the PGT-121.60 ADCC reporter cell based assay.

All four of the variants have the same heavy chain amino acid sequence provided below:

(SEQ ID NO: 94)
QMQLQESGPGLVKPSETLSLTCSVSGASISDSYWSWIRRSP

GKGLEWIGYVHKSGDTNYNPSLKSRVHLSLDTSKNQVSLSL

TGVTAADSGKYYCARTLHGRRIYGIVAFNEWFTYFYMDVWG

TGTQVTVSSASTKGPSVFPLAPSSKSTSGGTAALGCLVKDY

FPEPVTVSWNSGALTSGVHTFPAVLQSSGLYSLSSVVTVPS

SSLGTQTYICNVNHKPSNTKVDKKVEPKSCDKTHTCPPCPA

PELLAGPDVFLFPPKPKDTLMISRTPEVTCVVVDVSHEDPE

VKFNWYVDGVEVHNAKTKPREEQYNSTYRVVSVLTVLHQDW

LNGKEYKCKVSNKALPLPEEKTISKAKGQPREPQVYTLPPS

REEMTKNQVSLTCLVKGFYPSDIAVEWESNGQPENNYKTTP

PVLDSDGSFFLYSKLTVDKSRWQQGNVFSCSVLHEALHSHY

TQKSLSLSPGK

Variant 1 has the light chain sequence set forth in SEQ ID NO: 40. Variant 2 has the light chain sequence set forth in SEQ ID NO: 78. Variant 3 has the light chain sequence set forth in SEQ ID NO: 79. Variant 4 has the light chain sequence set forth in SEQ ID NO: 80.

Binding Studies

The binding of the various Variant antibodies described above to gp120 HIV ENV protein were determined. A 384 well Maxisorp plate was coated with 25 μl of 5 μg/ml gp120. The plate was incubated overnight at 4° C. The plate was washed 4 times with PBS 0.05% Tween 20 washing buffer and blocked with 75 μl of PBS 5% BSA for 1 hr at room temperature shaking at 600 rpm. The plate was incubated with 3-fold serial dilution of primary antibody for 1 hr at room temperature shaking at 600 rpm. The plate was then washed 4 times with PBS 0.05% Tween 20 and 25 μl of goat anti-human IgG (H+L) HRP secondary antibody was diluted in PBS 1% BSA and incubated at room temperature shaking at 600 rpm for 40 mins. The plates where washed 4 times with PBS 0.05% Tween 20 and 25 μl fresh TMB substrate was added. The plates were developed for 90 secs with shaking at 600 rpm and quenched with 25 μl 1M HCl. The plates were read at A450 on a Spectramax m5 plate reader.

Relative to PGT-121.60, the variant antibodies of the present disclosure comprising of mutations in the aspartate isomerization site in the framework insertion loop had both improved and decreased binding to gp120. Sequence activity relationship analysis showed a clear and strong preference for maintenance of aspartate at residue 59. Glycine was tolerated at residue 59 while glutamine, glutamate and asparagine negatively impacted the antibodies ability to bind gp120. At residue 60, the bulkier side groups of the introduced amino acids were tolerated. Data is shown in Table 14 below.

TABLE 14 gp120 biding data for PGT121.60 and Variants.

| Molecule | WITO EC50 (nM) |
|---|---|
| PGT121.60 (DS) | 0.36 |
| Variant 2 (DS -> DF) | 0.15 |
| Variant 4 (DS -> GS) | 0.84 |
| Variant 5 (DS -> GF) | 0.91 |
| Variant 6 (DS -> ES) | 21 |
| Variant 7 (DS -> NS) | 59 |
| Variant 1 (DS -> DY) | 0.05 |
| Variant 3 (DS -> DT) | 0.20 |
| Variant 8 (DS -> QS) | 1.37 |
| Variant 9 (DS -> EY) | 19 |
| Variant 10 (DS -> ET) | 18 |

(In the table above, the letters next to the molecules correspond to the amino acids at positions 59 and 60 (Kabat numbering) of the light chain. The mutated residue(s) is/are boldened.)

This data shows improvement in gp120 binding of Variant 2, Variant 1, and Variant 3 over PGT121.60 and the other variants suggesting that mutating the aspartate isomerization site can affect binding to gp120. These variants were tested with the DEAL+LS Fc (i.e., an Fc with the S239D, I332E, G236A, A330L, M428L and N434S mutations ("DEALLS")).

Potency Studies

The PGT-121.60 ADCC assay was selected since it incorporates an HT593-expressing target cell line and HT593 is known to be sensitive to the isoAsp liability in PGT-121.60. The ADCC Reporter Cell-Based assay measures the ability of PGT-121.60 to induce Nuclear Factor of Activated T cells (NFAT)-mediated luciferase expression as a surrogate measure of ADCC activity. In the assay, Jurkat cells expressing FcγRIIIa receptor (V158) and NFAT-regulated luciferase are incubated with gp120-expressing human embryonic kidney (HEK) cells in the presence of increasing concentrations of PGT-121.60 reference standard, control, and samples. PGT-121.60 binds to gp120 on the HEK cell surface, effectively crosslinking FcγRIIIa on the Jurkat cells and activating luciferase gene expression via NFAT. Relative Luminescence Units (RLU) are plotted against PGT-121.60 concentrations, and a parallel line analysis program is used to determine the potency of the control and samples relative to the reference standard. As the first reference standard (RS), PGT-121.60 was assigned a relative potency (RP) value of 100%.

Samples of the PGT-121.60 variants—i.e., Variant 1, Variant 2, Variant 3, and Variant 4—were diluted to an intermediate concentration of 0.5 mg/mL and protein concentration confirmed by UV spectrophotometry (Absorbance maximum of 280 nm-absorbance 320 nm). Intermediates were subsequently diluted to an initial concentration range of 0.6 ng/mL 4.96 µg/mL. Samples (control, 25° C., 4 weeks) were then tested according to the ADCC assay described above with the exception that the thermal stressed samples were quantitated against their respective controls (assigned as 100% RP) rather than the PGT-121.60 reference standard.

Samples of the PGT.121.60 variants, Variant 1, Variant 2, Variant 3, and Variant 4, were subjected to thermal stress by incubation at 25° C. for 4 weeks. They were then tested in the PGT.121.60 ADCC reporter cell based assay along with their respective untreated controls, which had been stored at 2-8° C. The results are shown in Table 15.

TABLE 15

ADCC Activity of thermally-stressed PGT-121.60 and isoAsp variants

| Molecule | % ADCC Activity (n = 2) |
|---|---|
| PGT-121.60 | 65[a] |
| Variant 2 | 96 |
| Variant 4 | 95 |
| Variant 1 | 100 |
| Variant 3 | 104 |

[a]PGT-121.60 was tested only one time and results consistent with historical data.

The results indicate that, while thermally-treated PGT-121.60 exhibits decreased activity (65% RP), the ADCC activity of the variants Variant 2, Variant 3, Variant 4, and Variant 1 (96%, 104%, 95%, and 100%, respectively) were not affected by treatment at 25° C. for 4 weeks.

Example 7: Assessing HIV Neutralization Activity

The potency (measured as IC50 or IC95) and breadth (% of isolates neutralized from the panel tested) of HIV-1 neutralization by antibodies were examined in the (i) the CEM-NKr-CCR5-LucR reporter cell-line based assay and the ii) the Monogram HIV PhenoSense Neutralization Assay (Monogram Biosciences) as described in Example 1.

In the CEM-NKr-CCR5-LucR reporter cell-line-based neutralization assay, the antibodies were examined against a panel of 40 clade B replication-competent HIV-1 isolates and clones.

The neutralization potency of Variants 1-4 was similar to that of PGT-121.60 (Student's paired T-test P value for each variant compared to PGT-121.60 was ≥0.372). Compared to PGT-121.60, the geometric mean fold-change in IC50 values of the variants ranged from 1.035 for Variant 1 to 1.539 for Variant 2, indicating that the mutations that abrogate the isoaspartate liability in PGT-121.60 did not significantly impact the HIV neutralization activity of PGT-121.60. The neutralization activity of Variants 1-4 was entirely abrogated for 1 of the 40 viruses tested (virus 8339). The results are displayed in Table 16.

TABLE 16

Neutralization activity using the CEM.NKr.CCR5.LucR based assay. Data represents mean of 2 repetitions.

| | IC50 (ug/mL) | | | | | Fold-change vs PGT-121.60 | | | |
|---|---|---|---|---|---|---|---|---|---|
| Isolate | PGT-121.60 | Variant 1 | Variant 2 | Variant 3 | Variant 4 | Variant 1 | Variant 2 | Variant 3 | Variant 4 |
| 7552 | 0.006 | 0.007 | 0.005 | 0.009 | 0.007 | 0.879 | 1.205 | 0.679 | 0.843 |
| 92US727 | 0.013 | 0.010 | 0.016 | 0.019 | 0.013 | 1.273 | 0.816 | 0.705 | 0.993 |
| BaL | 0.015 | 0.018 | 0.010 | 0.008 | 0.014 | 0.811 | 1.450 | 1.812 | 1.019 |
| 92US712 | 0.019 | 0.005 | 0.019 | 0.022 | 0.027 | 3.717 | 1.027 | 0.865 | 0.703 |
| 92HT593 | 0.024 | 0.018 | 0.017 | 0.018 | 0.018 | 1.289 | 1.420 | 1.287 | 1.296 |
| 7406 | 0.027 | 0.030 | 0.013 | 0.012 | 0.013 | 0.901 | 2.108 | 2.247 | 2.139 |
| 8398 | 0.028 | 0.033 | 0.023 | 0.036 | 0.041 | 0.864 | 1.207 | 0.785 | 0.691 |
| 8176 | 0.028 | 0.036 | 0.027 | 0.020 | 0.021 | 0.781 | 1.042 | 1.408 | 1.380 |
| 7051 | 0.030 | 0.023 | 0.017 | 0.040 | 0.038 | 1.278 | 1.737 | 0.741 | 0.772 |
| 7576 | 0.032 | 0.056 | 0.012 | 0.014 | 0.007 | 0.565 | 2.575 | 2.334 | 4.431 |
| 1489 | 0.047 | 0.075 | 0.019 | 0.027 | 0.021 | 0.625 | 2.482 | 1.752 | 2.249 |
| 8318 | 0.048 | 0.051 | 0.037 | 0.053 | 0.037 | 0.937 | 1.308 | 0.896 | 1.277 |
| 8134 | 0.062 | 0.065 | 0.012 | 0.025 | 0.010 | 0.949 | 5.173 | 2.439 | 6.408 |
| CH058 | 0.063 | 0.090 | 0.023 | 0.026 | 0.019 | 0.702 | 2.766 | 2.464 | 3.259 |
| 7467 | 0.082 | 0.144 | 0.030 | 0.043 | 0.045 | 0.568 | 2.698 | 1.921 | 1.835 |
| 8089 | 0.085 | 0.101 | 0.055 | 0.071 | 0.054 | 0.844 | 1.549 | 1.208 | 1.574 |
| 8106 | 0.091 | 0.155 | 0.021 | 0.025 | 0.026 | 0.586 | 4.247 | 3.561 | 3.532 |
| 7007 | 0.099 | 0.078 | 0.093 | 0.108 | 0.072 | 1.268 | 1.065 | 0.915 | 1.369 |
| 7141 | 0.112 | 0.205 | 0.025 | 0.037 | 0.016 | 0.546 | 4.530 | 3.061 | 6.920 |
| 7103 | 0.129 | 0.213 | 0.047 | 0.053 | 0.033 | 0.604 | 2.758 | 2.452 | 3.889 |
| 92US657 | 0.168 | 0.049 | 0.089 | 0.100 | 1.396 | 3.426 | 1.901 | 1.691 | 0.121 |
| 8359 | 0.337 | 0.515 | 0.091 | 0.139 | 0.335 | 0.654 | 3.714 | 2.431 | 1.005 |
| 8339 | 0.362 | 0.375 | >100 | >100 | >100 | 0.967 | 0.004 | 0.004 | 0.004 |
| 7595 | 0.475 | 0.342 | 0.068 | 0.099 | 0.116 | 1.389 | 7.003 | 4.807 | 4.106 |
| 8110 | 0.514 | 0.484 | 0.203 | 0.259 | 0.485 | 1.062 | 2.527 | 1.986 | 1.058 |
| RHPA | 0.534 | 0.434 | 0.547 | 0.692 | 0.737 | 1.229 | 0.975 | 0.771 | 0.724 |
| WITO | 1.049 | 0.095 | 6.706 | 12.110 | 5.299 | 11.018 | 0.156 | 0.087 | 0.198 |
| 1003 | 20.801 | 30.010 | 5.390 | 6.032 | 5.884 | 0.693 | 3.859 | 3.448 | 3.535 |
| 302076 | >100 | >100 | >100 | >100 | >100 | na | na | na | na |
| 7015 | >100 | >100 | 13.390 | 10.894 | >100 | na | 3.734 | 4.590 | na |
| 8339 | >100 | >100 | >100 | >100 | >100 | na | na | na | na |
| 8117 | >100 | >100 | >100 | >100 | >100 | na | na | na | na |
| CH077 | >100 | >100 | >100 | >100 | >100 | na | na | na | na |
| CH106 | >100 | >100 | >100 | >100 | >100 | na | na | na | na |
| REJO | >100 | >100 | >100 | >100 | >100 | na | na | na | na |
| THRO | >100 | >100 | >100 | >100 | >100 | na | na | na | na |
| 1413 | >100 | >100 | >100 | >100 | >100 | na | na | na | na |
| 8320 | >100 | >100 | >100 | >100 | >100 | na | na | na | na |
| 7714 | >100 | >100 | >100 | >100 | >100 | na | na | na | na |
| 1012 | >100 | >100 | >100 | >100 | >100 | na | na | na | na |
| Geomean† | 0.090 | 0.087 | 0.056 | 0.071 | 0.058 | 1.035 | 1.539 | 1.222 | 1.186 |
| T-test vs PGT-121.60 | na | 0.372 | 0.502 | 0.799 | 0.525 | na | na | na | na | a. na refers to "not applicable"
†Geometric mean calculated excluding resistant viruses (IC50 > 100 ug/mL)

In the Monogram HIV PhenoSense Neutralization Assay, the HIV neutralization activity of Variants 1-3 was assessed in a bispecific format with a FEAR/FEAL Fc against the Gilead Clinical Isolates panel (n=142 viruses). When evaluated in the FEAR/FEAL bispecific format, the potency of Variants 1-3 was between 4.1- and 5.3-fold reduced compared to PGT-121.60 DEAL+LS (Table 17). Taken together with the results of the CEM.NKr.CCR5.LucR based assay in which the variants were evaluated in the DEAL+LS format, the results indicate that the bispecific Duobody® format, but not the mutations to abrogate the isoaspartate liability in PGT-121.60, impair the HIV neutralization activity 4- to 5-fold.

TABLE 17

Neutralization activity using the Monogram HIV PhenoSense Neutralization Assay. Data represents a single experiment.

| | IC50 (ug/mL) | | | | Fold-change vs PGT-121.60 | | |
|---|---|---|---|---|---|---|---|
| Virus ID | PGT-121.60 | Variant 1 | Variant 2 | Variant 3 | Variant 1 | Variant 2 | Variant 3 |
| 15-124936 | 0.002 | 0.022 | 0.019 | 0.023 | 10.381 | 8.810 | 11.000 |
| 15-101755 | 0.002 | 0.032 | 0.037 | 0.028 | 13.333 | 15.500 | 11.833 |
| 15-124984 | 0.003 | 0.027 | 0.031 | 0.022 | 10.600 | 12.240 | 8.680 |
| 15-102242 | 0.003 | 0.014 | 0.020 | 0.013 | 4.091 | 6.091 | 3.788 |
| 15-102240 | 0.003 | 0.012 | 0.007 | 0.010 | 3.382 | 2.176 | 2.853 |
| 15-124942 | 0.003 | 0.012 | 0.023 | 0.019 | 3.441 | 6.676 | 5.529 |
| 15-124900 | 0.004 | 0.022 | 0.022 | 0.021 | 6.143 | 6.229 | 5.886 |

TABLE 17-continued

Neutralization activity using the Monogram HIV PhenoSense Neutralization Assay.
Data represents a single experiment.

| | IC50 (ug/mL) | | | | Fold-change vs PGT-121.60 | | |
|---|---|---|---|---|---|---|---|
| Virus ID | PGT-121.60 | Variant 1 | Variant 2 | Variant 3 | Variant 1 | Variant 2 | Variant 3 |
| 15-124918 | 0.005 | 0.030 | 0.038 | 0.023 | 6.061 | 7.837 | 4.653 |
| 15-124974 | 0.007 | 0.044 | 0.026 | 0.042 | 6.754 | 4.000 | 6.477 |
| 15-101605 | 0.007 | 0.047 | 0.055 | 0.048 | 6.438 | 7.493 | 6.575 |
| 15-101610 | 0.009 | 0.026 | 0.038 | 0.023 | 3.011 | 4.391 | 2.655 |
| 15-124940 | 0.009 | 0.023 | 0.023 | 0.028 | 2.602 | 2.636 | 3.148 |
| 15-124919 | 0.011 | 0.088 | 0.069 | 0.126 | 8.196 | 6.486 | 11.766 |
| 15-101609 | 0.011 | 0.040 | 0.025 | 0.043 | 3.679 | 2.275 | 3.945 |
| 15-124887 | 0.011 | 0.133 | 0.134 | 0.184 | 11.857 | 12.000 | 16.420 |
| 15-124914 | 0.011 | 0.023 | 0.046 | 0.015 | 2.027 | 4.089 | 1.304 |
| 15-124895 | 0.012 | 0.056 | 0.059 | 0.070 | 4.697 | 4.950 | 5.908 |
| 15-102508 | 0.013 | 0.040 | 0.070 | 0.043 | 3.151 | 5.548 | 3.381 |
| 15-124967 | 0.013 | 0.057 | 0.065 | 0.043 | 4.293 | 4.865 | 3.195 |
| 15-124891 | 0.013 | 0.023 | 0.028 | 0.021 | 1.731 | 2.090 | 1.597 |
| 15-124881 | 0.014 | 0.051 | 0.044 | 0.070 | 3.745 | 3.182 | 5.139 |
| 15-102505 | 0.014 | 0.079 | 0.050 | 0.061 | 5.698 | 3.612 | 4.353 |
| 15-124986 | 0.015 | 0.020 | 0.032 | 0.017 | 1.362 | 2.141 | 1.161 |
| 15-124969 | 0.016 | 0.070 | 0.057 | 0.073 | 4.354 | 3.553 | 4.547 |
| 15-124903 | 0.017 | 0.059 | 0.046 | 0.053 | 3.444 | 2.696 | 3.117 |
| 15-102230 | 0.020 | 0.022 | 0.038 | 0.035 | 1.144 | 1.964 | 1.785 |
| 15-124976 | 0.020 | 0.043 | 0.048 | 0.056 | 2.149 | 2.393 | 2.761 |
| 15-102232 | 0.023 | 0.092 | 0.062 | 0.052 | 3.957 | 2.652 | 2.219 |
| 15-124937 | 0.025 | 0.096 | 0.124 | 0.146 | 3.856 | 4.960 | 5.820 |
| 15-124964 | 0.026 | 0.178 | 0.127 | 0.209 | 6.754 | 4.811 | 7.898 |
| 15-124924 | 0.028 | 0.129 | 0.111 | 0.138 | 4.580 | 3.961 | 4.911 |
| 15-124907 | 0.028 | 0.183 | 0.172 | 0.170 | 6.454 | 6.067 | 6.000 |
| 15-124978 | 0.029 | 0.115 | 0.157 | 0.108 | 3.918 | 5.348 | 3.686 |
| 15-124935 | 0.029 | 0.081 | 0.090 | 0.096 | 2.738 | 3.044 | 3.262 |
| 15-124922 | 0.030 | 0.193 | 0.169 | 0.255 | 6.525 | 5.736 | 8.634 |
| 15-101763 | 0.030 | 0.208 | 0.199 | 0.352 | 7.007 | 6.707 | 11.865 |
| 15-124959 | 0.031 | 0.177 | 0.114 | 0.180 | 5.771 | 3.732 | 5.873 |
| 15-124958 | 0.031 | 0.162 | 0.106 | 0.082 | 5.239 | 3.432 | 2.642 |
| 15-124933 | 0.031 | 0.125 | 0.093 | 0.116 | 3.990 | 2.958 | 3.696 |
| 15-101612 | 0.035 | 0.137 | 0.125 | 0.113 | 3.948 | 3.594 | 3.251 |
| 15-124938 | 0.035 | 0.152 | 0.128 | 0.214 | 4.343 | 3.660 | 6.106 |
| 15-124912 | 0.035 | 0.358 | 0.306 | 0.551 | 10.144 | 8.680 | 15.606 |
| 15-102241 | 0.040 | 0.139 | 0.090 | 0.105 | 3.529 | 2.289 | 2.666 |
| 15-124902 | 0.040 | 0.315 | 0.254 | 0.477 | 7.826 | 6.321 | 11.873 |
| 15-101754 | 0.041 | 0.125 | 0.101 | 0.086 | 3.089 | 2.504 | 2.111 |
| 15-124880 | 0.041 | 0.134 | 0.140 | 0.159 | 3.274 | 3.433 | 3.883 |
| 15-124917 | 0.041 | 0.189 | 0.131 | 0.189 | 4.602 | 3.188 | 4.600 |
| 15-102234 | 0.046 | 0.219 | 0.234 | 0.351 | 4.773 | 5.114 | 7.657 |
| 15-124928 | 0.050 | 0.232 | 0.188 | 0.446 | 4.642 | 3.754 | 8.920 |
| 15-102231 | 0.051 | 0.221 | 0.195 | 0.234 | 4.341 | 3.818 | 4.580 |
| 15-124909 | 0.052 | 0.152 | 0.150 | 0.147 | 2.938 | 2.899 | 2.843 |
| 15-124894 | 0.055 | 0.382 | 0.348 | 0.619 | 6.956 | 6.335 | 11.268 |
| 15-124968 | 0.059 | 0.180 | 0.198 | 0.175 | 3.032 | 3.337 | 2.949 |
| 15-101759 | 0.063 | 0.569 | 0.444 | 0.871 | 9.083 | 7.093 | 13.907 |
| 15-101757 | 0.065 | 0.639 | 0.533 | 1.206 | 9.777 | 8.151 | 18.440 |
| 15-124906 | 0.068 | 0.379 | 0.433 | 0.515 | 5.612 | 6.405 | 7.612 |
| 15-124966 | 0.073 | 0.850 | 0.485 | 0.935 | 11.611 | 6.630 | 12.770 |
| 15-124899 | 0.098 | 0.352 | 0.354 | 0.461 | 3.596 | 3.609 | 4.706 |
| 15-102514 | 0.100 | 0.671 | 0.614 | 1.379 | 6.740 | 6.166 | 13.844 |
| 15-124971 | 0.120 | 0.470 | 0.407 | 0.631 | 3.929 | 3.405 | 5.277 |
| 15-102510 | 0.121 | 0.286 | 0.399 | 0.380 | 2.365 | 3.304 | 3.144 |
| 15-124953 | 0.125 | 0.481 | 0.432 | 0.548 | 3.858 | 3.461 | 4.393 |
| 15-124952 | 0.129 | 0.733 | 0.577 | 0.885 | 5.676 | 4.472 | 6.857 |
| 15-102243 | 0.133 | 0.352 | 0.279 | 0.440 | 2.645 | 2.102 | 3.312 |
| 15-124931 | 0.134 | 0.540 | 0.513 | 0.718 | 4.043 | 3.839 | 5.378 |
| 15-124987 | 0.157 | 1.218 | 0.848 | 1.357 | 7.739 | 5.389 | 8.622 |
| 15-102509 | 0.158 | 0.519 | 0.474 | 0.675 | 3.289 | 3.004 | 4.282 |
| 15-101617 | 0.171 | 0.555 | 0.474 | 0.909 | 3.250 | 2.777 | 5.326 |
| 15-101613 | 0.172 | 1.021 | 1.044 | 1.471 | 5.929 | 6.060 | 8.543 |
| 15-101934 | 0.176 | 0.897 | 0.928 | 1.549 | 5.092 | 5.266 | 8.791 |
| 15-124904 | 0.190 | 0.669 | 0.616 | 0.760 | 3.527 | 3.246 | 4.006 |
| 15-102515 | 0.224 | 1.124 | 0.904 | 2.000 | 5.009 | 4.032 | 8.918 |
| 15-124970 | 0.230 | 0.698 | 0.593 | 0.737 | 3.037 | 2.582 | 3.206 |
| 15-124961 | 0.232 | 0.691 | 0.691 | 0.948 | 2.983 | 2.983 | 4.094 |
| 15-124962 | 0.252 | 0.898 | 1.039 | 1.879 | 3.568 | 4.129 | 7.469 |
| 15-102513 | 0.255 | 1.178 | 1.622 | 1.779 | 4.620 | 6.359 | 6.976 |
| 15-101611 | 0.284 | 1.554 | 1.070 | 2.456 | 5.476 | 3.771 | 8.656 |
| 15-124905 | 0.317 | 0.635 | 0.589 | 0.747 | 2.002 | 1.855 | 2.353 |
| 15-124921 | 0.326 | 1.293 | 1.196 | 2.044 | 3.969 | 3.671 | 6.276 |
| 15-124879 | 0.330 | 1.658 | 1.378 | 1.401 | 5.029 | 4.179 | 4.249 |

TABLE 17-continued

Neutralization activity using the Monogram HIV PhenoSense Neutralization Assay.
Data represents a single experiment.

| | IC50 (ug/mL) | | | | Fold-change vs PGT-121.60 | | |
|---|---|---|---|---|---|---|---|
| Virus ID | PGT-121.60 | Variant 1 | Variant 2 | Variant 3 | Variant 1 | Variant 2 | Variant 3 |
| 15-124920 | 0.367 | 0.765 | 0.881 | 0.951 | 2.085 | 2.401 | 2.592 |
| 15-124975 | 0.401 | 2.475 | 1.753 | 2.800 | 6.173 | 4.372 | 6.985 |
| 15-124916 | 0.418 | 1.362 | 1.220 | 1.478 | 3.260 | 2.920 | 3.538 |
| 15-124977 | 0.478 | 2.538 | 3.746 | 3.917 | 5.309 | 7.837 | 8.194 |
| 15-124957 | 0.485 | 2.278 | 2.015 | 3.928 | 4.697 | 4.155 | 8.101 |
| 15-124911 | 0.492 | 1.696 | 1.804 | 3.619 | 3.447 | 3.668 | 7.358 |
| 15-102511 | 0.851 | 3.036 | 3.129 | 5.469 | 3.567 | 3.676 | 6.426 |
| 15-102229 | 0.856 | 25.241 | 12.867 | 21.072 | 29.504 | 15.040 | 24.631 |
| 15-124926 | 0.879 | 3.074 | 3.561 | 4.674 | 3.497 | 4.051 | 5.317 |
| 15-102516 | 1.051 | 2.616 | 1.945 | 5.084 | 2.490 | 1.851 | 4.839 |
| 15-124979 | 1.091 | 6.649 | 6.305 | 11.820 | 6.097 | 5.782 | 10.838 |
| 15-101607 | 1.460 | 4.161 | 5.955 | 4.808 | 2.849 | 4.078 | 3.292 |
| 15-124950 | 1.719 | 9.020 | 6.032 | 9.074 | 5.247 | 3.509 | 5.279 |
| 15-102507 | 2.743 | 10.042 | 9.008 | 24.434 | 3.661 | 3.284 | 8.908 |
| 15-101616 | 2.752 | 7.449 | 6.074 | 14.832 | 2.707 | 2.207 | 5.390 |
| 15-124973 | 4.811 | 14.646 | 15.639 | 36.306 | 3.044 | 3.251 | 7.546 |
| 15-124934 | 8.578 | 41.167 | >50 | >50 | 4.799 | >5.829 | >5.829 |
| 15-101608 | 9.958 | 18.100 | 14.184 | 23.143 | 1.818 | 1.424 | 2.324 |
| 15-124913 | 12.542 | 19.034 | 19.607 | 24.081 | 1.518 | 1.563 | 1.920 |
| 15-124963 | 13.294 | 15.314 | 24.216 | >50 | 1.152 | 1.822 | >3.761 |
| 15-101758 | 18.164 | >50 | 26.993 | >50 | >2.753 | 1.486 | >2.753 |
| 15-124897 | 19.659 | 39.036 | >50 | >50 | 1.986 | >2.543 | >2.543 |
| 15-124910 | 20.643 | >50 | >50 | >50 | >2.422 | >2.422 | >2.422 |
| 15-124932 | >50 | >50 | >50 | >50 | na | na | na |
| 15-124949 | >50 | >50 | >50 | >50 | na | na | na |
| 15-124893 | >50 | >50 | >50 | >50 | na | na | na |
| 15-124892 | >50 | >50 | >50 | >50 | na | na | na |
| 15-124960 | >50 | >50 | >50 | >50 | na | na | na |
| 15-124956 | >50 | >50 | >50 | >50 | na | na | na |
| 15-124888 | >50 | >50 | >50 | >50 | na | na | na |
| 15-101752 | >50 | >50 | >50 | >50 | na | na | na |
| 15-101760 | >50 | >50 | >50 | >50 | na | na | na |
| 15-124947 | >50 | >50 | >50 | >50 | na | na | na |
| 15-124980 | >50 | >50 | >50 | >50 | na | na | na |
| 15-101751 | >50 | >50 | >50 | >50 | na | na | na |
| 15-124983 | >50 | >50 | >50 | >50 | na | na | na |
| 15-124908 | >50 | >50 | >50 | >50 | na | na | na |
| 15-102504 | >50 | >50 | >50 | >50 | na | na | na |
| 15-101750 | >50 | >50 | >50 | >50 | na | na | na |
| 15-101595 | >50 | >50 | >50 | >50 | na | na | na |
| 15-101764 | >50 | >50 | >50 | >50 | na | na | na |
| 15-101761 | >50 | >50 | >50 | >50 | na | na | na |
| 15-101591 | >50 | >50 | >50 | >50 | na | na | na |
| 15-102512 | >50 | >50 | >50 | >50 | na | na | na |
| 15-124929 | >50 | >50 | >50 | >50 | na | na | na |
| 15-124972 | >50 | >50 | >50 | >50 | na | na | na |
| 15-102518 | >50 | >50 | >50 | >50 | na | na | na |
| 15-124898 | >50 | >50 | >50 | >50 | na | na | na |
| 15-124925 | >50 | >50 | >50 | >50 | na | na | na |
| 15-124945 | >50 | >50 | >50 | >50 | na | na | na |
| 15-101606 | >50 | >50 | >50 | >50 | na | na | na |
| 15-124965 | >50 | >50 | >50 | >50 | na | na | na |
| 15-124985 | >50 | >50 | >50 | >50 | na | na | na |
| 15-124941 | >50 | >50 | >50 | >50 | na | na | na |
| 15-124944 | >50 | >50 | >50 | >50 | na | na | na |
| 15-124954 | >50 | >50 | >50 | >50 | na | na | na |
| 15-102506 | >50 | >50 | >50 | >50 | na | na | na |
| 15-101765 | >50 | >50 | >50 | >50 | na | na | na |
| 15-124930 | >50 | >50 | >50 | >50 | na | na | na |
| 15-124982 | >50 | >50 | >50 | >50 | na | na | na |
| 15-124939 | >50 | >50 | >50 | >50 | na | na | na |
| 15-124886 | >50 | >50 | >50 | >50 | na | na | na |
| Geomean† | 0.089 | 0.340 | 0.306 | 0.339 | 4.238 | 4.014 | 5.239 |
| T-test vs PGT-121.60 | na | 0.001 | <0.001 | <0.001 | na | na | na | a. na refers to "not applicable"
†Geometric mean calculated excluding resistant viruses (IC50 > 100 ug/mL)

Example 8: T Cell Activation

Ligation of CD3+ T cells with target cells expressing the antigen of interest by CD3-bispecific antibodies results in T cell activation. No T cell activation is generally seen with CD3 bispecific antibodies in the absence of antigen-positive target cells. This dependence of T cell activation on the presence of antigen-positive target cells may prevent global T cell activation and limit adverse events associated with global T cell activation, such as cytokine release syndrome.

To assess the ability of gp120 X CD3 Duobody® to activate T cells only in the presence of both antigens, we incubated primary PBMCs isolated from HIV-uninfected donors (n=2) and HIV-infected donors (n=2) with gp120 X CD3 Duobody®-Variant 1, gp120 X CD3 Duobody®-Variant 2, or PGT-121.60 and CEM-NKr-CCR5-LucR CD4 T cells that were either (i) infected with a HIV-1 virus that was sensitive to killing by gp120 x CD3 Duobody® (7552), (ii) infected with a HIV-1 virus resistant to killing by gp120 x CD3 Duobody® (THRO), or (iii) uninfected. PBMCs and CEM-NKr-CCR5-LucR CD4 T cells were co-cultured at a 1:10 effector cell to target cell ratio to maximize the number of effector cells that engage the target cells, and thus, the ability to detect activated effector cells. Effector cells from both HIV-uninfected (n=2) and HIV-infected (n=2) donors were evaluated. The results are displayed in Tables 18-23.

Both gp120 X CD3 Duobody Variant 1 (Tables 18 and 19) and gp120 X CD3 Duobody Variant 2 (Tables 20 and 21) induced dose-dependent upregulation of T-cell activation markers CD69 and CD25 on primary CD4 T cells and CD8 T cells. Minor upregulation of PD-1 was also observed. No upregulation of Ki67 was observed. T cells from HIV-uninfected and HIV-infected donors responded similarly. Upregulation of activation markers was dependent on the gp120 X CD3 Duobody binding to both antigens since upregulation of activation markers was only observed in the presence of CEM-NKr-CCR5-LucR CD4 T cells infected with an HIV-1 virus sensitive to killing by gp120 x CD3 Duobody (7552). No upregulation of activation markers was observed when effector cells were co-cultured with CEM-NKr-CCR5-LucR CD4 T cells infected with an HIV virus resistant to killing by gp120 X CD3 Duobody (THRO) or uninfected CEM-NKr-CCR5-LucR CD4 T cells. PGT-121.60, which does not bind to T cells, did not induce upregulation of T cell activation markers regardless of whether the CEM-NKr-CCR5-LucR CD4 T cells were infected with a virus sensitive to killing by gp120 x CD3 Duobody® or not (Tables 22 and 23).

TABLE 18 gp120 × CD3 Duobody Variant 1 CD4 T-cell activation.

| | | | 7552 | | THRO | | Uninfected | |
|---|---|---|---|---|---|---|---|---|
| Donor | HIV-infected | Marker | Δ Emax (%) | EC50 (ug/mL) | Δ Emax (%) | EC50 (ug/mL) | Δ Emax (%) | EC50 (ug/mL) |
| D1597 | Yes | CD69 | 58 | 0.019 | 1 | >100 | 3 | >100 |
| | | CD25 | 36 | 0.128 | −4 | >100 | −2 | >100 |
| | | PD-1 | 7 | 0.057 | 3 | >100 | −1 | >100 |
| | | Ki-67 | 2 | >100 | 0 | >100 | 0 | >100 |
| D2256 | Yes | CD69 | 59 | 0.025 | 1 | >100 | 3 | >100 |
| | | CD25 | 21 | 0.213 | −4 | >100 | −1 | >100 |
| | | PD-1 | 12 | 0.012 | 1 | >100 | 2 | >100 |
| | | Ki-67 | 1 | >100 | 5 | 88.8 | 1 | >100 |
| D4246 | No | CD69 | 61 | 0.038 | 1 | >100 | 1 | >100 |
| | | CD25 | 30.4 | 0.093 | −2 | >100 | 3 | >100 |
| | | PD-1 | 5 | 0.465 | 0 | >100 | 0 | >100 |
| | | Ki-67 | 1 | >100 | 0 | >100 | 0 | >100 |
| D4279 | No | CD69 | 60 | 0.019 | 2 | >100 | −1 | >100 |
| | | CD25 | 24 | 0.156 | −2 | >100 | 0 | >100 |
| | | PD-1 | 10 | 0.024 | 2 | >100 | −1 | >100 |
| | | Ki-67 | 0 | >100 | −1 | >100 | 1 | >100 |

TABLE 19 gp120 × CD3 Duobody Variant 1 CD8 T-cell activation.

| | | | 7552 | | THRO | | Uninfected | |
|---|---|---|---|---|---|---|---|---|
| Donor | HIV-infected | Marker | Δ Emax (%) | EC50 (ug/mL) | Δ Emax (%) | EC50 (ug/mL) | Δ Emax (%) | EC50 (ug/mL) |
| D1597 | Yes | CD69 | 25 | 0.01 | 3 | >100 | 5 | 10.74 |
| | | CD25 | 21 | 0.245 | 0 | >100 | 1 | >100 |
| | | PD-1 | 2 | >100 | 0 | >100 | 1 | >100 |
| | | Ki-67 | 0 | >100 | 0 | >100 | 0 | >100 |
| D2256 | Yes | CD69 | 41 | 0.01 | 5 | 9.95 | 6 | 8.08 |
| | | CD25 | 18 | 0.08 | 0 | >100 | 0 | >100 |
| | | PD-1 | 9 | 0.053 | 1 | >100 | 1 | >100 |
| | | Ki-67 | 0 | >100 | 0 | >100 | 0 | >100 |
| D4246 | No | CD69 | 35 | 0.026 | 3 | >100 | 3 | >100 |
| | | CD25 | 18 | 0.272 | 0 | >100 | 0 | >100 |
| | | PD-1 | 1 | >100 | 0 | >100 | 0 | >100 |
| | | Ki-67 | 0 | >100 | 0 | >100 | 0 | >100 |
| D4279 | No | CD69 | 47 | 0.013 | 4 | >100 | 5 | 33.46 |
| | | CD25 | 14 | 0.6 | −1 | >100 | 1 | >100 |

TABLE 19-continued gp120 × CD3 Duobody Variant 1 CD8 T-cell activation.

| Donor | HIV-infected | Marker | 7552 Δ Emax (%) | 7552 EC50 (ug/mL) | THRO Δ Emax (%) | THRO EC50 (ug/mL) | Uninfected Δ Emax (%) | Uninfected EC50 (ug/mL) |
|---|---|---|---|---|---|---|---|---|
| | | PD-1 | 4 | >100 | 0 | >100 | 0 | >100 |
| | | Ki-67 | 0 | >100 | 0 | >100 | 0 | >100 |

TABLE 20 gp120 × CD3 Duobody Variant 2 CD4 T-cell activation.

| Donor | HIV-infected | Marker | 7552 Δ Emax (%) | 7552 EC50 (ug/mL) | THRO Δ Emax (%) | THRO EC50 (ug/mL) | Uninfected Δ Emax (%) | Uninfected EC50 (ug/mL) |
|---|---|---|---|---|---|---|---|---|
| D1597 | Yes | CD69 | 62 | 0.025 | 1 | >100 | 6 | 8.9 |
| | | CD25 | 37 | 0.077 | −3 | >100 | 0 | >100 |
| | | PD-1 | 6 | 0.094 | 0 | >100 | 0 | >100 |
| | | Ki-67 | 1 | >100 | 1 | >100 | 0 | >100 |
| D2256 | Yes | CD69 | 61 | 0.022 | 2 | >100 | 8 | 32.6 |
| | | CD25 | 25 | 0.093 | −2 | >100 | 0 | >100 |
| | | PD-1 | 14 | 0.024 | 0 | >100 | 0 | >100 |
| | | Ki-67 | 1 | >100 | −1 | >100 | −1 | >100 |
| D4246 | No | CD69 | 60 | 0.04 | 1 | >100 | 2 | >100 |
| | | CD25 | 30 | 0.1 | 0 | >100 | 2 | >100 |
| | | PD-1 | 6 | 0.07 | 0 | >100 | 0 | >100 |
| | | Ki-67 | 0 | >100 | 0 | >100 | 0 | >100 |
| D4279 | No | CD69 | 60 | 0.02 | 3 | >100 | 2 | >100 |
| | | CD25 | 22 | 0.08 | 2 | >100 | 4 | >100 |
| | | PD-1 | 9 | 0.01 | 1 | >100 | 1 | >100 |
| | | Ki-67 | 2 | >100 | 0 | >100 | 0 | >100 |

TABLE 21 gp120 × CD3 Duobody Variant 2 CD8 T-cell activation.

| Donor | HIV-infected | Marker | 7552 Δ Emax (%) | 7552 EC50 (ug/mL) | THRO Δ Emax (%) | THRO EC50 (ug/mL) | Uninfected Δ Emax (%) | Uninfected EC50 (ug/mL) |
|---|---|---|---|---|---|---|---|---|
| D1597 | Yes | CD69 | 31 | 0.016 | 7 | 3.118 | 7 | 2.869 |
| | | CD25 | 24 | 0.165 | 0 | >100 | 1 | >100 |
| | | PD-1 | 2 | >100 | 0 | >100 | 1 | >100 |
| | | Ki-67 | 0 | >100 | 0 | >100 | 0 | >100 |
| D2256 | Yes | CD69 | 42 | 0.011 | 11 | 2.652 | 13 | 3.563 |
| | | CD25 | 19 | 0.08 | 1 | >100 | 0 | >100 |
| | | PD-1 | 9 | 0.026 | 1 | >100 | 2 | >100 |
| | | Ki-67 | 0 | >100 | 0 | >100 | 0 | >100 |
| D4246 | No | CD69 | 39 | 0.016 | 4 | >100 | 5 | 6.281 |
| | | CD25 | 24 | 0.548 | −1 | >100 | 0 | >100 |
| | | PD-1 | 1 | >100 | 0 | >100 | 0 | >100 |
| | | Ki-67 | 0 | >100 | 0 | >100 | 0 | >100 |
| D4279 | No | CD69 | 45 | 0.009 | 5 | 6.244 | 4 | >100 |
| | | CD25 | 15 | 0.441 | 0 | >100 | 0 | >100 |
| | | PD-1 | 3 | >100 | 0 | >100 | 0 | >100 |
| | | Ki-67 | 0 | >100 | 0 | >100 | 0 | >100 |

TABLE 22

PGT-121.60 CD4 T-cell activation.

| Donor | HIV-infected | Marker | 7552 Δ Emax (%) | 7552 EC50 (ug/mL) | THRO Δ Emax (%) | THRO EC50 (ug/mL) | Uninfected Δ Emax (%) | Uninfected EC50 (ug/mL) |
|---|---|---|---|---|---|---|---|---|
| D1597 | Yes | CD69 | 0 | >100 | 0 | >100 | 1 | >100 |
| | | CD25 | 0 | >100 | −2 | >100 | 3 | >100 |

TABLE 22-continued

PGT-121.60 CD4 T-cell activation.

| | | | 7552 | | THRO | | Uninfected | |
|---|---|---|---|---|---|---|---|---|
| Donor | HIV-infected | Marker | Δ Emax (%) | EC50 (ug/mL) | Δ Emax (%) | EC50 (ug/mL) | Δ Emax (%) | EC50 (ug/mL) |
| | | PD-1 | 0 | >100 | 1 | >100 | 0 | >100 |
| | | Ki-67 | 1 | >100 | −1 | >100 | 1 | >100 |
| D2256 | Yes | CD69 | 0 | >100 | 0 | >100 | 0 | >100 |
| | | CD25 | 2 | >100 | −1 | >100 | −1 | >100 |
| | | PD-1 | −2 | >100 | 1 | >100 | 3 | >100 |
| | | Ki-67 | 0 | >100 | −2 | >100 | 0 | >100 |
| D4246 | No | CD69 | 3 | >100 | 1 | >100 | −1 | >100 |
| | | CD25 | −2 | >100 | −2 | >100 | 0 | >100 |
| | | PD-1 | 2 | >100 | 0 | >100 | 0 | >100 |
| | | Ki-67 | 0 | >100 | 0 | >100 | 0 | >100 |
| D4279 | No | CD69 | 3 | >100 | 0 | >100 | 0 | >100 |
| | | CD25 | −1 | >100 | −2 | >100 | 0 | >100 |
| | | PD-1 | 1 | >100 | −2 | >100 | −1 | >100 |
| | | Ki-67 | −1 | >100 | 1 | >100 | 1 | >100 |

TABLE 23

PGT-121.60 CD8 T-cell activation.

| | | | 7552 | | THRO | | Uninfected | |
|---|---|---|---|---|---|---|---|---|
| Donor | HIV-infected | Marker | Δ Emax (%) | EC50 (ug/mL) | Δ Emax (%) | EC50 (ug/mL) | Δ Emax (%) | EC50 (ug/mL) |
| D1597 | Yes | CD69 | 0 | >100 | 0 | >100 | 0 | >100 |
| | | CD25 | −1 | >100 | 0 | >100 | 0 | >100 |
| | | PD-1 | 0 | >100 | 0 | >100 | 0 | >100 |
| | | Ki-67 | 0 | >100 | 0 | >100 | 0 | >100 |
| D2256 | Yes | CD69 | 0 | >100 | 0 | >100 | 0 | >100 |
| | | CD25 | 0 | >100 | −1 | >100 | 0 | >100 |
| | | PD-1 | 0 | >100 | −1 | >100 | 0 | >100 |
| | | Ki-67 | 0 | >100 | 0 | >100 | 0 | >100 |
| D4246 | No | CD69 | 0 | >100 | 0 | >100 | 0 | >100 |
| | | CD25 | 1 | >100 | 0 | >100 | 0 | >100 |
| | | PD-1 | 0 | >100 | 0 | >100 | −1 | >100 |
| | | Ki-67 | 0 | >100 | 0 | >100 | 0 | >100 |
| D4279 | No | CD69 | −4 | >100 | 0 | >100 | 0 | >100 |
| | | CD25 | 0 | >100 | 1 | >100 | 0 | >100 |
| | | PD-1 | 0 | >100 | 0 | >100 | 0 | >100 |
| | | Ki-67 | 0 | >100 | 0 | >100 | 0 | >100 |

Methods

Gp120 X CD3 Duobody-induced upregulation of T cell activation markers was assessed by co-culturing $1 \times 10^4$ human primary T cells isolated by Ficol paque from leukopaks obtained from HIV-uninfected (n=2) and HIV-infected donors (n=2) with $1 \times 10^5$ CEM-NKr-CCR5-LucR CD4 T cells that were either (i) infected with a HIV-1 virus that was sensitive to killing by gp120 x CD3 Duobody® (7552), (ii) infected with a HIV-1 virus resistant to killing by gp120 x CD3 Duobody® (THRO), or (iii) uninfected at 37° C. for 24 hours. Wells were then washed 3X with FACS buffer, stained with Live/Dead Amcyan (Thermo Fisher, Cat. No. L34966) according to the manufacturer's instruction, washed 3X with FACS buffer and incubated at room temperature with the following antibodies diluted in FACS buffer for 20 minutes: anti-CD4-BV711 (BD Biosciences Cat. No. 563028); anti-CD8-APC/Cy7 (BD Biosciences, Cat. No. 560179); anti-CD25-PE/Cy7 (BD Biosciences, Cat. No. 557741); anti-CD69-PerCP/Cy5.5 (BioLegend, Cat. No. 310926); anti-PD-1-BV605 (BioLegend, Cat. No. 329924); anti-Ki67-AF700 (BD Biosciences. Cat. No. 561277). The cells were then washed 3X with FACS Buffer and fixed and permeabilized with 100 μL of Cytofix/Cytoperm for 10 mins, washed once with PermWash, resuspended in 120 μL of FACS buffer and flow cytometry data acquired on a LSR Fortessa or X20 FACS (BD Biosciences, San Jose, Calif.), and analyzed using FlowJo software (TreeStar).

The maximal fraction of CD4 and CD8 T cells expressing each activation marker (Emax) and the concentration that gave 50% Emax (EC50) were obtained from dose-response curves fitted by three parameter nonlinear regression (equation 1), using GraphPad Prism (La Jolla, Calif.) software.

$$Y = \text{Bottom} + \frac{\text{Top} - \text{Bottom}}{1 + 10^{(LogEC50 - X)}} \quad \text{Equation 1}$$

where Y=% activation, X=antibody concentration, Bottom=response in absence of antibody, and Top=maximal response.

The dose-response curves that had an Emax<5% above baseline (no antibody control wells) for T cell activation, the $EC_{50}$ values were reported as >100 μg/mL (maximum concentration tested).

Example 9: Killing of HIV-Infected CEM-NKr-CCR5-LucR CD4 T Cells Using PBMC Effector Cells The killing activity was assessed against 4 primary HIV-1 isolates or molecular clones. Each virus was assessed using PBMC effector cells from 2 healthy donors and results are displayed in Table 24. The proportion of infected cells killed (Emax) was significantly higher with the gp120 X CD3 Duobodies® (Exemplary, Variant 1 and Variant 2) (median, 76%) than with PGT-121.60 (median, 18%, Mann-Whitney, P<0.0001) and PGT-121 (median, 0%, Mann-Whitney, P<0.0001).

In addition to killing a significantly greater number of infected cells (Emax) compared to PGT-121.60 and PGT-121, gp120 X CD3 Duobodies (Exemplary, Variants 1 and 2; median EC50, 0.042 ug/mL) were also significantly more potent at killing infected cells than PGT-121 (median EC50, >100 ug/mL; Mann-Whitney, P<0.0001) and tended to be more potent than PGT-121.60 (median EC50, >100 ug/mL; Mann-Whitney, P=0.1157).

The difference in infected-cell-killing efficacy (Emax) between PGT-121.60 (median 18%) and PGT-121 (median 0%) was statistically significant (Mann Whitney, P=0.018). Furthermore, PGT-121.60 tended to be more potent than PGT-121 (P=0.128). The results suggest that CD3-bispecific Duobodies exhibited increased killing HIV-infected cells than PGT-121.60 (an effector-enhanced IgG1 mAb) or PGT-121 (IgG1 mAb).

Luciferase reagent and relative luminescence units (RLU) was measured in a luminometer according to the manufacturer's instructions.

Killing of HIV-infected CEM-NKr-CCR5-LucR CD4 T cells by gp120 x CD3 Duobody® and PGT-121.60 was determined from the RLU of gp120 x CD3 Duobody- or PGT-121.60-treated wells and compared to the RLU of HIV-infected CEM-NKr-CCR5-LucR CD4 T cells in the untreated wells (treated with human serum IgG only, n=2-10 per 96-well plate). The percent killing of HIV-infected CEM-NKr-CCR5-LucR CD4 T cells was calculated using the following equation:

100−((RLU of HIV-infected target cells in treated wells/RLU of HIV-infected target cells in untreated wells)*100).

The maximal fraction of infected cells killed (Emax) and the concentration that gave 50% killing ($IC_{50}$) were obtained from dose-response curves fitted by three parameter nonlinear regression (equation 1), using GraphPad Prism (La Jolla, Calif.) software.

$$Y = \text{Bottom} + \frac{\text{Top} - \text{Bottom}}{1 + 10^{(LogEC50-X)}} \qquad \text{Equation 1}$$

where Y=% killing, X=antibody concentration, Bottom=response in absence of antibody, and Top=maximal response.

TABLE 24

Killing of HIV-infected CEM-NKr-CCR5-LucR CD4 T cells.

| | | Emax (%) | | | | | EC50 (ug/mL) | | | | |
|---|---|---|---|---|---|---|---|---|---|---|---|
| Donor | Virus | Exemplary gp120 x CD3 | gp120 x CD3 V1 | gp120 x CD3 V2 | PGT-121.60 | PGT-121 | Exemplary gp120 x CD3 | gp120 x CD3 V1 | gp120 x CD3 V2 | PGT-121.60 | PGT-121 |
| 4288 | WITO | 63 | 80 | 76 | 46 | 0 | 0.046 | 0.06 | 0.03 | 0.767 | >100 |
| | 1489 | 85 | 86 | 87 | 48 | 0 | 0.005 | 0.002 | 0.002 | 0.014 | >100 |
| | 7015 | 68 | 78 | 74 | 26 | 15 | 0.446 | 0.362 | 0.289 | 0.004 | 0.334 |
| | 7552 | 81 | 87 | 86 | 54 | 0 | 0.003 | 0.008 | 0.001 | 0.016 | >100 |
| 4176 | WITO | 51 | 70 | 62 | 0 | 0 | 0.248 | 0.186 | 0.969 | >100 | >100 |
| | 1489 | 76 | 84 | 83 | 9 | 0 | 0.028 | 0.026 | 0.016 | >100 | >100 |
| | 7015 | 48 | 76 | 73 | 0 | 0 | 1.041 | 1.722 | 1.509 | >100 | >100 |
| | 7552 | 66 | 75 | 74 | 7 | 0 | 0.038 | 0.051 | 0.034 | >100 | >100 |

Methods

CEM-NKr-CCR5-LucR CD4 T cells were infected with HIV-1 isolates 92US657, 1489, 8398, and 7552 in R10+1+1 (RMPI plus 10% FBS, 1% penicillin/streptomycin, 1% HEPES) medium containing 20 Tg/mL DEAE Dextran and incubated for 4 hours at 37° C. Four hours after inoculation, CEM-NKr-CCR5-LucR CD4 T cells were diluted 3x with R10+1+1 and cultured for 48-72 hrs to allow de novo expression of HIV Env. Infected CEM-NKr-CCR5-LucR CD4 T cells were washed 3 times to remove free virus, plated in white, 96-well plates at 2×10$^4$ cells/well, and incubated with 10-fold serial dilutions of 7 concentrations of gp120 X CD3 Duobody® or PGT-121.60 in the presence of human serum IgG (5 mg/mL final concentration) for 1 hour, after which, 2×10$^5$ PBMCs/well were added to the opsonizing CEM-NKr-CCR5-LucR CD4 T cells and incubated at 37° C. for 48 hrs in a final volume of 100 µL. The killing of HIV-infected CEM-NKr-CCR5-LucR CD4 T cells was determined by addition of 100 µL/well of ONE-Glo™

The dose-response curves that had apparent Emax<10% for infected-cell killing, the IC50 values were reported as >100m/mL and the Emax with absolute value of ≤0% were assigned 0%.

Example 10: Killing of HIV-Infected Primary CD4 T Cells Using Tonsil-Derived Mononuclear Cells A major reservoir of latent HIV-infected cells in cART-suppressed, HIV-infected subjects resides in lymph nodes. The ability of antibodies to utilize effector cells present in lymphoid tissue was examined in an in vitro killing assay using mononuclear cells isolated from HIV-1 seronegative tonsils as effector cells and HIV-1-infected primary CD4 T cells as target cells. Due to the unavailability of autologous PBMCs from tonsil donors, heterologous primary CD4 T cells were used as target cells and a source of PBMC effector cells.

The results from tonsil-derived mononuclear cells (TDMCs) from a single donor, peripheral blood mononuclear cells (PBMCs) from two donors, and target cells infected with two HIV-1 viruses (CH058 and 92US727) are shown in Tables 25 and 26. Both TDMCs and PBMCs mediated robust killing of HIV-infected CD4 T cells by exemplary gp120 x CD3 Duobody and Duobodies comprised of Variant 1 or Variant 2, with Emaxes and IC50 concentrations ranging from 66%-82.6% and 0.013-0.053 μg/mL, respectively for TDMCs and Emaxes and IC50 concentrations ranging from 62%-84% and 0.001-0.024 ug/mL, respectively for PBMCs. In contrast, only PBMCs, but not TDMCs, were able to utilize PGT121.60 (or the negative control Duobody, Palivizumab×CD3) to mediate killing of HIV-infected CD4 T cells.

gp120 X CD3 Duobody® or PGT-121.60 in the presence of human serum IgG (5 mg/mL final concentration) for 1 hour. While the CD4$^+$ T-cell targets were opsonizing, the effector cells were prepared. The cryopreserved PBMCs and TDMCs were thawed and membrane-stained using PKH67 according to the manufacturer's instructions and added to the opsonizing target cells at 4×10$^5$ cells/well to yield an E:T ratio of 2:1. The effector cells were co-cultured with the opsonized target cells in a final volume of 200 per well for 48 hours.

The killing of HIV-infected target cells were determined by flow cytometry. At the end of the co-culture period, the cells were washed 2× with PBS, stained with 100 μL

TABLE 25

Maxmium percent of HIV-infected cells killed using tonsil-derived- and peripheral blood-derived-mononuclear effector cells.

| | | Tonsil-derived Effector Cells | | | | | PBMC-derived Effector Cells | | | | |
|---|---|---|---|---|---|---|---|---|---|---|---|
| Donor | Virus | 121 × CD3 | .66 | .71 | PGT121 DEALLS | Pali × CD3 | 121 × CD3 | .66 | .71 | PGT121 DEALLS | Pali × CD3 |
| 1003277 | CHO589 | 66 | 79.9 | 72 | 10.9 | 15.1 | 81.1 | 81.9 | 83.5 | 66.2 | 32.3 |
| 1004344 | CHO588 | 72.1 | 72.8 | 82.6 | 0 | 0 | 75.4 | 61.7 | 80.2 | 82.8 | 0 |
| 1004344 | 92US727 | 72.4 | 78.6 | 71.8 | 0 | 0 | 73.2 | 67.7 | 71.2 | 63.7 | 0 |

TABLE 26

Potency (IC50) of killing HIV-infected cells using tonsil-derived- and peripheral blood-derived-mononuclear effector cells.

| | | Tonsil-derived Effector Cells | | | | | PBMC-derived Effector Cells | | | | |
|---|---|---|---|---|---|---|---|---|---|---|---|
| Donor | Virus | 121 × CD3 | .66 | .71 | PGT121 DEALLS | Pali × CD3 | 121 × CD3 | .66 | .71 | PGT121 DEALLS | Pali × CD3 |
| 1003277 | CHO58 | 0.024 | 0.013 | 0.034 | >10 | >10 | 0.002 | 0.001 | 0.008 | 0.706 | >10 |
| 1004344 | CHO58 | 0.031 | 0.054 | 0.053 | >10 | >10 | 0.001 | 0.001 | 0.024 | 0.094 | >10 |
| 1004344 | 92US727 | 0.051 | 0.029 | 0.028 | >10 | >10 | 0.012 | 0.009 | 0.022 | 0.014 | >10 |

Methods gp120 X CD3 Duobody®- and PGT-121.60-dependent killing of HIV-infected CD4 T-cells was investigated in vitro using primary quiescent HIV-infected CD4$^+$ T-cells as target cells and peripheral blood derived-mononuclear cells and tonsil-derived mononuclear cells as effector cells. Non-diseased tonsils were obtained from healthy, consenting donors undergoing tonsillectomy. Tonsils were transported to the lab in DMEM medium containing antibiotics and processed within 8 hrs of the tonsillectomy. To isolate tonsil-derived mononuclear cells (TDMCs), fat and quarterized tissue was first removed. The tonsils were cut into 2-mm$^3$ pieces using a scalpel and dispersed through a 100 μm nylon cell strainer (Falcon). After washing with DMEM plus 1% FBS, TDMCs were recovered from the cell suspension by Ficol paque, cryopreserved in 90% DMSO, 10% FBS and stored in liquid nitrogen.

Primary CD4' cells were infected by spinfection with 50-100 ng p24/million cells at 1200×g for 2 hours and cultured for 5 days at 37° C. in RPMI media (supplemented with 10% FBS and 1% penicillin/streptomycin) with 30 U/mL IL2 (Roche Cat #11011456001). Following a 5-day rest to allow de novo antigen expression, the spinfected CD4$^+$ T-cell culture was washed 3 times to remove free virus, plated in 96-well plates at 2×10$^5$ cells/well, and incubated with 10-fold serial dilutions of 7 concentrations of Live/Dead Aqua (1/1000 diluted in PBS) for 10 minutes until stain was inactivated with addition of 100 FACS buffer (PBS+2% FBS). The cells were then washed with FACS Buffer and incubated with anti-CD4-PE/Cy7 mAb (1/50 dilution in FACS buffer) for 20 mins, then washed 3X with FACS Buffer and fixed and permeabilized with 100 μL of Cytofix/Cytoperm for 10 minutes. The cells were then washed once with PermWash and incubated with anti-p24-PE mAb in FACS buffer+10% PermWash for 25 minutes. Finally, the cells were washed 3X with FACS buffer, resuspended in 120 μL of FACS buffer, and flow cytometry data acquired on a LSR Fortessa or X20 FACS (BD Biosciences, San Jose, Calif.) and analyzed using FlowJo software (TreeStar).

In the killing of infected primary CD4$^+$ T-cells by PBMCs and TDMCs, the enumeration of HIV-infected target cells by flow cytometry used the following gating strategy: lymphocytes were selected based on forward and side scatter and live lymphocytes by negative staining for Live/Dead Aqua. The PKH67-negative live lymphocytes, representing the inoculated CD4$^+$ T-cells, were then selected and HIV-infected cells were identified as p24 Gag+, CD4low (due to HIV-mediated CD4 down-modulation) cells. The percent HIV-infection was represented by the percent of the inoculated (PKH67-negative) CD4$^+$ T cells that were HIV-infected (p24 Gag$^+$, CD4$^{low}$ positive).

The percent of HIV-infected target cells in PGT-121.60-treated wells was compared to the mean percent of HIV-infected target cells in the untreated wells (treated with human serum IgG only, n=2-10 per 96-well plate). The percent killing of HIV-infected target-cells was calculated using the following equation:

100−((% HIV-infected target cells in treated wells/% HIV-infected target cells in untreated wells) *100).

The maximal fraction of infected cells killed by PGT-121.60 (Emax) and the concentration that gave 50% killing (IC50) were obtained from dose-response curves fitted by three parameter nonlinear regression (equation 1), using GraphPad Prism (La Jolla, Calif.) software.

$$Y = \text{Bottom} + \frac{\text{Top} - \text{Bottom}}{1 + 10^{(LogEC50-X)}} \quad \text{Equation 1}$$

where Y=% killing, X=antibody concentration, Bottom=response in absence of antibody, and Top=maximal response.

The dose-response curves that had apparent Emax<40% for infected-cell killing, the IC50 values were reported as >10 μg/mL and the Emax with absolute value of ≤0% were assigned 0%.

Example 11: Killing of HIV-Infected CD4 T Cells by T-Cell Subsets

To investigate which T-cell subsets are capable of mediating gp120 x CD3 Duobody-dependent killing of HIV-infected cells, we assessed the ability of isolated T-cell subsets, namely memory CD8 T cells, naïve CD4 T cells, memory CD4 T cells, effector memory CD4 T cells, and γΔ T cells, to mediate killing of HIV-infected CD4 T cells.

The results shown in Table 27 indicate that all T cell subsets examined (i.e. memory CD8 T cells, naïve CD4 T cells, memory CD4 T cells, effector memory CD4 T cells and γΔ T cells) were able to mediate potent (EC50; 0.006-0.14 μg/mL), effective (Emax; 27%-68%) Duobody-dependent killing of T cells infected with HIV-1 WITO infectious molecular clone utilizing Exemplary gp120 x CD3 Duobody®, gp120 x CD3 Duobody® Variant 1, and gp120 x CD3 Duobody® Variant 2. In contrast, CD8 and CD4 T cells subsets were unable to mediate effective killing of HIV-infected T cells utilizing PGT-121.60. Results also showed that γΔ T cells were able to mediate effective killing of HIV-infected T cells by PGT-121.60, with Emax comparable to that achieved by gp120 x CD3 Duobodies (48% vs 43%-68%), albeit with reduced potency than the gp120 x CD3 Duobodies (EC50 12 ug/mL vs 0.02 ug/mL-0.14 ug/mL). The ability of PGT-121.60 to mediate antibody-dependent killing of HIV-infected T cells by γΔ T cells is consistent with publications that γΔ T cells express FcγR CD16 and are capable of mediating antibody-dependent cellular cytotoxicity (Tokuyama et al, 2008; Seidel et al, 2014; Chen & Freedman, 2008).

TABLE 27

Emax (%) and Potency (IC50) of killing HIV-infected cells by various T cell subsets.

| | Emax (%) | | | | | EC50 (ug/mL) | | | | |
|---|---|---|---|---|---|---|---|---|---|---|
| Effector Cell Type | Exemplary | PGT121.71 (V1)6 | PGT121.66 (V2) | 9722 DEALLS | Pali x CD3 | Exemplary | PGT121.71 (V1)6 | PGT121.66 (V2) | 9722 DEALLS | Pali x CD3 |
| Memory CD8 | 40 | 57 | 62 | 9 | 10 | 0.02 | 0.1 | 0.009 | >10 | >10 |
| Naïve CD4 | 35 | 38 | 44 | nd | nd | 0.03 | 0.03 | 0.005 | nd | nd |
| Memory CD4 | 27 | 47 | 49 | 9 | 3 | 0.02 | 0.02 | 0.007 | >10 | >10 |
| Eff Memory CD4 | 41 | 47 | 49 | 0 | 0 | 0.02 | 0.03 | 0.01 | >10 | >10 |
| γ Δ CD4 | 46 | 66 | 65 | 18 | 0 | 0.09 | 0.14 | 0.02 | 0.36 | >10 |

Methods gp120 X CD3 Duobody®- and PGT-121.60-dependent killing of HIV-infected CD4 T-cells by T cell subsets was investigated in vitro using the Infected-Cell Killing by PBMC Effector Cells Assay described in Example 5 with the following modification: rather than using whole PBMCs as effector cells, T cell subsets isolated according to the manufacturers protocol using the cell isolation kits detailed in Table 21 were used as effector cells at a 2:1 effector to target ratio. EC50 values were reported as >10 ug/mL (maximum concentration tested) if Emax was ≤10%.

TABLE 28

T cell subset isolation kits

| T cell subset | Supplier | Catalogue # |
|---|---|---|
| Memory CD8 T cells | Miltenyi Biotec | 130-094-412 |
| Naïve CD4 T cells | Miltenyi Biotec | 130-094-131 |
| Memory CD4 T cells | Miltenyi Biotec | 130-094-893 |
| Eff memory CD4 T cells | Miltenyi Biotec | 130-094-125 |
| γΔ CD4 | Miltenyi Biotec | 130-092-892 |

Example 11: Human Platelet Binding

To assess the binding to human platelets, flow cytometry-based platelet binding assays were conducted and compared with PGT-121.60. Platelet rich plasma (PRP) samples were prepared from whole blood of 3 human healthy donors and treated with tested articles at 1000 µg/ml or 250 µg/ml concentration. The RSV fusion protein targeting monoclonal antibody palivizumab (Pali) and its derived duobody, Pali×CD3, were used as non-anti-HIV Env control antibodies.

The results shown in Table 29 indicate that MFI of 1000 µg/ml PGT-121.60 binding to human platelets was increased 40-100 fold over the staining background in the samples from 3 donors, while MFIs of the gp120 X CD3 Duobody variants were increased 15-50 fold in the same samples. The platelet staining MFI reduced to 4-7 fold compared to PGT-121.60 and 1-3 fold for variants when the articles were tested at 250 µg/ml in the binding assay. MFIs of non-anti-HIV Env control antibodies Pali and Pali×CD3 were at background levels at both tested concentrations. Compared to PGT-121.60, variants showed lower human platelet binding activity. The average binding MFI of the Duobody variants was 35-47% of PGT-121.60 at 1000 µg/ml concentration (Table 30).

Methods

Platelet-rich plasma (PRP) samples were prepared from human whole blood samples. Briefly, whole blood samples were centrifuged at 170×g for 15 minutes without brakes at room temperature. After centrifugation, PRP was collected from the top layer of each sample, and then diluted 5-fold in modified HT (mHT) buffer (10 mM HEPES, 137 mM NaCl, 2.8 mM KCl, 1 mM $MgCl_2$, 12 mM $NaHCO_3$, 0.4 mM $Na_2HPO_4$, 0.35% BSA, 5.5 mM glucose, pH 7.4). Diluted test antibodies (50 µL) were added to equal volumes of the PRP samples and incubated 45 minutes at room temperature. At the end of incubation, an equal volume of BD FACS Stain buffer (phosphate buffered saline with 2% fetal bovine serum) was added and assay plates were centrifuged at 2000×g for 5 minutes at room temperature. The supernatant was aspirated and the washed PRP samples were re-suspended in mHT buffer and stained with PE anti-CD61, FITC anti-CD41 and APC anti-human IgG secondary antibodies for 30 minutes at 4° C. Following staining, PRP samples were washed with BD FACS buffer and re-suspended in 125 µL BD FACS Stain buffer and analyzed by flow cytometry with a BD LSRFortessa™ cell analyzer (BD Biosciences, San Jose, Calif.) and FlowJo software (TreeStar, Ashland, Oreg.).

The platelet population was defined as PE anti-CD41 and FITC anti-CD61 double positive FACS events. The mean fluorescence intensity (MFI) values of the APC anti-human IgG of the platelet populations were quantified. The fold-increase of MFI of each test article over staining background (determined by APC anti-human IgG secondary antibody only) was then calculated. To compare platelet-binding activities of the gp120 X CD3 duobody variants to that of PGT-121.60, the MFI percentage of each duobody variant to PGT-121.60 at 1000 µg/ml in each sample was calculated.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 29

Fold increase of human platelet binding MFI over staining background.

| Test Article | Donor ID | Conc (µg/ml) 1000.00 | 250.00 |
|---|---|---|---|
| Pali | 1 | 1.34 | 0.96 |
|  | 2 | 1.02 | 0.98 |
|  | 3 | 0.76 | 0.71 |
| Pali × CD3 | 1 | 2.32 | 1.39 |
|  | 2 | 0.88 | 0.59 |
|  | 3 | 0.95 | 1.48 |
| 9722 × CD3 | 1 | 21.23 | 1.37 |
|  | 2 | 15.95 | 1.57 |
|  | 3 | 32.07 | 0.98 |
| gp120 × CD3 variant 1 | 1 | 24.32 | 2.53 |
|  | 2 | 46.79 | 2.39 |
|  | 3 | 16.75 | 2.47 |
| gp120 × CD3 variant 2 | 1 | 41.85 | 2.91 |
|  | 2 | 51.03 | 2.72 |
|  | 3 | 24.02 | 2.07 |
| PGT-121.60 | 1 | 118.32 | 6.06 |
|  | 2 | 108.26 | 6.97 |
|  | 3 | 41.76 | 4.28 |

TABLE 30

Comparison of gp120 × CD3 Duobody variants and PGT-121.60 binding to human platelets.

| mAb | 9722 × CD3 | | | gp120 X CD3 variant 1 | | | gp120 X CD3 variant 2 | | |
|---|---|---|---|---|---|---|---|---|---|
| Donor | 1 | 2 | 3 | 1 | 2 | 3 | 1 | 2 | 3 |
| % of PGT-121.60 at 1000 µg/ml | 17.94 | 14.73 | 76.79 | 20.55 | 43.23 | 40.10 | 35.37 | 47.13 | 57.52 |
| mean | | 36.49 | | | 34.63 | | | 46.68 | |

What is claimed is:

1. A bispecific antibody that binds to human immunodeficiency virus-1 (HIV-1) Envelope (Env) glycoprotein gp120 (gp120) and human CD3ε, wherein the antibody comprises:
    (a) a first antigen-binding domain that comprises a first heavy chain variable domain (VH) and a first light chain variable domain (VL), wherein the first antigen-binding domain binds to gp120 and comprises:
        (i) a first VH-complementarity determining region (CDR) 1 comprising the amino acid sequence of SEQ ID NO:1;
        (ii) a first VH-CDR2 comprising the amino acid sequence of SEQ ID NO:2;
        (iii) a first VH-CDR3 comprising the amino acid sequence of SEQ ID NO:3;
        (iv) a first VL-CDR1 comprising the amino acid sequence of SEQ ID NO:4;
        (v) a first VL-CDR2 comprising the amino acid sequence of SEQ ID NO:5; and
        (vi) a first VL-CDR3 comprising the amino acid sequence of SEQ ID NO:6, and wherein the VL comprises a tyrosine at position 67A (Kabat numbering), a phenylalanine at position 67A (Kabat numbering), a threonine at position 67A (Kabat numbering), or a glycine at position 67 (Kabat numbering); and
    (b) a second antigen-binding domain that binds to human CD3ε.

2. The antibody of claim 1, wherein the first VH comprises an amino acid sequence of SEQ ID NO:7.

3. The antibody of claim 1, wherein the first VL comprises an amino acid sequence that is an amino acid sequence selected from the group consisting of SEQ ID NO:8, SEQ ID NO:81, SEQ ID NO:82, SEQ ID NO:83 and SEQ ID NO:84.

4. The antibody of claim 1, wherein the first antigen-binding domain comprises a heavy chain having an amino acid sequence of SEQ ID NO:9.

5. The antibody of claim 1, wherein the first antigen-binding domain comprises a light chain having an amino acid sequence of SEQ ID NO:10.

6. The antibody of claim 1, wherein the first VH comprises the amino acid sequence of SEQ ID NO:7 and the first VL comprises an amino acid sequence selected from the group consisting of SEQ ID NO:8, SEQ ID NO:81, SEQ ID NO:82, SEQ ID NO:83 and SEQ ID NO:84.

7. The antibody of claim 1, wherein the antibody is a kappa-lambda body, a dual-affinity re-targeting molecule (DART), a knob-in-hole, a strand-exchange engineered domain body (SEEDbody), a Bispecific T cell engager (BiTe), a CrossMab, an Fcab, a Diabody, a Tandem diabody (TandAb), or a DuoBody.

8. The antibody of claim 1, wherein the first antigen-binding domain is fused directly or via an intervening amino acid sequence to a first heavy chain constant region selected from the group consisting of human $IgG_1$, human $IgG_2$, human $IgG_3$, human $IgG_4$, human $IgA_1$, and human $IgA_2$, and wherein the second antigen-binding domain is fused directly or via an intervening amino acid sequence to a second heavy chain constant region selected from the group consisting of human $IgG_1$, human $IgG_2$, human $IgG_3$, human $IgG_4$, human $IgA_1$, and human $IgA_2$.

9. The antibody of claim 8, wherein the first heavy chain constant region is human $IgG_1$, and wherein the second heavy chain constant region is human $IgG_1$.

10. The antibody of claim 9, wherein the first antigen-binding domain is fused directly or via an intervening amino acid sequence to a first light chain constant region that is a human lambda constant region, and wherein the second antigen-binding domain is fused directly or via an intervening amino acid sequence to a second light chain constant region that is a human lambda constant region.

11. The antibody of claim 8, wherein the effector function of the first heavy chain constant region and the second heavy chain constant region are reduced or abrogated.

12. The antibody of claim 8, wherein the first heavy chain constant region comprises a human $IgG_1$ heavy chain constant region that comprises a N297A mutation or a N297Q mutation and/or the second heavy chain constant region comprises a human $IgG_1$ heavy chain constant region that comprises a N297A mutation or a N297Q mutation.

13. The antibody of claim 1, further comprising a cytotoxic agent, a radioisotope, a therapeutic agent, an anti-viral agent, or a detectable label.

14. A pharmaceutical composition comprising the antibody of claim 1, and a pharmaceutically acceptable excipient.

* * * * *